US012263216B2

(12) United States Patent
Kassiotis et al.

(10) Patent No.: US 12,263,216 B2
(45) Date of Patent: Apr. 1, 2025

(54) CANCER ANTIGENS AND METHODS

(71) Applicants: The Francis Crick Institute Limited, London (GB); Enara Bio Limited, Oxford (GB)

(72) Inventors: George Kassiotis, London (GB); George Young, London (GB); Jan Attig, London (GB); Bram Snijders, London (GB); David Perkins, London (GB); Fabio Marino, London (GB); Nicola Ternette, London (GB)

(73) Assignees: The Francis Crick Institute Limited, London (GB); Enara Bio Limited, Oxfordshire (GB)

( * ) Notice: Subject to any disclaimer, the term of this patent is extended or adjusted under 35 U.S.C. 154(b) by 921 days.

(21) Appl. No.: 17/232,597

(22) Filed: Apr. 16, 2021

(65) Prior Publication Data

US 2021/0353729 A1 Nov. 18, 2021

Related U.S. Application Data

(63) Continuation of application No. PCT/GB2019/052980, filed on Oct. 18, 2019.

(30) Foreign Application Priority Data

Oct. 19, 2018 (EP) .................................... 18201634

(51) Int. Cl.

| | |
|---|---|
| ***A61K 39/39*** | (2006.01) |
| ***A61K 39/00*** | (2006.01) |
| ***A61P 35/00*** | (2006.01) |
| ***C07K 14/47*** | (2006.01) |
| ***C07K 16/32*** | (2006.01) |
| ***C12N 5/0783*** | (2010.01) |
| ***C12N 5/0784*** | (2010.01) |

(52) U.S. Cl.

CPC .......... *A61K 39/39* (2013.01); *A61K 39/4611* (2023.05); *A61K 39/46449* (2023.05); *A61K 39/464491* (2023.05); *A61P 35/00* (2018.01); *C07K 14/4748* (2013.01); *C07K 16/32* (2013.01); *C12N 5/0636* (2013.01); *C12N 5/0639* (2013.01); *A61K 2039/55505* (2013.01); *A61K 2039/55522* (2013.01); *A61K 2039/55538* (2013.01); *A61K 2039/55561* (2013.01); *A61K 2039/55566* (2013.01); *A61K 2039/55572* (2013.01); *A61K 2039/55577* (2013.01); *A61K 2039/6031* (2013.01); *A61K 2039/876* (2018.08); *A61K 2239/57* (2023.05); *C07K 2319/00* (2013.01)

(58) Field of Classification Search

CPC .......... A61K 2039/55522; A61K 2039/55538; A61K 2039/55572; A61K 2039/55505; A61K 2039/55561; A61K 2039/55566; A61K 2039/55577; A61K 2039/876; A61K 2239/57; A61K 38/00; A61K 39/39; A61K 39/46449; C07K 14/4748; C07K 16/32; C07K 2319/00

See application file for complete search history.

(56) References Cited

U.S. PATENT DOCUMENTS

| | | | |
|---|---|---|---|
| 7,504,490 B1 | 3/2009 | Weinstock et al. | |
| 7,745,391 B2 * | 6/2010 | Mintz ..................... | A61P 37/00 514/19.3 |
| 2002/0082206 A1 | 6/2002 | Leach et al. | |
| 2007/0072175 A1 | 3/2007 | Cooper et al. | |
| 2007/0083334 A1 | 4/2007 | Mintz et al. | |
| 2010/0136518 A1 | 6/2010 | Humer et al. | |
| 2010/0285509 A1 | 11/2010 | Mayer et al. | |
| 2011/0183924 A1 | 7/2011 | Mintz et al. | |
| 2011/0217326 A1 | 9/2011 | Kudo et al. | |
| 2014/0099324 A1 | 4/2014 | Wang-Johanning | |
| 2015/0119265 A1 | 4/2015 | Perot et al. | |
| 2016/0160295 A1 | 6/2016 | Chinnaiyan et al. | |
| 2019/0322721 A1 | 10/2019 | Sonntag et al. | |
| 2019/0351040 A1 | 11/2019 | Valiente et al. | |
| 2021/0353729 A1 | 11/2021 | Kassiotis et al. | |
| 2022/0211760 A1 | 7/2022 | Kassitois et al. | |
| 2022/0213159 A1 | 7/2022 | Kassiotis et al. | |
| 2022/0218807 A1 | 7/2022 | Kassiotis et al. | |
| 2022/0220175 A1 | 7/2022 | Kassiotis et al. | |

FOREIGN PATENT DOCUMENTS

| | | | |
|---|---|---|---|
| EP | 1580263 | A1 | 9/2005 |
| JP | 2003304877 | A | 10/2003 |
| WO | WO-0006598 | A1 | 2/2000 |
| WO | 2001064835 | A2 | 9/2001 |
| WO | 200175067 | A2 | 10/2001 |
| WO | 2001077330 | A2 | 10/2001 |

(Continued)

OTHER PUBLICATIONS

Attermann et al., "Human endogenous retroviruses and their implication for immunotherapeutics of cancer," Ann Oncol. Nov. 1, 2018;29(11):2183-2191.

Attig et al., "Physiological and Pathological Transcriptional Activation of Endogenous Retroelements Assessed by RNA-Sequencing of B Lymphocytes," Front Microbiol. Dec. 12, 2017;8:2489.

Bannert et al., "HERVs new role in cancer: from accused perpetrators to cheerful protectors," Front Microbiol. Feb. 13, 2018;9:178.

Bulik-Sullivan et al., "Deep learning using tumor HLA peptide mass spectrometry datasets improves neoantigen identification," Nat Biotechnol. Jan. 2019;37(1):55-63.

Cegolon et al., "Human endogenous retroviruses and cancer prevention: evidence and prospects," BMC Cancer. Jan. 3, 2013;13:4.

(Continued)

*Primary Examiner* — Bao Q Li

(74) *Attorney, Agent, or Firm* — Dechert LLP; Andrew T. Wilkins; Sean Coughlin

(57) ABSTRACT

There are disclosed inter alia polypeptides and nucleic acids encoding said polypeptides which are useful in the treatment, prevention and diagnosis of cancer, particularly melanoma, especially cutaneous melanoma and uveal melanoma.

3 Claims, 64 Drawing Sheets

Specification includes a Sequence Listing.

(56) References Cited

FOREIGN PATENT DOCUMENTS

| | | | |
|---|---|---|---|
| WO | 2004038003 | A2 | 5/2004 |
| WO | WO-2005099750 | A1 | 10/2005 |
| WO | 2006105642 | A1 | 10/2006 |
| WO | WO-2006103562 | A2 | 10/2006 |
| WO | WO-2006119527 | A2 | 11/2006 |
| WO | 2007073478 | A2 | 6/2007 |
| WO | WO-2007109583 | A2 | 9/2007 |
| WO | WO-2007137279 | A2 | 11/2007 |
| WO | 2008016356 | A2 | 2/2008 |
| WO | 2008118258 | A2 | 10/2008 |
| WO | 2009026116 | A2 | 2/2009 |
| WO | 2009039244 | A2 | 3/2009 |
| WO | 2013033333 | A1 | 3/2013 |
| WO | 2013040142 | A2 | 3/2013 |
| WO | 2014004385 | A2 | 1/2014 |
| WO | 2017097699 | A1 | 6/2017 |
| WO | 2020079448 | A1 | 4/2020 |
| WO | 2020260897 | A1 | 12/2020 |
| WO | 2020260898 | A2 | 12/2020 |
| WO | 2021005338 | A2 | 1/2021 |
| WO | 2021005339 | A1 | 1/2021 |

OTHER PUBLICATIONS

Escudier et al., "Vaccination of metastatic melanoma patients with autologous dendritic cell (DC) derived-exosomes: results of thefirst phase I clinical trial," J Transl Med. Mar. 2, 2005;3:10.
Ferrucci et al., "Newly identified tumor antigens as promising cancer vaccine targets for malignant melanoma treatment," Curr Top Med Chem. 2012; 12(1):11-31.
"*Homo sapiens* isolate KOREF chromosome 13 KOREF.81120, whole genome shotgun sequence," EBI Accession No. LWKW01081120.
"*Homo sapiens* isolate KOREF chromosome 18 KOREF.98780, whole genome shotgun sequence," EBI Accession No. LWKW01098780.
Jayson et al., "Ovarian cancer," Lancet. Oct. 11, 2014;384(9951): 1376-88.
"Macaca fuscata fuscata DNA, clone: MSB2-228H05_R, genomic survey sequence," EBI Accession No. AG759599.
PCT International Search Report and Written Opinion from PCT/US2021/028029, dated Aug. 9, 2021.
Schuster et al., "The immunopeptidomic landscape of ovarian carcinomas," Proc Natl Acad Sci U S A. Nov. 14, 2017;114(46):E9942-E9951.
"SubName: Full = Acetyltransferase {ECO : 0000313 | EMBL : EFE74977.2}," EBI Accession No. UNIPROT: D6AHI5.
Ternette et al., "Immunopeptidomic Profiling of HLA-A2-Positive Triple Negative Breast Cancer Identifies Potential Immunotherapy Target Antigens," Proteomics. Jun. 2018;18(12):e1700465.
"UI-H-DPO-avc-g-14-0-UI.s1 NCI_CGAP_Fs1 *Homo sapiens* cDNA clone UI-H-DPO-avc-g-14-0-UI 3', mRNA sequence," EBI Accession No. CA441646.
UniParc—UPI00060150B7.
Yin et al., "Immature dendritic cell-derived exosomes: a promise subcellular vaccine for autoimmunity," Inflammation. Feb. 2013;36(1):232-40.
PCT International Search Report and Written Opinion from PCT/GB2021/050940, dated Aug. 3, 2021.
Pandiani, Charlotte, et al. "Focus on cutaneous and uveal melanoma specificities." Genes & development 31.8 (2017):724-743.
Attig et al., Supplemental Material—"LTR retroelement expansion of the human cancer transcriptome and immunopeptidome revealed by de novo transcript assembly," Genome Res. Oct. 2019;29(10): (160 pages).
Acha-Orbea, et al., "Superantigens of Mouse Mammary Tumor Virus," Ann Rev Immunol. 13: 459-486 (1995).
Andersson et al., "Expression of Human Endogenous Retrovirus ERV3 (HERV-R) mRNA in Normal and Neoplastic Tissues," International Journal of Oncology 12(2): 309-322 (1998).
Aspergillus fumigatus ORF amino acid sequence SEQ ID No. 31732 EBI Accession No. GSP: AWP60286.
Attig et al., "LTR Retroelement Expansion of the Human Cancer Transcriptome and Immunopeptidome Revealed by De Novo Transcript Assembly," Genome Res. 10: 1578-1590 (2019).
Aung et al., "Expression of New York Esophageal Squamous Cell Carcinoma-1 in Primary and Metastatic Melanoma," Hum Pathol. 45(2): 259-267 (2014).
Babaian et al., "Endogenous Retroviral Promoter Exaptation in Human Cancer." Mobile DNA 7(1): 1-21 (2016).
Bassani-Sternberg et al., "Direct Identification of Clinically Relevant Neoepitopes Presented on Native Human Melanoma Tissue by Mass Spectrometry," Nature Communications 7(1): 1-16 (2016).
Cherkasova et al., "Endogenous Retroviruses as Targets for Antitumor Immunity in Renal Cell Cancer and Other Tumors," Front Oncol. 3: 243 (2013).
"DNA fragments of a human Tox gene, 47247" EBI Accession No. GSN: ARC03196.
Gigoux et al., "Refusing to TAP Out: 16 New Human TEIPPs Identified," The Journal of Experimental Medicine 215(9): 2233 (2018).
Hoyos et al., "Cancer-Specific Splicing Changes and the Potential for Splicing-Derived Neoantigens," Cancer Cell 34(2): 181-183 (2018).
Human 0RF553 EBI Accession No. GSP: ABP64183.
Human derived non-coding RNA CAT2186.2 SEQ: 1274 EBI accession No. GSN: BCQ57982.
Human derived non-coding RNA MEAT62.1, SEQ: 1895 EBI Accession No. GSN: BCQ58603.
Humer et al., "Identification of a Melanoma Marker Derived from Melanoma-Associated Endogenous Retroviruses," Cancer Research 66(3): 1658-1663 (2006).
Hurst et al., "Activation of the Innate Immune Response by Endogenous Retroviruses," J Gen Virol., 96(6): 1207-1218 (2015).
Kahles et al., "Comprehensive Analysis of Alternative Splicing Across Tumors From 8,705 Patients," Cancer Cell 4(2): 211-224 (2018).
Kassiotis et al., "Immune Responses to Endogenous Retroelements: Taking the Bad With the Good," Nat Rev Immunol., 16(4): 207-219 (2016).
Katoh et al., "Association of Endogenous Retroviruses and Long Terminal Repeats With Human Disorders," Front Oncol. 3: 234 (2013).
Kershaw et al., "Immunization Against Endogenous Retroviral Tumor-Associated Antigens," Cancer Research 61(21): 7920-7924 (2001).
Laumont et al., "Noncoding Regions Are The Main Source of Targetable Tumor-Specific Antigens," Sci Transl Med. 10: 470 (2018).
Lauss et al., "Mutational and Putative Neoantigen Load Predict Clinical Benefit of Adoptive T Cell Therapy in Melanoma," Nature Communications 8(1): 1-11 (2017).
Lock et al., "Distinct isoform of FABP7 revealed by screening for retroelement-activated genes in diffuse large B-cell lymphoma." Proceedings of the National Academy of Sciences 111.34 (2014): E3534-E3543.
Mangeney et al., "The Full-Length Envelope of an HERV-H Human Endogenous Retrovirus has Immunosuppressive Properties." Journal of General Virology 82(10): 2515-2518 (2001).
Marijt et al., "Identification of Non-Mutated Neoantigens Presented by TAP-Deficient Tumors," Journal of Experimental Medicine 215(9): 2325-2337 (2018).
Ribas et al., "Cancer Immunotherapy Using Checkpoint Blockade," Science 359(6382): 1350-1355 (2018).
Ruprecht et al., "Endogenous Retroviruses and Cancer," Cell Mol Life Sci., 65(21): 3366-3382 (2008).
Sacha et al., "Vaccination With Cancer-and HIV Infection-Associated Endogenous Retrotransposable Elements is Safe and Immunogenic," The Journal of Immunology 189(3): 1467-1479 (2012).
Schiavetti et al., "A Human Endogenous Retroviral Sequence Encoding an Antigen Recognised on Melanoma by Cytolytic T Lymphocytes," Cancer Res. 62(19): 5510-5516 (2002).

(56) References Cited

OTHER PUBLICATIONS

Slansky et al., "Enhanced Antigen-Specific Antitumor Immunity with Altered Peptide Ligands that Stabilize the MHC-Peptide-TCR Complex," Immunity 13(4): 529-538 (2000).
Wold et al. "Adenovirus Vectors for Gene Therapy, Vaccination and Cancer Gene Therapy," Current Gene Therapy 13(6): 421-433 (2013).
Smart et al., "Intron Retention is a Source of Neoepitopes in Cancer," Nature Biotechnology 36(11): 1056-1058 (2018).
Acetyltransferase EBI Accession No. UNIPROT: D6AHI5.
Wang-Johanning et al., "Detecting the Expression of Human Endogenous Retrovirus E Envelope Transcripts in Human Prostate Adenocarcinoma," Cancer 98:(1): 187-197 (2003).
Yossef et al., "Enhanced Detection of Neoantigen-Reactive T Cells Targeting Unique and Shared Oncogenes for Personalized Cancer Immunotherapy," JCI Insight 3(19): (2018).

* cited by examiner

| b+ | # | seq | # | y+ |
|---|---|---|---|---|
| 114.0550 | 1 | A | 18 | |
| 171.0764 | 2 | G | 17 | 1763.7943 |
| 258.1084 | 3 | S | 16 | 1706.7729 |
| 386.1670 | 4 | Q | 15 | 1619.7408 |
| 473.1991 | 5 | S | 14 | 1491.6823 |
| 560.2311 | 6 | S | 13 | 1404.6502 |
| 647.2631 | 7 | S | 12 | 1317.6182 |
| 794.3315 | 8 | F | 11 | 1230.5862 |
| 895.3792 | 9 | T | 10 | 1083.5178 |
| 1051.4803 | 10 | R | 9 | 982.4701 |
| 1108.5018 | 11 | G | 8 | 826.3690 |
| 1245.5607 | 12 | H | 7 | 769.3475 |
| 1346.6084 | 13 | T | 6 | 632.2886 |
| 1403.6298 | 14 | G | 5 | 531.2409 |
| 1532.6724 | 15 | E | 4 | 474.2195 |
| 1633.7201 | 16 | T | 3 | 345.1769 |
| 1730.7729 | 17 | P | 2 | 244.1292 |
| | 18 | Q | 1 | 147.0764 |

| b+ | # | seq | # | y+ |
|---|---|---|---|---|
| 129.1022 | 1 | K | 10 | |
| 230.1499 | 2 | T | 9 | 994.5680 |
| 358.2449 | 3 | K | 8 | 893.5203 |
| 415.2663 | 4 | G | 7 | 765.4254 |
| 502.2984 | 5 | S | 6 | 708.4039 |
| 615.3824 | 6 | L | 5 | 621.3719 |
| 702.4145 | 7 | S | 4 | 508.2878 |
| 801.4829 | 8 | V | 3 | 421.2558 |
| 948.5513 | 9 | F | 2 | 322.1874 |
| | 10 | R | 1 | 175.1190 |

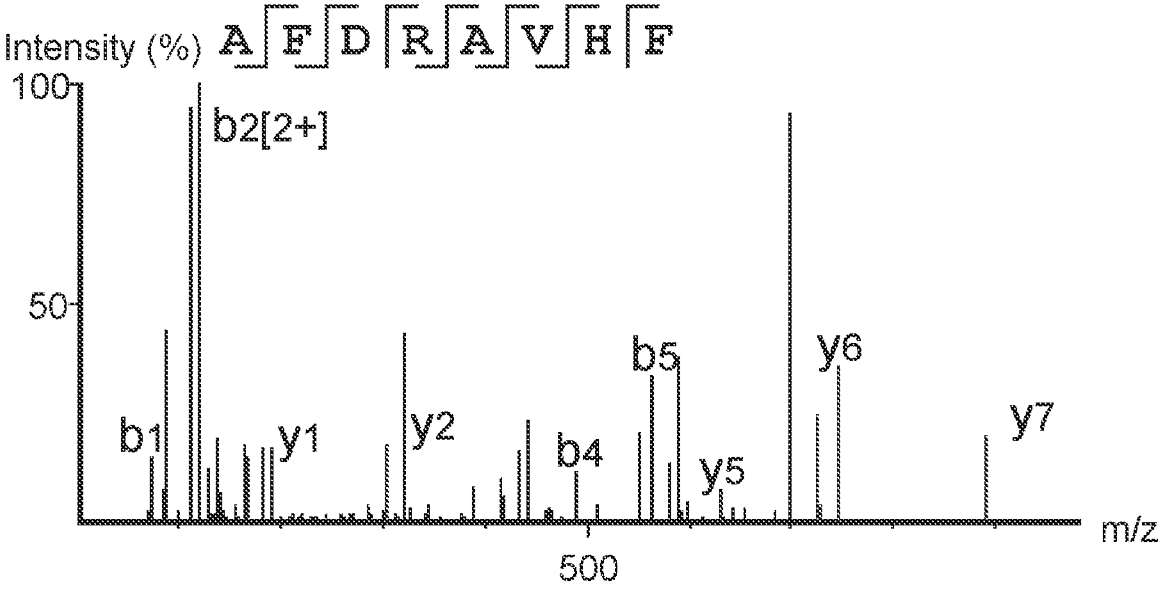
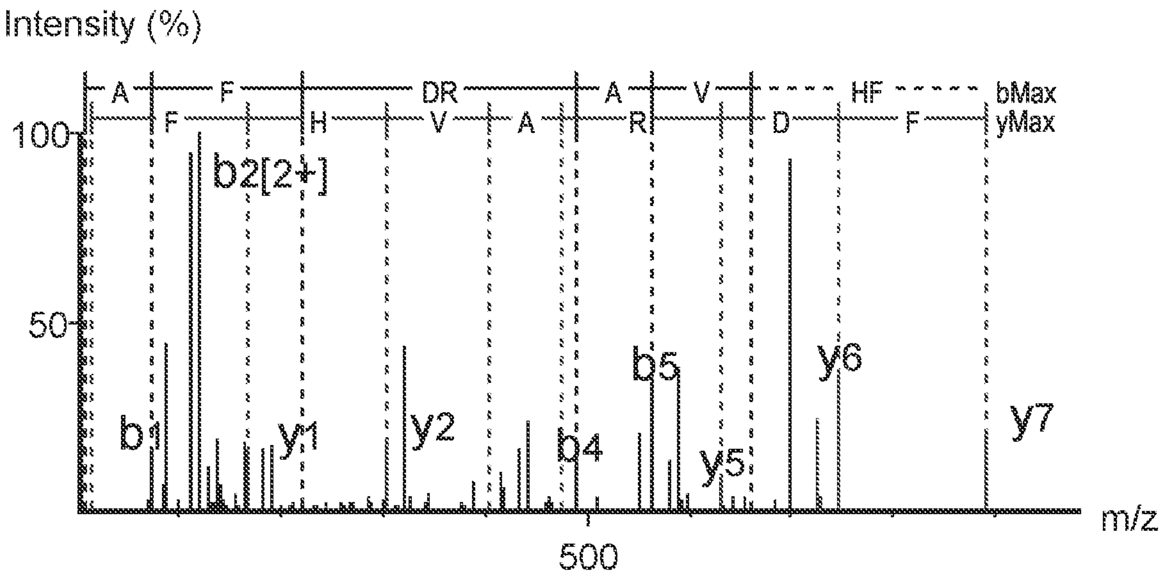
FIG. 31

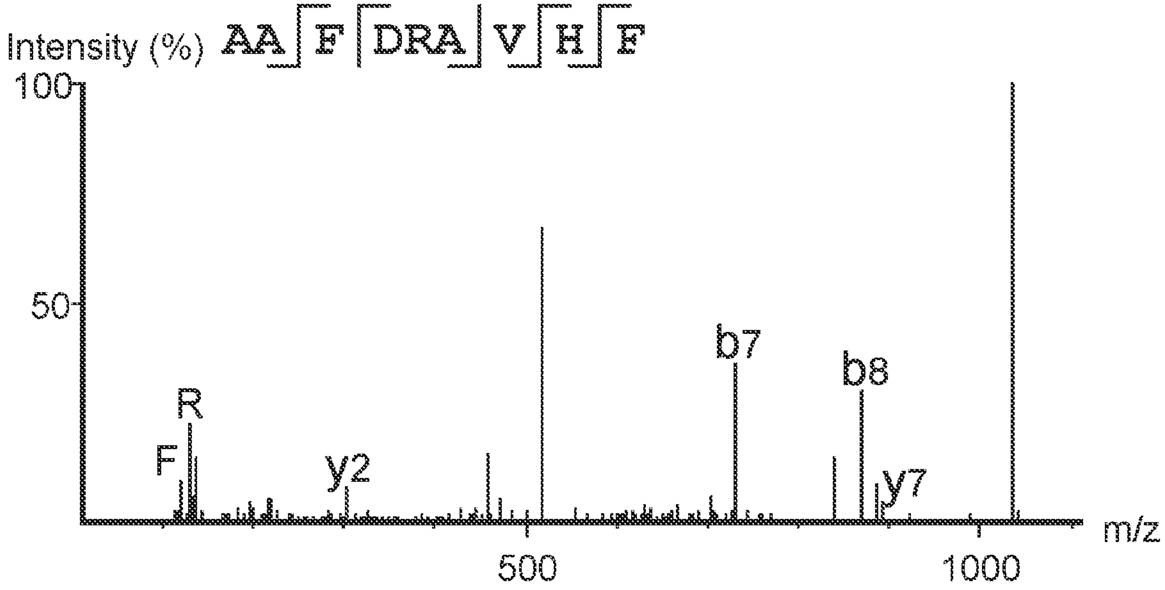
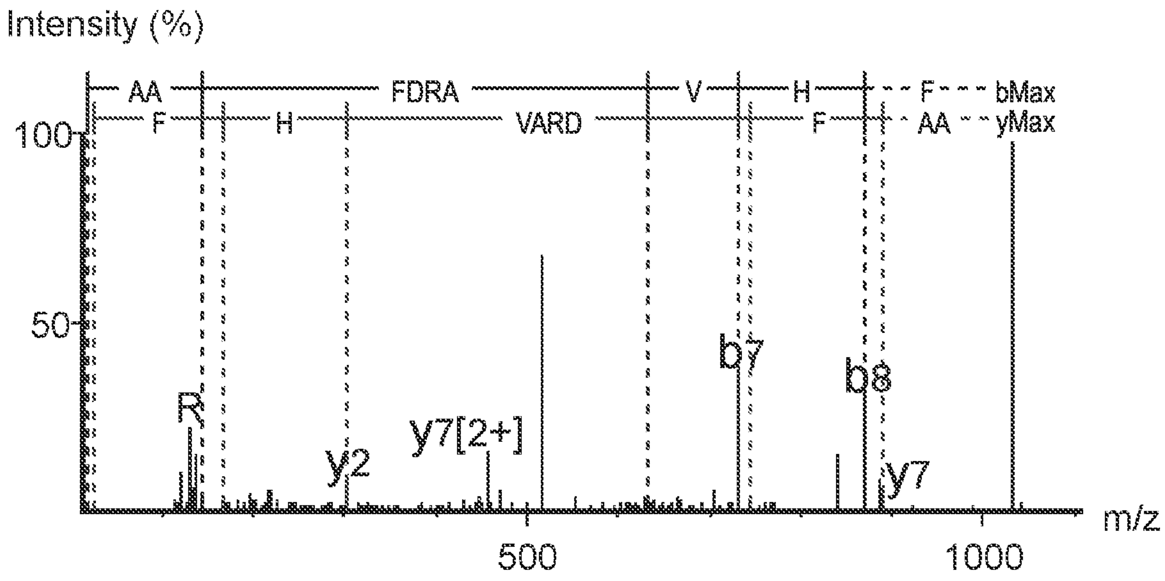
FIG. 39

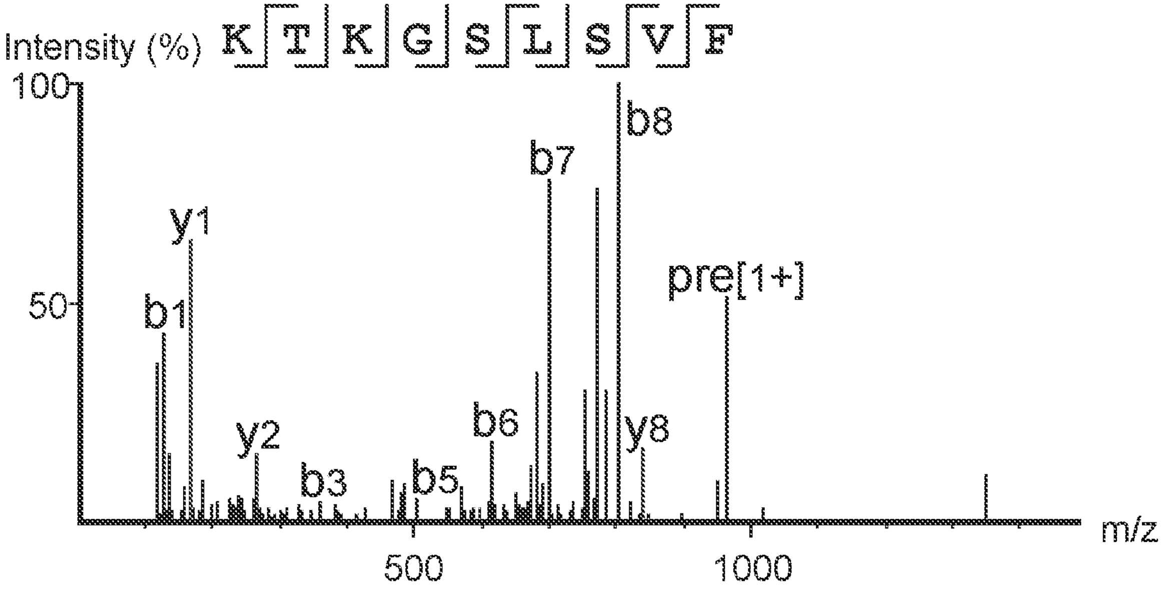
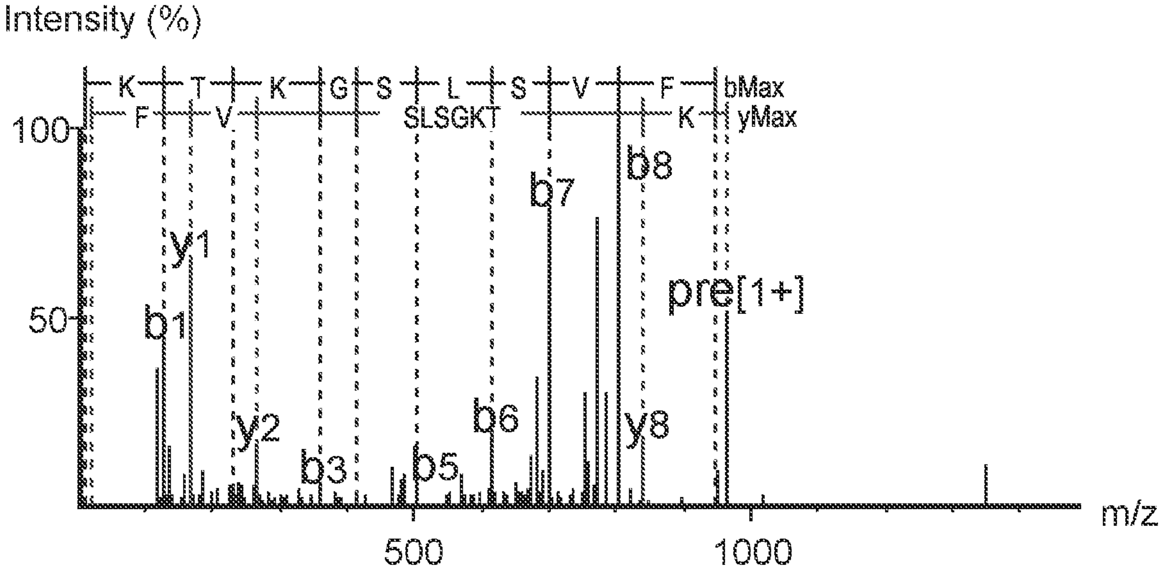
FIG. 42

Panel B:

Panel A: CLT Antigen 1 sequence (annotated with mass spectrometry-discovered peptides) above HERVFEST detected peptides

| | |
|---|---|
| CLT Ant 1 > | MWNFFRRELTSNGFPENFSLDVPANTYNALKSRLCDPNADHTSCPSPCSLHAAGALPGTGRQRWRVELA**HLADRKLSL**RDVSRLRQG |
| **Pat.188B** | **ANTYNALKSR (A*11)** |
| **Pat.188B** | **HLADRKLSL (B*07)** |
| **Pat.224B** | **VPANTYNALK (A*03)** |
| CLT Ant 1 > | GERRSGIAK**VVRGGAGFAAR**LQGSVTL**VQQGWFFPR**LGGCQAWWRMGAVVWCGELLTCTS |
| **Pat.224B** | **RLGGCQAWWR (A*03)** |

FIG. 52

*LILDFQPLQL* (A*02)

Panel B: CLT Antigen 2 sequence (annotated with mass spectrometry-discovered peptides) above HERVFEST detected peptides

| | |
|---|---|
| CLT Ant. 2 > | MTGVLIRRGDLVTDMVACRIKTFRGHTEKAAICKTRKESSAETSP**ADSLILDF**QPLQLM**SSFSTLASLDK** |
| Pat.222B | *LILDFQPLQL* (A*02) |
| Pat.222B | **LMSSFSTLASL** (A*02) |
| Pat.222B | SLILDFQPL |
| Pat.224B | **LMSSFSTLA** (A*02) |
| Pat.224B | **QLMSSFSTLA** (A*02) |
| Pat.224B | *MVACRIKTFR* (A*03) |
| Pat.254C | *MVACRIKTFR* (A*11) |
| Pat.254C | VTDMVACRIK (A*11) |
| Pat.225B | **SSFSTLASLDK** (A*03) |
| Pat.225B | **SPADSLIL** (B*07) |
| Pat.225B | SLILDFQPL |
| Pat.271B | **LVTDMVACRI** (A*01) |
| Pat.271B | **LILDFQPLQL** (A*01) |
| Pat.271B | **MSSFSTLASL** (A*01) |
| Pat.188B | **SLILDFQPL** |
| Pat.293B | SLILDFQPL |

FIG. 52 (cont.)

Panel C: CLT Antigen 3 sequence (annotated with mass spectrometry-discovered peptides) above HERVFEST detected peptides

| | |
|---|---|
| CLT Ant 3 > | MNTPNIVSLRAHQPEVGIIPSVLLMRPLRIKGVFHHIHSPLHGENQGFTLCLQGAPPSSSV |
| Pat.254C | VLLMRPLRIK (A*11) |
| Pat.225B | MRPLRIKGVF (B*07) |
| Pat.271B | NTPNIVSLRA (A*01) |

Panel D: CLT Antigen 4 sequence (annotated with mass spectrometry-discovered peptides) above HERVFEST detected peptides

| | |
|---|---|
| CLT Ant 4 > | MAKTKGSLSVFRELHPAAAFDRAVHFLFLELWLPEPMLSSSPPSSTAPLLGSEPLRHWEASLSR |
| Pat.222B | *FLFLELWL* (A*02) |
| Pat.222B | *SVFRELHPA* (A*02) |
| Pat.224B | FLFLELWL (A*02) |
| Pat.225B | SPPSSTAPL (B*07) |

FIG. 52 (cont.)

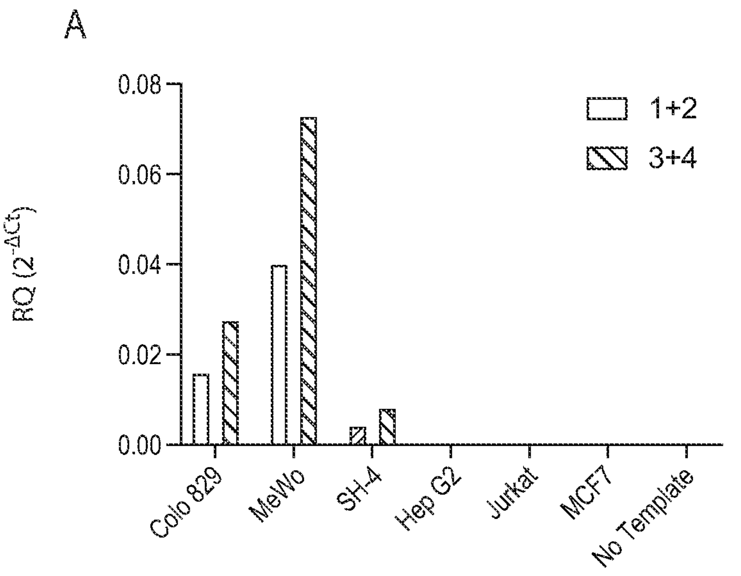
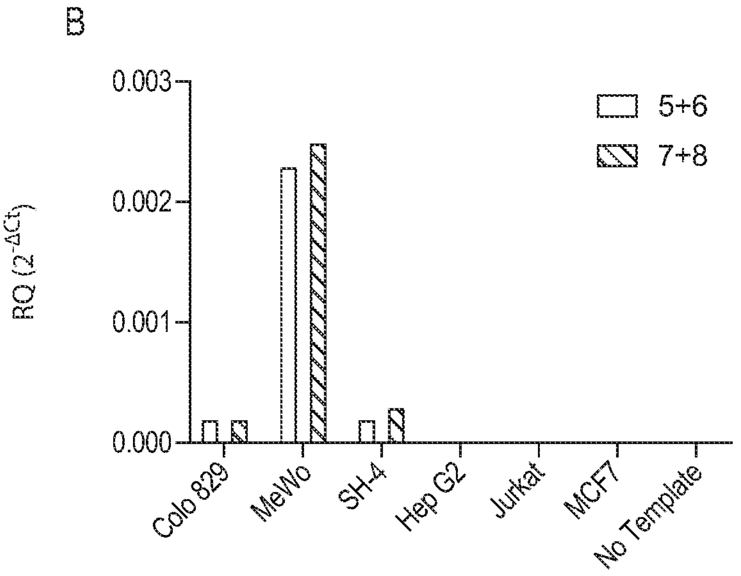
FIG. 59

SEQUENCE LISTING

<160> NUMBER OF SEQ ID NOS: 78

<210> SEQ ID NO 1
<211> LENGTH: 148
<212> TYPE: PRT
<213> ORGANISM: Homo sapiens

<400> SEQUENCE: 1

```
Met Trp Asn Phe Phe Arg Arg Glu Leu Thr Ser Asn Gly Phe Pro Glu
1               5                   10                  15

Asn Phe Ser Leu Asp Val Pro Ala Asn Thr Tyr Asn Ala Leu Lys Ser
            20                  25                  30

Arg Leu Cys Asp Pro Asn Ala Asp His Thr Ser Cys Pro Ser Pro Cys
        35                  40                  45

Ser Leu His Ala Ala Gly Ala Leu Pro Gly Thr Gly Arg Gln Arg Trp
    50                  55                  60

Arg Val Glu Leu Ala His Leu Ala Asp Arg Lys Leu Ser Leu Arg Asp
65                  70                  75                  80

Val Ser Arg Leu Arg Gln Gly Gly Glu Arg Arg Ser Gly Ile Ala Val
                85                  90                  95

Lys Val Val Arg Gly Gly Ala Gly Phe Ala Ala Arg Leu Gln Gly Ser
            100                 105                 110

Val Thr Leu Val Gln Gln Gly Trp Phe Phe Pro Arg Leu Gly Gly Cys
        115                 120                 125

Gln Ala Trp Trp Arg Met Gly Ala Val Val Trp Cys Gly Glu Leu Leu
    130                 135                 140

Thr Cys Thr Ser
145
```

<210> SEQ ID NO 2
<211> LENGTH: 70
<212> TYPE: PRT
<213> ORGANISM: Homo sapiens

<400> SEQUENCE: 2

```
Met Thr Gly Val Leu Ile Arg Arg Gly Asp Leu Val Thr Asp Met Val
1               5                   10                  15

Ala Cys Arg Ile Lys Thr Phe Arg Gly His Thr Glu Lys Ala Ala Ile
            20                  25                  30

Cys Lys Thr Arg Lys Glu Ser Ser Ala Glu Thr Ser Pro Ala Asp Ser
        35                  40                  45

Leu Ile Leu Asp Phe Gln Pro Leu Gln Leu Met Ser Ser Phe Ser Thr
    50                  55                  60

Leu Ala Ser Leu Asp Lys
65                  70
```

<210> SEQ ID NO 3
<211> LENGTH: 61
<212> TYPE: PRT
<213> ORGANISM: Homo sapiens

<400> SEQUENCE: 3

```
Met Asn Thr Pro Asn Ile Val Ser Leu Arg Ala His Gln Pro Glu Val
1               5                   10                  15

Gly Ile Ile Pro Ser Val Leu Leu Met Arg Pro Leu Arg Ile Lys Gly
            20                  25                  30

Val Phe His His Ile His Ser Pro Leu His Gly Glu Asn Gln Gly Phe
        35                  40                  45

Thr Leu Cys Leu Gln Gly Ala Pro Pro Ser Ser Ser Val
    50                  55                  60
```

<210> SEQ ID NO 4
<211> LENGTH: 64

```
<212> TYPE: PRT
<213> ORGANISM: Homo sapiens

<400> SEQUENCE: 4

Met Ala Lys Thr Lys Gly Ser Leu Ser Val Phe Arg Glu Leu His Pro
1               5                   10                  15

Ala Ala Ala Phe Asp Arg Ala Val His Phe Leu Phe Leu Glu Leu Trp
            20                  25                  30

Leu Pro Glu Pro Met Leu Ser Ser Ser Pro Pro Ser Ser Thr Ala Pro
        35                  40                  45

Leu Leu Gly Ser Glu Pro Leu Arg His Trp Glu Ala Ser Leu Ser Arg
    50                  55                  60


<210> SEQ ID NO 5
<211> LENGTH: 44
<212> TYPE: PRT
<213> ORGANISM: Homo sapiens

<400> SEQUENCE: 5

Met Lys Arg Lys Ala Asn Arg Trp Arg Leu Ser Leu Arg Asn Gly Leu
1               5                   10                  15

Leu Pro Ser Thr Pro Arg Ala Thr Gln Gln Ile Pro Met Glu Phe Leu
            20                  25                  30

Asn Ser Arg Val Ala Asp Ile Pro Ile Lys Pro Trp
        35                  40


<210> SEQ ID NO 6
<211> LENGTH: 44
<212> TYPE: PRT
<213> ORGANISM: Homo sapiens

<400> SEQUENCE: 6

Met Arg Gly Phe Leu Trp Arg Val Glu Thr Arg Gly Val Glu Gly Ser
1               5                   10                  15

Met Arg Gly Pro Gln Lys Val Leu Gly Asn Arg Leu Pro Gly Ala Gly
            20                  25                  30

Arg Asn Ala Arg Ser Arg Asp Asn Phe Ala Val Trp
        35                  40


<210> SEQ ID NO 7
<211> LENGTH: 46
<212> TYPE: PRT
<213> ORGANISM: Homo sapiens

<400> SEQUENCE: 7

Met Val Tyr Tyr Gly Asn Pro Glu Ser Ser Pro Gly Ile Ser Leu Val
1               5                   10                  15

Phe Gly Leu Leu Arg Leu Asp Arg Met Gln Pro Gly Phe Ser Val Ser
            20                  25                  30

Gln Glu Gly Asp Pro Val Gly Ile Thr Asp His Leu Gly Cys
        35                  40                  45


<210> SEQ ID NO 8
<211> LENGTH: 49
<212> TYPE: PRT
<213> ORGANISM: Homo sapiens

<400> SEQUENCE: 8

Met Pro Ala Gln Leu Lys Phe Thr Leu Gln Val Asn Pro Ala Thr Lys
1               5                   10                  15
```

```
Met Arg Val Thr Leu Leu Ser Gln Pro Met Glu Thr Tyr Glu Gly Asp
            20                  25                  30

Val Leu Gly Val Gln Thr Pro Tyr Ser Ser Asp Ser Thr Ile Leu Val
        35                  40                  45

Leu


<210> SEQ ID NO 9
<211> LENGTH: 173
<212> TYPE: PRT
<213> ORGANISM: Homo sapiens

<400> SEQUENCE: 9

Met Gly Ser Ser Arg Val Gly Glu Arg Met Met Glu Glu Glu Ser Arg
1               5                   10                  15

Thr Gly Gln Lys Val Asn Pro Gly Asn Thr Gly Lys Leu Phe Val Gly
            20                  25                  30

Val Gly Ile Ser Arg Ile Ala Lys Val Lys Tyr Gly Glu Cys Gly Gln
        35                  40                  45

Gly Phe Ser Asp Lys Ser Asp Val Ile Thr His Gln Arg Thr His Thr
    50                  55                  60

Gly Gly Lys Pro Tyr Val Cys Arg Glu Cys Gly Arg Ala Leu Ala Gly
65                  70                  75                  80

Ser Gln Thr Ser Ser Val Thr Arg Gly His Thr Gln Gly Arg Ser Leu
                85                  90                  95

Met Ser Ala Glu Ser Val Ser Gly Ala Leu Ala Gly Ser Gln Ser Ser
            100                 105                 110

Ser Phe Thr Arg Gly His Thr Gly Glu Thr Pro Gln Ser Ala Gly Arg
        115                 120                 125

Met Ser Lys Ser Leu Val Ile Lys Pro Tyr Leu Asn Ser His Lys Lys
    130                 135                 140

Thr Asn Val Ile Thr Thr His Leu His Thr Pro Ala Leu Arg Trp Leu
145                 150                 155                 160

Gln Arg Lys Ser Ala Asn Pro Leu His Ser Pro Arg Val
                165                 170


<210> SEQ ID NO 10
<211> LENGTH: 106
<212> TYPE: PRT
<213> ORGANISM: Homo sapiens

<400> SEQUENCE: 10

Met His Ser Leu Gln Ile Phe Ser Leu Cys Leu Phe Thr Leu Leu Ile
1               5                   10                  15

Val Ser Phe Ile Val Gln Lys Pro Phe Asn Leu Ile Arg Ser Asn Leu
            20                  25                  30

Ser Ile Phe Leu Leu Val Glu Ile Ala Phe Glu Asp Leu Val Met Asn
        35                  40                  45

Tyr Leu Pro Lys Leu Thr Ser Arg Arg Val Phe Ser Arg Phe Ser Tyr
    50                  55                  60

Met Thr Phe Tyr Ser Phe Arg Ser Tyr Ile Lys Val Phe Val Ser Ser
65                  70                  75                  80

Gln Ile Asp Phe Phe Ser Leu Val Lys Gly Arg Gly Pro Val Gln Ala
                85                  90                  95

His Phe Ser Met Trp Phe Cys Tyr Ser Gly
            100                 105
```

-continued

```
<210> SEQ ID NO 11
<211> LENGTH: 9
<212> TYPE: PRT
<213> ORGANISM: Homo sapiens

<400> SEQUENCE: 11

Val Gln Gln Gly Trp Phe Phe Pro Arg
1               5


<210> SEQ ID NO 12
<211> LENGTH: 11
<212> TYPE: PRT
<213> ORGANISM: Homo sapiens

<400> SEQUENCE: 12

Val Val Arg Gly Gly Ala Gly Phe Ala Ala Arg
1               5                   10


<210> SEQ ID NO 13
<211> LENGTH: 9
<212> TYPE: PRT
<213> ORGANISM: Homo sapiens

<400> SEQUENCE: 13

His Leu Ala Asp Arg Lys Leu Ser Leu
1               5


<210> SEQ ID NO 14
<211> LENGTH: 9
<212> TYPE: PRT
<213> ORGANISM: Homo sapiens

<400> SEQUENCE: 14

Ala Arg Leu Gln Gly Ser Val Thr Leu
1               5


<210> SEQ ID NO 15
<211> LENGTH: 8
<212> TYPE: PRT
<213> ORGANISM: Homo sapiens

<400> SEQUENCE: 15

Ala Asp Ser Leu Ile Leu Asp Phe
1               5


<210> SEQ ID NO 16
<211> LENGTH: 11
<212> TYPE: PRT
<213> ORGANISM: Homo sapiens

<400> SEQUENCE: 16

Ser Ser Phe Ser Thr Leu Ala Ser Leu Asp Lys
1               5                   10


<210> SEQ ID NO 17
<211> LENGTH: 9
<212> TYPE: PRT
<213> ORGANISM: Homo sapiens

<400> SEQUENCE: 17

Asn Thr Pro Asn Ile Val Ser Leu Arg
1               5


<210> SEQ ID NO 18
<211> LENGTH: 15
```

<212> TYPE: PRT
<213> ORGANISM: Homo sapiens

<400> SEQUENCE: 18

Gln Pro Glu Val Gly Ile Ile Pro Ser Val Leu Leu Met Arg Pro
1               5                   10                  15

<210> SEQ ID NO 19
<211> LENGTH: 10
<212> TYPE: PRT
<213> ORGANISM: Homo sapiens

<400> SEQUENCE: 19

Lys Thr Lys Gly Ser Leu Ser Val Phe Arg
1               5                   10

<210> SEQ ID NO 20
<211> LENGTH: 10
<212> TYPE: PRT
<213> ORGANISM: Homo sapiens

<400> SEQUENCE: 20

Arg Val Ala Asp Ile Pro Ile Lys Pro Trp
1               5                   10

<210> SEQ ID NO 21
<211> LENGTH: 7
<212> TYPE: PRT
<213> ORGANISM: Homo sapiens

<400> SEQUENCE: 21

Asp Ile Pro Ile Lys Pro Trp
1               5

<210> SEQ ID NO 22
<211> LENGTH: 9
<212> TYPE: PRT
<213> ORGANISM: Homo sapiens

<400> SEQUENCE: 22

Arg Val Ala Asp Ile Pro Ile Lys Pro
1               5

<210> SEQ ID NO 23
<211> LENGTH: 9
<212> TYPE: PRT
<213> ORGANISM: Homo sapiens

<400> SEQUENCE: 23

Arg Ser Arg Asp Asn Phe Ala Val Trp
1               5

<210> SEQ ID NO 24
<211> LENGTH: 7
<212> TYPE: PRT
<213> ORGANISM: Homo sapiens

<400> SEQUENCE: 24

Arg Ser Arg Asp Asn Phe Ala
1               5

<210> SEQ ID NO 25
<211> LENGTH: 8
<212> TYPE: PRT
<213> ORGANISM: Homo sapiens

<400> SEQUENCE: 25

Ser Pro Gly Ile Ser Leu Val Phe
1 5

<210> SEQ ID NO 26
<211> LENGTH: 9
<212> TYPE: PRT
<213> ORGANISM: Homo sapiens

<400> SEQUENCE: 26

Ser Ser Asp Ser Thr Ile Leu Val Leu
1 5

<210> SEQ ID NO 27
<211> LENGTH: 11
<212> TYPE: PRT
<213> ORGANISM: Homo sapiens

<400> SEQUENCE: 27

Ala Gly Arg Met Ser Lys Ser Leu Val Ile Lys
1 5 10

<210> SEQ ID NO 28
<211> LENGTH: 7
<212> TYPE: PRT
<213> ORGANISM: Homo sapiens

<400> SEQUENCE: 28

Pro Gln Ser Ala Gly Arg Met
1 5

<210> SEQ ID NO 29
<211> LENGTH: 18
<212> TYPE: PRT
<213> ORGANISM: Homo sapiens

<400> SEQUENCE: 29

Ala Gly Ser Gln Ser Ser Ser Phe Thr Arg Gly His Thr Gly Glu Thr
1 5 10 15

Pro Gln

<210> SEQ ID NO 30
<211> LENGTH: 8
<212> TYPE: PRT
<213> ORGANISM: Homo sapiens

<400> SEQUENCE: 30

Arg Ser Asn Leu Ser Ile Phe Leu
1 5

<210> SEQ ID NO 31
<211> LENGTH: 8
<212> TYPE: PRT
<213> ORGANISM: Homo sapiens

<400> SEQUENCE: 31

Phe Ser Leu Cys Leu Phe Thr Leu
1 5

<210> SEQ ID NO 32
<211> LENGTH: 24
<212> TYPE: PRT
<213> ORGANISM: Homo sapiens -continued

<400> SEQUENCE: 32

Ser Arg Arg Val Phe Ser Arg Phe Ser Tyr Met Thr Phe Tyr Ser Phe
1 5 10 15

Arg Ser Tyr Ile Lys Val Phe Val
20

<210> SEQ ID NO 33
<211> LENGTH: 1063
<212> TYPE: DNA
<213> ORGANISM: Homo sapiens

<400> SEQUENCE: 33
cggggccagt ctttcccgtg ctattctcgt gatagtgaat aagtctcaca agatctgatg 60
ggtttatcag ggttttcat tttgcttctt cctcattttc ttttgctgct gtaatgtaag 120
aaacgccttt tgcctcctgc cataattctg aggcctcaca gccatgtgga acttcttcag 180
gagagaatta acatccaatg gattcccaga aaacttttcc ctcgatgtac cagcaaacac 240
ctacaatgcc ctgaaaagcc gcctctgcga ccccaatgca gatcacacgt cctgtcccag 300
cccctgcagc ctccacgcgg cgggtgcact gccaggcacg ggaaggcagc gctggcgagt 360
agaactggcc catctcgcag ataggaagct gagcctcagg gacgtttcac gccttcgtca 420
aggtggtgag aggaggagcg ggattgccgt gaaggtggtg agaggaggag cggggtttgc 480
tgcccgactt cagggatctg tcaccctcgt ccagcagggt tggttcttcc cgaggctggg 540
aggatgccaa gcctggtgga ggatgggggc ggtggtgtgg tgtggggagc ttctgacttg 600
cacatcctga gggaaccttc tgcagctgat gtgtgaactg gaccccaggc cgtgcctccg 660
aggaatcccc aaggctatgg cccctcaggt cctgctgggg tgttggcccc cacctctgcc 720
tcagaatgca ggggttctgc agggaagccg cagaccagcc tgctgccttg ggccctaggg 780
acactgcagc cccagaaagt actgtggggg acaaaagagt tgtttctcgg gggagaaaac 840
acctgtgagg aaatgcaggt gccacagagg gaaatcctcc tggggaggag ggtacctgtt 900
ccatcctcgg ccgacacggg actgcctggt gcctggtacc cacagccgct acctgccgca 960
cgcatctctc catggtttgc taattacttc cattagtttt aaacaaactt gacaagagac 1020
agaagggtcc agagagaaat taaatctaac tgtttaaaca tgt 1063

<210> SEQ ID NO 34
<211> LENGTH: 2851
<212> TYPE: DNA
<213> ORGANISM: Homo sapiens

<400> SEQUENCE: 34
cacctccatc actgcgaatt ataattcgac atgagatttg ggagatgaca caaaaccaaa 60
ccatatcagt ctttaaagag ttaagttaaa ataagctctt taaagtgggc cctaatccag 120
tatgactggt gttcttataa gaagaggaga tttggtcaca gacatggttg catgcagaat 180
aaagactttt cgaggacaca ctgagaaggc agccatctgc aaaacaagga aagagtcctc 240
agcagaaacc agtcctgcag actccttgat cttggacttc cagccactgc aattgatgtc 300
aagcttcagc acccttgcat ctctggataa atgaaatgtc accccagctg ccgtccttgt 360
tcagatctgt gcaataaaga gcaaagcata aaaccaagtc aaggctttga gggagtgacc 420
tacaaaatgc ataatgtgaa acaatgcaaa agcgaaaggt gcaaaatccc catcaaagag 480
ctggaggctg acagatgcgc cagtgataat tcccatcttc caacacagga gcacagcttc 540

-continued

```
cattttccat aacagaacaa cagccagagc agctggaagg cagggccgca tcccagactt    600
ccaccaacaa tgggatgaga cttgacatct ggaatcacaa ccacaacaga cctgagagac    660
ccaccagctt gatgacaagc ttcttctttc aaagaaaggt atcagtctgg gggacctagt    720
gctgcaaacc atgacaaatt aagtgtggca tccctcactt gcataatgga actcagtgat    780
attttttaat taacaagagt tatttttatg taagcttctc tcattcctcc actgtgcgtg    840
ctcgggggct ggtggtgagg aaaaagaaaa cagctgtgcg ggaagcatca agaaaaggca    900
agtcatgaag tcttagagat cagtgacatg taagaaaaag agtgaggaga aaaatattcc    960
tactaaagtt ttccatttgt ttaccttcct tgtcacatag acttccaaga gttagaagtc   1020
taggatttga tctccaaatc ttcctggcag attactcatc ttcatttcat tcatatagtc   1080
caggggtttg tacaaaggaa gatgccagtt cttccccaat cataactaag atatcaagag   1140
atattctttt gaaatgtaac aaaggagatc tgaagttcat ctgaaaaaaa taaatggttt   1200
taggcggtca tgaccatggg atgctggacc aggatggtaa gcttcaggaa acagaatctg   1260
gagaatgccc agctgctccc acaggaagca tcagggaaga agaagaagag gtgtgaagtc   1320
tgccttctgc tctgctggga tccctttcac atctcctttg cctccaggca gttttggttc   1380
ctggccattt ccaggtgtga ctcactcagg atggtaagca tcttctctcc tacccagagt   1440
agaggatgaa gacctcatct cagaggttga agggagctcc agagagaggt ctcaaacttc   1500
cagcattaac tgctaaagaa gcttcatgag ctgctggaga acctgggaaa tgaccaatta   1560
tagggacaga gctcaaatac tctgggacac tctagtagct gagaaagttc caactccagg   1620
gtgatagagg actgcctggc aaaccatcat caaagcagaa gacctgatac taacatcaca   1680
ggctatggtt tattactgaa gatcagtgct tacaccctgc cagaggttca gaagcaaact   1740
tatcattgtt ctccctggag atgttggccc acattctgaa aagtgtggtc agtagtagca   1800
acagaaagca attgtgcttg ccaagcacaa tgtcactgtc cccagccctt cccccaacac   1860
aacccagtag gtgcttcctg gctgcaaact tgggaaagtc acttgacctg tctgaggttc   1920
cacttcctaa tctggcctgg cgaagataag aaaaacagtt tatttaaagt gtctagcaaa   1980
gtgcttggac caaaatagga cctctgaaat ggttatggta gtgctgttaa ggtgatgttt   2040
taagtgctga tgagcacaaa gatgggtaag atattccttc tgttaaaatc tacagtctaa   2100
tgagagagaa caagatgaat gcacaataac tgtcattcag aacaggatta tgagaaggtg   2160
tgaatttctg tgaaaaatca gaacagggag taatatgatc ccaggtgatt ggcagggggt   2220
gggggtctgg attcaactgg agagggagct ggcagggaag gcttcctgga ggatgagagt   2280
tcaacaaggg gcaggtgtag gatgtgggtg gccaagtgac tgggcagaag gagctgcaga   2340
agtaagaccc caaatcagga agacaagggc ctgctgagaa acacgagcta caaagtgcaa   2400
gtgcaggaag agttgggatg agattagaag gggtctgggg gccagactgt ggaaggccca   2460
aatgccgggc taaggagttt gtacttaatt cagtggtcaa cggggagtca ttggaggctg   2520
ttgagcagga gagttgcttt ctttacagct gtgccagact aaattaaacc taaacagtac   2580
tttatagctg gaaagggaag gcccaggaat agctcttgac tcagaaacag gcattgggga   2640
aggtaatgag aaacagccgt gactgatcaa agcagagagg ttaattaaat ttgtaattat   2700
tgtgaaaggc cattaaaaac cctagttcac tagagataac tgctctagtg gggcttcaaa   2760
gacaaacgct tcttttaacc ttgaataggg ggatgtttgc ttctctgtgg aggagatatg   2820
attaagatac ttaataaatg gtagataaac a                                  2851
```

```
<210> SEQ ID NO 35
<211> LENGTH: 2614
<212> TYPE: DNA
<213> ORGANISM: Homo sapiens

<400> SEQUENCE: 35

aaacacacta agggctttgt tatggactga aatgtgtcct ctccccagag tcacaggatt     60

atgaagccat aatcctcaat gtgactatat ttggagcagg ggcctttaca gacataatta    120

aattaaatga ggtcataaga gtggggccct agtctgatag gactggtgtc cttacaagaa    180

gagggagagt cctcagagag tcctctctct cggcatggac acaaaagaaa agccatgtga    240

ggacacagag agaaggtggc tgtctacgag ctaggaagaa aggcctcacc ggaaaccaac    300

cctcacagca gctccatctt ggacttccag cctccggaac tgtgagaaaa taaatgtttg    360

caattcaggt cggttgtatt ttgtgaaggc catcctagca aatgaatact cctaacattg    420

tctctttaag agctcaccag cctgaggtag gaatcattcc atctgtgtta ctaatgagac    480

cgctgaggat caaaggggtt ttccaccaca tccactcacc tctacatggc gaaaaccaag    540

ggttcactct ctgtcttcag ggagctccac ccagcagcag cgtttgacag agctgttcac    600

ttcctcttcc tggagctgtg gcttccagag cccatgctca gcagttcccc tccttcttcg    660

actgctcctc tcttaggctc agagccactc agacattggg aagcaagttt gtcaagatga    720

cagagaaccg aggtaatgga ttcgagtgat gaaacaggaa gttcattcat gagtttttgg    780

ccacacctcc aaagtgacga cttagccaga aatgggataa ctgggtttcc ctacttctct    840

tttatcatcc tcaatgagag tgaccaaata ttagagctag atggaacctt agtgaaaatc    900

tggctactcg tcccgtccca ccagcctgcc acccatttca agtttgaaga gacaaagaca    960

catggacctt atgtaattac tggggattac cccaggagtc tgtggcaaaa gtcagcttct   1020

tccctccctg cttccccgcc ctgtctctgg tactttctac caacactggg ctgtttctgt   1080

gatcacactt aagcgtacct aacctgcgaa tgctgtatag aaggtgctaa tgaacatgat   1140

ttagctttaa cactcagttt tctaaaggga cacgtggggg cagcaaatgt ttaggcaaaa   1200

acaattccag ttctagcctc tactgtctac atatgtgtat acatttggga aacgtttggg   1260

aaagggatat ttgagagctt ctttttcttt tttgtggttt agttatttga tgatattgag   1320

attgtttctg agccatgtgc ttcaacatcg gattggggat ttcagaaaaa gttttagtca   1380

ctgtgattcc atttagcttc caaatgtgtc tctgctaaga gacttaaaag cactcataaa   1440

tagcacgtgt gtcttctttg cagtgtttgc taattttgag tcacatcttt ttagaaaatc   1500

atgagatttg gtgtcacaga gactggaata aatatagtca aacttattgg tgaagatttc   1560

ctttagctgt tttcataatc catttccatt gttatgatta ttgatgaata aaacattttc   1620

tttaggtaga tacttctttt ttccccccac cttgatttaa tgtttccact cttattgtca   1680

agtttcttat tactccctaa taactctcaa taaaataatg attcctggga gattattcct   1740

gctttcctac tatcacctgt tgatttgaaa agacagaaca ataccgtaga agcttcacta   1800

atacattgaa agataaaatg ataatactaa atactaaaat atgaaaagtg atactaaaag   1860

tggagtcctg gcactagtat tttttttttt gagtctttaa attttattta tttatttttg   1920

aatttttaa aattatatgt tatgttctgg gatacatgtg cagaacgtgc aggtttgtta    1980

cataggtata caggtctggc actagtattt tgttgccaca aaatatcaag catgtatcca   2040

aactgctcaa gacacattaa agacacaggt aatctgtagg catattcagg cttgtagttt   2100

gcatttttg gttttcttgt ggctttcagt gcaagttgag gtaattcatg ggaaacagtc    2160
```

```
accaaagaag tgccagtatt agaaatccaa gagccatttc tctagcttct tccagaatca   2220

agactttaga ggtaatttct atcaacactg gacatttcct gtctgcaatt aacaatgaac   2280

acatagcatt atgtttaatt gcaacctgtt taaagcagat tggatgctaa ggtttaagaa   2340

cactcttcag tcaaaaaggt cttttaatca ggtttttaat cttgagcaca atctaggaca   2400

cagcatcata gactaactca ttcgagaata ggtgttgtca tctaatccta accaccccca   2460

ccaccaacaa gctgaatagc tctgggctca gtatatacat ttgtactggg ctcagtacac   2520

acacctaagc tgggttcagt atatgccact ttatagtgag aggcattttg taatgagagc   2580

tctgggttca ctatatacat ttgtactggg ctca                               2614


<210> SEQ ID NO 36
<211> LENGTH: 1858
<212> TYPE: DNA
<213> ORGANISM: Homo sapiens

<400> SEQUENCE: 36

gggaggggc catggcgggg ccacttcaaa ggaaaagctc tagctcccct acctctctca      60

catcctaagg ctgcctttgt gggattccac acagaacagc ctggaagctt ggggccctgg    120

cttccttttc tggcctggga gtcaggtcat ggggccatcg cttcacagca atcatgaggg    180

cccaggccca agtgctcaca tgctcctcat ggggactgct cctcttaaag ggtgggccct    240

cctcacccag ctccctgccc tggccaagga ggaggctgaa agagcctgag ctgtgccctc    300

tccattccac tgctgtggca gggtcagaaa tcttggatag agaaaacctt ttgcaaacgg    360

gaatgtatct ttgtaattcc tagcatgaaa gactctaaca ggtgttgctg tggccagttc    420

accaaccagc atatcccccc tctgccaagt gcaacaccca gcaaaaatga agaggaaagc    480

aaacaggtgg agactcagcc tgagaaatgg tctgttgcca agcacaccca gagctaccca    540

acagattcct atggagttct tgaattccag ggtggcggat attccaataa agccatggtg    600

agaaaggcat tcagacatgg tgccactagg atcacagctt tcattggcgg ccagtctccc    660

agccccaaac tgcagatacc tggtcttctt catggctgtg gctcaatctt cctagatatt    720

tcattgaaaa accaagagat atatctgtgc acatggcttt tagccatgag gcttggaaac    780

tggacaccac tgtaaagaac atctagtgtc ccgtaaatcc ataccaaagc tctgaatcca    840

caaaccaggc tctggcccaa ccctgcaaac acactccatt gctccatctt cagtaaagga    900

agacaaattc atttttctaa taactgtgga cctgcagccc ccttagatgt gttgagagtc    960

tttggaaata ttttcctctg aggtctgtcc acagcttccc tgggcctgcg ctcagctggc   1020

ccgagaagga ccaaggtccc tcacatttgc atgtaaacag ggagtgccct ctgcccttcc   1080

agtgagccct gccagcgtgg gggaggcttc agctctgtga tccgttccag ctcactctga   1140

attacactcc tacatgccca gtcacagact ttttgcaatt tcattttatt tcactggccc   1200

aacatcattg ttaaaataaa atttagctgt gttccaaatg ctgcaatata cagtcttctg   1260

aaatggcacc ctacatatta gcccagacac aaagaagcag tttataggag acaaggcatc   1320

tgagcattat tagcctcctc ctcactttga agaggtcaag ttcatgggtg ggcccatgat   1380

cgcctgaccc atttactcaa caacatcctc atccaacttc ttgggccact gttctagcta   1440

agccagcttt ggaacctatt cctccaacat taggattgcc agataaaata caggacaccc   1500

agttatattt gaacttcaga catacattgg ataaattttc agtacaagta tgtcccaaat   1560

attgcatgat ttattgcatt taataaaaat gttgtactga aacatttttc attgttcctc   1620

taaaattcaa atttaactgg gtgtcttggt ctgtttggct gctataacaa attgccttag   1680
```

gctggggaat ttataaacaa cagaaattta ttgctcacat ttctagagtc tgggaggccc 1740
aagatcaagg tgccagcaga tttggtgcct ggcgagggcc catcctctgc ttcatagata 1800
gcaccttctt gctgtgtcct cacatggcag aagcagagaa caagctctct gagtcctc 1858

<210> SEQ ID NO 37
<211> LENGTH: 2538
<212> TYPE: DNA
<213> ORGANISM: Homo sapiens

<400> SEQUENCE: 37
cttggacttc ccagcctcca gaactgtgag aaataaattt ttgttgttta atccatccag 60
tctgtgatat tttgttatgg cagctgaagc agtcaggaaa ggatcctccc catctctgca 120
gaagcctgac catcccccta gagggcctgg gaggaagtgg gttttgcata cagtccctgt 180
tgactctagt gccccctgct ggccccagac gcgagttccg gcgaggcttc agggtacagc 240
tcccccgcag ccagaagccg ggcctgcagc gcctcagcac cgctccggga caccccaccc 300
gcttcccagg cgtgacctgt caacaggtct gtattggcga caaaaggagc agccctgaat 360
gtagggaaag cagggcggag tcctctgcag gctcggggga ggggaggggc gtgaatgcgt 420
ggatttctgt ggagagtgga aacacgggga gtcgagggga gcatgcgcgg gcctcagaaa 480
gttctgggaa accgactccc gggagcaggg aggaacgcgc gctccagaga caacttcgcg 540
gtgtggtgaa ctctctgagg aaaaacacgt gcgtggcaac aagtgactga gacctagaaa 600
tccaagcgtt ggaggtcctg aggccagcct aagtcgcttc aaaatggaac gaaggcgttt 660
gtggggttcc attcagagcc gatacatcag catgagtgtg tggacaagcc cacggagact 720
tgtggagctg gcagggcaga gcctgctgaa ggatgaggcc ctggccattg ccgccctgga 780
gttgctgccc agggagctct tcccgccact cttcatggca gcctttgacg ggagacacag 840
ccagaccctg aaggcaatgg tgcaggcctg gcccttcacc tgcctccctc tgggagtgct 900
gatgaaggga caacatcttc acctggagac cttcaaagct gtgcttgatg gacttgatgt 960
gctccttgcc caggaggttc gccccaggag gtggaaactt caagtgctgg atttacggaa 1020
gaactctcat caggacttct ggactgtatg gtctggaaac agggccagtc tgtactcatt 1080
tccagagcca gaagcagctc agcccatgac aaagaagcga aaagtagatg gtttgagcac 1140
agaggcagag cagcccttca ttccagtaga ggtgctcgta gacctgttcc tcaaggaagg 1200
tgcctgtgat gaattgttct cctacctcat tgagaaagtg aagcgaaaga aaaatgtact 1260
acgcctgtgc tgtaagaagc tgaagatttt tgcaatgccc atgcaggata tcaagatgat 1320
cctgaaaatg gtgcagctgg actctattga agatttggaa gtgacttgta cctggaagct 1380
acccaccttg gcgaaatttt ctccttacct gggccagatg attaatctgc gtagactcct 1440
cctctcccac atccatgcat cttcctacat ttccccggag aaggaagagc agtatatcgc 1500
ccagttcacc tctcagttcc tcagtctgca gtgcctgcag gctctctatg tggactcttt 1560
atttttcctt agaggccgcc tggatcagtt gctcaggcac gtgatgaacc ccttggaaac 1620
cctctcaata actaactgcc ggctttcgga aggggatgtg atgcatctgt cccagagtcc 1680
cagcgtcagt cagctaagtg tcctgagtct aagtggggtc atgctgaccg atgtaagtcc 1740
cgagcccctc caagctctgc tggagagagc ctctgccacc ctccaggacc tggtctttga 1800
tgagtgtggg atcacggatg atcagctcct tgccctcctg ccttccctga gccactgctc 1860
ccagcttacg accttaagct tctacgggaa ttccatctcc atatctgccc tgcagagtct 1920

-continued

```
cctgcagcac ctcatcgggc tgagcaatct gacccacgtg ctgtatcctg tccccctgga   1980

gagttatgag gacatccatg gtaccctcca cctggagagg cttgcctatc tgcatgccag   2040

gctcagggag ttgctgtgtg agttggggcg gcccagcatg gtctggctta gtgccaaccc   2100

ctgtcctcac tgtggggaca gaaccttcta tgacccggag cccatcctgt gcccctgttt   2160

catgcctaat tagctgggtg cacatatcaa atgcttcatt ctgcatactt ggacactaaa   2220

gccaggatgt gcatgcatct tgaagcaaca aagcagccac agtttcagac aaatgttcag   2280

tgtgagtgag gaaaacatgt tcagtgagga aaaaacattc agacaaatgt tcagtgagga   2340

aaaaaagggg aagttggggg taggcagatg ttgacttgag gagttaatgt gatctttggg   2400

gagatacatc ttatagagtt agaaatagaa tctgaatttc taaagggaga ttctggcttg   2460

ggaagtacat gtaggagtta atccctgtgt agactgttgt aaagaaactg ttgaaaataa   2520

agagaagcaa tgtgaagc                                                 2538
```

```
<210> SEQ ID NO 38
<211> LENGTH: 1256
<212> TYPE: DNA
<213> ORGANISM: Homo sapiens

<400> SEQUENCE: 38

gagacaggtc tcactctgtt gcccggtcag gaaagtggca caatcacagc tcactgcagt     60

ctcagtctcc caggctcaag atggatacat ttaaggtatg gtgatccggt ccaccgtgtg    120

gttaggattc ccaaattttg ttgacagcgt ctcggatatg aaccacacgg aaatttggcc    180

tgctgctttc tgcgtgggga gtgcgatgtg gatccagctg ttgtacagtg cctgcttctg    240

gtggctgttt tgctatgcag tggatgctta tctggtgatc cggagatcgg caggactgag    300

caccatcctg ctgtatcaca tcatggcgtg gggcctggcc accctgctct gtgtggaggg    360

agccgccatg ctctactacc cttccgtgtc caggtgtgag cggggcctgg accacgccat    420

cccccactat gtcaccatgt acctgcccct gctgctggtt ctcgtggcga accccatcct    480

gttccaaaag acagtgactg cagtggcctc tttacttaaa ggaagacaag gcatttacac    540

ggagaacgag aggaggatgg gagccgtgat caagatccga tttttcaaaa tcatgctggt    600

tttaattatt tgttggttgt cgaatatcat caatgaaagc cttttattct atcttgagat    660

gcaaacagat atcaatggag gttctttgaa acctgtcaga actgcagcca agaccacatg    720

gtttattatg ggaatcctga atccagccca gggatttctc ttgtctttgg ccttctacgg    780

ctggacagga tgcagcctgg gttttcagtc tcccaggaag gagatccagt gggaatcact    840

gaccacctcg gctgctgagg gggctcaccc atccccactg atgccccatg aaaaccctgc    900

ttccgggaag gtgtctcaag tgggtgggca gacttctgac gaagccctga gcatgctgtc    960

tgaaggttct gatgccagca caattgaaat tcacactgca agtgaatcct gcaacaaaaa   1020

tgagggtgac cctgctctcc caacccatgg agacctatga aggggatgtg ctgggggtcc   1080

agaccccata ttcctcagac tcaacaattc ttgttcttta gaactgtgtt ctcaccttcc   1140

caacactgca ctgccgaagt gtagcggccc ccaaaccttg ctctcatcac cagctagagc   1200

ttcttcccga agggccttta ggataggaga aagggttcat gcacacacgt gtgaga       1256

<210> SEQ ID NO 39
<211> LENGTH: 2657
<212> TYPE: DNA
<213> ORGANISM: Homo sapiens
```

<400> SEQUENCE: 39

```
cctgtagtcc cagctactca ggaggctgag gcaggagaat tgcttgaatc cgggaggcgg     60
aggttgcagt gaggggagat tgtgccactg cactccagcc tgggcgacag agggagactc    120
catatcaaaa agaaaaaaaa atctctagag tttggaaaca tttaccaacc aaaccactga    180
tttctcatca cctcttagtc aaacctcctt ggatggcctt cagaggagaa cagagtaaac    240
accagaagaa ctcaggagga aggagactga aggaaagatg tatagcctgc gagaaagaaa    300
gggtcatgca tacaaagaga tcagcgagcc acaggatgat gactacctct attgtgagat    360
gtgtcagaac ttcttcattg acagctgtgc tgctcatggg ccccctacat ttgtaaagga    420
cagtgcagtg gacaaggggc atcccaaccg ttcagccctc agtctgcccc cggggctgag    480
aattgggcca tcaggcatcc ctcaggctgg gcttggagta tggaacgagg catctgatct    540
gccactgggt ctgcactttg gcccctatga gggccgaatt acagaagacg aagaggcagc    600
caacagtgga tattcctggc taatcaccaa ggggagaaac tgctatgagt atgtggatgg    660
aaaagataaa tcctcggcca actggatgag aaccaaagcc agagatccat ccatgtccct    720
catgctgtct ggcctttttca agtcaaaaat ttctcagtca acatgtggaa cgcaatcact    780
cctctcagaa cttcccagga ccatctgcaa gaaaacttct ccaaccagag aatccctgcc    840
caggggatca gaatcaggag cggcaatatt ctgatccacg ctgctgtaat gacaaaacca    900
aaggtcaaga gatcaaagaa aggtccaaac tcttgaataa aaggacatgg cagagggaga    960
tttcaagggc cttttctagc ccacccaaag gacaaatggg gagctctaga gtgggagaaa   1020
gaatgatgga agaagagtcc agaacaggcc agaaagtgaa tccagggaac acaggcaaat   1080
tatttgtggg ggtaggaatc tcaagaattg cgaaagtcaa atatggagag tgtgggcaag   1140
gtttcagtga taagtcagat gttattacac accaaaggac acacacaggg gggaagccct   1200
acgtctgcag agagtgtggg agggctttag ccggaagtca gacctcctca gtcaccagag   1260
gacacacaca ggggagaagc cttatgtctg cagagagtgt gagcggggct ttagccggaa   1320
gtcagtcctc ctcattcacc agaggacaca caggggagac gccccagtct gcaggaagga   1380
tgagtaagtc attagtaata aaaccttatc tcaatagcca caagaagaca aacgtgatca   1440
ccacacactt gcacacccca gctctgaggt ggcttcagcg aaagtctgct aaccccttac   1500
attccccgag agtgtaaaga gatcggaaat aactaattaa acaaatccgc cactttcatg   1560
actagagttg aggaagaaca ggggatagtt ctgtaagtgt tcgggggacg tcaacatgtg   1620
tggttgtttc ccgcactgat cccctccatt ttttgtgttt tgcctcctgt tctaattaat   1680
tttgtctcca tacatatctg aaccccaagt gtgtacctca ttcttccctt atcactgaag   1740
gaaggaagag tccagaaggg ccacagagaa ctcaaacgtt cagttcaagt ctccacagga   1800
attcaacccc agaaagacat aaacttggag tccatctggt ttaattattg gagaatcgat   1860
tcccaagtcc aggaagagaa atgtagggtt ttacagagtc gcagcaggaa agagagctcc   1920
ctggtctcct gggaagtgtg acctcttcta atggacccct ctcctctgct gccatactcc   1980
cccttggctc cccctgtctc ctctcctgat ttcctccaat ctctgtagcc ccagaagtga   2040
acgccagaca ggaacacgca tgtgtgtata tatgtgttca cgtgtgctat gtgtgttaag   2100
cctgcatgca tgggtgtggg ggtatgtgcc ctctgtgtac gtatctgtgt gagtgtgggg   2160
gtttcaaggg tgtattagga ataacgctca aaatcctaag gaaattgaat actctgagag   2220
aagagagaca gaccctctca tactgtttta tattgtttta tactcagaaa aggaaaaaga   2280
```

-continued

```
agcaaaacta aaggcaggta gcctggcgcc taggaaccag acctgaaacc aaggaaccag   2340

acccgaaacc aggcctgggc cggcctgacc taagcctggt agttaaaatt cgacccctga   2400

cctagcaact gatgttatct atagattata gaaagacatt gtgaaacttc ccggtctgtt   2460

ctgttccact ctgaccatcg gtgcatgcag cccctgtcac ctacccccctg cttgctcaat   2520

cgatcacgac cctctcacgt ggaccccctt agagttgtga gcccttaaaa gggacaggaa   2580

ttgctcactc ggggagctcg gctcttgaga cagcagtctt gctgatgctc ctggccgaat   2640

aaaccgcttc cttcttt                                                  2657
```

<210> SEQ ID NO 40
<211> LENGTH: 1319
<212> TYPE: DNA
<213> ORGANISM: Homo sapiens

<400> SEQUENCE: 40

```
cccacctact gatttaccaa ctctttttca tttcaacttt tattttaggt ccagagggta     60

catgtgtgag tttgttgcat gagtatattg tgtgacactc atgtatgggg tacaaataat    120

cccaacacca atgtagagaa cacaatatcc aataggcagt tcttcaggcc ctttctccat    180

cctgccctcc cccacatggt agatcccagt gtctattgtg cccatcttta tgtccatgca    240

taaccaatgt ttagttccca cttataagtg agagcatgca gtattgggct ttctgtgccc    300

acattaattc acttaagata atggtctcca gctggatcca tattgatgca aagtacataa    360

tttctttcat tttatggctg catagtattc catgttatgt ttgtaccaca ttttctttat    420

ccagtccata gctgatggac atctacattg attccatgtc ctcattaatg tgaatagtgt    480

tttgatgaac atatgaatgt atgtgtcttt ttggtagaat aatttatttt cctttggata    540

taaagccagt aatggaattg ctgggtcgaa tcgtcgttct tttgtaagtt ctttgagata    600

tctccaagtt tcgttccaca ggcactgaaa tagtttacat tcccaccaat aatgaacacg    660

cattcccttt tctccacaac cctgtcaaca tctgttattt ttttactttt taatagtagc    720

cattctgact ggtgtgtgat ggtacttcat tatggctttc attcgcattt ctttcctgac    780

ttgtgatttt gagtagtttt tcatatgttt gttggcgaca tgtatgtctt ctgagaagag    840

cctgttcatg ttttttgccc acttcttaac agggctgttc atcttttgct tgttgatttg    900

ttcaagtttc ttagagatag tggatattag atctctgttg gatgcatagt ttgcaaatat    960

tttctctctg tctgtttacc ctgttgatag tttcttttat tgtgcagaaa ccctttaatt   1020

taatcaggtc caacttatcc atttttcttt tggttgaaat tgcttttgag gacttagtta   1080

tgaattattt gccaaagctg acgtcaagaa gggtattctc taggttttct tatatgacat   1140

tttatagttt taggtcttat attaaagtct ttgtttcatc tcaaattgac tttttttctc   1200

tggtaaaagg taggggtcca gttcaagctc atttttccat gtggttttgt tacagtgggt   1260

agctgcagac atgagctggg caggagaggc ctcttcctaa caggaatgtc aggtgacca    1319
```

<210> SEQ ID NO 41
<211> LENGTH: 444
<212> TYPE: DNA
<213> ORGANISM: Homo sapiens

<400> SEQUENCE: 41

```
atgtggaact tcttcaggag agaattaaca tccaatggat tcccagaaaa cttttccctc     60

gatgtaccag caaacaccta caatgccctg aaaagccgcc tctgcgaccc caatgcagat    120

cacacgtcct gtcccagccc ctgcagcctc cacgcggcgg gtgcactgcc aggcacggga    180
```

aggcagcgct ggcgagtaga actggcccat ctcgcagata ggaagctgag cctcagggac 240
gtttcacgcc ttcgtcaagg tggtgagagg aggagcggga ttgccgtgaa ggtggtgaga 300
ggaggagcgg ggtttgctgc ccgacttcag ggatctgtca ccctcgtcca gcagggttgg 360
ttcttcccga ggctgggagg atgccaagcc tggtggagga tgggggcggt ggtgtggtgt 420
ggggagcttc tgacttgcac atcc 444

<210> SEQ ID NO 42
<211> LENGTH: 210
<212> TYPE: DNA
<213> ORGANISM: Homo sapiens

<400> SEQUENCE: 42
atgactggtg ttcttataag aagaggagat ttggtcacag acatggttgc atgcagaata 60
aagacttttc gaggacacac tgagaaggca gccatctgca aaacaaggaa agagtcctca 120
gcagaaacca gtcctgcaga ctccttgatc ttggacttcc agccactgca attgatgtca 180
agcttcagca cccttgcatc tctggataaa 210

<210> SEQ ID NO 43
<211> LENGTH: 183
<212> TYPE: DNA
<213> ORGANISM: Homo sapiens

<400> SEQUENCE: 43
atgaatactc ctaacattgt ctctttaaga gctcaccagc ctgaggtagg aatcattcca 60
tctgtgttac taatgagacc gctgaggatc aaaggggttt tccaccacat ccactcacct 120
ctacatggcg aaaaccaagg gttcactctc tgtcttcagg gagctccacc cagcagcagc 180
gtt 183

<210> SEQ ID NO 44
<211> LENGTH: 192
<212> TYPE: DNA
<213> ORGANISM: Homo sapiens

<400> SEQUENCE: 44
atggcgaaaa ccaagggttc actctctgtc ttcagggagc tccacccagc agcagcgttt 60
gacagagctg ttcacttcct cttcctggag ctgtggcttc cagagcccat gctcagcagt 120
tcccctcctt cttcgactgc tcctctctta ggctcagagc cactcagaca ttgggaagca 180
agtttgtcaa ga 192

<210> SEQ ID NO 45
<211> LENGTH: 132
<212> TYPE: DNA
<213> ORGANISM: Homo sapiens

<400> SEQUENCE: 45
atgaagagga aagcaaacag gtggagactc agcctgagaa atggtctgtt gccaagcaca 60
cccagagcta cccaacagat tcctatggag ttcttgaatt ccagggtggc ggatattcca 120
ataaagccat gg 132

<210> SEQ ID NO 46
<211> LENGTH: 132
<212> TYPE: DNA
<213> ORGANISM: Homo sapiens

<400> SEQUENCE: 46
atgcgtggat ttctgtggag agtggaaaca cggggagtcg aggggagcat gcgcgggcct 60
cagaaagttc tgggaaaccg actcccggga gcagggagga acgcgcgctc cagagacaac 120
ttcgcggtgt gg 132

<210> SEQ ID NO 47
<211> LENGTH: 138
<212> TYPE: DNA
<213> ORGANISM: Homo sapiens

<400> SEQUENCE: 47
atggtttatt atgggaatcc tgaatccagc ccagggattt ctcttgtctt tggccttcta 60
cggctggaca ggatgcagcc tgggttttca gtctcccagg aaggagatcc agtgggaatc 120
actgaccacc tcggctgc 138

<210> SEQ ID NO 48
<211> LENGTH: 147
<212> TYPE: DNA
<213> ORGANISM: Homo sapiens

<400> SEQUENCE: 48
atgccagcac aattgaaatt cacactgcaa gtgaatcctg caacaaaaat gagggtgacc 60
ctgctctccc aacccatgga gacctatgaa ggggatgtgc tgggggtcca gaccccatat 120
tcctcagact caacaattct tgttctt 147

<210> SEQ ID NO 49
<211> LENGTH: 519
<212> TYPE: DNA
<213> ORGANISM: Homo sapiens

<400> SEQUENCE: 49
atggggagct ctagagtggg agaaagaatg atggaagaag agtccagaac aggccagaaa 60
gtgaatccag ggaacacagg caaattattt gtgggggtag gaatctcaag aattgcgaaa 120
gtcaaatatg gagagtgtgg gcaaggtttc agtgataagt cagatgttat tacacaccaa 180
aggacacaca cagggggaa gccctacgtc tgcagagagt gtgggagggc tttagccgga 240
agtcagacct cctcagtcac cagaggacac acacagggga gaagccttat gtctgcagag 300
agtgtgagcg gggctttagc cggaagtcag tcctcctcat tcaccagagg acacacaggg 360
gagacgcccc agtctgcagg aaggatgagt aagtcattag taataaaacc ttatctcaat 420
agccacaaga agacaaacgt gatcaccaca cacttgcaca ccccagctct gaggtggctt 480
cagcgaaagt ctgctaaccc cttacattcc ccgagagtg 519

<210> SEQ ID NO 50
<211> LENGTH: 318
<212> TYPE: DNA
<213> ORGANISM: Homo sapiens

<400> SEQUENCE: 50
atgcatagtt tgcaaatatt ttctctctgt ctgtttaccc tgttgatagt ttcttttatt 60
gtgcagaaac cctttaattt aatcaggtcc aacttatcca tttttctttt ggttgaaatt 120
gcttttgagg acttagttat gaattatttg ccaaagctga cgtcaagaag ggtattctct 180
aggttttctt atatgacatt ttatagtttt aggtcttata ttaaagtctt tgtttcatct 240
caaattgact ttttttctct ggtaaaaggt aggggtccag ttcaagctca tttttccatg 300
tggttttgtt acagtggg 318

<210> SEQ ID NO 51
<211> LENGTH: 9
<212> TYPE: PRT
<213> ORGANISM: Homo sapiens

<400> SEQUENCE: 51

Ala Ala Phe Asp Arg Ala Val His Phe
1 5

<210> SEQ ID NO 52
<211> LENGTH: 8
<212> TYPE: PRT
<213> ORGANISM: Homo sapiens

<400> SEQUENCE: 52

Ala Phe Asp Arg Ala Val His Phe
1 5

<210> SEQ ID NO 53
<211> LENGTH: 9
<212> TYPE: PRT
<213> ORGANISM: Homo sapiens

<400> SEQUENCE: 53

Arg Pro Leu Arg Ile Lys Gly Val Phe
1 5

<210> SEQ ID NO 54
<211> LENGTH: 9
<212> TYPE: PRT
<213> ORGANISM: Homo sapiens

<400> SEQUENCE: 54

Lys Thr Lys Gly Ser Leu Ser Val Phe
1 5

<210> SEQ ID NO 55
<211> LENGTH: 10
<212> TYPE: PRT
<213> ORGANISM: Homo sapiens

<400> SEQUENCE: 55

Val Pro Ala Asn Thr Tyr Asn Ala Leu Lys
1 5 10

<210> SEQ ID NO 56
<211> LENGTH: 10
<212> TYPE: PRT
<213> ORGANISM: Homo sapiens

<400> SEQUENCE: 56

Arg Leu Gly Gly Cys Gln Ala Trp Trp Arg
1 5 10

<210> SEQ ID NO 57
<211> LENGTH: 10
<212> TYPE: PRT
<213> ORGANISM: Homo sapiens

<400> SEQUENCE: 57

Ala Asn Thr Tyr Asn Ala Leu Lys Ser Arg
1 5 10

<210> SEQ ID NO 58
<211> LENGTH: 10
<212> TYPE: PRT
<213> ORGANISM: Homo sapiens

<400> SEQUENCE: 58

Leu Val Thr Asp Met Val Ala Cys Arg Ile
1 5 10

<210> SEQ ID NO 59
<211> LENGTH: 10
<212> TYPE: PRT
<213> ORGANISM: Homo sapiens

<400> SEQUENCE: 59

Leu Ile Leu Asp Phe Gln Pro Leu Gln Leu
1 5 10

<210> SEQ ID NO 60
<211> LENGTH: 10
<212> TYPE: PRT
<213> ORGANISM: Homo sapiens

<400> SEQUENCE: 60

Met Ser Ser Phe Ser Thr Leu Ala Ser Leu
1 5 10

<210> SEQ ID NO 61
<211> LENGTH: 11
<212> TYPE: PRT
<213> ORGANISM: Homo sapiens

<400> SEQUENCE: 61

Leu Met Ser Ser Phe Ser Thr Leu Ala Ser Leu
1 5 10

<210> SEQ ID NO 62
<211> LENGTH: 9
<212> TYPE: PRT
<213> ORGANISM: Homo sapiens

<400> SEQUENCE: 62

Leu Met Ser Ser Phe Ser Thr Leu Ala
1 5

<210> SEQ ID NO 63
<211> LENGTH: 10
<212> TYPE: PRT
<213> ORGANISM: Homo sapiens

<400> SEQUENCE: 63

Gln Leu Met Ser Ser Phe Ser Thr Leu Ala
1 5 10

<210> SEQ ID NO 64
<211> LENGTH: 10
<212> TYPE: PRT
<213> ORGANISM: Homo sapiens

<400> SEQUENCE: 64

Met Val Ala Cys Arg Ile Lys Thr Phe Arg
1 5 10

<210> SEQ ID NO 65
<211> LENGTH: 10
<212> TYPE: PRT
<213> ORGANISM: Homo sapiens

<400> SEQUENCE: 65

Val Thr Asp Met Val Ala Cys Arg Ile Lys
1 5 10

<210> SEQ ID NO 66
<211> LENGTH: 8
<212> TYPE: PRT
<213> ORGANISM: Homo sapiens

<400> SEQUENCE: 66

Ser Pro Ala Asp Ser Leu Ile Leu
1 5

<210> SEQ ID NO 67
<211> LENGTH: 10
<212> TYPE: PRT
<213> ORGANISM: Homo sapiens

<400> SEQUENCE: 67

Asn Thr Pro Asn Ile Val Ser Leu Arg Ala
1 5 10

<210> SEQ ID NO 68
<211> LENGTH: 10
<212> TYPE: PRT
<213> ORGANISM: Homo sapiens

<400> SEQUENCE: 68

Val Leu Leu Met Arg Pro Leu Arg Ile Lys
1 5 10

<210> SEQ ID NO 69
<211> LENGTH: 10
<212> TYPE: PRT
<213> ORGANISM: Homo sapiens

<400> SEQUENCE: 69

Met Arg Pro Leu Arg Ile Lys Gly Val Phe
1 5 10

<210> SEQ ID NO 70
<211> LENGTH: 8
<212> TYPE: PRT
<213> ORGANISM: Homo sapiens

<400> SEQUENCE: 70

Phe Leu Phe Leu Glu Leu Trp Leu
1 5

<210> SEQ ID NO 71
<211> LENGTH: 9
<212> TYPE: PRT
<213> ORGANISM: Homo sapiens

<400> SEQUENCE: 71

Ser Val Phe Arg Glu Leu His Pro Ala
1               5

<210> SEQ ID NO 72
<211> LENGTH: 9
<212> TYPE: PRT
<213> ORGANISM: Homo sapiens

<400> SEQUENCE: 72

Ser Pro Pro Ser Ser Thr Ala Pro Leu
1               5

<210> SEQ ID NO 73
<211> LENGTH: 9
<212> TYPE: PRT
<213> ORGANISM: Homo sapiens

<400> SEQUENCE: 73

Arg Leu Gln Gly Ser Val Thr Leu Val
1               5

<210> SEQ ID NO 74
<211> LENGTH: 9
<212> TYPE: PRT
<213> ORGANISM: Homo sapiens

<400> SEQUENCE: 74

Val Pro Ala Asn Thr Tyr Asn Ala Leu
1               5

<210> SEQ ID NO 75
<211> LENGTH: 9
<212> TYPE: PRT
<213> ORGANISM: Homo sapiens

<400> SEQUENCE: 75

Gln Leu Met Ser Ser Phe Ser Thr Leu
1               5

<210> SEQ ID NO 76
<211> LENGTH: 11
<212> TYPE: PRT
<213> ORGANISM: Homo sapiens

<400> SEQUENCE: 76

Phe Leu Glu Leu Trp Leu Pro Glu Pro Met Leu
1               5                   10

<210> SEQ ID NO 77
<211> LENGTH: 9
<212> TYPE: PRT
<213> ORGANISM: Homo sapiens

<400> SEQUENCE: 77

Ala Pro Leu Leu Gly Ser Glu Pro Leu
1               5

<210> SEQ ID NO 78
<211> LENGTH: 9
<212> TYPE: PRT
<213> ORGANISM: Homo sapiens

-continued

<400> SEQUENCE: 78

```
Ser Leu Ile Leu Asp Phe Gln Pro Leu
1               5
```

CANCER ANTIGENS AND METHODS

CROSS-REFERENCE TO RELATED APPLICATIONS

This application is a continuation of International (PCT) Patent Application Serial No. PCT/GB2019/052980, filed Oct. 18, 2019, which claims the benefit of and priority to European Patent Application Serial No. 18201634.5, filed Oct. 19, 2018; the entire contents of these applications are incorporated herein by reference in their entirety.

FIELD OF THE INVENTION

The present invention relates to antigenic polypeptides and corresponding polynucleotides for use in the treatment or prevention of cancer, in particular for use in treating or preventing melanoma (e.g. cutaneous melanoma or uveal melanoma). The present invention further relates inter alia to pharmaceutical and immunogenic compositions comprising said nucleic acids and polypeptides, immune cells loaded with and/or stimulated by said polypeptides and polynucleotides, antibodies specific for said polypeptides and cells (autologous or otherwise) genetically engineered with molecules that recognize said polypeptides.

BACKGROUND OF THE INVENTION

As part of normal immunosurveillance for pathogenic microbes, all cells degrade intracellular proteins to produce peptides that are loaded onto Major Histocompatibility Complex (MHC) Class I molecules that are expressed on the surface of all cells. Most of these peptides, which are derived from the host cell, are recognized as self, and remain invisible to the adaptive immune system. However, peptides that are foreign (non-self), are capable of stimulating the expansion of naïve CD8+ T-cells that encode a T-cell receptor (TCR) that tightly binds the MHC I-peptide complex. This expanded T-cell population can produce effector CD8+ T-cells (including cytotoxic T-lymphocytes—CTLs) that can eliminate the foreign antigen-tagged cells, as well as memory CD8+ T-cells that can be re-amplified when the foreign antigen-tagged cells appear later in the animal's life.

MHC Class II molecules, whose expression is normally limited to professional antigen-presenting cells (APCs) such as dendritic cells (DCs), are usually loaded with peptides which have been internalised from the exogenous environment. Binding of a complementary TCR from a naïve CD4+ T-cell to the MHC II-peptide complex, in the presence of various factors, including T-cell adhesion molecules (CD54, CD48) and co-stimulatory molecules (CD40, CD80, CD86), induces the maturation of CD4+ T-cells into effector cells (e.g., $T_H1$, $T_H2$, $T_H17$, $T_{FH}$, $T_{reg}$ cells). These effector CD4+ T-cells can promote B-cell differentiation to antibody-secreting plasma cells as well as facilitate the differentiation of antigen-specific CD8+ CTLs, thereby helping induce the adaptive immune response to foreign antigens, that include both short-term effector functions and longer-term immunological memory. DCs can perform the process of cross-presentation of peptide antigens by delivering exogenously-derived antigens (such as a peptide or protein released from a pathogen or a tumor cell) onto their MHC I molecules, contributing to the generation of immunological memory by providing an alternative pathway to stimulating the expansion of naïve CD8+ T-cells.

Immunological memory (specifically antigen-specific B cells/antibodies and antigen-specific CTLs) are critical players in controlling microbial infections, and immunological memory has been exploited to develop numerous vaccines that prevent the diseases caused by important pathogenic microbes. Immunological memory is also known to play a key role in controlling tumor formation, but very few efficacious cancer vaccines have been developed.

Cancer is the second leading cause of morbidity, accounting for nearly 1 in 6 of all deaths globally. Of the 8.8 million deaths caused by cancer in 2015, the cancers which claimed the most lives were from lung (1.69 million), liver (788,000), colorectal (774,000), stomach (754,000) and breast (571,000) carcinomas. The economic impact of cancer in 2010 was estimated to be USD1.16 Trillion, and the number of new cases is expected to rise by approximately 70% over the next two decades (World Health Organisation Cancer Facts 2017).

Current therapies for cutaneous melanoma are varied and are highly dependent on the location of the tumor and stage of the disease. The main treatment for a non-metastatic melanoma is surgery to remove the tumor and surrounding tissue. Later stage melanomas may require treatment comprising lymph node dissection, radiotherapy, or chemotherapy. Immune checkpoint blockade strategies, including the use of antibodies targeting negative immune regulators such PD-1/PD-L1 and CTLA4, have recently revolutionised treatments to a variety of malignancies, including melanoma (Ribas, A., & Wolchok, J. D. (2018) *Science,* 359:1350-1355. ). The extraordinary value of checkpoint blockade therapies, and the well-recognized association of their clinical benefit with patient's adaptive immune responses (specifically T-cell based immune responses) to their own cancer antigens has re-invigorated the search for effective cancer vaccines, vaccine modalities, and cancer vaccine antigens.

Human endogenous retroviruses (HERVs) are remnants of ancestral germline integrations of exogenous infectious retroviruses. HERVs belong to the group of endogenous retroelements that are characterised by the presence of Long Terminal Repeats (LTRs) flanking the viral genome. This group also includes the Mammalian apparent LTR Retrotransposons (MaLRs) and are therefore collectively known as LTR elements (here referred to collectively as ERV to mean all LTR elements). ERVs constitute a considerable proportion of the mammalian genome (8%), and can be grouped into approximately 100 families based on sequence homology. Many ERV sequences encode defective proviruses which share the prototypical retroviral genomic structure consisting of gag, pro, pol and env genes flanked by LTRs. Some intact ERV ORFs produce retroviral proteins which share features with proteins encoded by exogenous infectious retroviruses such as HIV-1. Such proteins may serve as antigens to induce a potent immune response (Hurst & Magiorkinis, 2015, J. Gen. Virol 96:1207-1218), suggesting that polypeptides encoded by ERVs can escape T and B-cell receptor selection processes and central and peripheral tolerance. Immune reactivity to ERV products may occur spontaneously in infection or cancer, and ERV products have been implicated as a cause of some autoimmune diseases (Kassiotis & Stoye, 2016, Nat. Rev. Immunol. 16:207-219).

Due to the accumulation of mutations and recombination events during evolution, most ERV-derived sequences have lost functional open reading frames for some or all of their genes and therefore their ability to produce infectious virus. However, these ERV elements are maintained in germline DNA like other genes and still have the potential to produce proteins from at least some of their genes. Indeed, HERV-encoded proteins have been detected in a variety of human cancers. For example, splice variants of the HERV-K env gene, Rec and Np9, are found exclusively in malignant testicular germ cells and not in healthy cells (Ruprecht et. al, 2008, Cell Mol Life Sci 65:3366-3382). Increased levels of HERV transcripts have also been observed in cancers such as those of the prostate, as compared to healthy tissue (Wang-Johanning, 2003, Cancer 98:187-197; Andersson et al., 1998, Int. J. Oncol, 12:309-313). Additionally, overexpression of HERV-E and HERV-H has been demonstrated to be immunosuppressive, which could also contribute to the development of cancer (Mangeney et al., 2001, J. Gen. Virol. 82:2515-2518). However, the exact mechanism(s) by which HERVs could contribute to the development or pathogenicity of cancer remains unknown.

In addition to deregulating the expression of surrounding neighbouring host genes, the activity and transposition of ERV regulatory elements to new genomic sites may lead to the production of novel transcripts, some of which may have oncogenic properties (Babaian & Mager, *Mob. DNA,* 2016, Lock et al., *PNAS,* 2014, 111:3534-3543).

A wide range of vaccine modalities are known. One well-described approach involves directly delivering an antigenic polypeptide to a subject with a view to raising an immune response (including B- and T-cell responses) and stimulating immunological memory. Alternatively, a polynucleotide may be administered to the subject by means of a vector such that the polynucleotide-encoded immunogenic polypeptide is expressed in vivo. The use of viral vectors, for example adenovirus vectors, has been well explored for the delivery of antigens in both prophylactic vaccination and therapeutic treatment strategies against cancer (Wold et al. Current Gene Therapy, 2013, Adenovirus Vectors for Gene Therapy, Vaccination and Cancer Gene Therapy, 13:421-433). Immunogenic peptides, polypeptides, or polynucleotides encoding them, can also be used to load patient-derived antigen presenting cells (APCs), that can then be infused into the subject as a vaccine that elicits a therapeutic or prophylactic immune response. An example of this approach is Provenge, which is presently the only FDA-approved anti-cancer vaccine.

Cancer antigens, may also be exploited in the treatment and prevention of cancer by using them to create a variety of non-vaccine therapeutic modalities. These therapies fall into two different classes: 1) antigen-binding biologics, 2) adoptive cell therapies.

Antigen-binding biologics typically consist of multivalent engineered polypeptides that recognize antigen-decorated cancer cells and facilitate their destruction. The antigen-binding components of these biologics may consist of TCR-based biologicals, including, but not limited to TCRs, high-affinity TCRs, and TCR mimetics produced by various technologies (including those based on monoclonal antibody technologies). Cytolytic moieties of these types of multivalent biologics may consist of cytotoxic chemicals, biological toxins, targeting motifs and/or immune stimulating motifs that facilitate targeting and activation of immune cells, any of which facilitate the therapeutic destruction of tumor cells.

Adoptive cell therapies may be based on a patient's own T-cells that are removed and stimulated ex vivo with vaccine antigen preparations (cultivated with T-cells in the presence or absence of other factors, including cellular and acellular components) (JCI Insight. 2018 Oct. 4; 3(19). pii: 122467. doi: 10.1172/jci.insight.122467). Alternatively, adoptive cell therapies can be based on cells (including patient- or non-patient-derived cells) that have been deliberately engineered to express antigen-binding polypeptides that recognize cancer antigens. These antigen-binding polypeptides fall into the same classes as those described above for antigen-binding biologics. Thus, lymphocytes (autologous or non-autologous), that have been genetically manipulated to express cancer antigen-binding polypeptides can be administered to a patient as adoptive cell therapies to treat their cancer.

Use of ERV-derived antigens in raising an effective immune response to cancer has shown promising results in promoting tumor regression and a more favourable prognosis in murine models of cancer (Kershaw et al., 2001, Cancer Res. 61:7920-7924; Slansky et al., 2000, Immunity 13:529-538). Thus, HERV antigen-centric immunotherapy trials have been contemplated in humans (Sacha et al.,2012, J.Immunol 189:1467-1479), although progress has been restricted, in part, due to a severe limitation of identified tumor-specific ERV antigens.

WO 2005/099750 identifies anchored sequences in existing vaccines against infectious pathogens, which are common in raising cross-reactive immune responses against the HERV-K Mel tumor antigen and confers protection to melanoma.

WO 00/06598 relates to the identification of HERV-AVL3-B tumor associated genes which are preferentially expressed in melanomas, and methods and products for diagnosing and treating conditions characterised by expression of said genes.

WO 2006/119527 provides antigenic polypeptides derived from the melanoma-associated endogenous retrovirus (MERV), and their use for the detection and diagnosis of melanoma as well as prognosis of the disease. The use of antigenic polypeptides as anticancer vaccines is also disclosed.

WO 2007/137279 discloses methods and compositions for detecting, preventing and treating HERV-K+ cancers, for example with use of a HERV-K+ binding antibody to prevent or inhibit cancer cell proliferation.

WO 2006/103562 discloses a method for treating or preventing cancers in which the immunosuppressive Np9 protein from the env gene of HERV-K is expressed. The invention also relates to pharmaceutical compositions comprising nucleic acid or antibodies capable of inhibiting the activity of said protein, or immunogen or vaccinal composition capable of inducing an immune response directed against said protein.

WO 2007/109583 provides compositions and methods for preventing or treating neoplastic disease in a mammalian subject, by providing a composition comprising an enriched immune cell population reactive to a HERV-E antigen on a tumor cell.

Humer J, et al., 2006, Canc. Res., 66:1658-63 identifies a melanoma marker derived from melanoma-associated endogenous retroviruses.

There is a need to identify further HERV-associated antigenic sequences which can be used in immunotherapy of cancer, particularly melanoma, especially cutaneous and uveal melanoma.

SUMMARY OF THE INVENTION

The inventors have surprisingly discovered certain RNA transcripts which comprise LTR elements or are derived from genomic sequences adjacent to LTR elements which are found at high levels in cutaneous melanoma cells, but are undetectable or found at very low levels in normal, healthy tissues (see Example 1). Such transcripts are herein referred to as cancer-specific LTR-element spanning transcripts (CLTs). Further, the inventors have shown that a subset of the potential polypeptide sequences (i.e., open reading frames (ORFs)) encoded by these CLTs are translated in cancer cells, processed by components of the antigen-processing apparatus, and presented on the surface of cells found in tumor tissue in association with the class I and class II major histocompatibility complex (MHC Class I, and MHC Class II) and class I and class II human leukocyte antigen (HLA Class I, HLA Class II) molecules (see Example 2). These findings demonstrate that these polypeptides (herein referred to as CLT antigens) are, ipso facto, antigenic. Thus, cancer cell presentation of CLT antigens is expected to render these cells susceptible to elimination by T-cells that bear cognate T-cell receptors (TCRs) for the CLT antigens, and CLT antigen-based vaccination methods/regimens that amplify T-cells bearing these cognate TCRs are expected to elicit immune responses against cancer cells (and tumors containing them), particularly melanoma particularly cutaneous melanoma tumors. T-cells from melanoma subjects are indeed reactive to peptides derived from CLT antigens disclosed herein and amplify T-cells and amplify T-cell receptor sequences (see Example 3). The inventors have confirmed that T-cells specific for CLT antigens have not been deleted from normal subject's T-cell repertoire by central tolerance (see Example 4). The presence and killing activity of CLT antigen specific T-cells in ex vivo cultures of healthy donor T-cells has been determined (see Example 5). Finally, qRT-PCR studies have confirmed that CLTs are specifically expressed in RNA extracted from melanoma cell lines as compared to non-melanoma cells lines (see Example 7).

The inventors have also surprisingly discovered that certain CLT antigen-encoding CLTs as well as being overexpressed in cutaneous melanoma are also overexpressed in uveal melanoma. The CLT antigen polypeptide sequences encoded by these CLTs are expected to elicit immune responses against uveal melanoma cells and tumors containing them.

The CLTs and the CLT antigens that are the subject of the present invention are not canonical sequences which can be readily derived from known tumor genome sequences found in the cancer genome atlas. The CLTs are transcripts resulting from complex transcription and splicing events driven by transcription control sequences of ERV origin. Since the CLTs are expressed at high level and since CLT antigen polypeptide sequences are not sequences of normal human proteins, it is expected that they will be capable of eliciting strong, specific immune responses (as indeed has been established—see Examples 3-5) and are thus suitable for therapeutic use in a cancer immunotherapy setting.

The CLT antigens discovered in the highly expressed transcripts that characterize tumor cells, which prior to the present invention were not known to exist and produce protein products in man and to stimulate immune responses, can be used in several formats. First, CLT antigen polypeptides of the invention can be directly delivered to a subject as a vaccine that elicits a therapeutic or prophylactic immune response to tumor cells. Second, nucleic acids of the invention, which may be codon optimised to enhance the expression of their encoded CLT antigens, can be directly administered or else inserted into vectors for delivery in vivo to produce the encoded protein products in a subject as a vaccine that elicits a therapeutic or prophylactic immune response to tumor cells. Third, polynucleotides and/or polypeptides of the invention can be used to load patient-derived antigen presenting cells (APCs), that can then be infused into the subject as a vaccine that elicits a therapeutic or prophylactic immune response to tumor cells. Fourth, polynucleotides and/or polypeptides of the invention can be used for ex vivo stimulation of a subject's T-cells, producing a stimulated T-cell preparation that can be administered to a subject as a therapy to treat cancer. Fifth, biological molecules such as T-cell receptors (TCRs) or TCR mimetics that recognize CLT antigens complexed to MHC I molecules and have been further modified to permit them to kill (or facilitate killing) of cancer cells may be administered to a subject as a therapy to treat cancer. Sixth, chimeric versions of biological molecules that recognize CLT antigens complexed to MHC cells may be introduced into T-cells (autologous our non-autologous), and the resulting cells may be administered to a subject as a therapy to treat cancer. These and other applications are described in greater detail below.

Thus, the invention provides inter alia an isolated polypeptide comprising a sequence selected from:

(a) the sequence of any one of SEQ ID NOs. 1-10 and (b) a variant of the sequences of (a); and (c) an immunogenic fragment of the sequences of (a)

(hereinafter referred to as "a polypeptide of the invention").

The invention also provides a nucleic acid molecule which encodes a polypeptide of the invention (hereinafter referred to as "a nucleic acid of the invention").

The polypeptides of the invention and the nucleic acids of the invention, as well as related aspects of the invention, are expected to be useful in a range of embodiments in cancer immunotherapy and prophylaxis, particularly immunotherapy and prophylaxis of melanoma, as discussed in more detail below.

DESCRIPTION OF THE FIGURES

For each of FIGS. 1-15, the top panel shows an extracted MS/MS spectrum (with assigned fragment ions) of a peptide isolated from a tumor sample of a patient and the bottom panel shows a rendering of the spectrum indicating the positions of the linear peptide sequences that have been mapped to the fragment ions.

For each of FIGS. 29-42, the top panel shows an extracted MS/MS spectrum (with assigned fragment ions) of a peptide isolated from a tumor sample of a patient and the bottom panel shows a rendering of the spectrum indicating the positions of the linear peptide sequences that have been mapped to the fragment ions.

Figure 1:
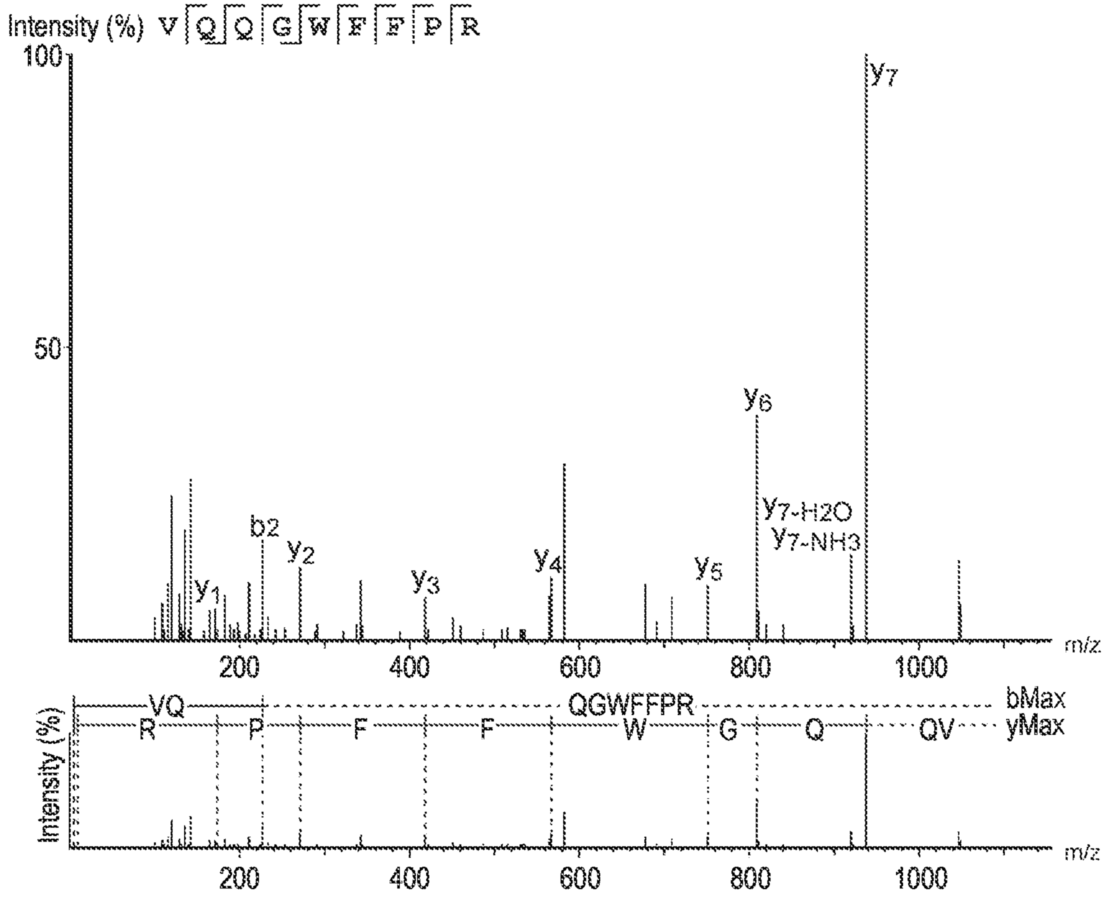
FIG. 1. Spectra for the peptide of SEQ ID NO. 11 isolated from a tumor sample of patient Mel-3.
Figure 2:
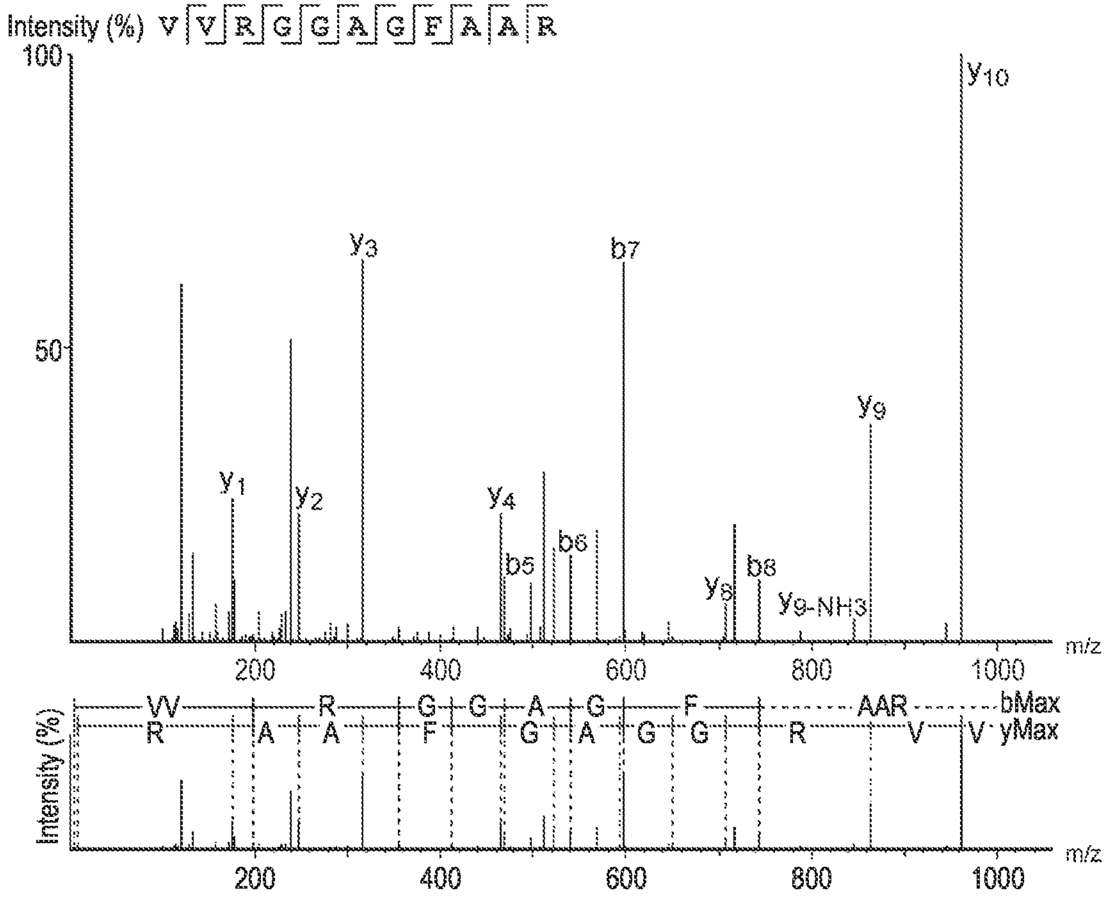
FIG. 2. Spectra for the peptide of SEQ ID NO. 12 isolated from a tumor sample of patient Mel-3.
Figure 3:
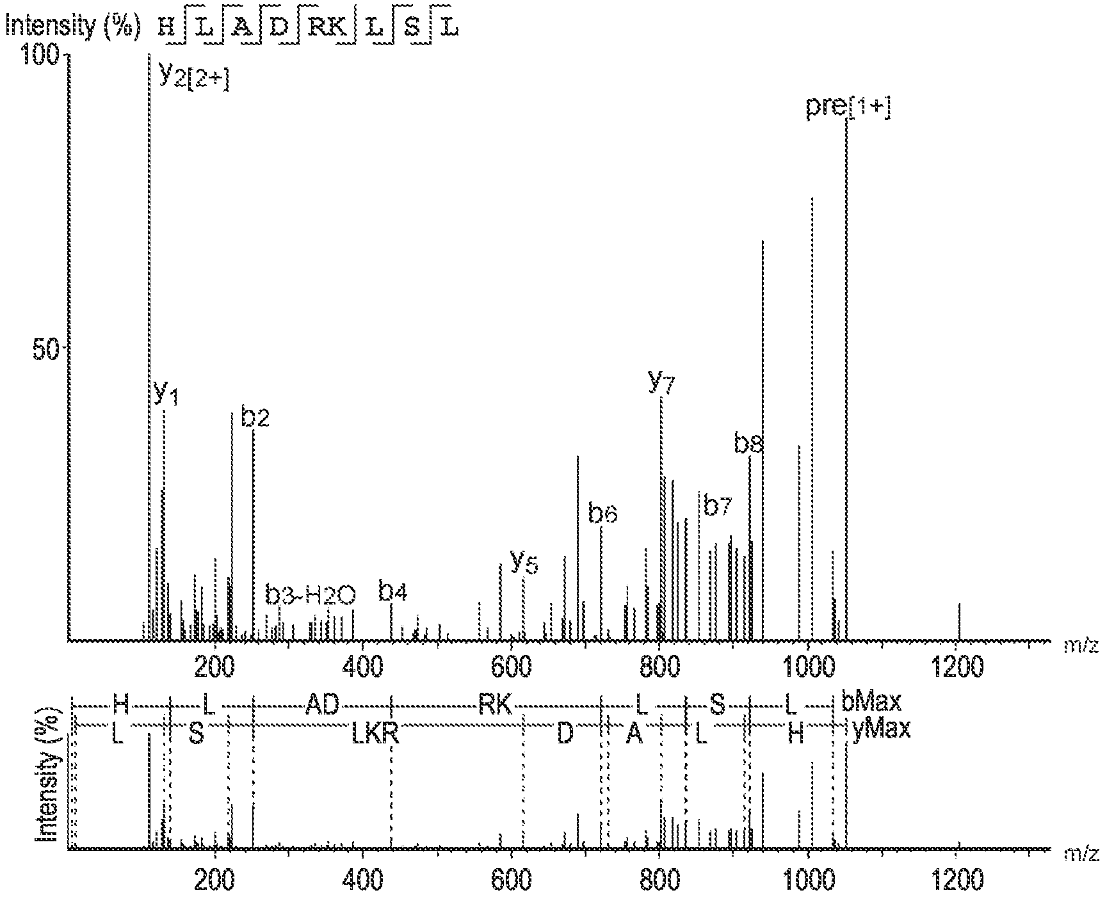
FIG. 3. Spectra for the peptide of SEQ ID NO. 13 isolated from a tumor sample of patient Mel-5.
Figure 4:
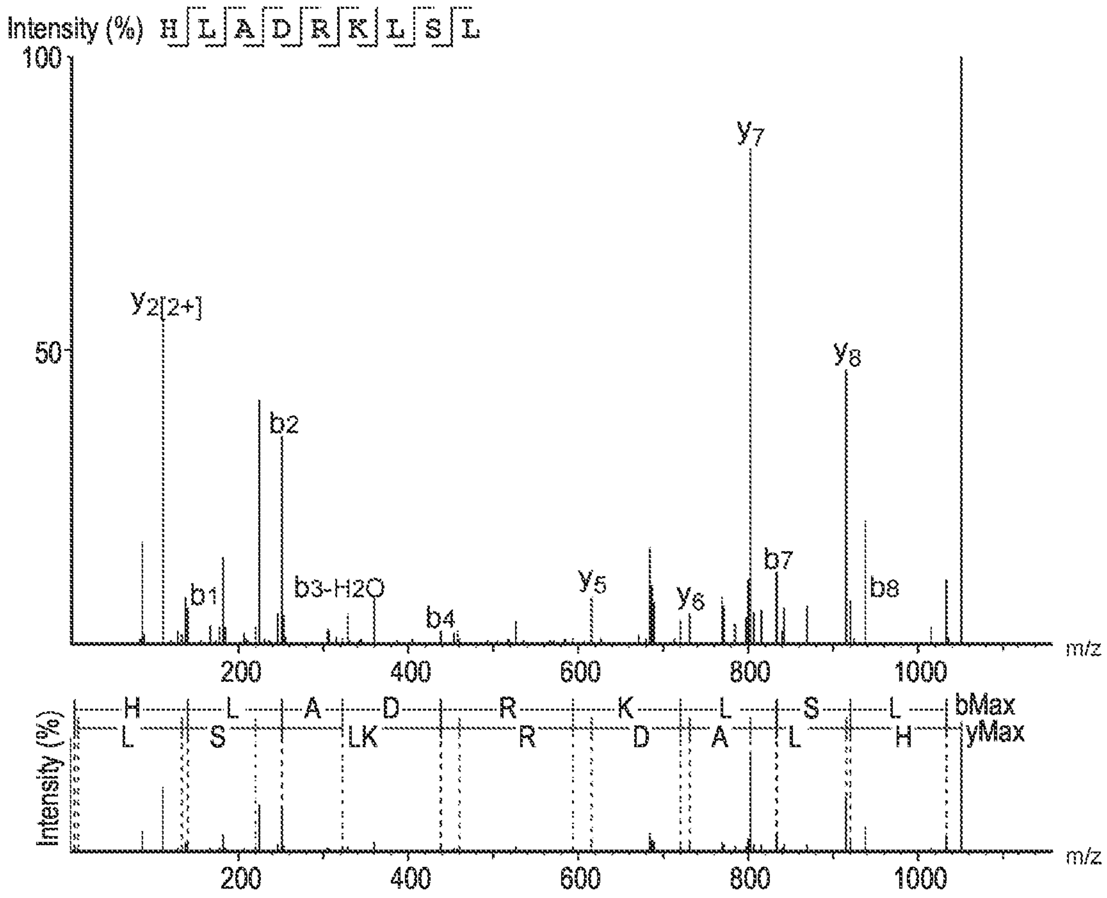
FIG. 4. Spectra for the peptide of SEQ ID NO. 13 isolated from a tumor sample of patient Mel-16.
Figure 5:
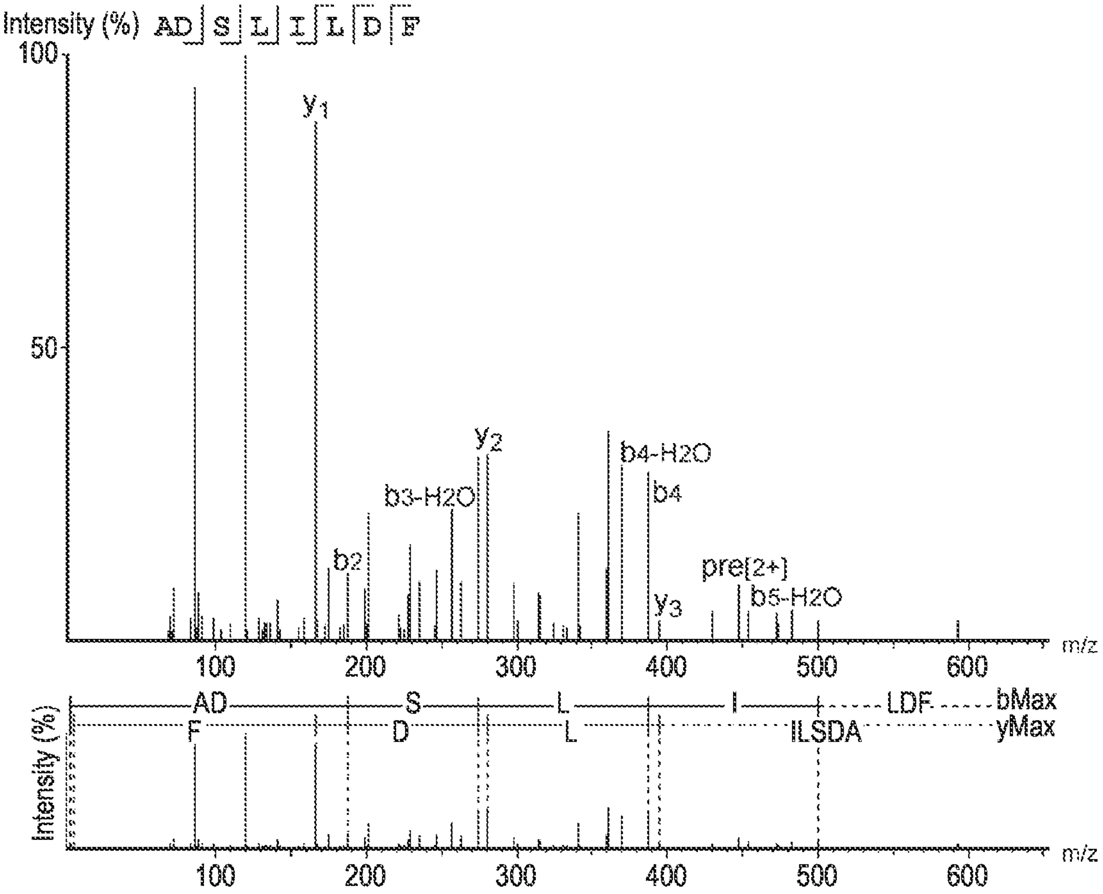
FIG. 5. Spectra for the peptide of SEQ ID NO. 15 isolated from a tumor sample of patient Mel-26.
Figure 6:
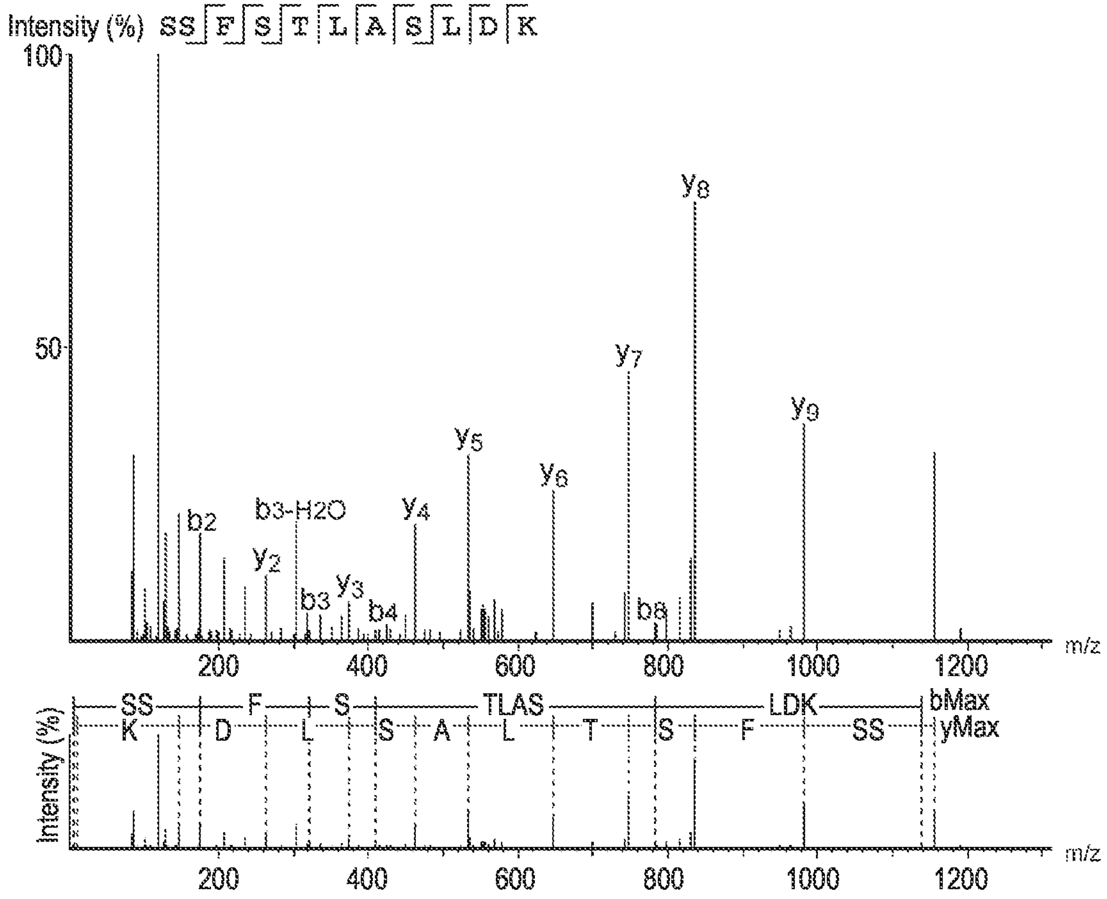
FIG. 6. Spectra for the peptide of SEQ ID NO. 16 isolated from a tumor sample of patient Mel-20.
Figure 7:
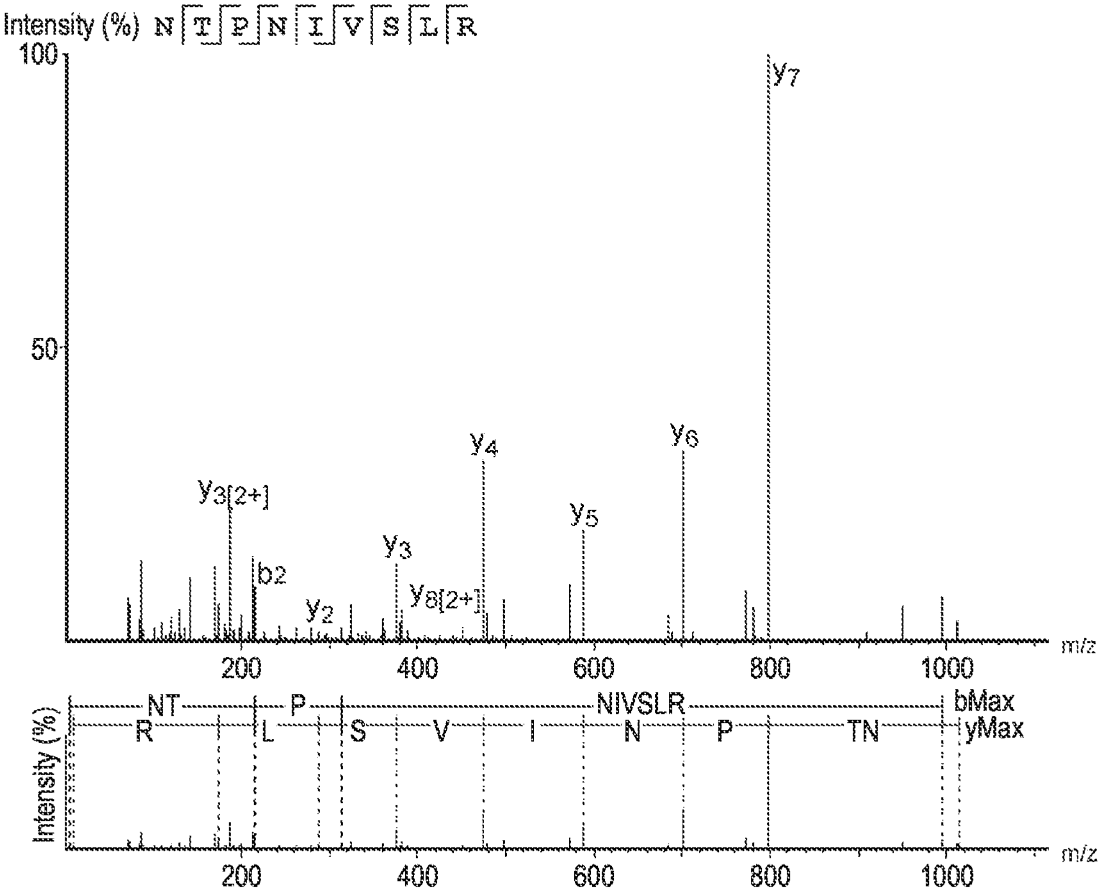
FIG. 7. Spectra for the peptide of SEQ ID NO. 17 isolated from a tumor sample of patient Mel-35.
Figure 8:
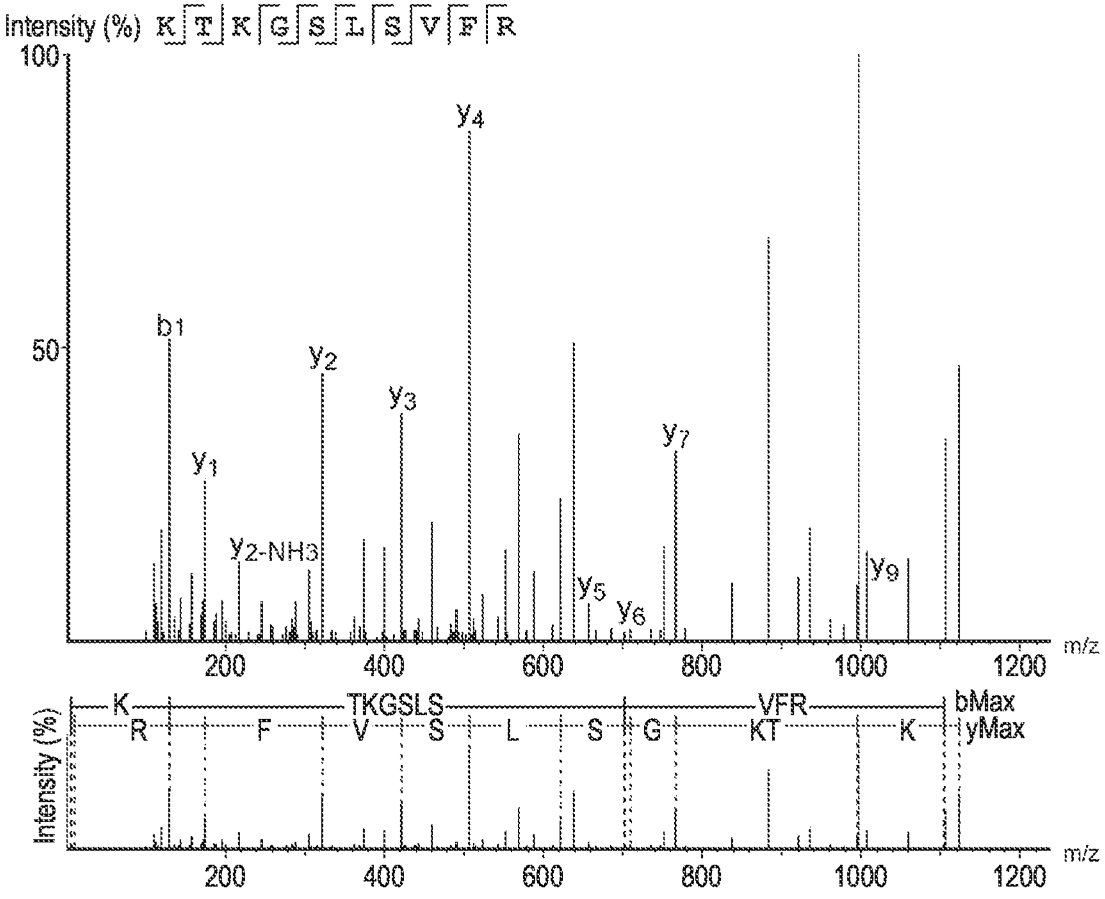
FIG. 8. Spectra for the peptide of SEQ ID NO. 19 isolated from a tumor sample of patient Mel-3.
Figure 9:
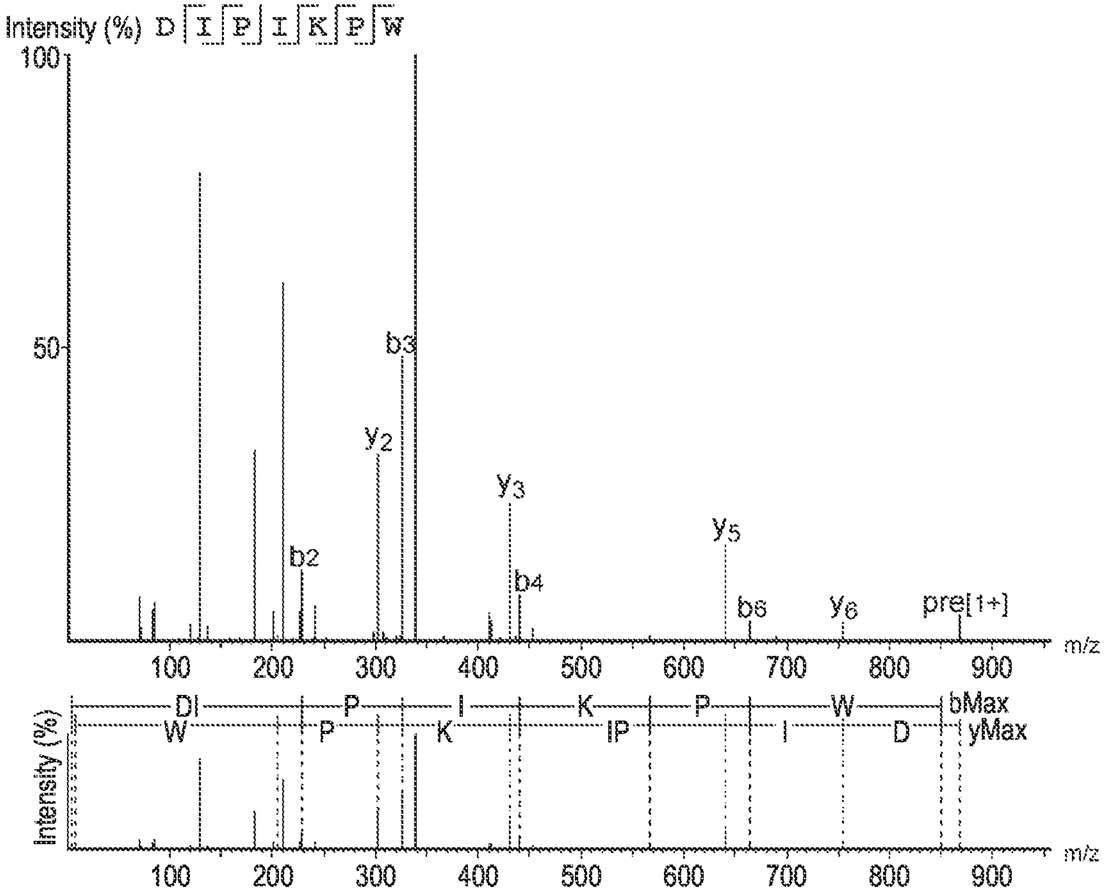
FIG. 9. Spectra for the peptide of SEQ ID NO. 21 isolated from a tumor sample of patient Mel-27.
Figure 10:
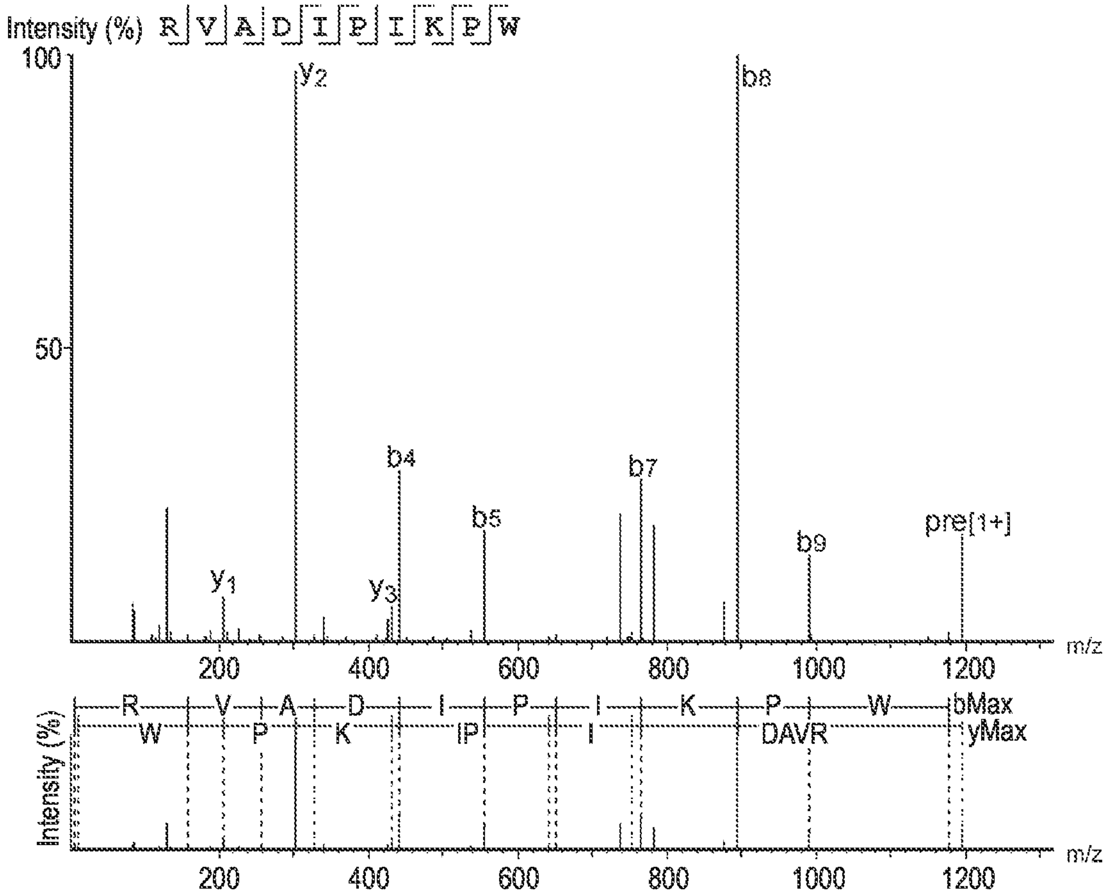
FIG. 10. Spectra for the peptide of SEQ ID NO. 20 isolated from a tumor sample of patient Mel-27.
Figure 11:
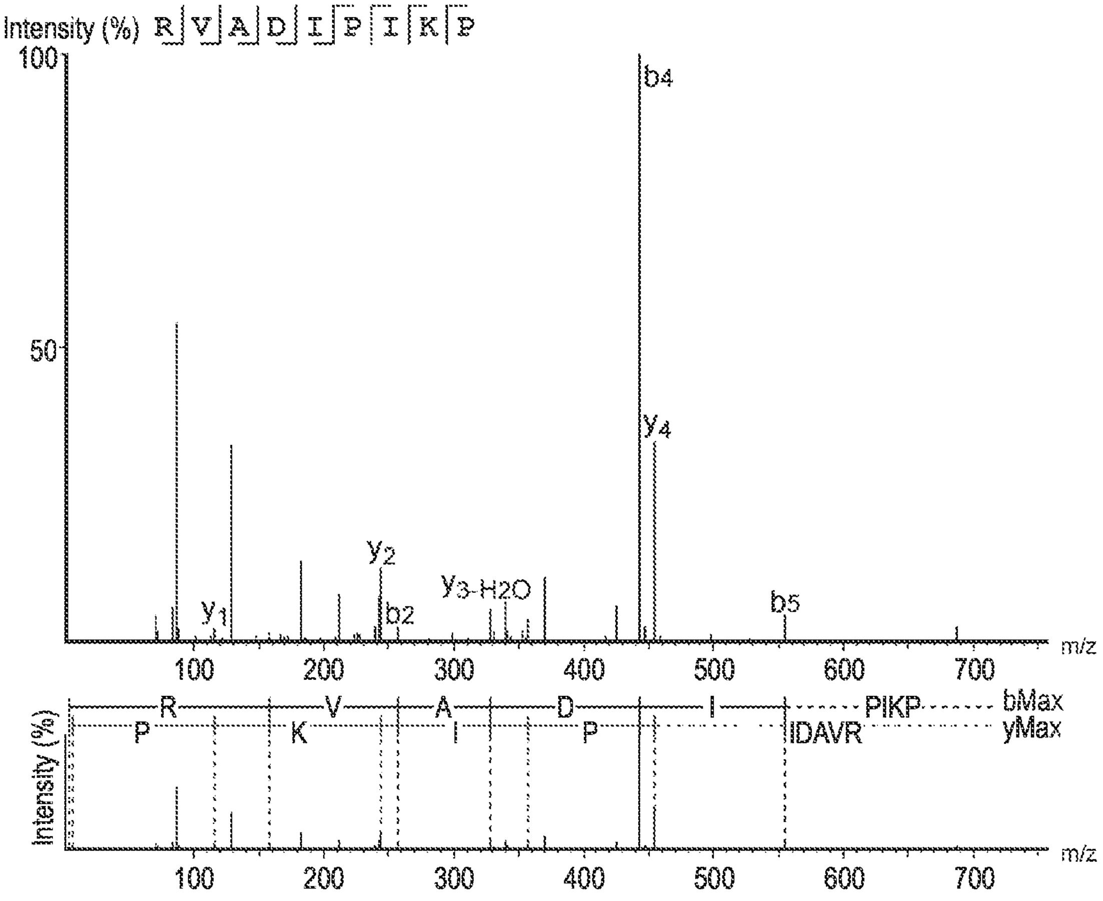
FIG. 11. Spectra for the peptide of SEQ ID NO. 22 isolated from a tumor sample of patient Mel-27.
Figure 12:
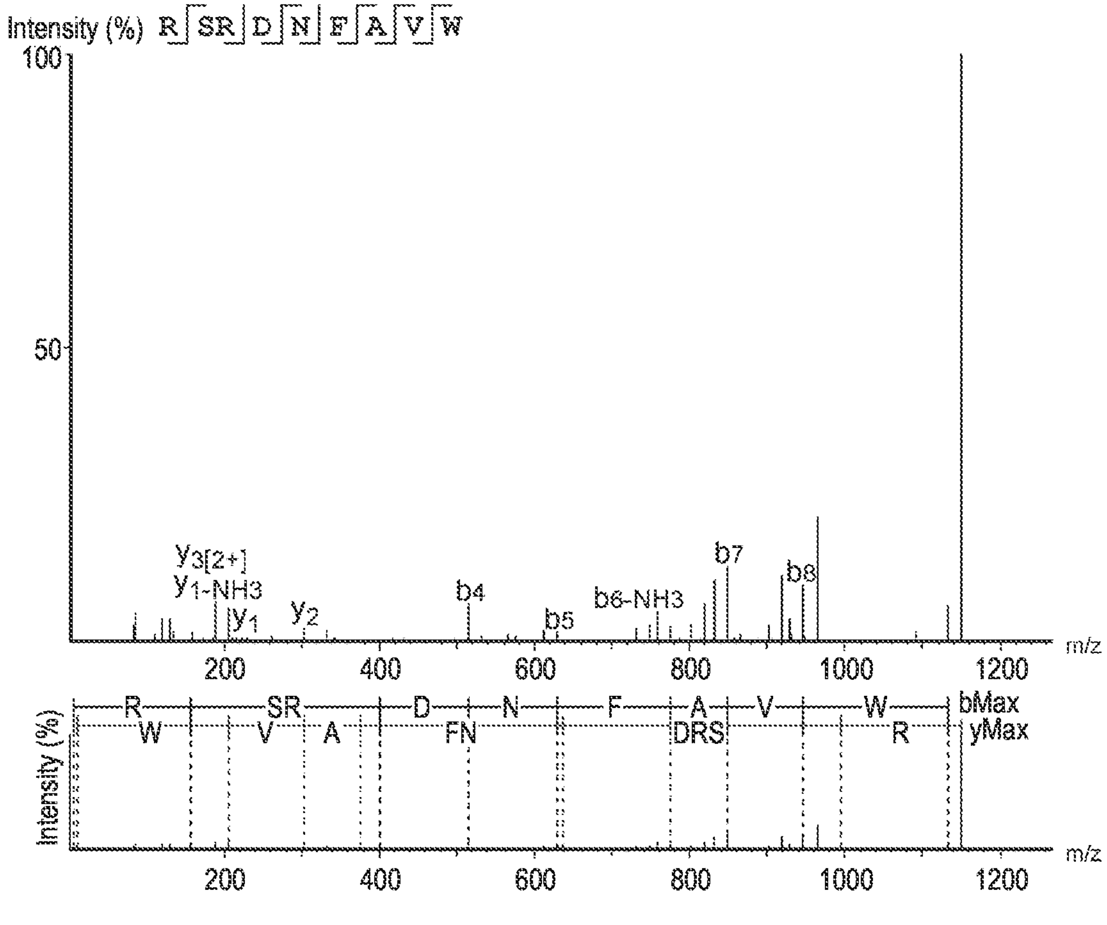
FIG. 12. Spectra for the peptide of SEQ ID NO. 23 isolated from a tumor sample of patient Mel-27.
Figure 13:
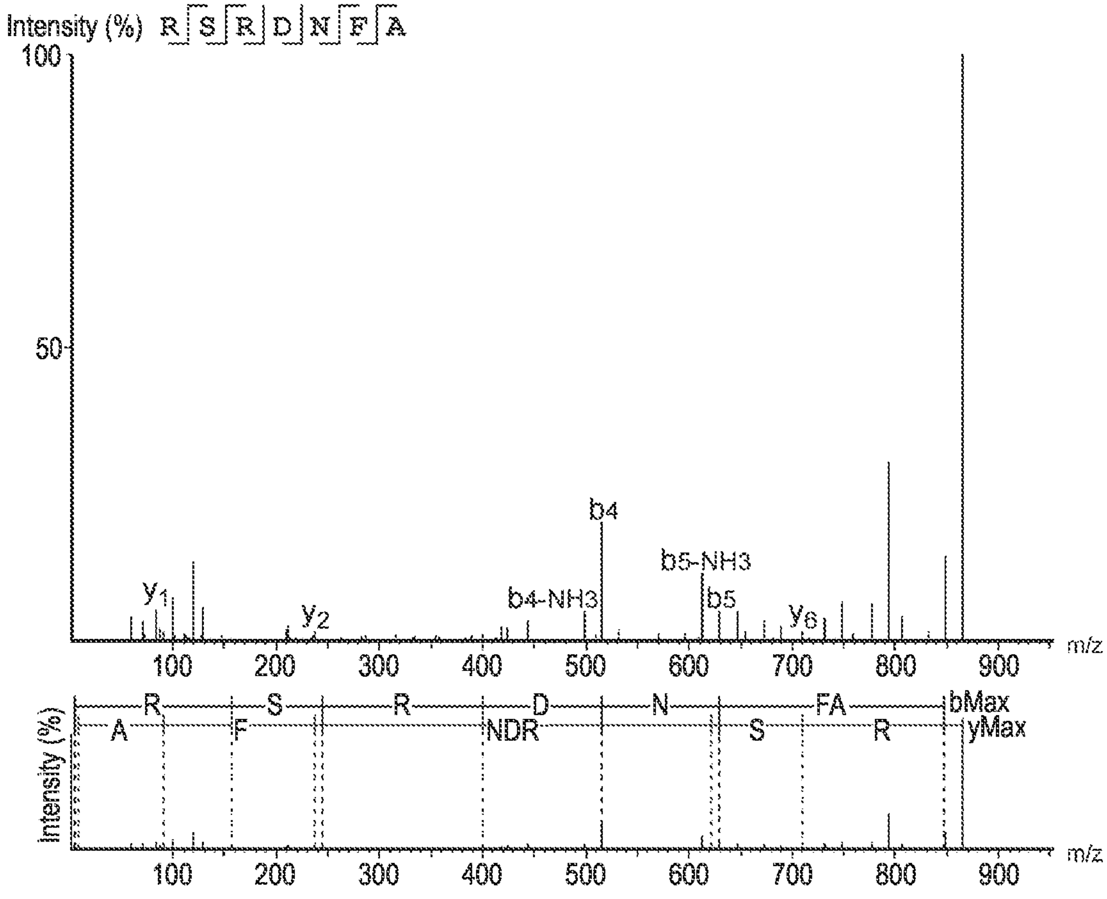
FIG. 13. Spectra for the peptide of SEQ ID NO. 24 isolated from a tumor sample of patient Mel-27.
Figure 14:
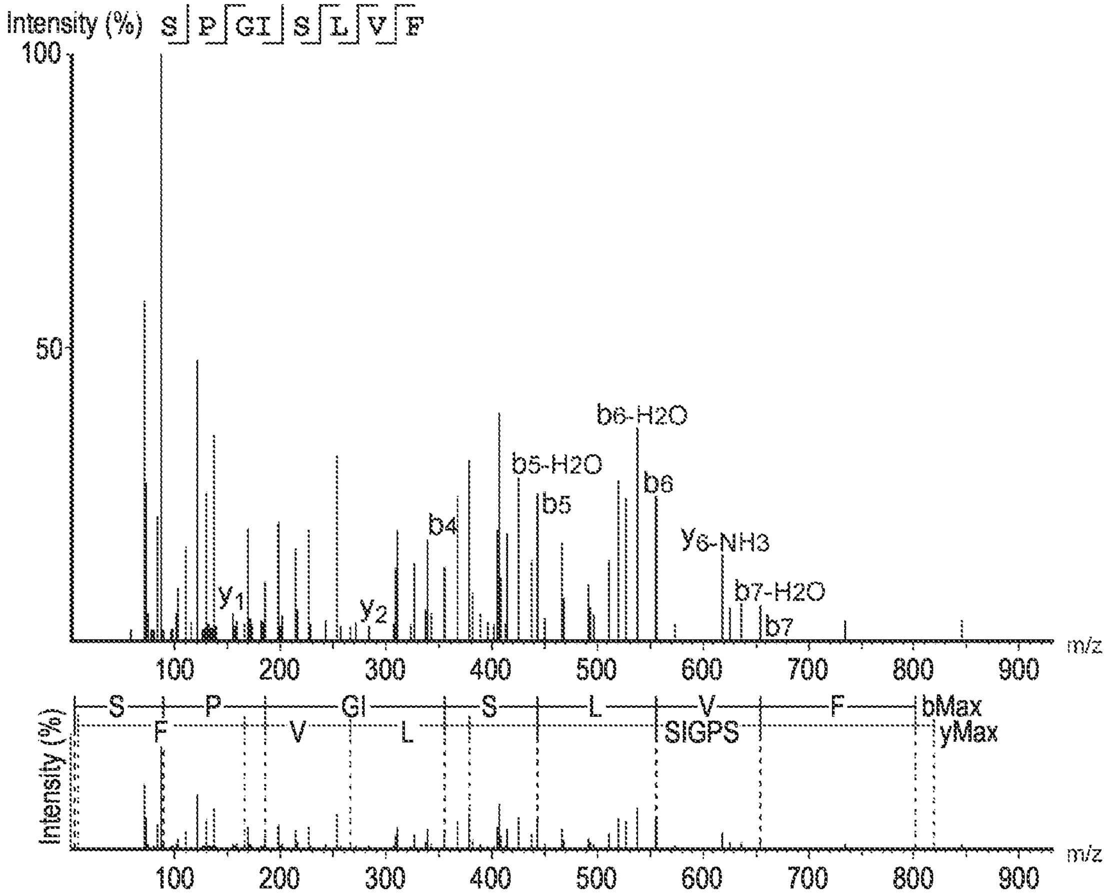
FIG. 14. Spectra for the peptide of SEQ ID NO. 25 isolated from a tumor sample of patient Mel-16.
Figure 15:
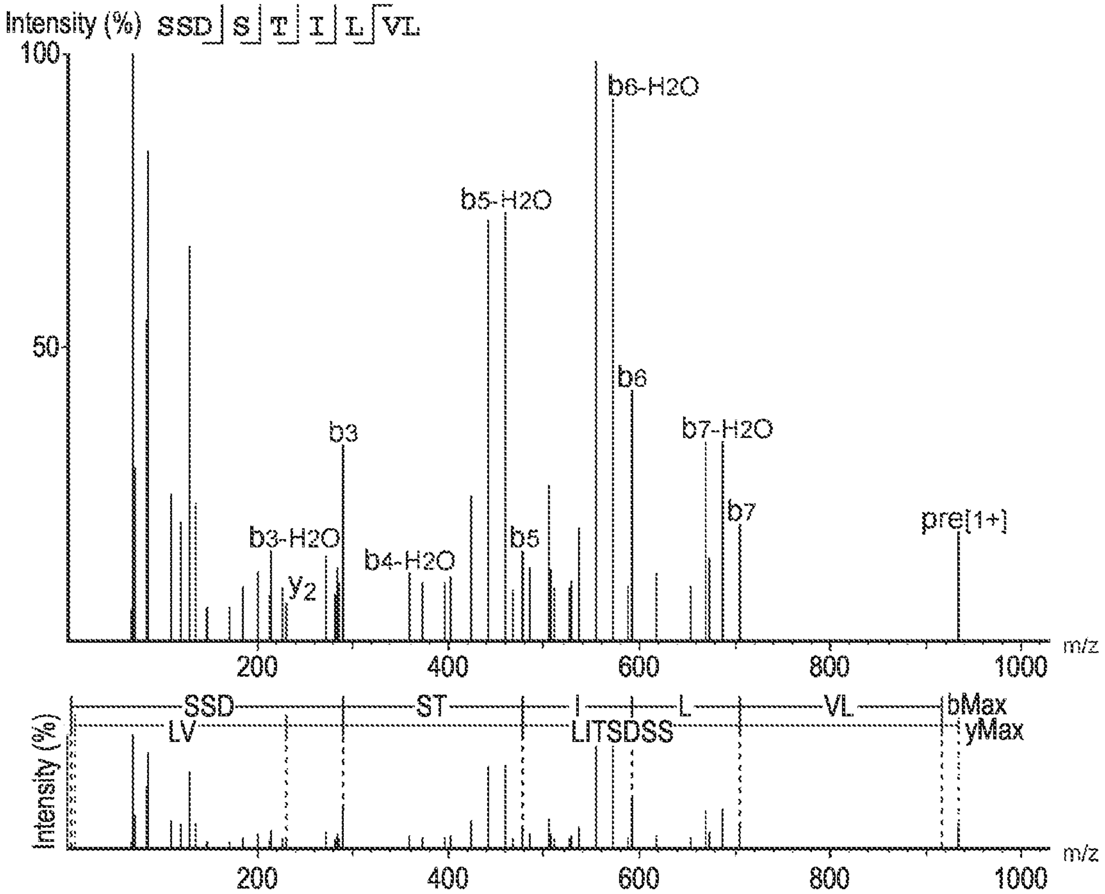
FIG. 15. Spectra for the peptide of SEQ ID NO. 26 isolated from a tumor sample of patient Mel-41.
Figure 16:
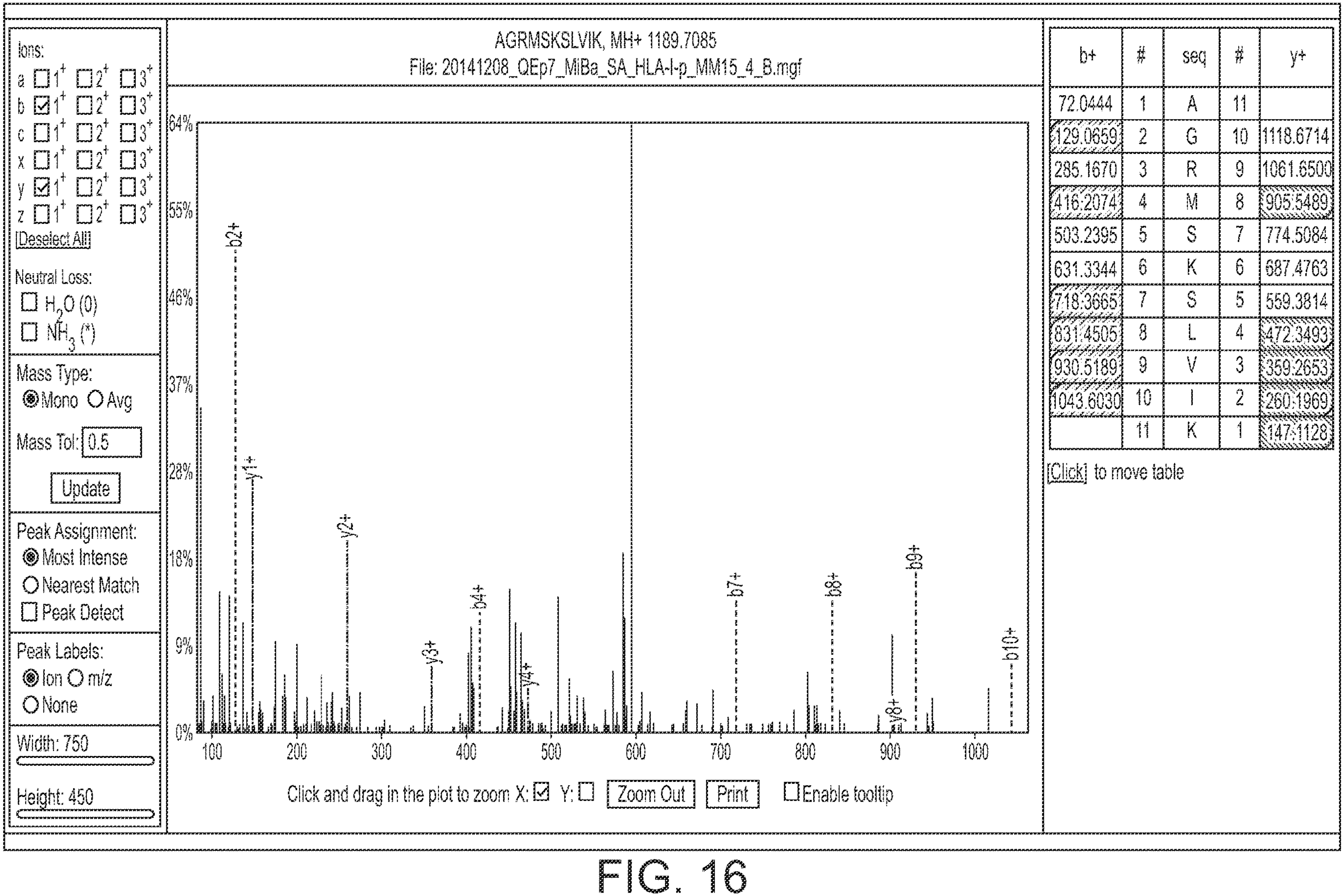
FIG. 16 shows a mass spectrometry spectrum of a peptide fragment from immunopeptidomic analysis of patient Mel-15 attributed to SEQ ID NO. 27.
Figure 17:
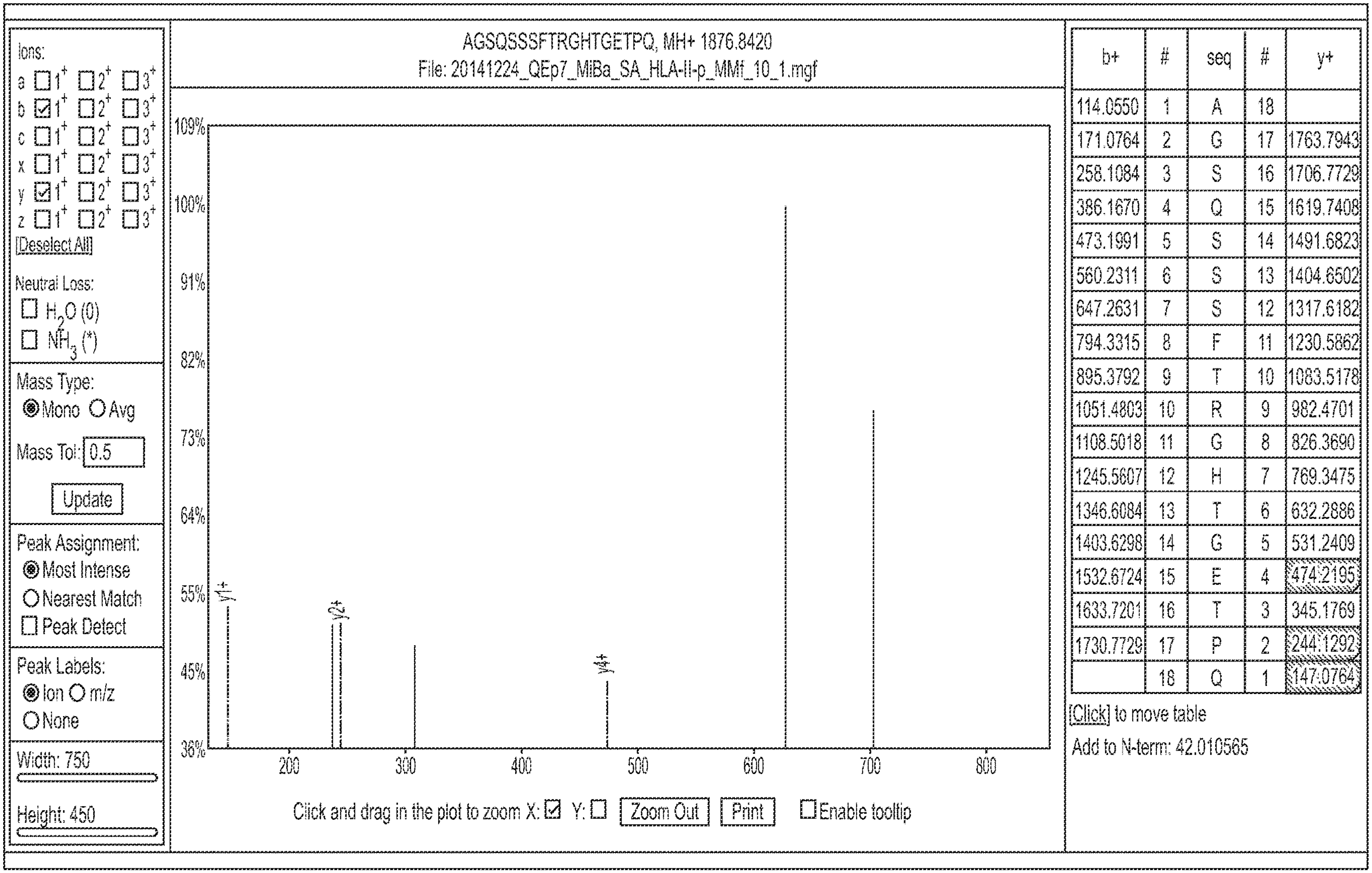
FIG. 17 shows a mass spectrometry spectrum of a peptide fragment from immunopeptidomic analysis of patient Mel-10 attributed to SEQ ID NO. 29.
Figure 18:
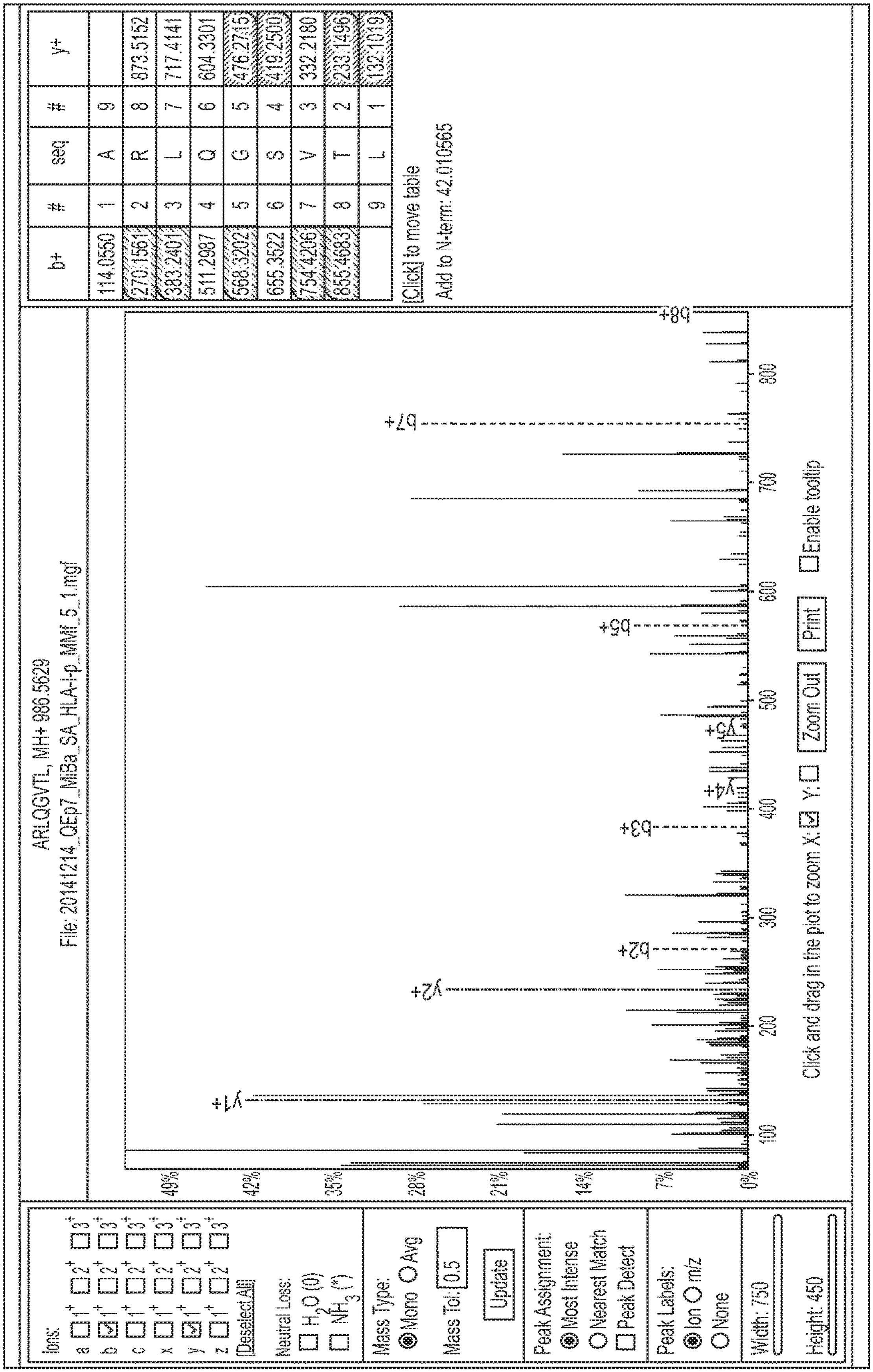
FIG. 18 shows a mass spectrometry spectrum of a peptide fragment from immunopeptidomic analysis of patient Mel-5 attributed to SEQ ID NO. 14.
Figure 19:
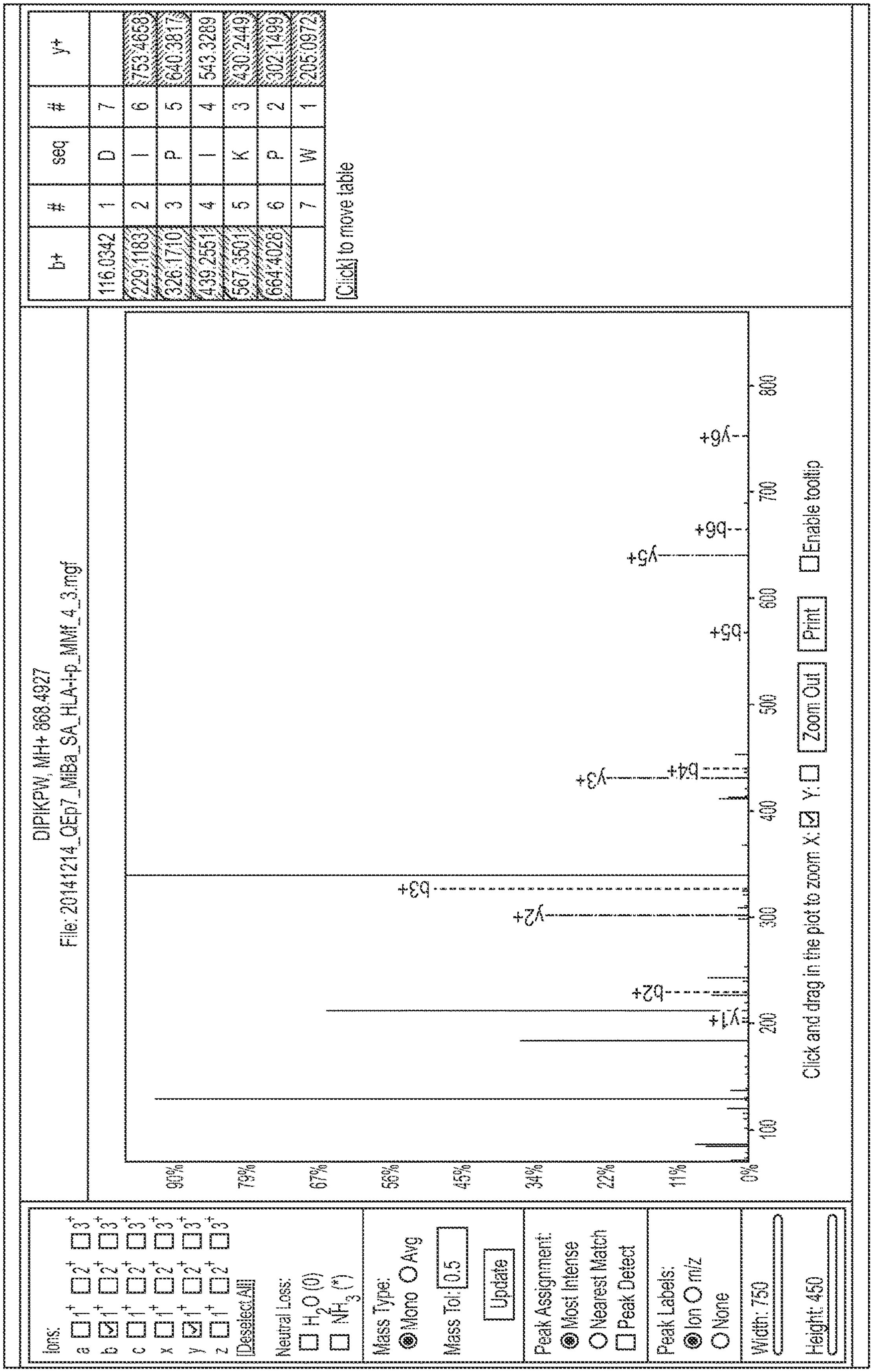
FIG. 19 shows a mass spectrometry spectrum of a peptide fragment from immunopeptidomic analysis of patient Mel-4 attributed to SEQ ID NO. 21.
Figure 20:
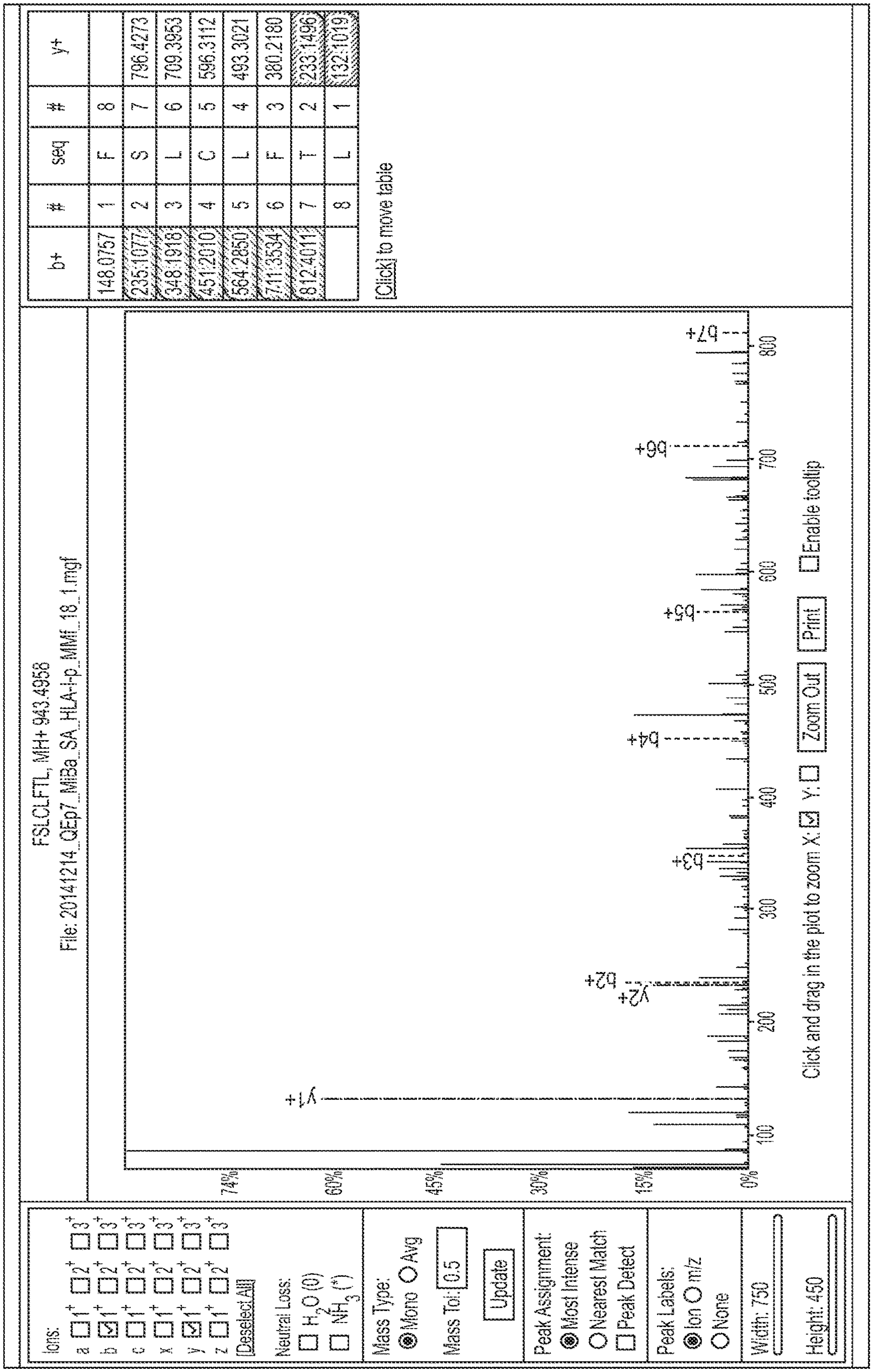
FIG. 20 shows a mass spectrometry spectrum of a peptide fragment from immunopeptidomic analysis of patient Mel-18 attributed to SEQ ID NO. 31.
Figure 21:
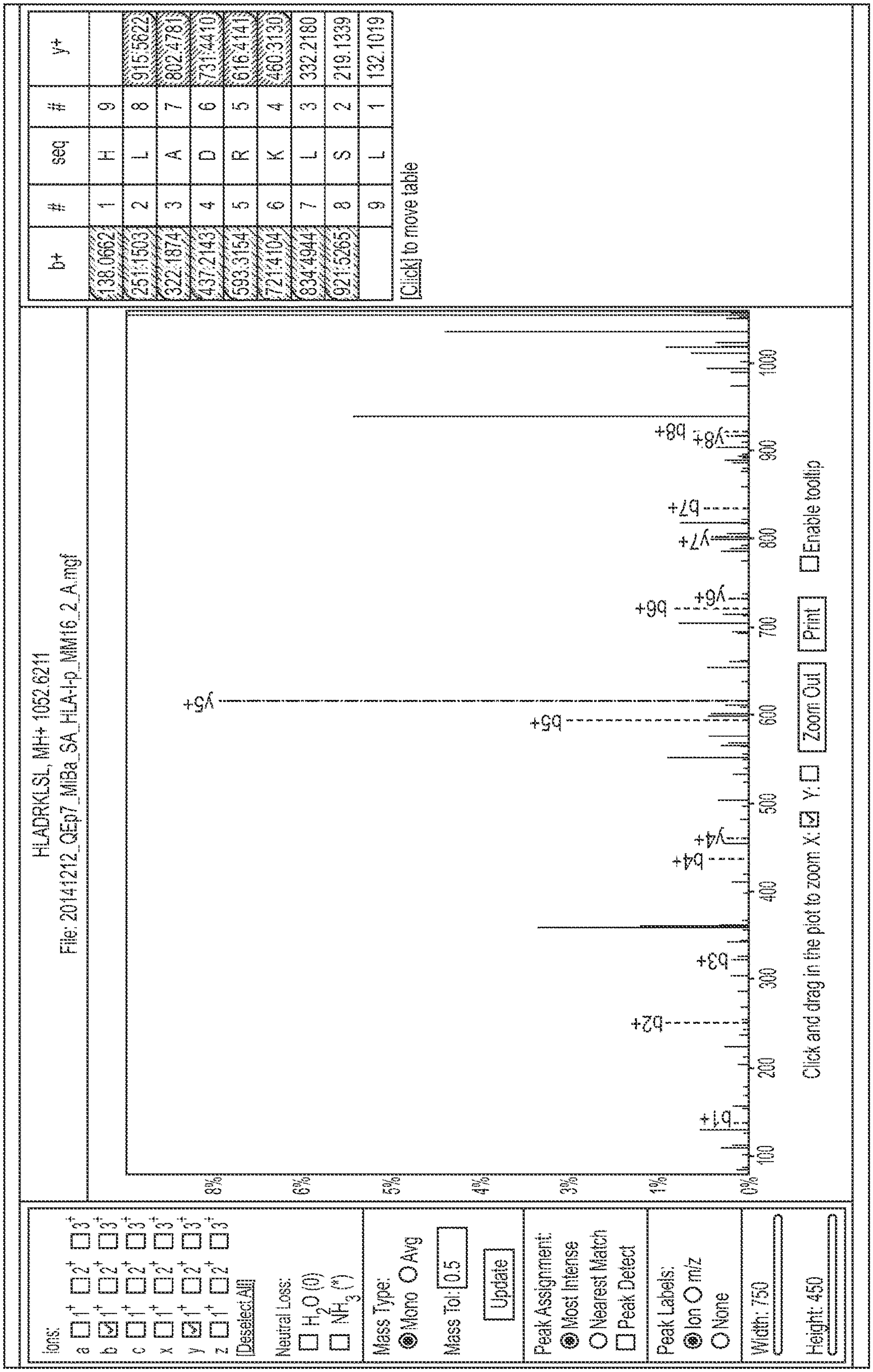
FIG. 21 shows a mass spectrometry spectrum of a peptide fragment from immunopeptidomic analysis of patient Mel-16 attributed to SEQ ID NO. 13.
Figure 22:
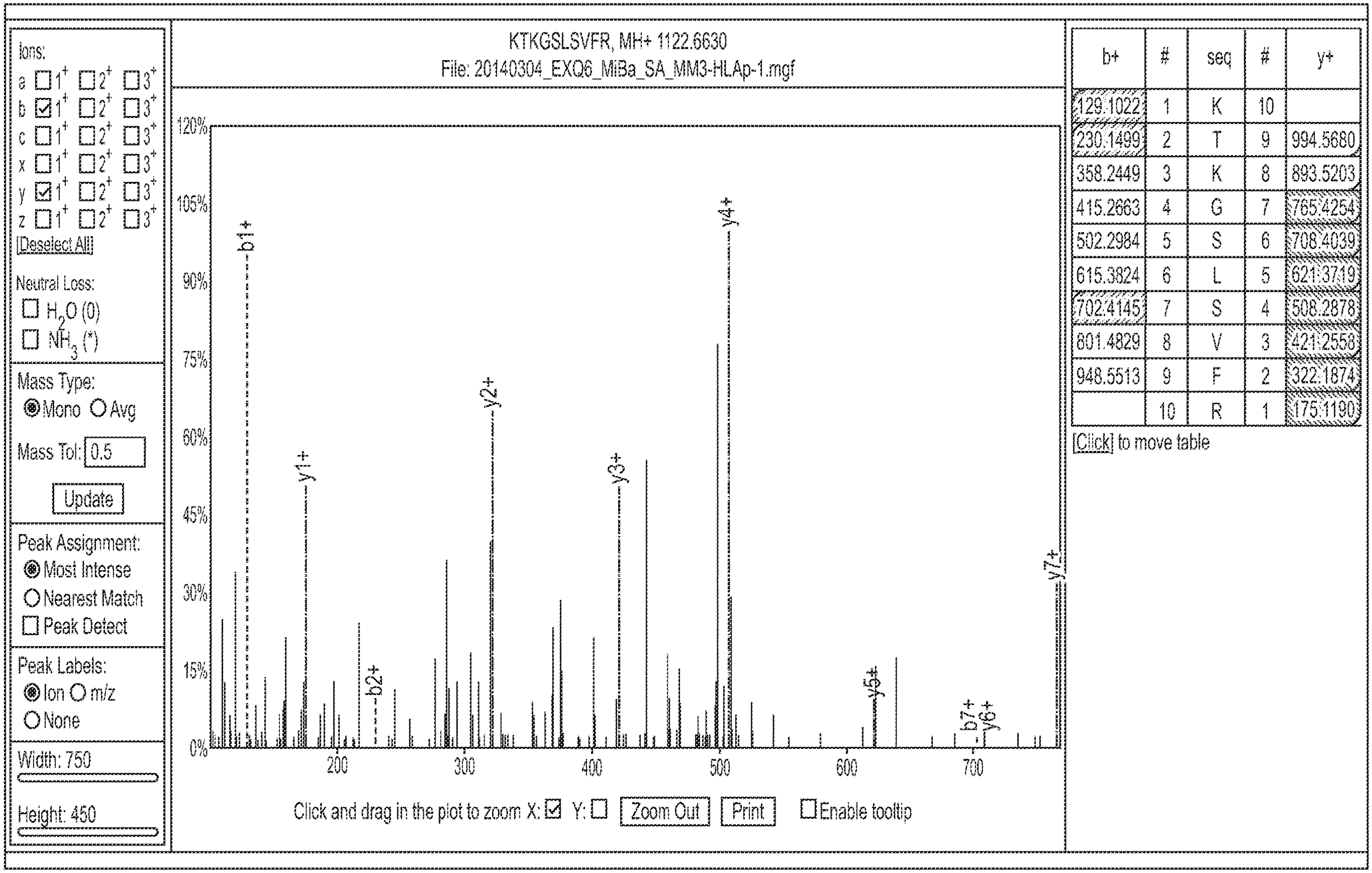
FIG. 22 shows a mass spectrometry spectrum of a peptide fragment from immunopeptidomic analysis of patient Mel-3 attributed to SEQ ID NO. 19.
Figure 23:
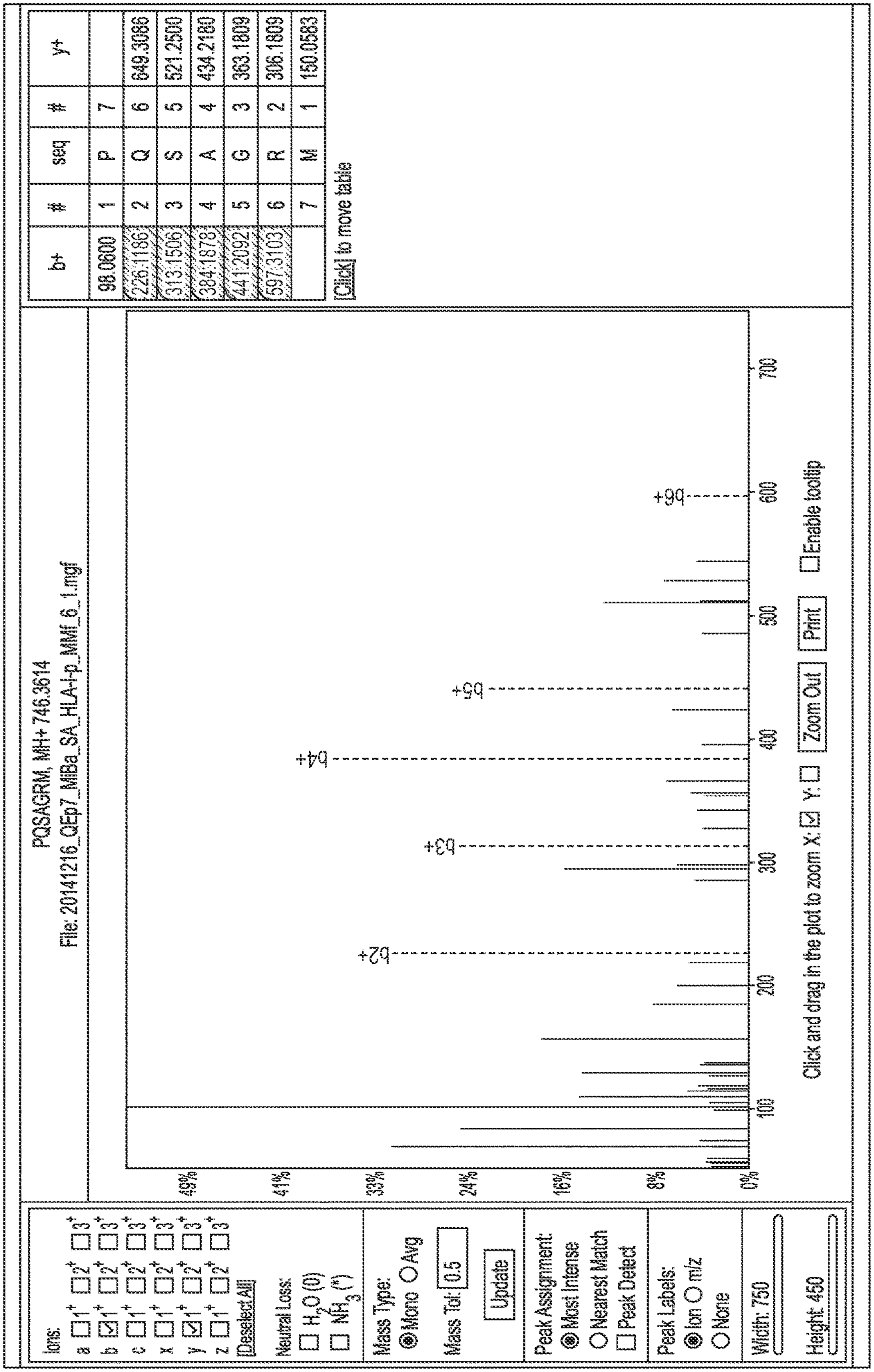
FIG. 23 shows a mass spectrometry spectrum of a peptide fragment from immunopeptidomic analysis of patient Mel-6 attributed to SEQ ID NO. 28.
Figure 24:
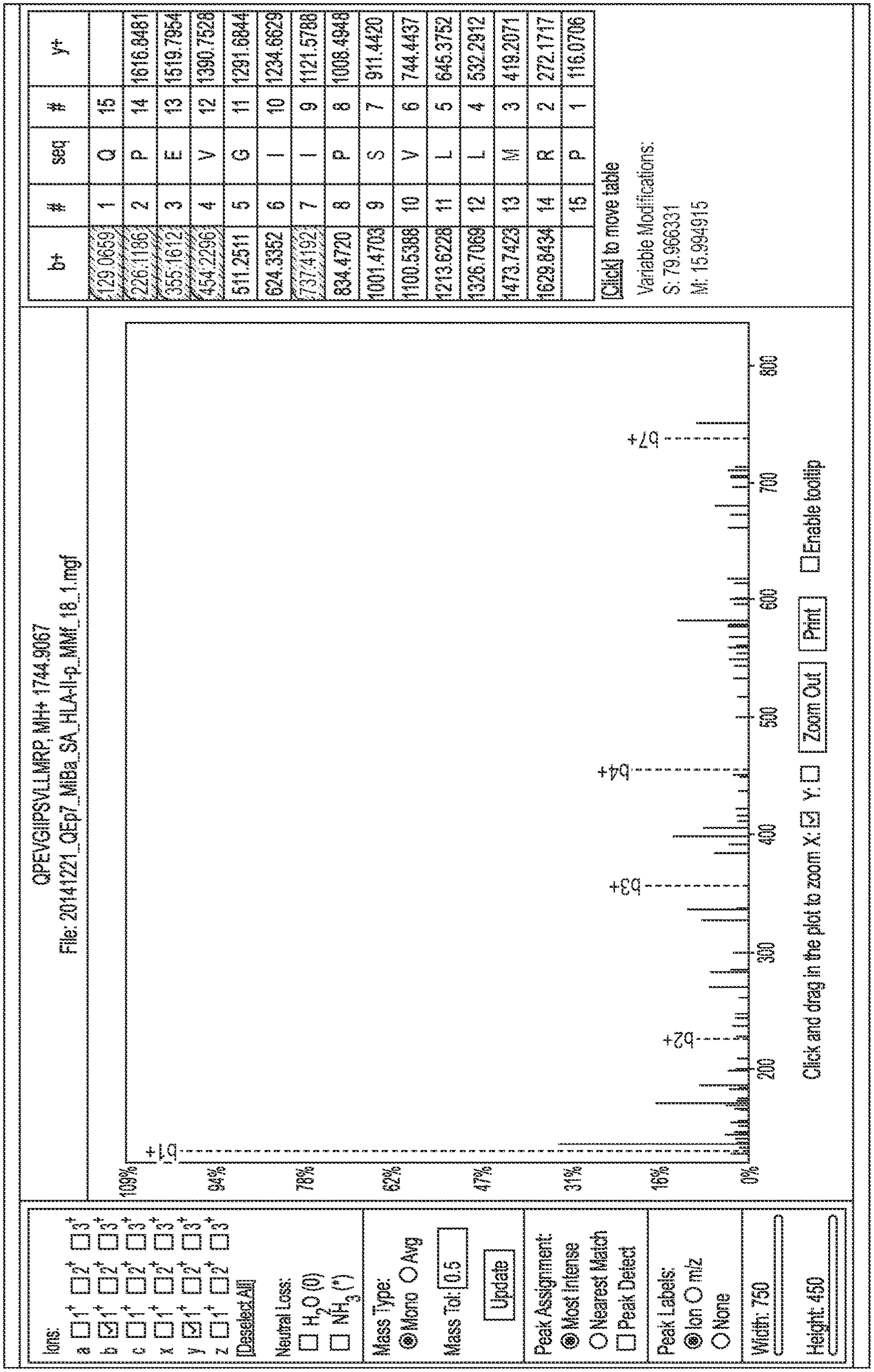
FIG. 24 shows a mass spectrometry spectrum of a peptide fragment from immunopeptidomic analysis of patient Mel-18 attributed to SEQ ID NO. 18.
Figure 25:
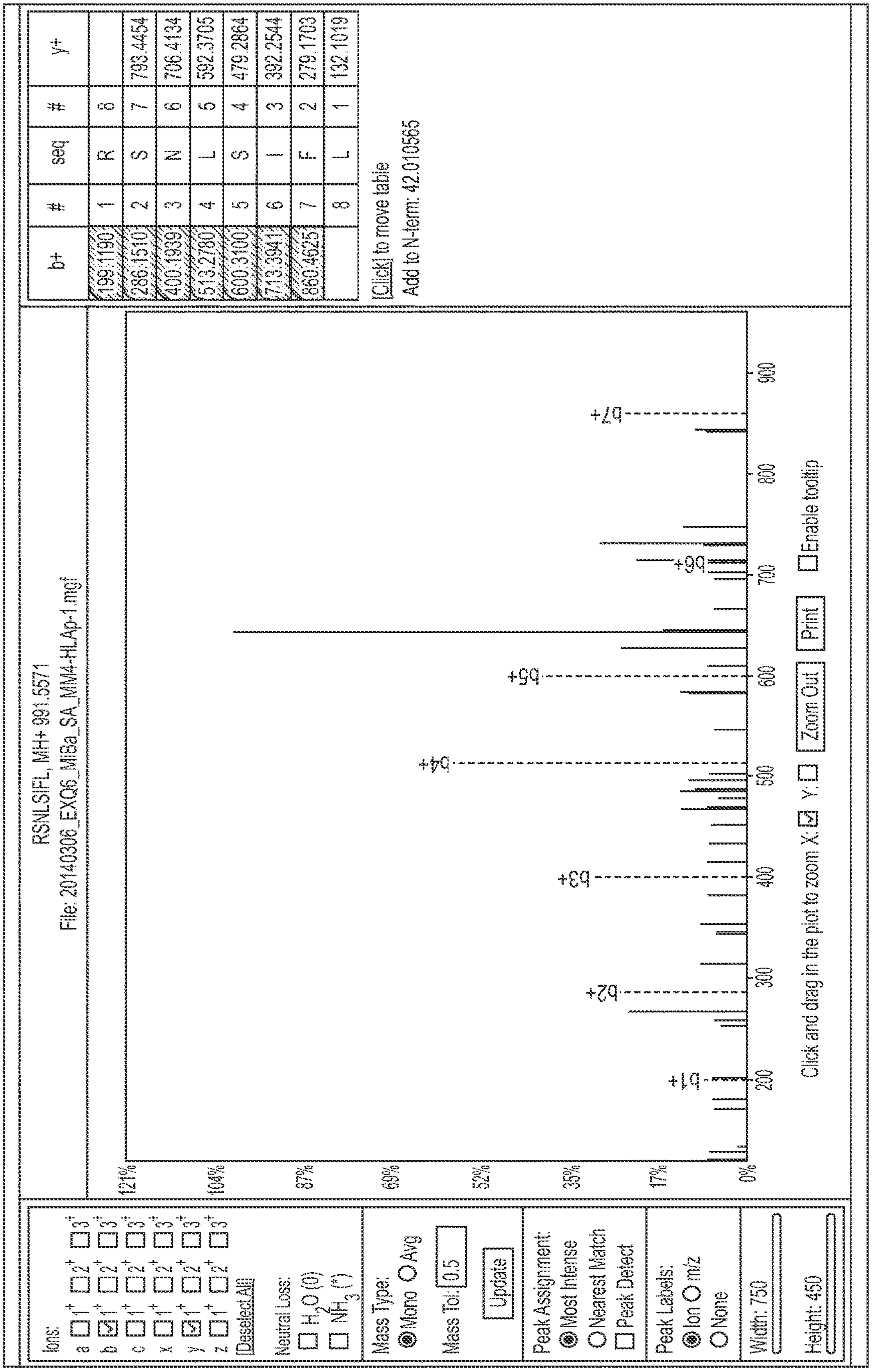
FIG. 25 shows a mass spectrometry spectrum of a peptide fragment from immunopeptidomic analysis of patient Mel-4 attributed to SEQ ID NO. 30.
Figure 26:
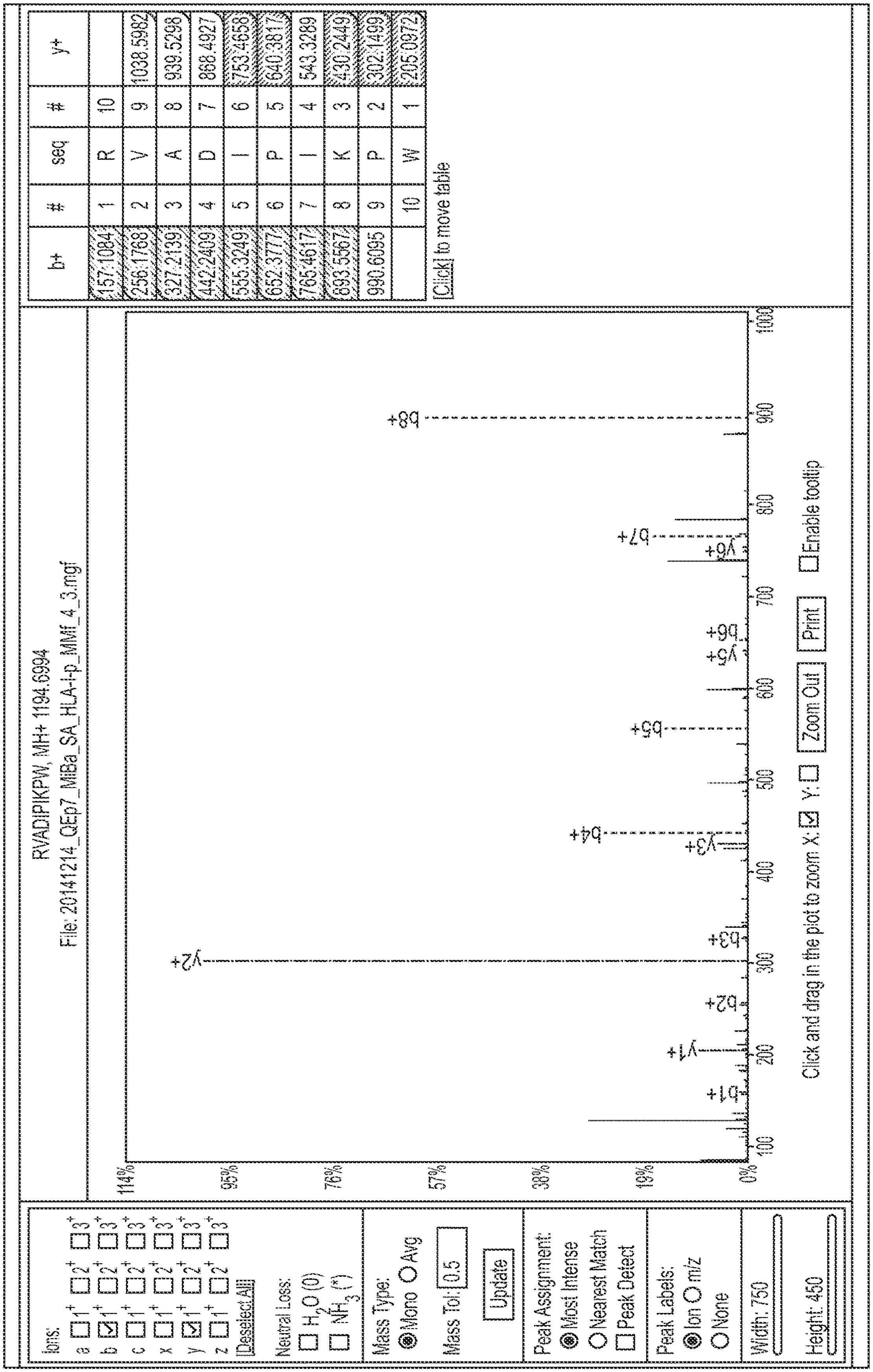
FIG. 26 shows a mass spectrometry spectrum of a peptide fragment from immunopeptidomic analysis of patient Mel-4 attributed to SEQ ID NO. 20.
Figure 27:
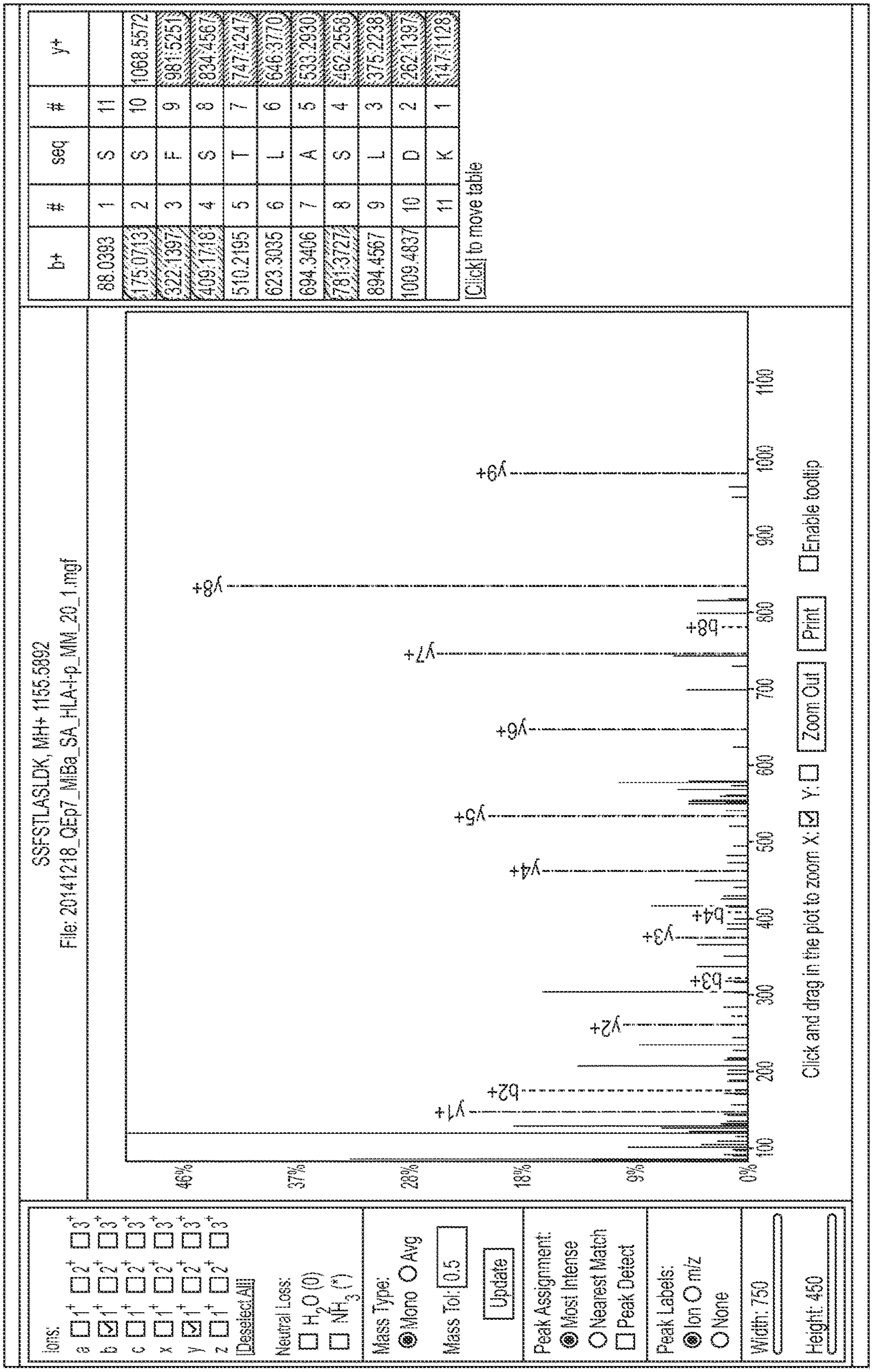
FIG. 27 shows a mass spectrometry spectrum of a peptide fragment from immunopeptidomic analysis of patient Mel-20 attributed to SEQ ID NO. 16.
Figure 28:
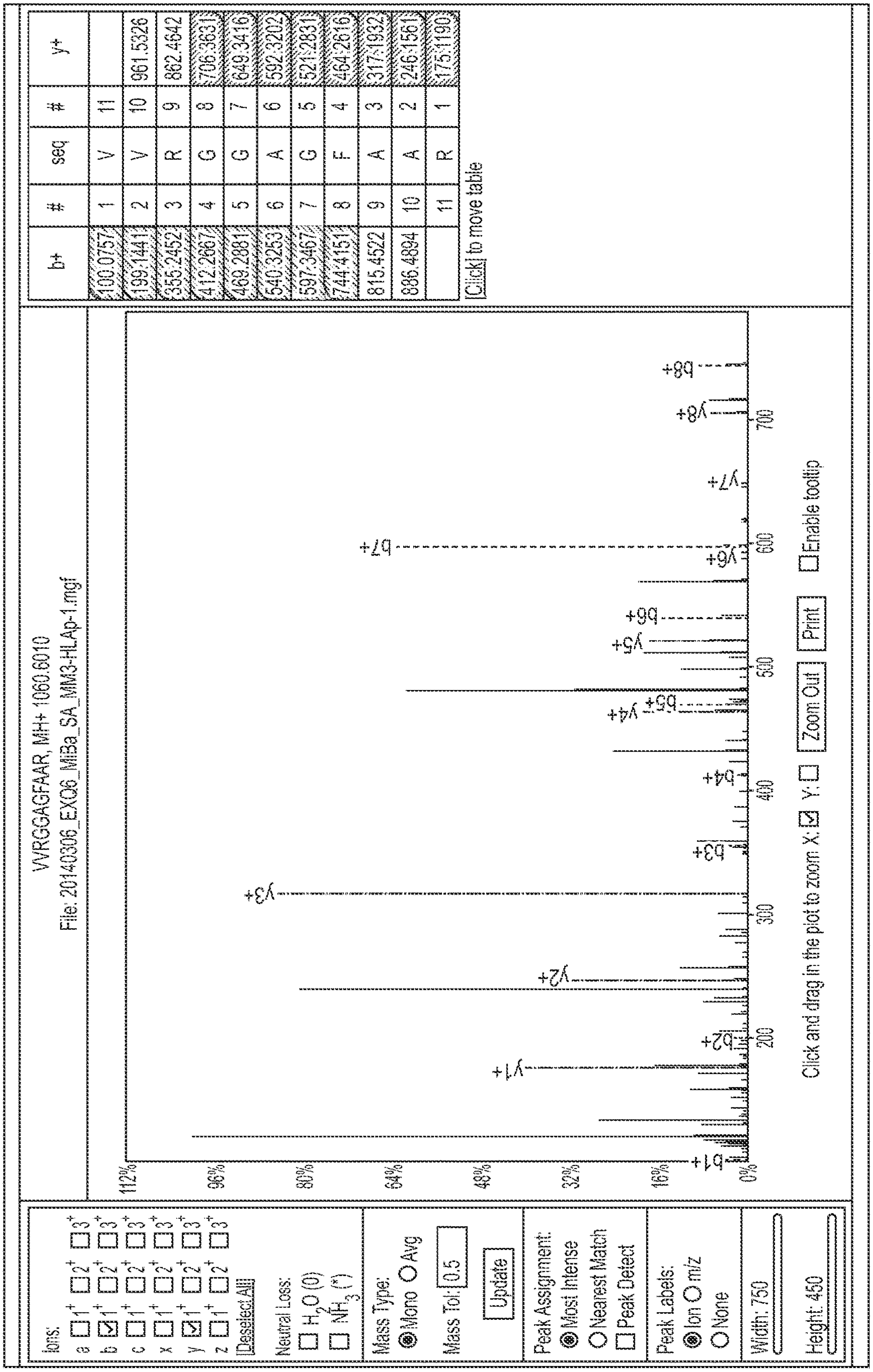
FIG. 28 shows a mass spectrometry spectrum of a peptide fragment from immunopeptidomic analysis of patient Mel-3 attributed to SEQ ID NO. 12.
Figure 29:
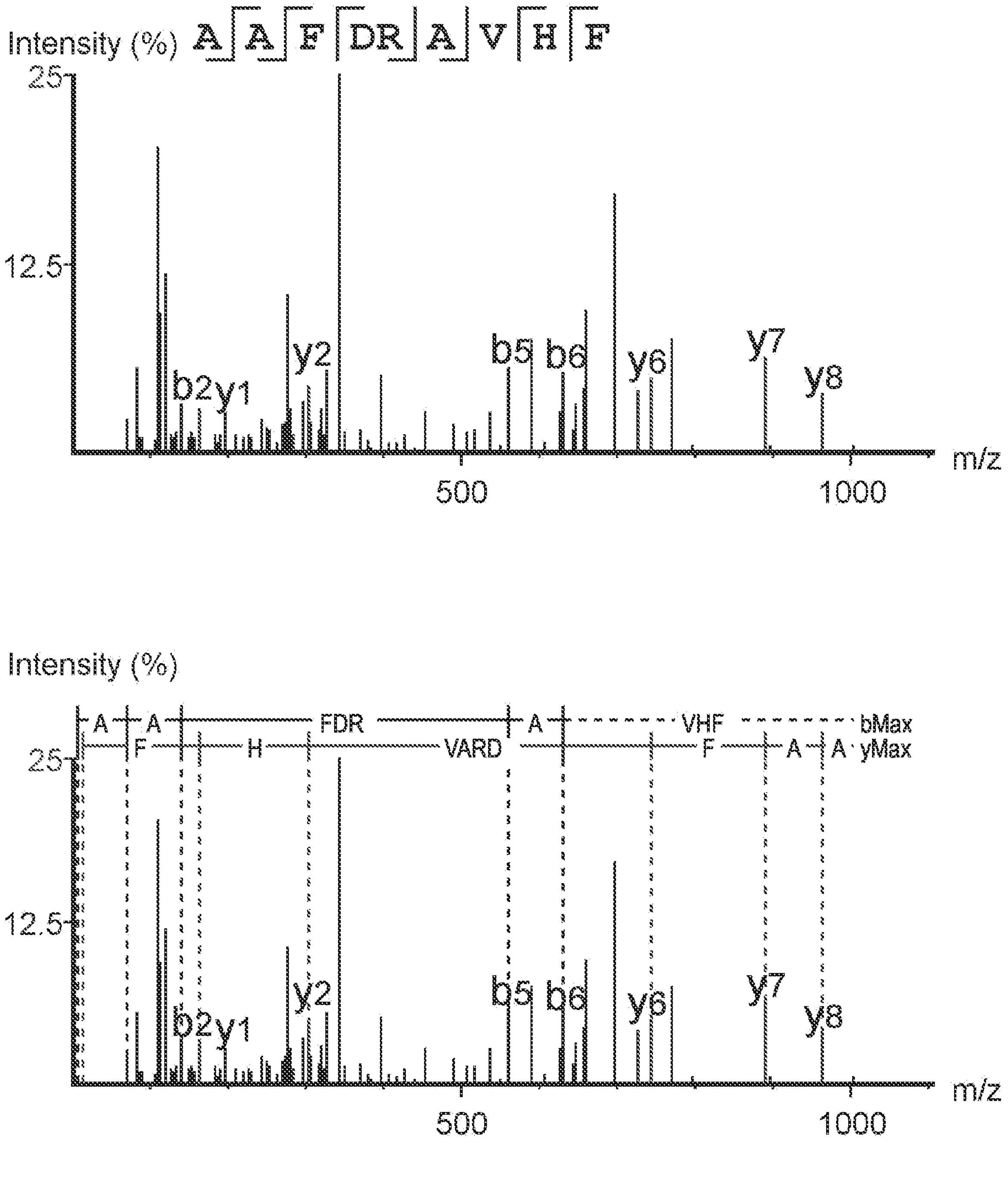

FIG. 29. Spectra for the peptide of SEQ ID NO. 51 isolated from a tumor sample of patient Mel-40.

Figure 30:
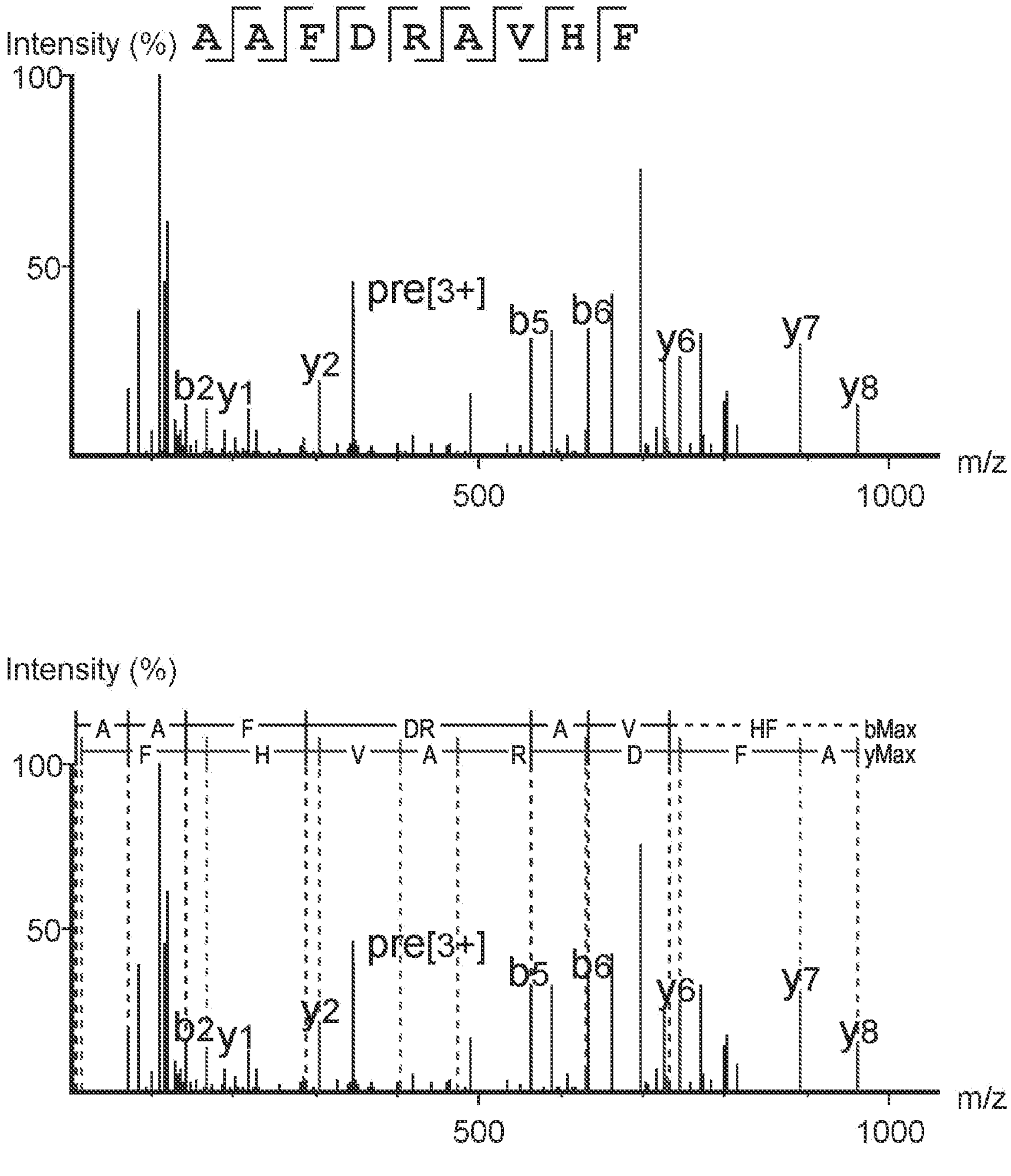

FIG. 30. Spectra for the peptide of SEQ ID NO. 51 isolated from a tumor sample of patient Mel-41.

FIG. 31. Spectra for the peptide of SEQ ID NO. 52 isolated from a tumor sample of patient Mel-27.

Figure 32:
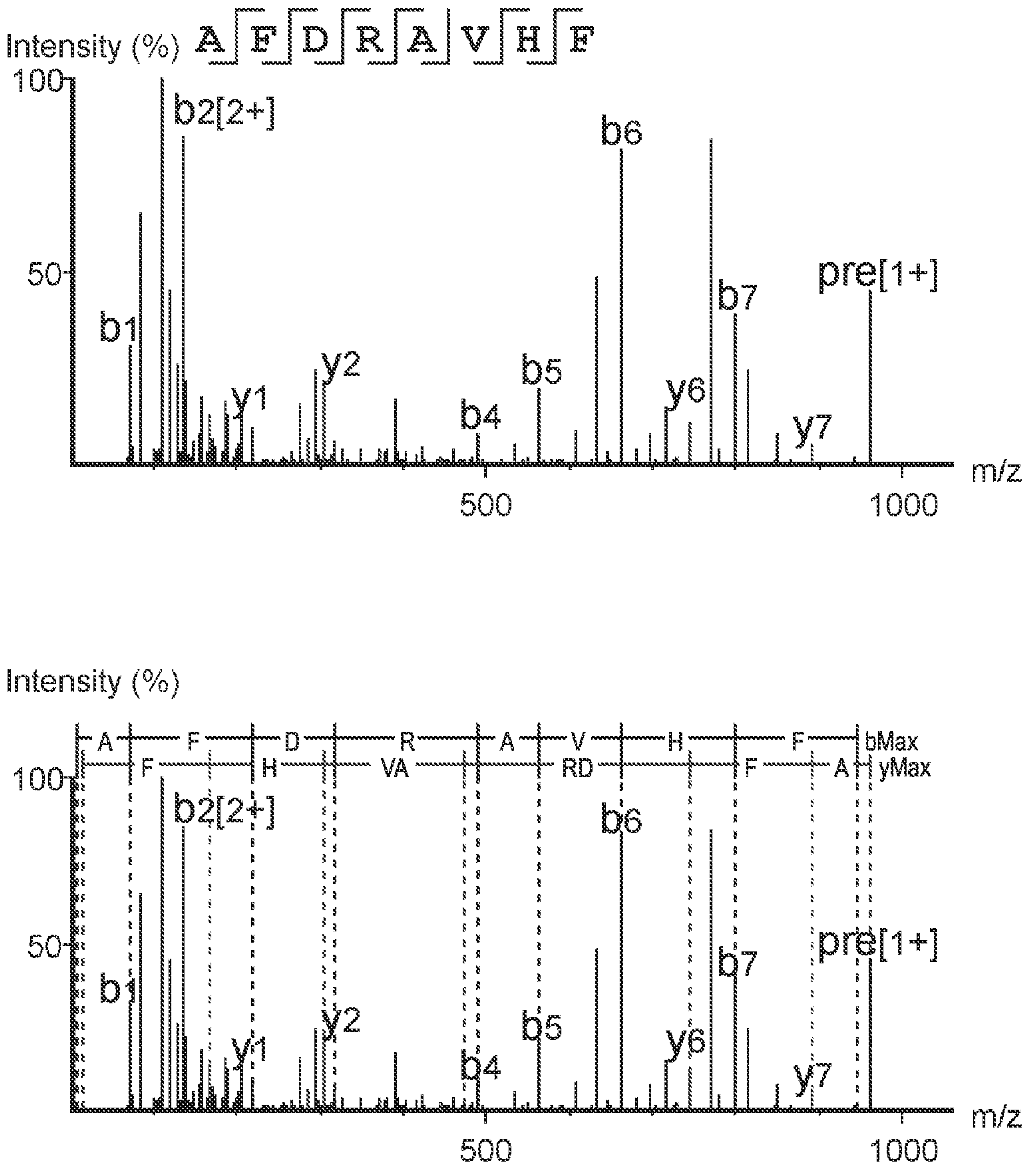

FIG. 32. Spectra for the peptide of SEQ ID NO. 52 isolated from a tumor sample of patient Mel-39.

Figure 33:
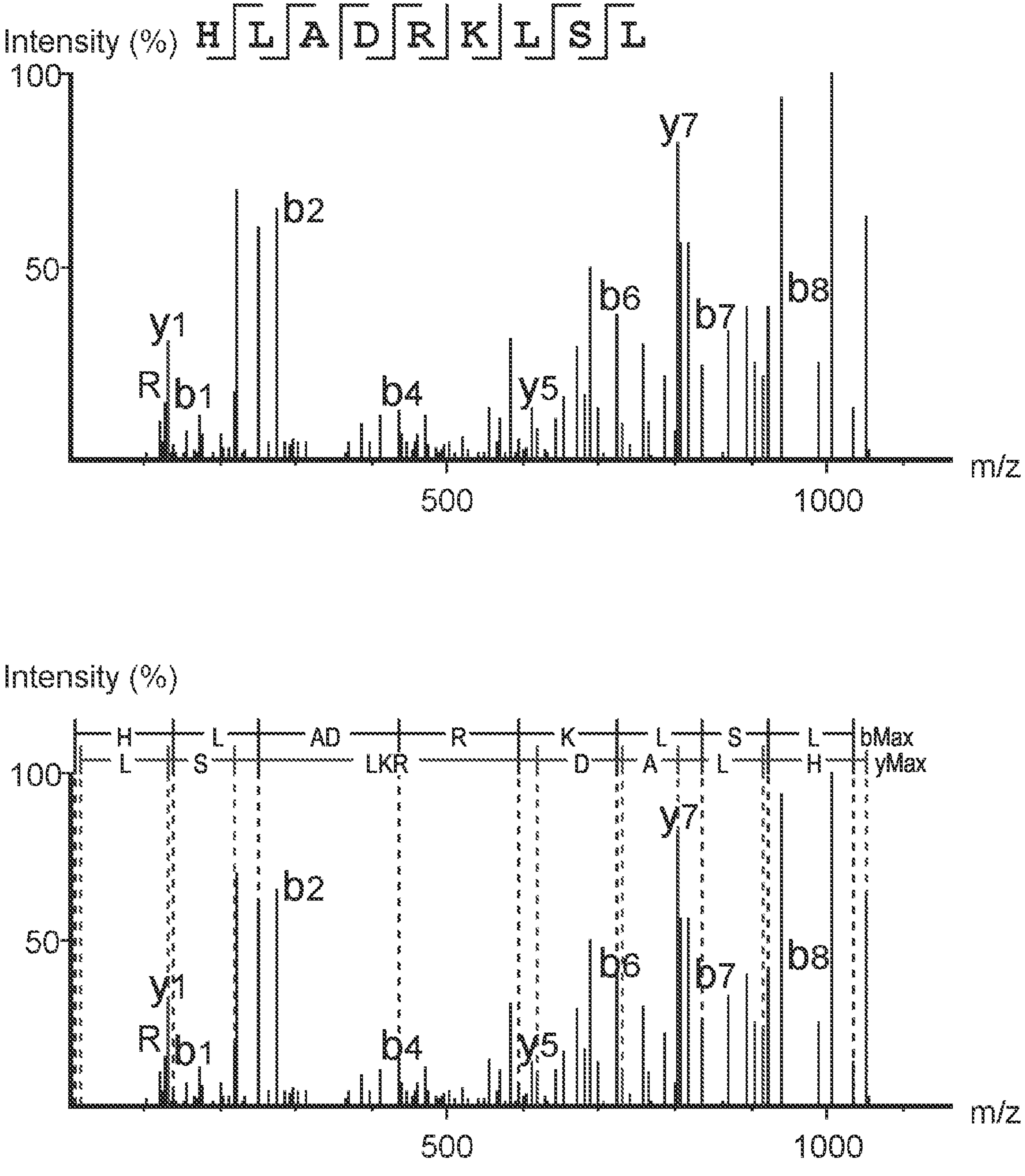

FIG. 33. Spectra for the peptide of SEQ ID NO. 13 isolated from a tumor sample of patient 2MT3.

Figure 34:
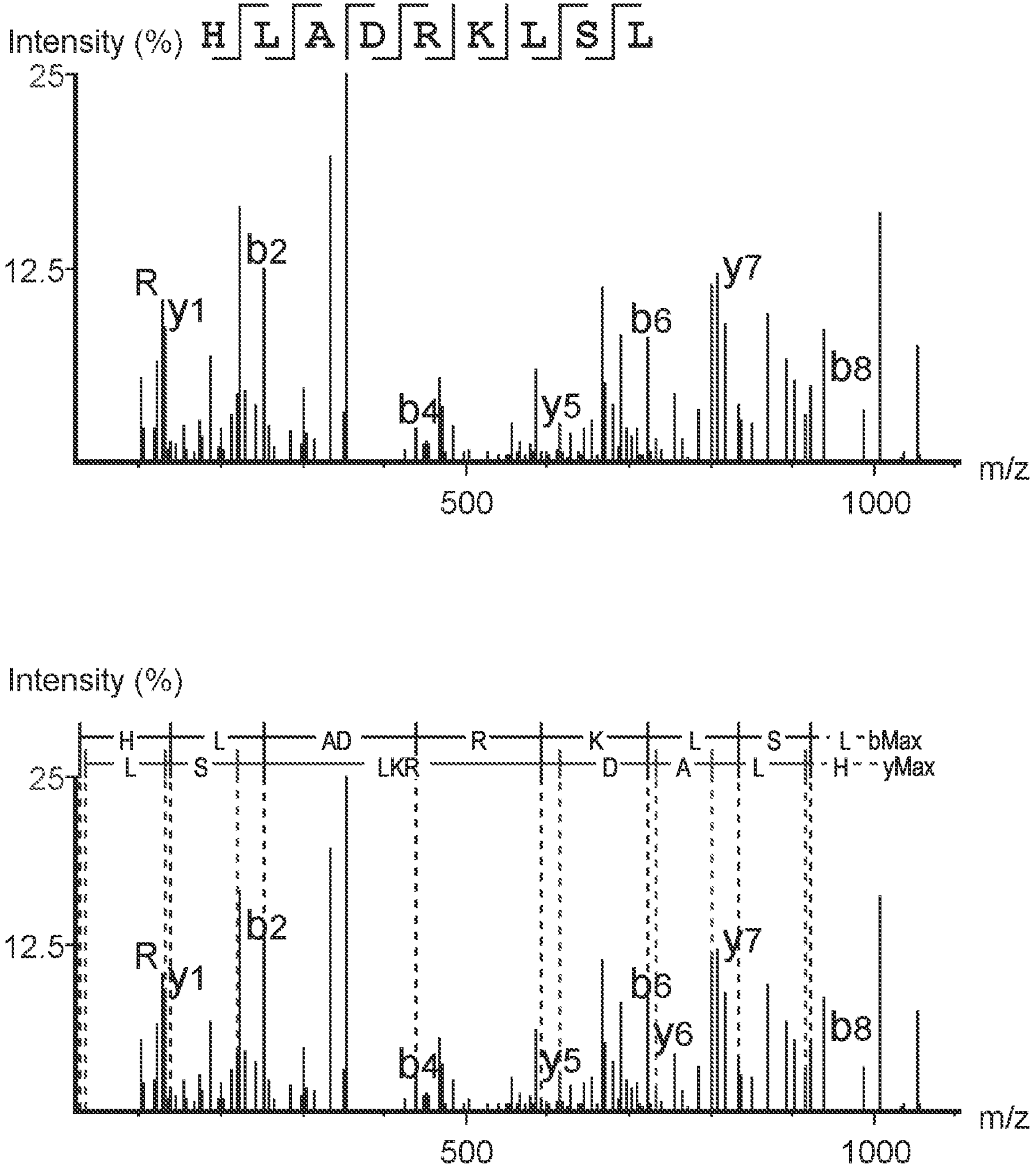

FIG. 34. Spectra for the peptide of SEQ ID NO. 13 isolated from a tumor sample of patient 2MT10.

Figure 35:
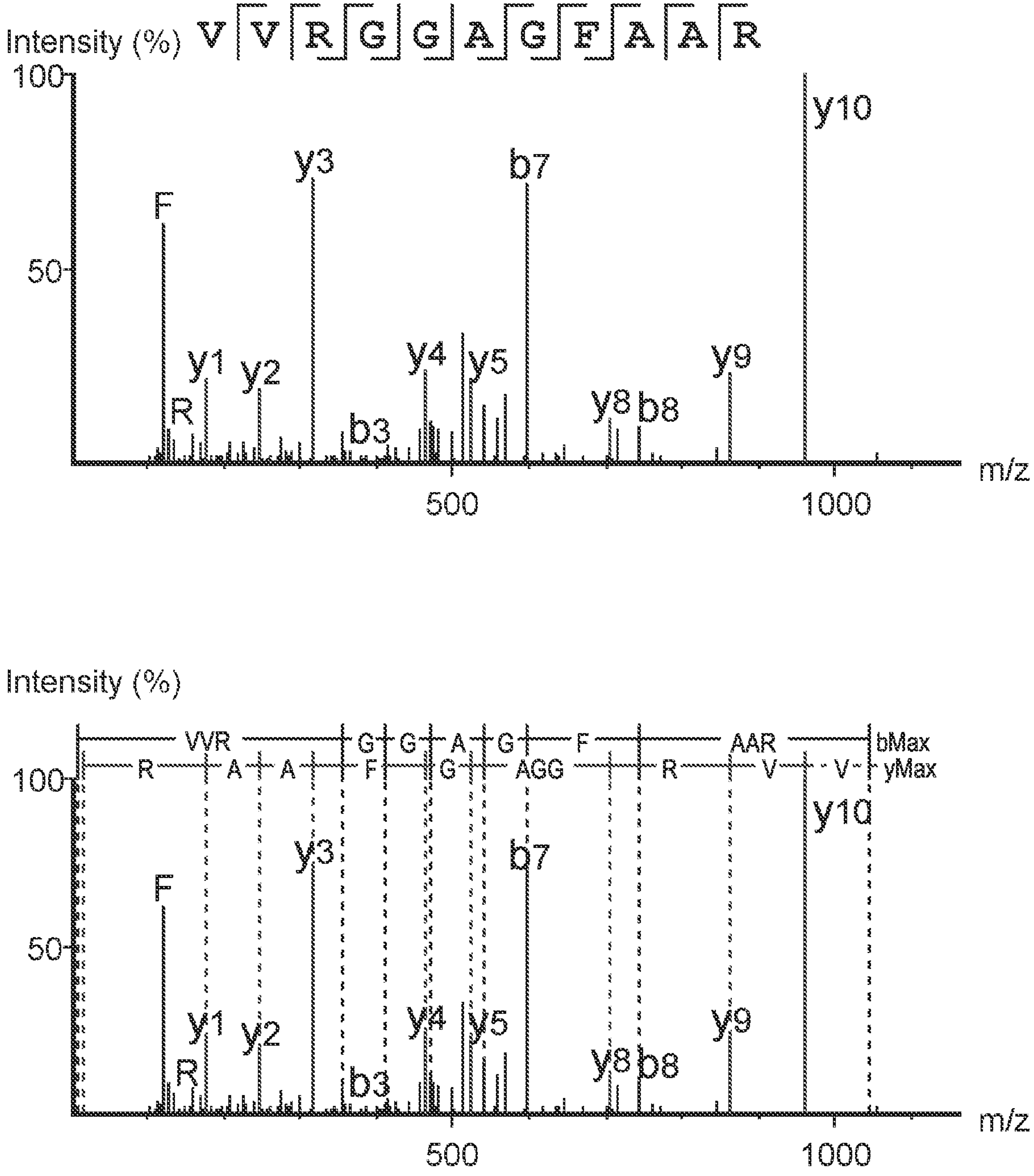

FIG. 35. Spectra for the peptide of SEQ ID NO. 12 isolated from a tumor sample of patient 2MT3.

Figure 36:
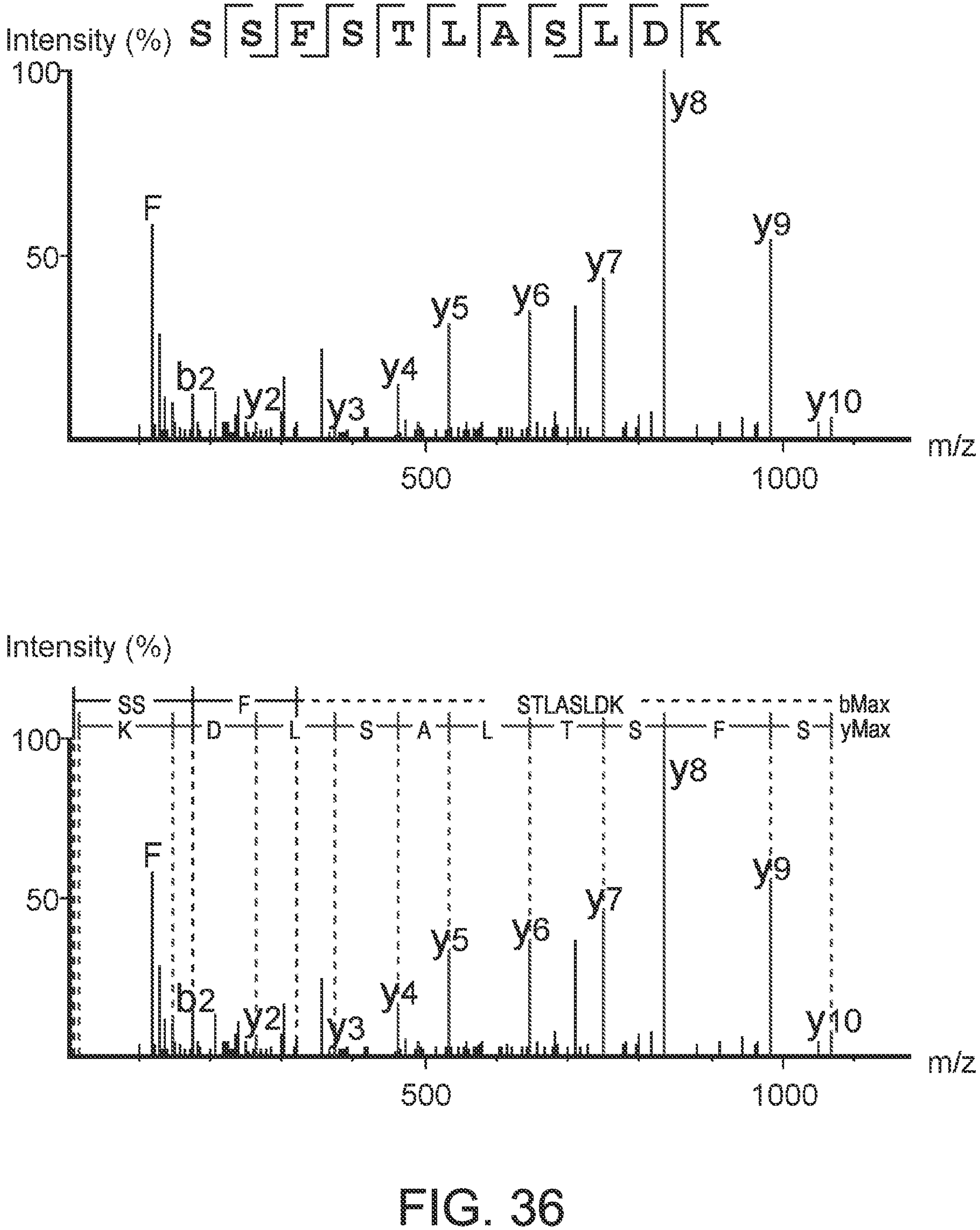

FIG. 36. Spectra for the peptide of SEQ ID NO. 16 isolated from a tumor sample of patient 2MT4.

Figure 37:
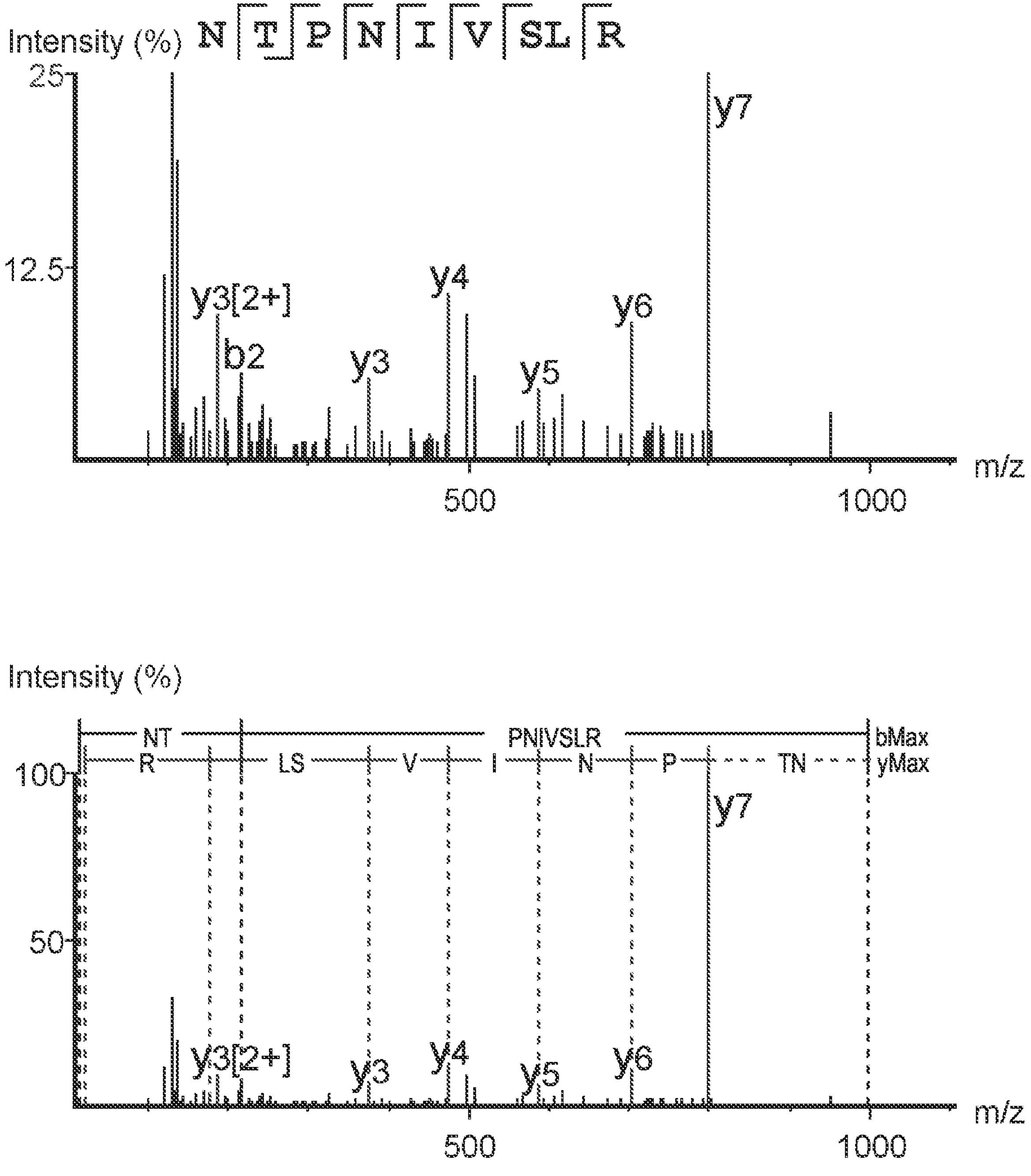

FIG. 37. Spectra for the peptide of SEQ ID NO. 17 isolated from a tumor sample of patient 2MT3.

Figure 38:
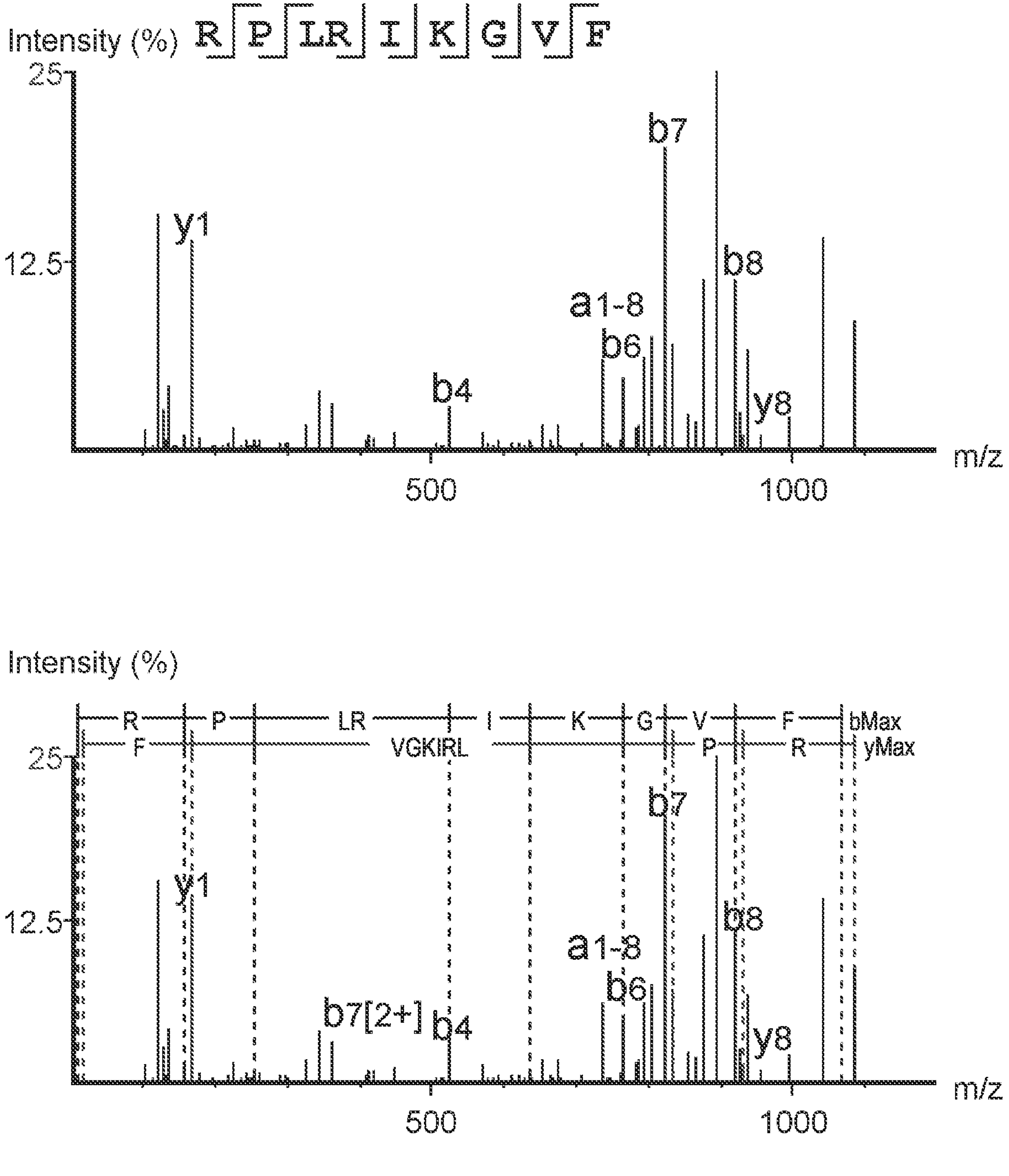

FIG. 38. Spectra for the peptide of SEQ ID NO. 53 isolated from a tumor sample of patient 1 MT1.

FIG. 39. Spectra for the peptide of SEQ ID NO. 51 isolated from a tumor sample of patient 2MT3.

Figure 40:
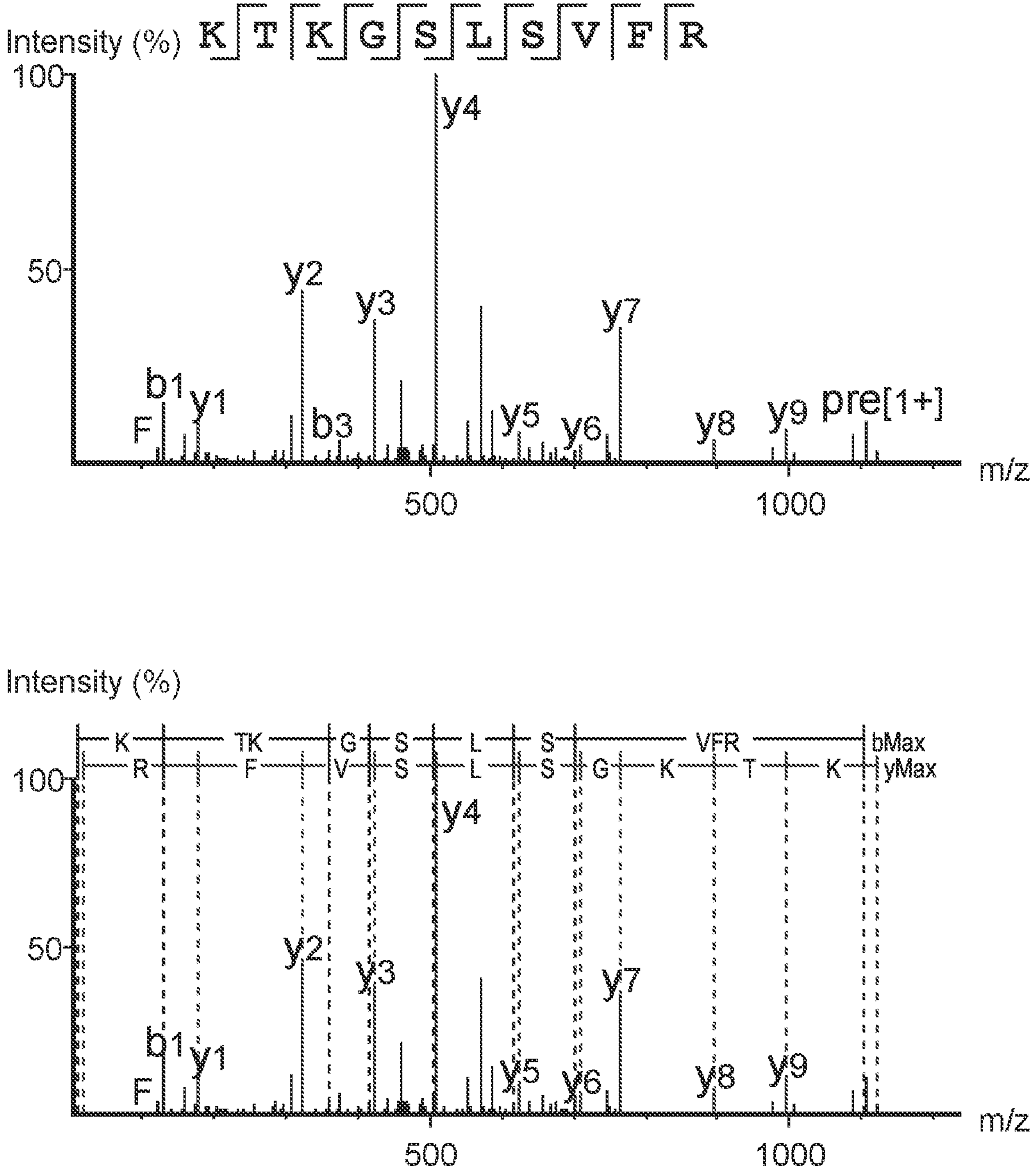

FIG. 40. Spectra for the peptide of SEQ ID NO. 19 isolated from a tumor sample of patient 2MT3.

Figure 41:
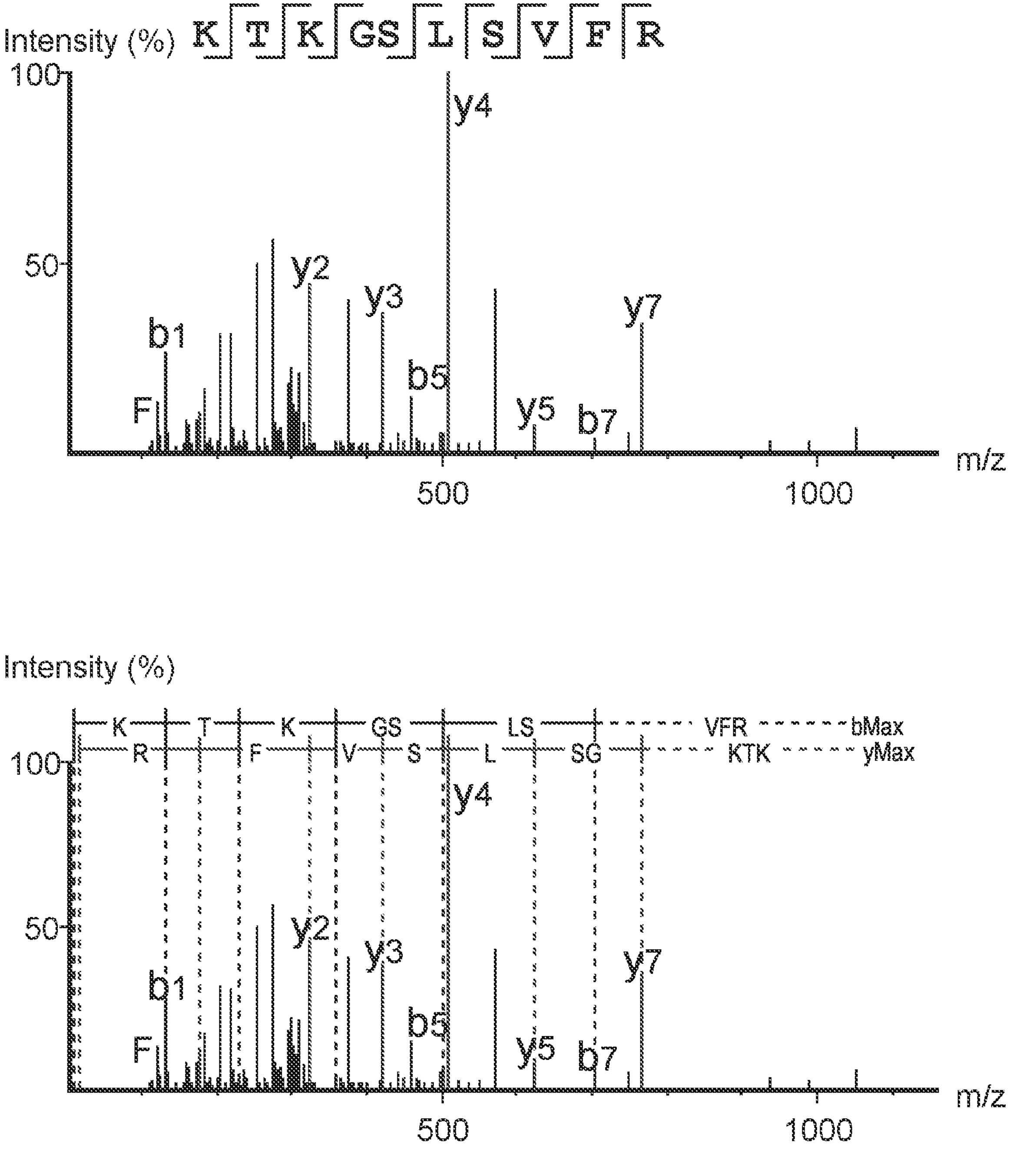

FIG. 41. Spectra for the peptide of SEQ ID NO. 19 isolated from a tumor sample of patient 2MT1.

FIG. 42. Spectra for the peptide of SEQ ID NO. 54 isolated from a tumor sample of patient 2MT12.

Each of FIGS. 43-50 shows an alignment of a native MS/MS spectrum of a peptide isolated from a patient tumor sample (upper) to the native spectrum of a synthetic peptide corresponding to the same sequence (lower).

Figure 43:
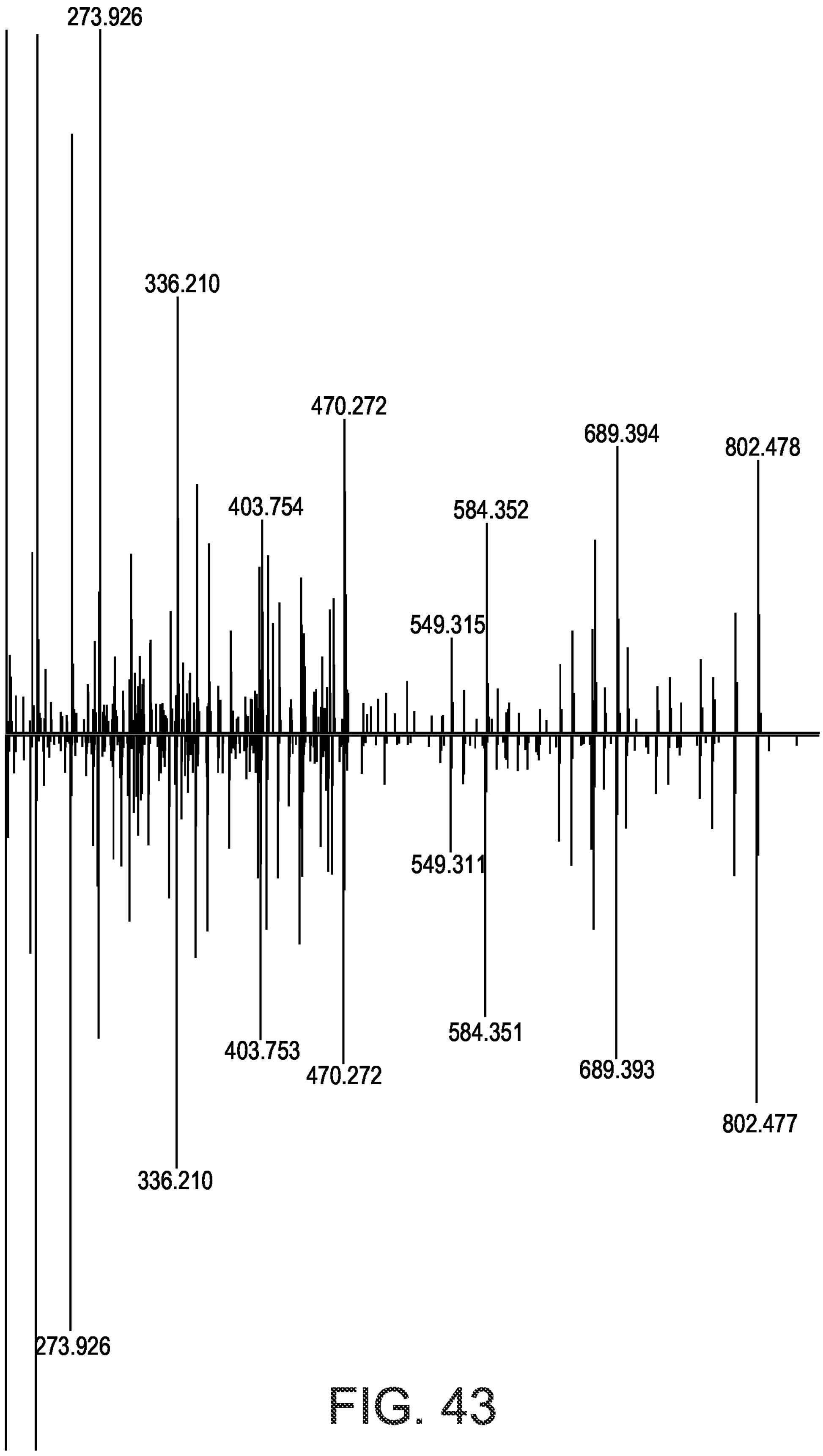

FIG. 43 shows a mass spectrometry spectrum of a peptide fragment from immunopeptidomic analysis of patient 2MT3 attributed to SEQ ID NO. 13.

Figure 44:
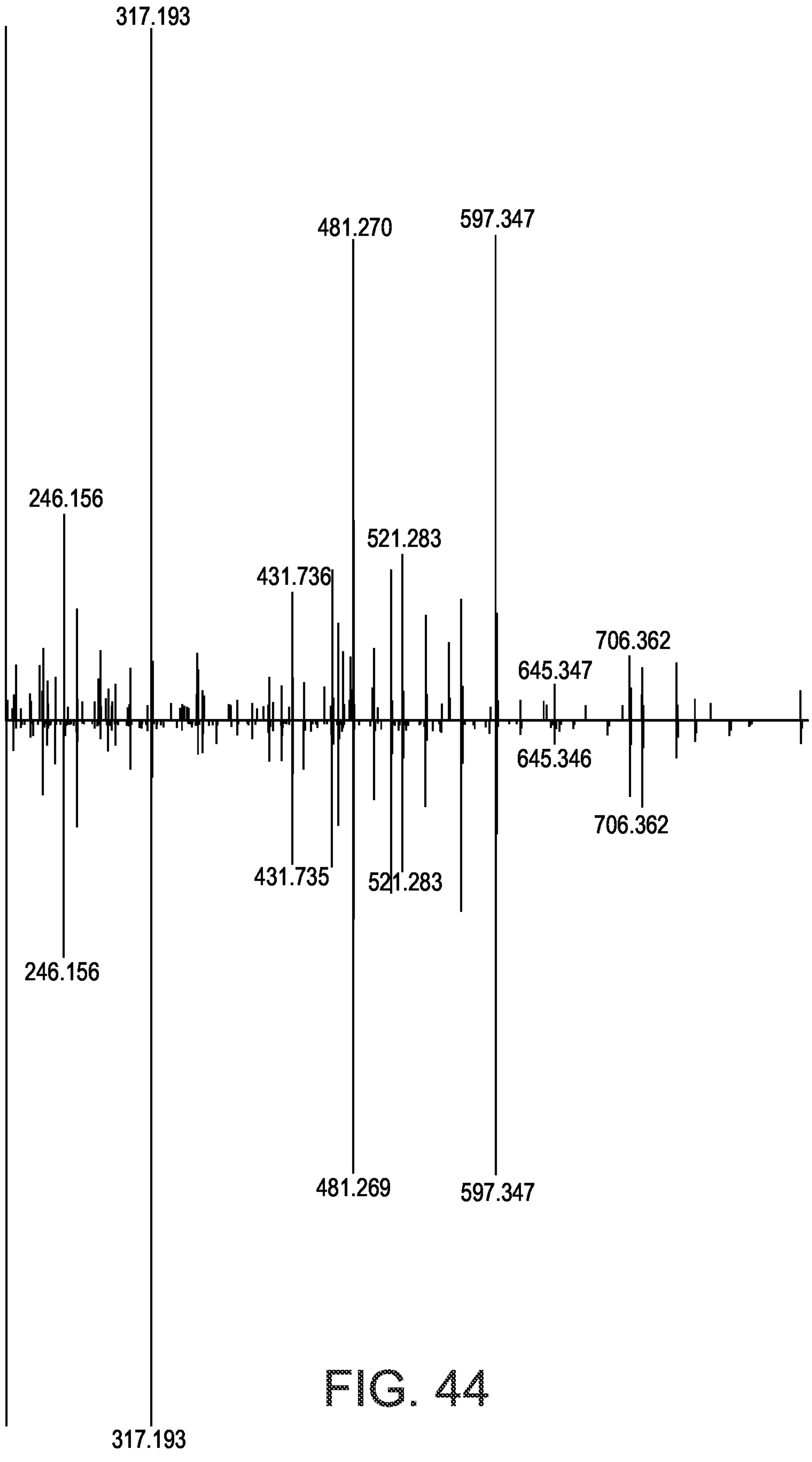

FIG. 44 shows a mass spectrometry spectrum of a peptide fragment from immunopeptidomic analysis of patient 2MT3 attributed to SEQ ID NO. 12.

Figure 45:
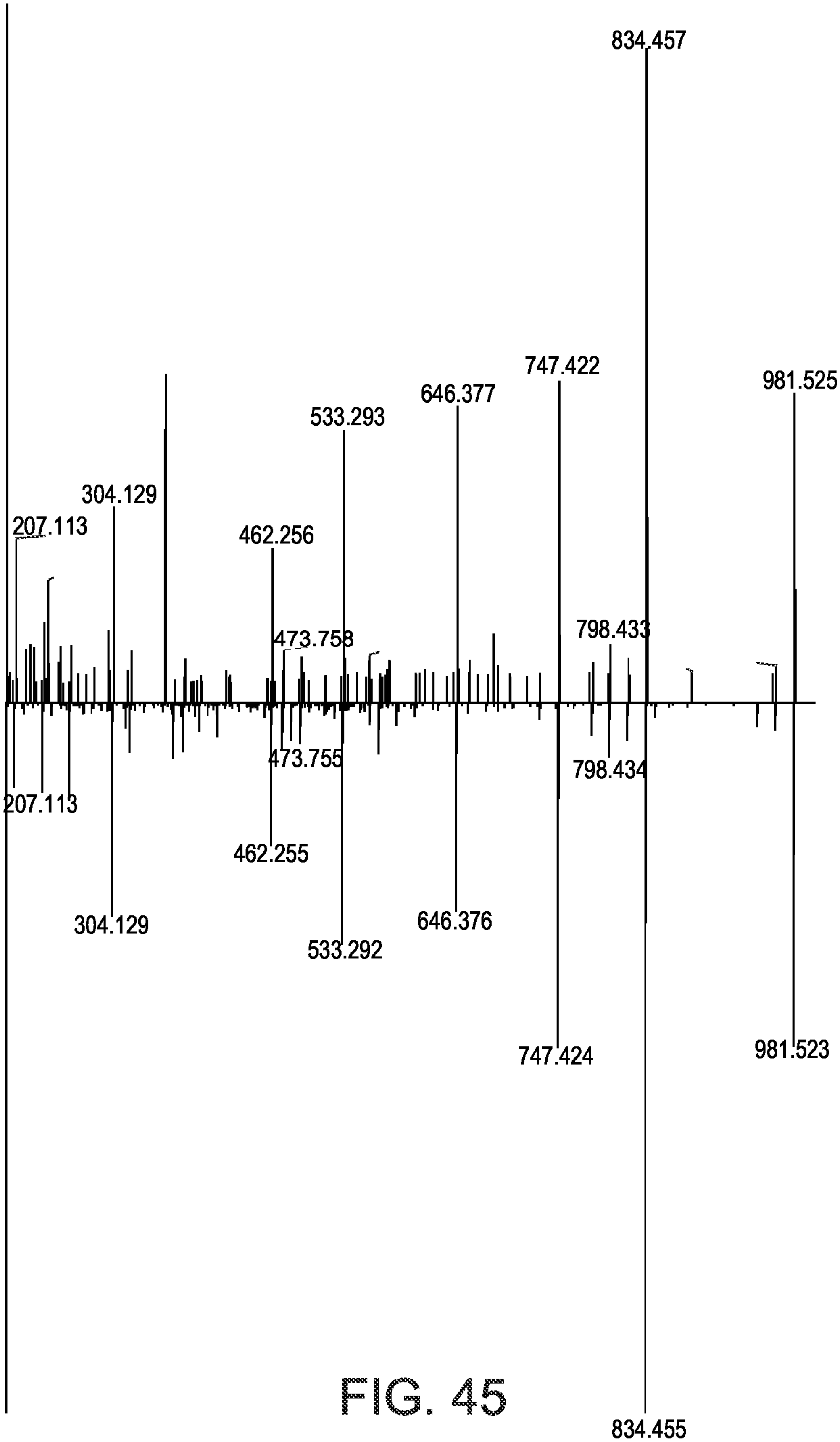

FIG. 45 shows a mass spectrometry spectrum of a peptide fragment from immunopeptidomic analysis of patient 2MT4 attributed to SEQ ID NO. 16.

Figure 46:
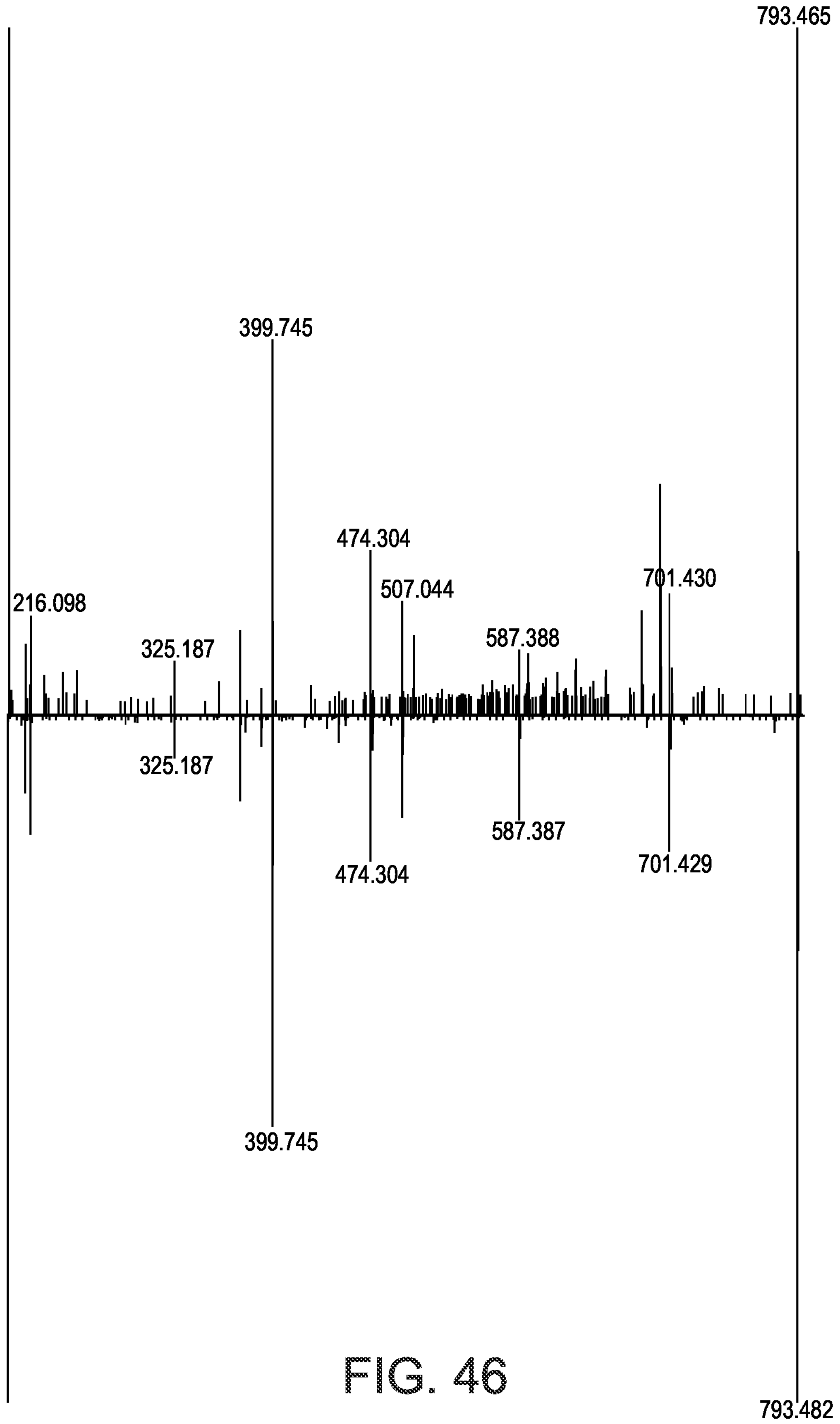

FIG. 46 shows a mass spectrometry spectrum of a peptide fragment from immunopeptidomic analysis of patient 2MT3 attributed to SEQ ID NO. 17.

Figure 47:
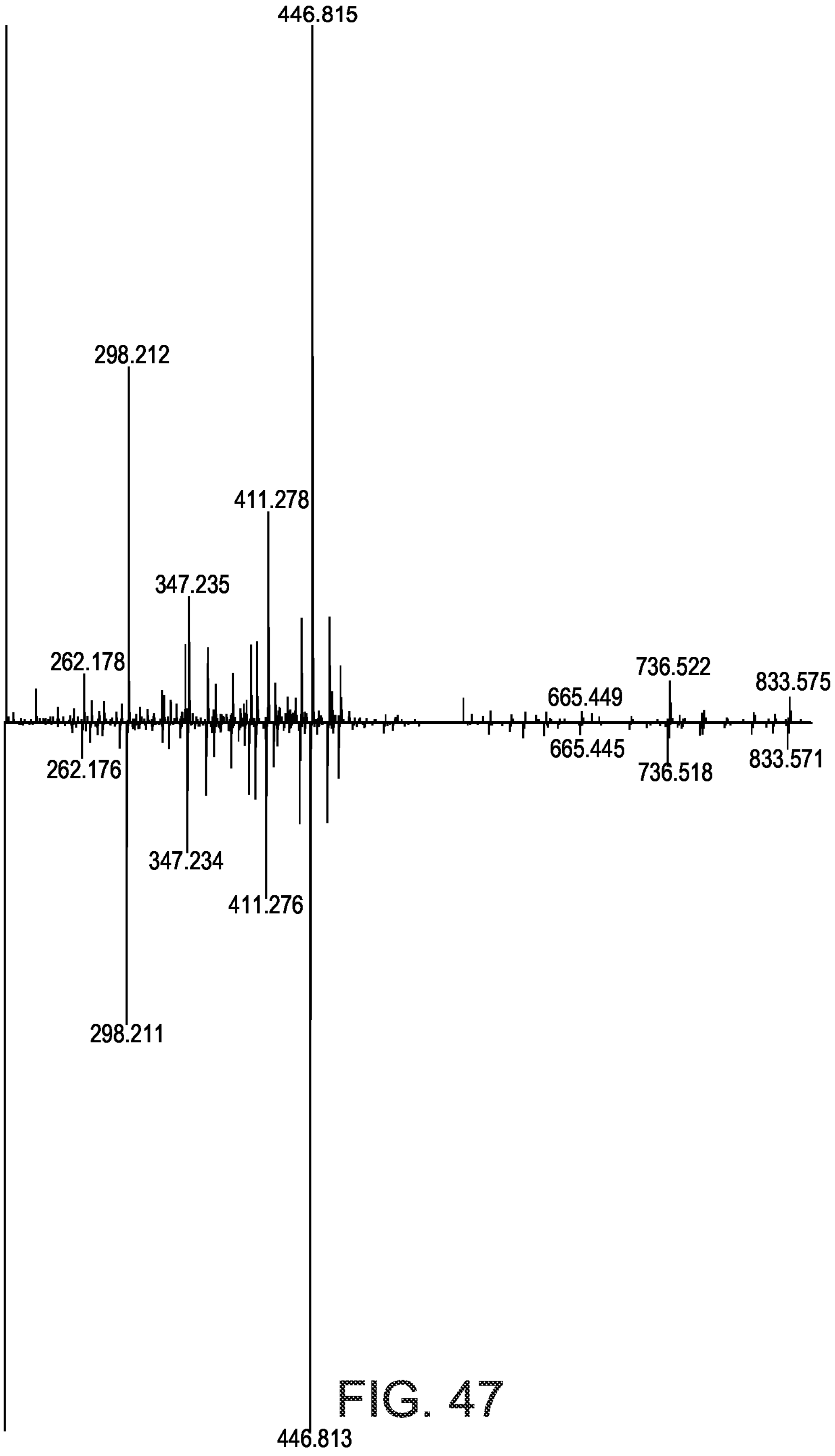

FIG. 47 shows a mass spectrometry spectrum of a peptide fragment from immunopeptidomic analysis of patient 1 MT1 attributed to SEQ ID NO. 53.

Figure 48:
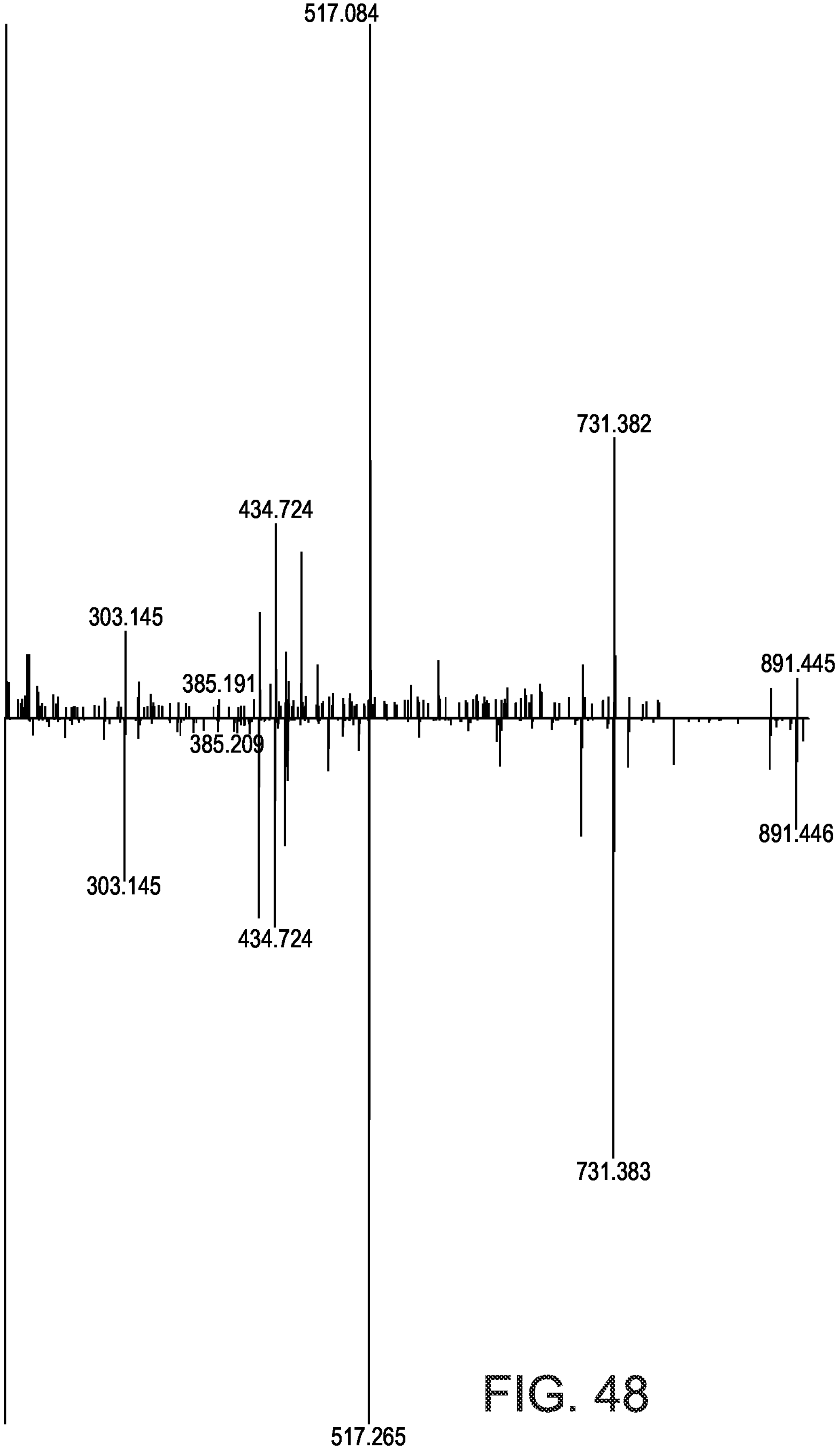

FIG. 48 shows a mass spectrometry spectrum of a peptide fragment from immunopeptidomic analysis of patient 2MT3 attributed to SEQ ID NO. 51.

Figure 49:
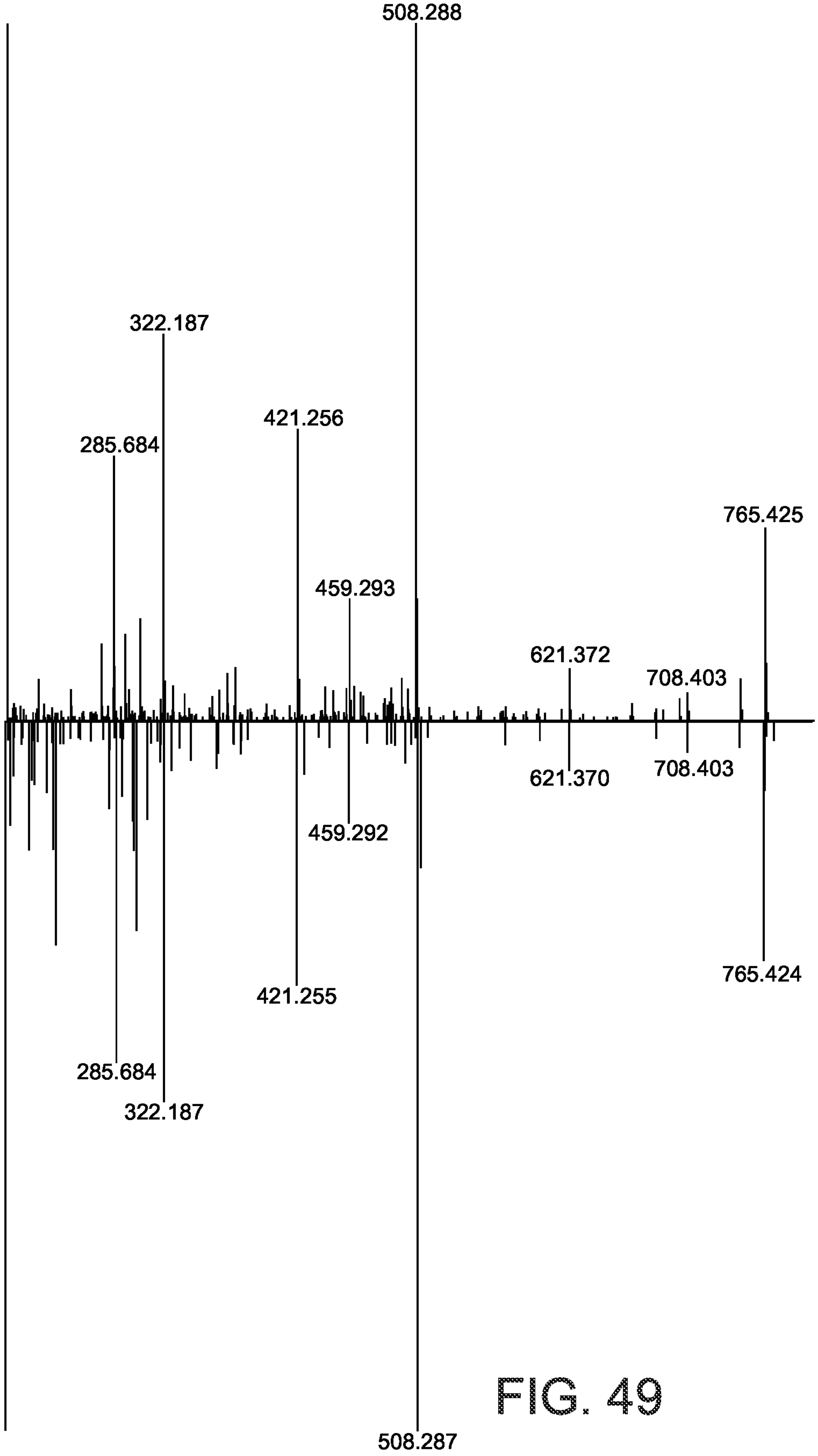

FIG. 49 shows a mass spectrometry spectrum of a peptide fragment from immunopeptidomic analysis of patient 2MT3 attributed to SEQ ID NO. 19.

Figure 50:
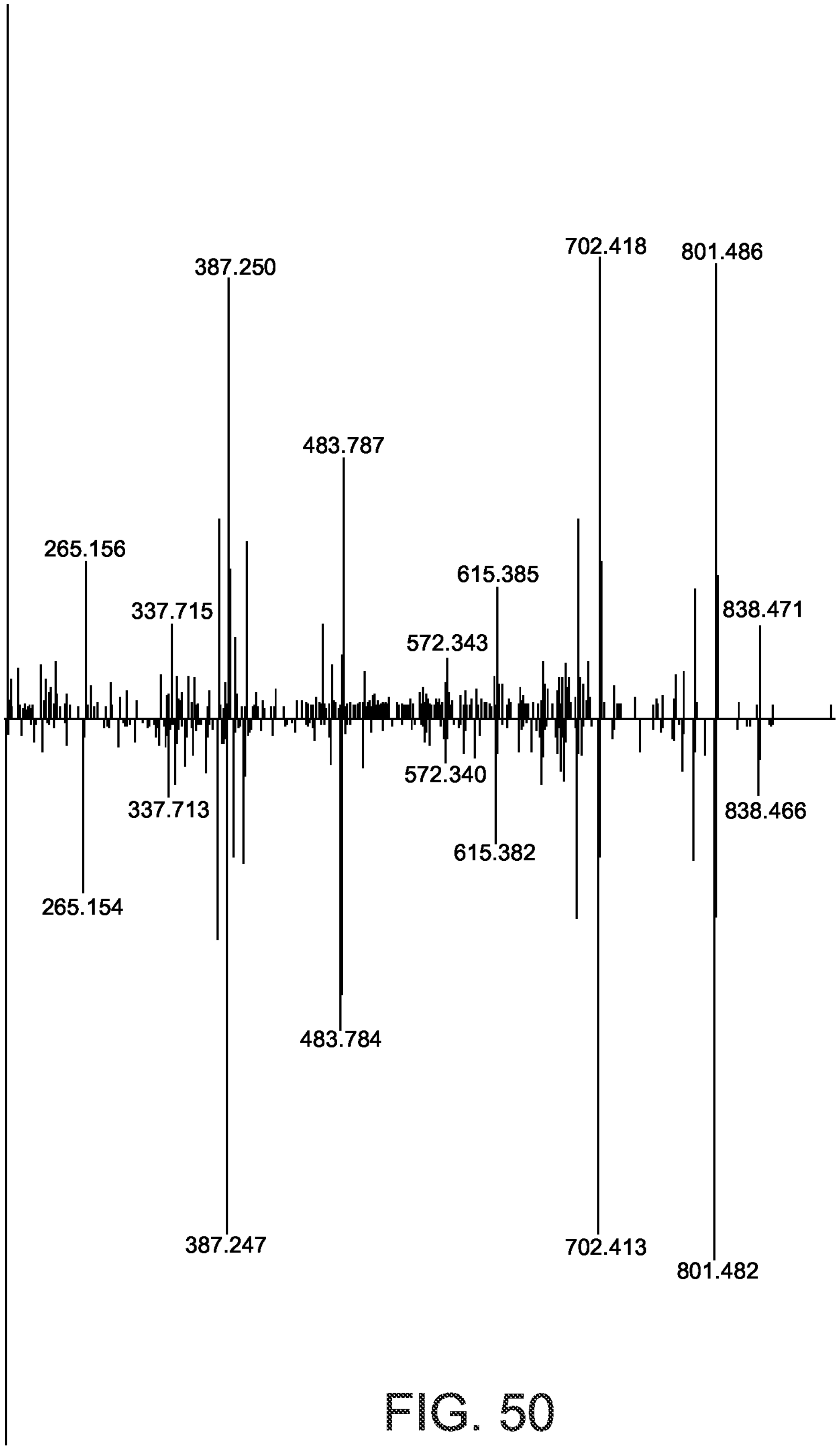

FIG. 50 shows a mass spectrometry spectrum of a peptide fragment from immunopeptidomic analysis of patient 2MT12 attributed to SEQ ID NO. 54.

Figure 51:
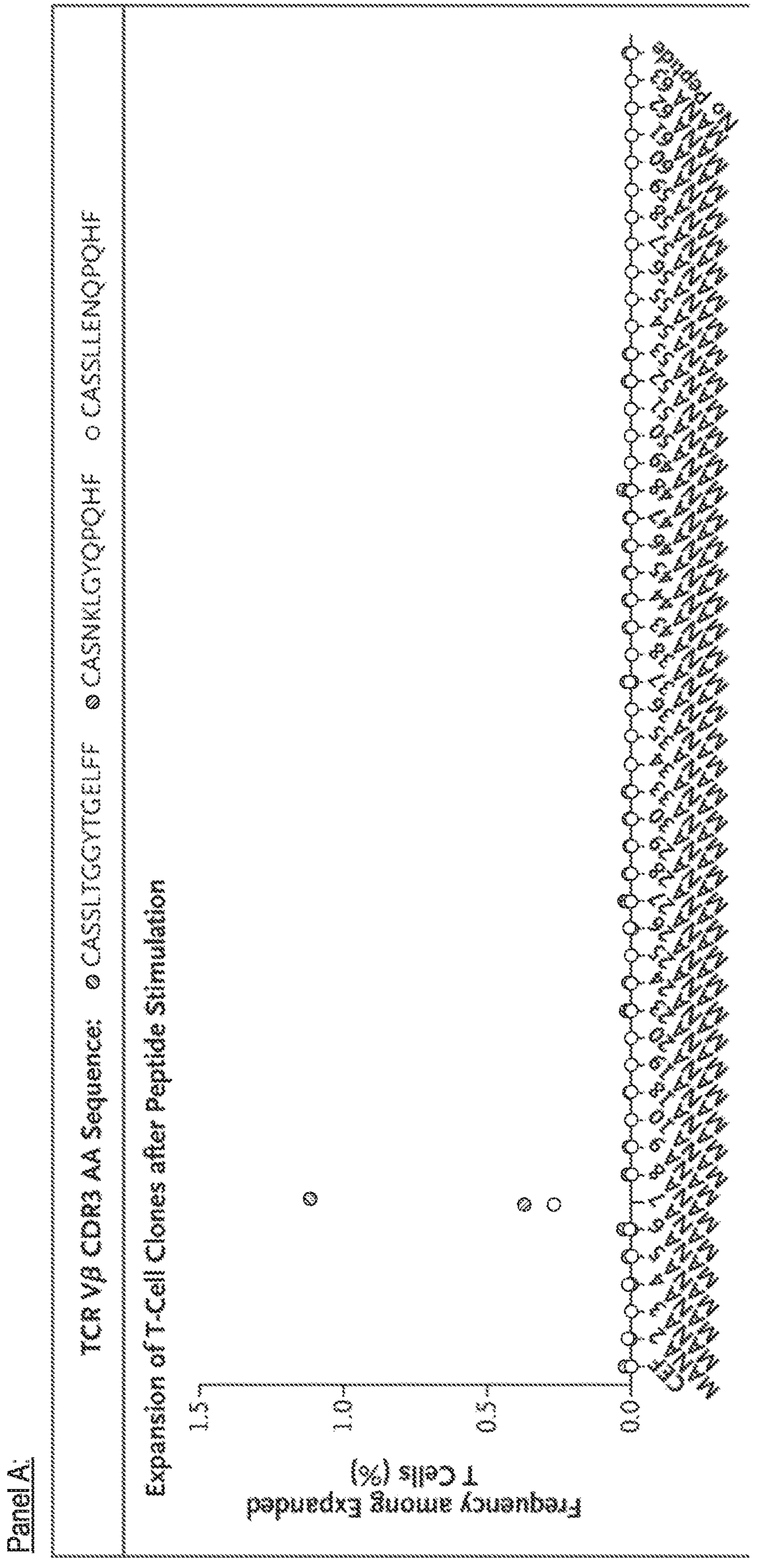
Figure 51:
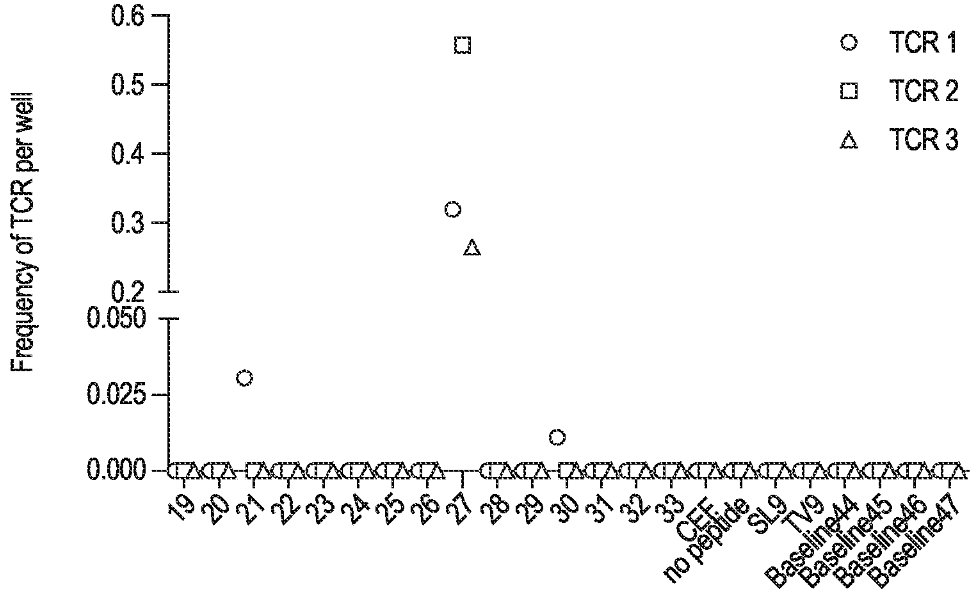
Figure 51:
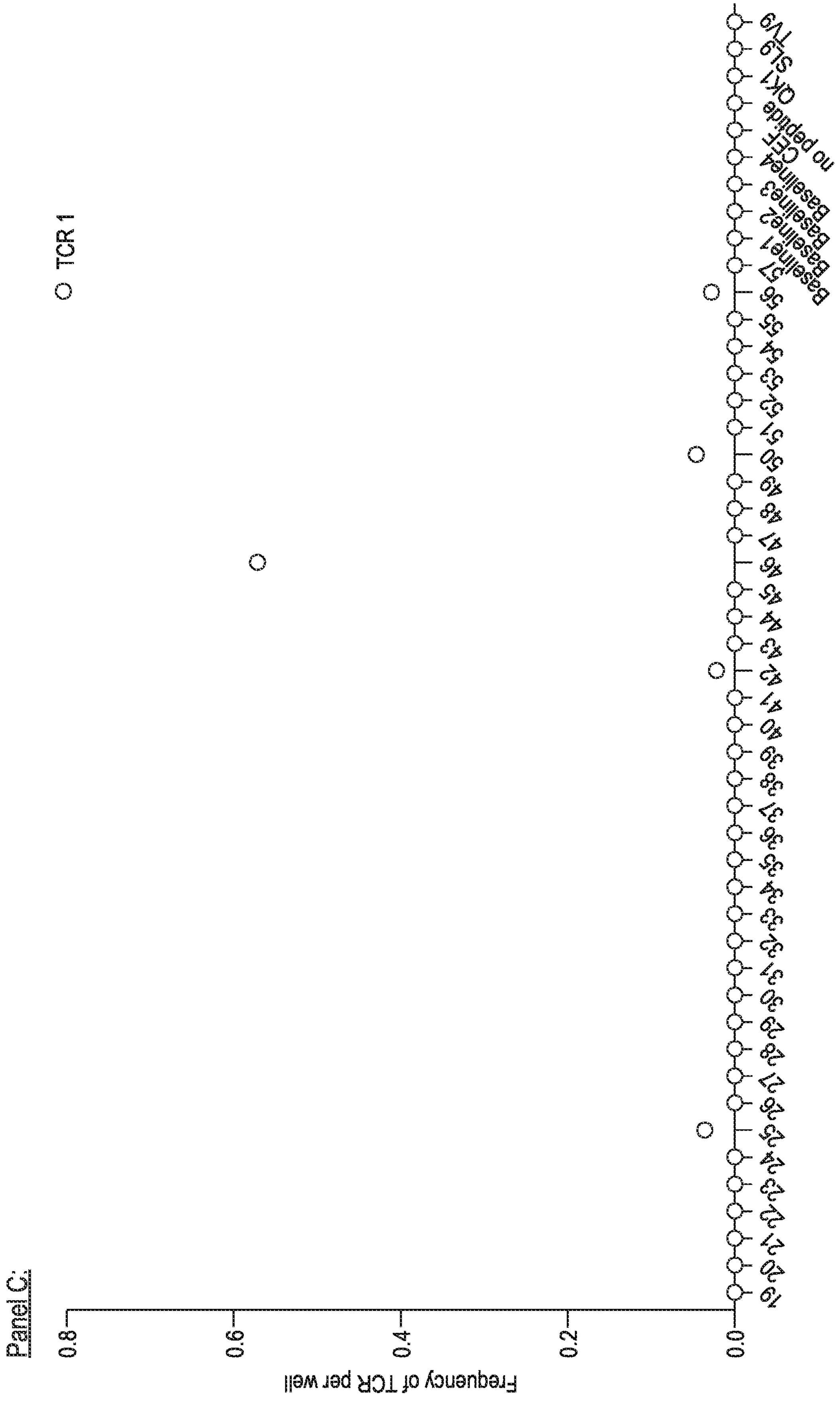

FIG. 51 panels A to C shows tumor antigen-specific T-cell amplification from patient PBMC cultures in response to cultivation with specific tumor antigen-derived peptides.

FIG. 52 panels A to D provides a summary of CLT Antigen-derived peptides (SEQ ID NO. 55 to SEQ ID NO. 72) that were capable of amplifying specific TCR-bearing T-cells from melanoma patient PBMCs. FIG. 52 panel A provides the CLT Antigen 1 sequence, FIG. 52 panel B provides the CLT Antigen 2 sequence, FIG. 52 panel C provides the CLT Antigen 3 sequence, and FIG. 52 panel D provides the CLT Antigen 4 sequence.

Figure 53:
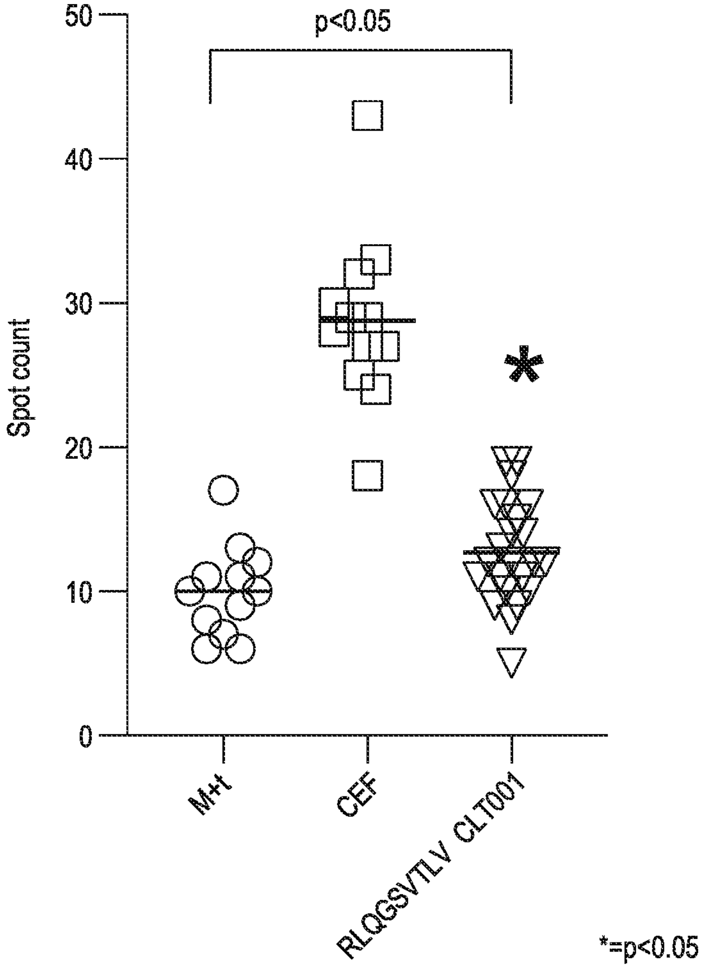

FIG. 53 shows CD8 T-cell responses from a normal blood donor to a HLA-A*0201-restricted peptide (SEQ ID NO. 73) from CLT Antigen 1.

Figure 54:
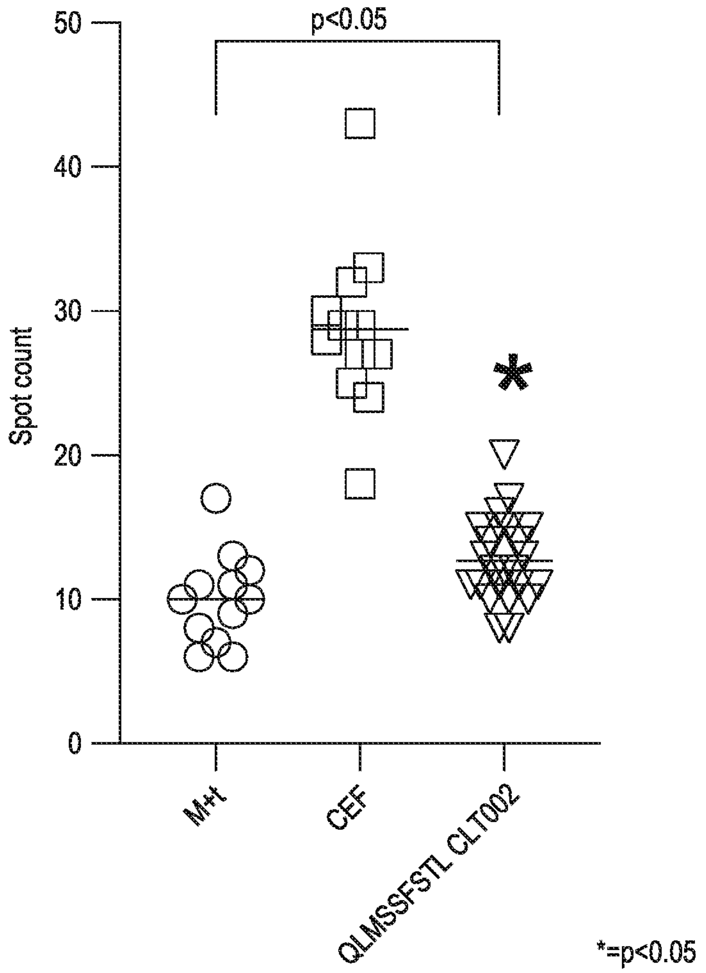

FIG. 54 shows CD8 T-cell responses from a normal blood donor to HLA-A*0201-restricted peptide (SEQ ID NO. 75) from CLT Antigen 2.

Figure 55:
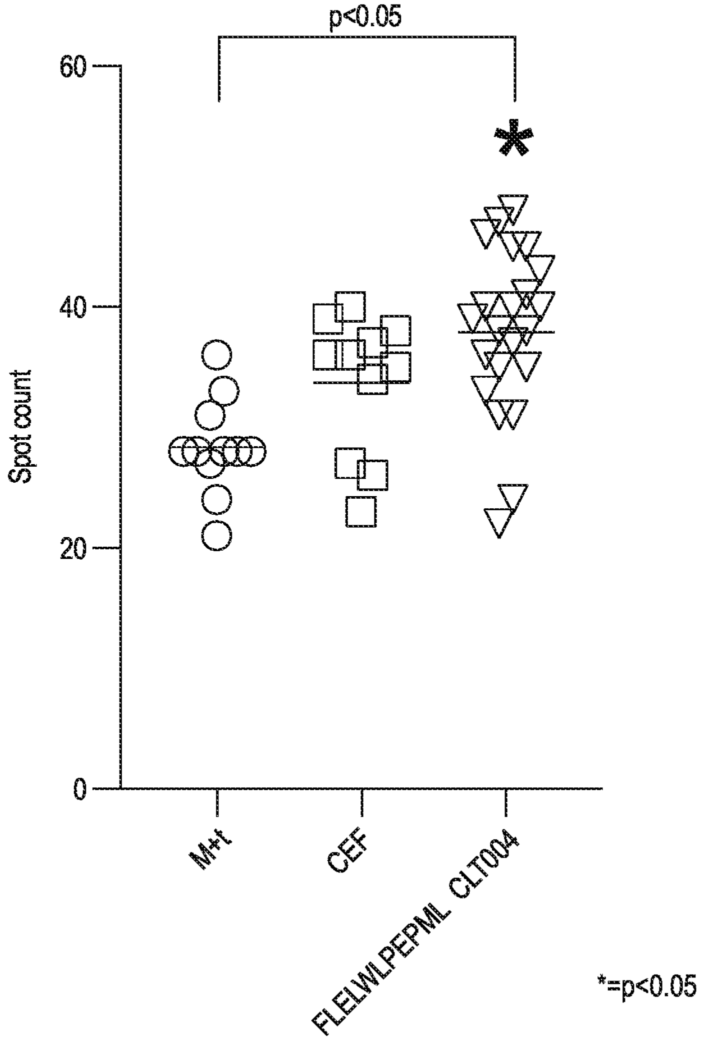

FIG. 55 shows CD8 T-cell responses from a normal blood donor to HLA-A*0201-restricted peptide (SEQ ID NO. 76) from CLT Antigen 4.

FIG. 56A to D shows responsiveness to HLA-B*0702 restricted peptides (SEQ ID NO. 74 and 77) from CLT Antigen 1 (FIG. 56A), CLT Antigen 2 (FIG. 56B), CLT Antigen 3 (FIG. 56C), and CLT Antigen 4 (FIG. 56D) in memory CD45RO-positive CD8 T-cells as compared with naïve CD45RO-negative CD8 T-cells from the same donor.

Figure 57:
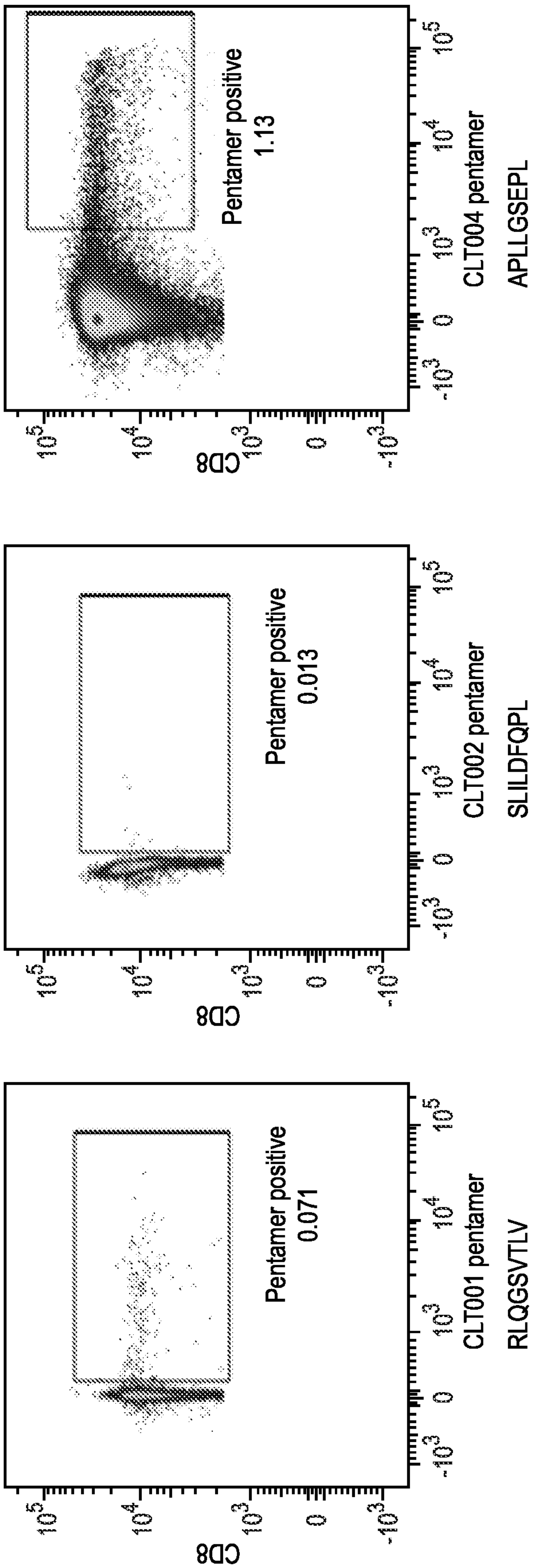

FIG. 57 shows HLA pentamer staining of normal CD8 T-cells specific for a peptide (SEQ ID NO. 73) derived from CLT Antigen 1, a peptide (SEQ ID NO. 78) derived from CLT Antigen 2 and a peptide (SEQ ID NO. 77) derived from CLT Antigen 4.

Figure 58:
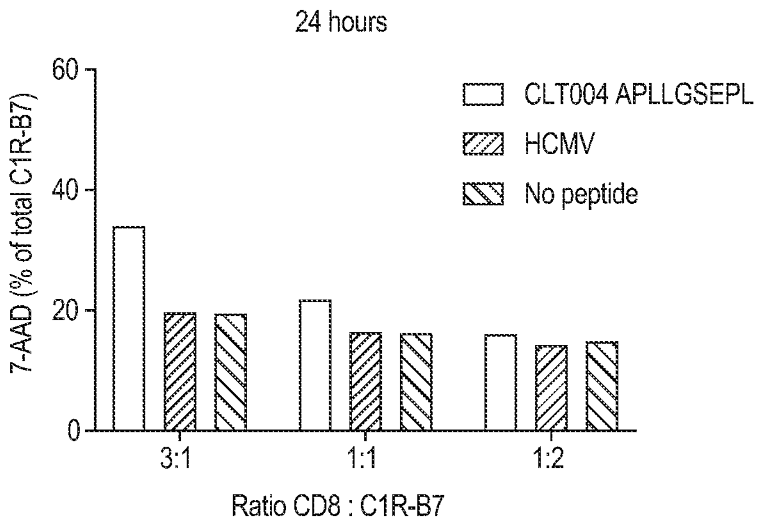

FIG. 58 shows expanded, pentamer-sorted CD8 T-cells killing Cl RB7-target cells pulsed with a peptide (SEQ ID NO. 77) derived from CLT Antigen 4.

FIG. 59A to C shows qRT-PCR assay results to verify the transcription of the CLT encoding CLT Antigen 1 (SEQ ID NO. 33; FIG. 59A), the CLT encoding CLT Antigen 2 (SEQ ID NO. 34; FIG. 59B) and the CLT encoding CLT Antigen 3 and 4 (SEQ ID NO. 35; FIG. 59C) in melanoma cancer cell lines.

DESCRIPTION OF THE SEQUENCES

SEQ ID NO. 1 is the polypeptide sequence of CLT Antigen 1

SEQ ID NO. 2 i is the polypeptide sequence of CLT Antigen 2

SEQ ID NO. 3 is the polypeptide sequence of CLT Antigen 3

SEQ ID NO. 4 is the polypeptide sequence of CLT Antigen 4

SEQ ID NO. 5 is the polypeptide sequence of CLT Antigen 5

SEQ ID NO. 6 is the polypeptide sequence of CLT Antigen 6

SEQ ID NO. 7 is the polypeptide sequence of CLT Antigen 7

SEQ ID NO. 8 is the polypeptide sequence of CLT Antigen 8

SEQ ID NO. 9 is the polypeptide sequence of CLT Antigen 9

SEQ ID NO. 10 is the polypeptide sequence of CLT Antigen 10

SEQ ID NOs. 11-14 are peptide sequences derived from CLT Antigen 1

SEQ ID NOs. 15 and 16 are peptide sequences derived from CLT Antigen 2

SEQ ID NOs. 17 and 18 are peptide sequences derived from CLT Antigen 3

SEQ ID NO. 19 is a peptide sequence derived from CLT Antigen 4

SEQ ID NOs. 20-22 are peptide sequences derived from CLT Antigen 5

SEQ ID NOs. 23 and 24 are peptide sequences derived from CLT Antigen 6

SEQ ID NO. 25 is a peptide sequence derived from CLT Antigen 7

SEQ ID NO. 26 is a peptide sequence derived from CLT Antigen 8

SEQ ID NOs. 27-29 are peptide sequences derived from CLT Antigen 9

SEQ ID NOs. 30-32 are peptide sequences derived from CLT Antigen 10

SEQ ID NO. 33 is the cDNA sequence of the CLT encoding CLT Antigen 1

SEQ ID NO. 34 is the cDNA sequence of the CLT encoding CLT Antigen 2

SEQ ID NO. 35 is the cDNA sequence of the CLT encoding CLT Antigens 3 and 4

SEQ ID NO. 36 is the cDNA sequence of the CLT encoding CLT Antigen 5

SEQ ID NO. 37 is the cDNA sequence of the CLT encoding CLT Antigen 6

SEQ ID NO. 38 is the cDNA sequence of the CLT encoding CLT Antigens 7 and 8

SEQ ID NO. 39 is the cDNA sequence of the CLT encoding CLT Antigen 9

SEQ ID NO. 40 is the cDNA sequence of the CLT encoding CLT Antigen 10

SEQ ID NO. 41 is a cDNA sequence encoding CLT Antigen 1

SEQ ID NO. 42 is a cDNA sequence encoding CLT Antigen 2

SEQ ID NO. 43 is a cDNA sequence encoding CLT Antigen 3

SEQ ID NO. 44 is a cDNA sequence encoding CLT Antigen 4

SEQ ID NO. 45 is a cDNA sequence encoding CLT Antigen 5

SEQ ID NO. 46 is a cDNA sequence encoding CLT Antigen 6

SEQ ID NO. 47 is a cDNA sequence encoding CLT Antigen 7

SEQ ID NO. 48 is a cDNA sequence encoding CLT Antigen 8

SEQ ID NO. 49 is a cDNA sequence encoding CLT Antigen 9

SEQ ID NO. 50 is a cDNA sequence encoding CLT Antigen 10

SEQ ID NOs. 51-52 are peptide sequences derived from CLT Antigen 4

SEQ ID NO. 53 is a peptide sequence derived from CLT Antigen 3

SEQ ID NO. 54 is a peptide sequences derived from CLT Antigen 4

SEQ ID NOs. 55-57 are peptide sequences derived from CLT Antigen 1

SEQ ID NOs. 58-66 are peptide sequences derived from CLT Antigen 2

SEQ ID NOs. 67-69 are peptide sequences derived from CLT Antigen 3

SEQ ID NOs. 70-72 are peptide sequences derived from CLT Antigen 4

SEQ ID NOs. 73-74 are peptide sequences derived from CLT Antigen 1

SEQ ID NO. 75 is a peptide sequence derived from CLT Antigen 2

SEQ ID NOs. 76-77 are peptide sequences derived from CLT Antigen 4

SEQ ID NO. 78 is a peptide sequence derived from CLT Antigen 2

DETAILED DESCRIPTION OF THE INVENTION

Polypeptides

The terms "protein", "polypeptide" and "peptide" are used interchangeably herein and refer to any peptide-linked chain of amino acids, regardless of length, co-translational or post-translational modification.

The term "amino acid" refers to any one of the naturally occurring amino acids, as well as amino acid analogs and amino acid mimetics that function in a manner which is similar to the naturally occurring amino acids. Naturally occurring amino acids are those 20 L-amino acids encoded by the genetic code, as well as those amino acids that are later modified, e.g., hydroxyproline, γ-carboxyglutamate, and O-phosphoserine. The term "amino acid analogue" refers to a compound that has the same basic chemical structure as a naturally occurring amino acid, i.e., an α carbon that is bound to a hydrogen, a carboxyl group, an amino group, and an R group but has a modified R group or a modified peptide backbone as compared with a natural amino acid. Examples include homoserine, norleucine, methionine sulfoxide, methionine methyl sulfonium and norleucine. Amino acid mimetics refers to chemical compounds that have a structure that is different from the general chemical structure of an amino acid, but that functions in a manner similar to a naturally occurring amino acid. Suitably an amino acid is a naturally occurring amino acid or an amino acid analogue, especially a naturally occurring amino acid and in particular one of those 20 L-amino acids encoded by the genetic code.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Thus, the invention provides an isolated polypeptide comprising a sequence selected from:

(a) the sequence of any one of SEQ ID NOs. 1-10; and
(b) a variant of the sequences of (a); and
(c) an immunogenic fragment of the sequences of (a)

The invention also provides an isolated polypeptide comprising a sequence selected from:

(a) the sequence of any one of SEQ ID NOs. 1-10 minus the initial methionine residue; and
(b) a variant of the sequences of (a); and
(c) an immunogenic fragment of the sequences of (a)

In general, variants of polypeptide sequences of the invention include sequences having a high degree of sequence identity thereto. For example variants suitably have at least about 80% identity, more preferably at least about 85% identity and most preferably at least about 90% identity (such as at least about 95%, at least about 98% or at least about 99%) to the associated reference sequence over their whole length.

Suitably the variant is an immunogenic variant. A variant is considered to be an immunogenic variant where it elicits a response which is at least 20%, suitably at least 50% and especially at least 75% (such as at least 90%) of the activity of the reference sequence (i.e. the sequence of which the variant is a variant) e.g., in an in vitro restimulation assay of PBMC or whole blood with the polypeptide as antigen (e.g., restimulation for a period of between several hours to up to 1 year, such as up to 6 months, 1 day to 1 month or 1 to 2 weeks), that measures the activation of the cells via lymphoproliferation (e.g., T-cell proliferation), production of cytokines (e.g., IFN-gamma) in the supernatant of culture (measured by ELISA etc.) or characterisation of T-cell responses by intra and extracellular staining (e.g., using antibodies specific to immune markers, such as CD3, CD4, CD8, IL2, TNF-alpha, IFNg, Type 1 IFN, CD40L, CD69 etc.) followed by analysis with a flow cytometer.

The variant may, for example, be a conservatively modified variant. A "conservatively modified variant" is one where the alteration(s) results in the substitution of an amino acid with a functionally similar amino acid or the substitution/deletion/addition of residues which do not substantially impact the biological function of the variant. Typically, such biological function of the variants will be to induce an immune response against a melanoma e.g. a cutaneous melanoma cancer antigen.

Conservative substitution tables providing functionally similar amino acids are well known in the art. Variants can include homologues of polypeptides found in other species.

A variant of a polypeptide of the invention may contain a number of substitutions, for example, conservative substitutions (for example, 1-25, such as 1-10, in particular 1-5, and especially 1 amino acid residue(s) may be altered) when compared to the reference sequence. The number of substitutions, for example, conservative substitutions, may be up to 20% e.g., up to 10% e.g., up to 5% e.g., up to 1% of the number of residues of the reference sequence. In general, conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins 1984).

Suitably such substitutions do not alter the immunological structure of an epitope (e.g., they do not occur within the epitope region as mapped in the primary sequence), and do not therefore have a significant impact on the immunogenic properties of the antigen.

Polypeptide variants also include those wherein additional amino acids are inserted compared to the reference sequence, for example, such insertions may occur at 1-10 locations (such as 1-5 locations, suitably 1 or 2 locations, in particular 1 location) and may, for example, involve the addition of 50 or fewer amino acids at each location (such as 20 or fewer, in particular 10 or fewer, especially 5 or fewer). Suitably such insertions do not occur in the region of an epitope, and do not therefore have a significant impact on the immunogenic properties of the antigen. One example of insertions includes a short stretch of histidine residues (e.g., 2-6 residues) to aid expression and/or purification of the antigen in question.

Polypeptide variants include those wherein amino acids have been deleted compared to the reference sequence, for example, such deletions may occur at 1-10 locations (such as 1-5 locations, suitably 1 or 2 locations, in particular 1 location) and may, for example, involve the deletion of 50 or fewer amino acids at each location (such as 20 or fewer, in particular 10 or fewer, especially 5 or fewer). Suitably such deletions do not occur in the region of an epitope, and do not therefore have a significant impact on the immunogenic properties of the antigen.

The skilled person will recognise that a particular protein variant may comprise substitutions, deletions and additions (or any combination thereof). For example, substitutions/deletions/additions might enhance (or have neutral effects) on binding to desired patient HLA molecules, potentially increasing immunogenicity (or leaving immunogenicity unchanged).

Immunogenic fragments according to the present invention will typically comprise at least 9 contiguous amino acids from the full-length polypeptide sequence (e.g., at least 9 or 10), such as at least 12 contiguous amino acids (e.g., at least 15 or at least 20 contiguous amino acids), in particular at least 50 contiguous amino acids, such as at least 100 contiguous amino acids (for example at least 200 contiguous amino acids) depending on the length of the CLT antigen. Suitably the immunogenic fragments will be at least 10%, such as at least 20%, such as at least 50%, such as at least 70% or at least 80% of the length of the full-length polypeptide sequence.

Immunogenic fragments typically comprise at least one epitope. Epitopes include B cell and T-cell epitopes and suitably immunogenic fragments comprise at least one T-cell epitope such as a CD4+ or a CD8+ T-cell epitope.

T-cell epitopes are short contiguous stretches of amino acids which are recognised by T-cells (e.g., CD4+ or CD8+ T-cells) when bound to HLA molecules. Identification of T-cell epitopes may be achieved through epitope mapping experiments which are well known to the person skilled in the art (see, for example, Paul, *Fundamental Immunology,* 3rd ed., 243-247 (1993); Beiβbarth et al., 2005, *Bioinformatics,* 21(Suppl. 1):i29-i37).

As a result of the crucial involvement of the T-cell response in cancer, it is readily apparent that fragments of the full-length polypeptides of SEQ ID NOs. 1-10 which contain at least one T-cell epitope may be immunogenic and may contribute to immunoprotection.

It will be understood that in a diverse outbred population, such as humans, different HLA types mean that specific epitopes may not be recognised by all members of the population. Consequently, to maximise the level of recognition and scale of immune response to a polypeptide, it is generally desirable that an immunogenic fragment contains a plurality of the epitopes from the full-length sequence (suitably all epitopes within a CLT antigen).

Particular fragments of the polypeptides of SEQ ID NOs. 1-10 which may be of use include those containing at least one CD8+ T-cell epitope, suitably at least two CD8+ T-cell epitopes and especially all CD8+ T-cell epitopes, particularly those associated with a plurality of HLA alleles, e.g., those associated with 2, 3, 4, 5 or more alleles). Particular fragments of the polypeptides of SEQ ID NOs. 1-10 which may be of use include those containing at least one CD4+ T-cell epitope, suitably at least two CD4+ T-cell epitopes and especially all CD4+ T-cell epitopes (particularly those associated with a plurality of HLA alleles, e.g., those associated with 2, 3, 4, 5 or more alleles). However, a person skilled in design of vaccines could combine exogenous CD4+ T-cell epitopes with CD8+ T-cells epitopes of this invention and achieve desired responses to the invention's CD8+ T-cell epitopes.

Where an individual fragment of the full-length polypeptide is used, such a fragment is considered to be immunogenic where it elicits a response which is at least 20%, suitably at least 50% and especially at least 75% (such as at least 90%) of the activity of the reference sequence (i.e., the sequence of which the fragment is a fragment) e.g., activity in an in vitro restimulation assay of PBMC or whole blood with the polypeptide as antigen (e.g., restimulation for a period of between several hours to up to 1 year, such as up to 6 months, 1 day to 1 month or 1 to 2 weeks,) that measures the activation of the cells via lymphoproliferation (e.g., T-cell proliferation), production of cytokines (e.g., IFN-gamma) in the supernatant of culture (measured by ELISA etc.) or characterisation of T-cell responses by intra and extracellular staining (e.g., using antibodies specific to immune markers, such as CD3, CD4, CD8, IL2, TNF-alpha, IFN-gamma, Type 1 IFN, CD4OL, CD69 etc.) followed by analysis with a flow cytometer.

In some circumstances a plurality of fragments of the full-length polypeptide (which may or may not be overlapping and may or may not cover the entirety of the full-length sequence) may be used to obtain an equivalent biological response to the full-length sequence itself. For example, at least two immunogenic fragments (such as three, four or five) as described above, which in combination provide at least 50%, suitably at least 75% and especially at least 90% activity of the reference sequence in an in vitro restimulation assay of PBMC or whole blood (e.g., a T-cell proliferation and/or IFN-gamma production assay).

Example immunogenic fragments of polypeptides of SEQ ID NOs. 1-10, and thus example peptides of the invention, include polypeptides which comprise or consist of the sequences of SEQ ID NOs. 11-32. Further example immunogenic fragments of polypeptides of SEQ ID NOs. 1-4, and thus example peptides of the invention, include polypeptides which comprise or consist of the sequences of SEQ ID NOs. 51-78. The sequences of SEQ ID NOs. 11-17, 19-28, 30-31 and 51-54 were identified as being bound to HLA Class I molecules from immunopeptidomic analysis (see Examples 2 and 2.1). The sequences of SEQ ID NOs. 18, 29 and 32 were identified as being bound to HLA Class II molecules from immunopeptidomic analysis (see Example 2). The sequences of SEQ ID NOs 55-78 were predicted by NetMHC software eas being bound to HLA Class I molecules and were used in immunological validation assays (see Examples 3, 4 and 5).

Nucleic Acids

The invention provides an isolated nucleic acid encoding a polypeptide of the invention (referred to as a nucleic acid of the invention). For example, the nucleic acid of the invention comprises or consists of a sequence selected from SEQ ID NOs. 33-40 or 41-50.

The terms "nucleic acid" and "polynucleotide" are used interchangeably herein and refer to a polymeric macromolecule made from nucleotide monomers particularly deoxyribonucleotide or ribonucleotide monomers. The term encompasses nucleic acids containing known nucleotide analogs or modified backbone residues or linkages, which are naturally occurring and non-naturally occurring, which have similar properties as the reference nucleic acid, and which are intended to be metabolized in a manner similar to the reference nucleotides or are intended to have extended half-life in the system. Examples of such analogs include, without limitation, phosphorothioates, phosphoramidates, methyl phosphonates, chiral-methyl phosphonates, 2-O-methyl ribonucleotides, peptide-nucleic acids (PNAs). Suitably the term "nucleic acid" refers to naturally occurring polymers of deoxyribonucleotide or ribonucleotide monomers. Suitably the nucleic acid molecules of the invention are recombinant. Recombinant means that the nucleic acid molecule is the product of at least one of cloning, restriction or ligation steps, or other procedures that result in a nucleic acid molecule that is distinct from a nucleic acid molecule found in nature (e.g., in the case of cDNA). In an embodiment the nucleic acid of the invention is an artificial nucleic acid sequence (e.g., a cDNA sequence or nucleic acid sequence with non-naturally occurring codon usage). In one embodiment, the nucleic acids of the invention are DNA. Alternatively, the nucleic acids of the invention are RNA.

DNA (deoxyribonucleic acid) and RNA (ribounucleic acid) refer to nucleic acid molecules having a backbone of sugar moieties which are deoxyribosyl and ribosyl moieties respectively. The sugar moieties may be linked to bases which are the 4 natural bases (adenine (A), guanine (G), cytosine (C) and thymine (T) in DNA and adenine (A), guanine (G), cytosine (C) and uracil (U) in RNA). As used herein, a "corresponding RNA" is an RNA having the same sequence as a reference DNA but for the substitution of thymine (T) in the DNA with uracil (U) in the RNA. The sugar moieties may also be linked to unnatural bases such as inosine, xanthosine, 7-methylguanosine, dihydrouridine and 5-methylcytidine. Natural phosphodiester linkages between sugar (deoxyribosyl/ribosyl) moieties may optionally be replaced with phosphorothioates linkages. Suitably nucleic acids of the invention consist of the natural bases attached to a deoxyribosyl or ribosyl sugar backbone with phosphodiester linkages between the sugar moieties.

In an embodiment the nucleic acid of the invention is a DNA. For example the nucleic acid comprises or consists of a sequence selected from SEQ ID NOs. 33-40 or 41-50. Also provided is a nucleic acid which comprises or consists of a variant of sequence selected from SEQ ID NOs. 33-40 or 41-50 which variant encodes the same amino acid sequence but has a different nucleic acid based on the degeneracy of the genetic code.

Thus, due to the degeneracy of the genetic code, a large number of different, but functionally identical nucleic acids can encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations lead to "silent" (sometimes referred to as "degenerate" or "synonymous") variants, which are one species of conservatively modified variations. Every nucleic acid sequence disclosed herein which encodes a polypeptide also enables every possible silent variation of the nucleic acid. One of skill will recognise that each codon in a nucleic acid (except AUG, which is ordinarily the only codon for methionine, and UGG, which is ordinarily the only codon for tryptophan) can be modified to yield a functionally identical molecule. Accordingly, each silent variation of a nucleic acid that encodes a polypeptide is implicit in each described sequence and is provided as an aspect of the invention.

Degenerate codon substitutions may also be achieved by generating sequences in which the third position of one or more selected (or all) codons is substituted with mixed-base and/or deoxyinosine residues (Batzer et al., 1991, Nucleic Acid Res. 19:5081; Ohtsuka et al., 1985, J. Biol. Chem. 260:2605-2608; Rossolini et al., 1994, Mol. Cell. Probes 8:91-98).

A nucleic acid of the invention which comprises or consists of a sequence selected from SEQ ID NOs. 33-40 or 41-50 may contain a number of silent variations (for example, 1-50, such as 1-25, in particular 1-5, and especially 1 codon(s) may be altered) when compared to the reference sequence.

In an embodiment the nucleic acid of the invention is an RNA. RNA sequences are provided which correspond to a DNA sequence provided herein and have a ribonucleotide backbone instead of a deoxyribonucleotide backbone and have the sidechain base uracil (U) in place of thymine (T).

Thus a nucleic acid of the invention comprises or consists of the RNA equivalent of a cDNA sequence selected from SEQ ID NOs. 33-40 or 41-50 and may contain a number of silent variations (for example, 1-50, such as 1-25, in particular 1-5, and especially 1 codon(s) may be altered) when compared to the reference sequence. By "RNA equivalent" is meant an RNA sequence which contains the same genetic information as the reference cDNA sequence (i.e. contains the same codons with a ribonucleotide backbone instead of a deoxyribonucleotide backbone and having the sidechain base uracil (U) in place of thymine (T)).

The invention also comprises sequences which are complementary to the aforementioned cDNA and RNA sequences.

In an embodiment, the nucleic acids of the invention are codon optimised for expression in a human host cell.

The nucleic acids of the invention are capable of being transcribed and translated into polypeptides of the invention in the case of DNA nucleic acids, and translated into polypeptides of the invention in the case of RNA nucleic acids.

Polypeptides and Nucleic Acids

Suitably, the polypeptides and nucleic acids used in the present invention are isolated. An "isolated" polypeptide or nucleic acid is one that is removed from its original environment. For example, a naturally-occurring polypeptide or nucleic acid is isolated if it is separated from some or all of the coexisting materials in the natural system. A nucleic acid is considered to be isolated if, for example, it is cloned into a vector that is not a part of its natural environment.

"Naturally occurring" when used with reference to a polypeptide or nucleic acid sequence means a sequence found in nature and not synthetically modified.

"Artificial" when used with reference to a polypeptide or nucleic acid sequence means a sequence not found in nature which is, for example, a synthetic modification of a natural sequence, or contains an unnatural sequence.

The term "heterologous" when used with reference to the relationship of one nucleic acid or polypeptide to another nucleic acid or polypeptide indicates that the two or more sequences are not found in the same relationship to each other in nature. A "heterologous" sequence can also mean a sequence which is not isolated from, derived from, or based upon a naturally occurring nucleic acid or polypeptide sequence found in the host organism.

As noted above, polypeptide variants preferably have at least about 80% identity, more preferably at least about 85% identity and most preferably at least about 90% identity (such as at least about 95%, at least about 98% or at least about 99%) to the associated reference sequence over their whole length.

For the purposes of comparing two closely-related polypeptide or polynucleotide sequences, the "% sequence identity" between a first sequence and a second sequence may be calculated. Polypeptide sequences are said to be the same as or identical to other polypeptide sequences, if they share 100% sequence identity over their entire length. Residues in sequences are numbered from left to right, i.e. from N- to C-terminus for polypeptides. The terms "identical" or percentage "identity", in the context of two or more polypeptide sequences, refer to two or more sequences or sub-sequences that are the same or have a specified percentage of amino acid residues that are the same (i.e., 70% identity, optionally 75%, 80%, 85%, 90%, 95%, 98% or 99% identity over a specified region), when compared and aligned for maximum correspondence over a comparison window. Suitably, the comparison is performed over a window corresponding to the entire length of the reference sequence.

For sequence comparison, one sequence acts as the reference sequence, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage sequence identities for the test sequences relative to the reference sequence, based on the program parameters.

A "comparison window", as used herein, refers to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerised implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, 1987, *J. Mol. Evol.* 35:351-360. The method used is similar to the method described by Higgins & Sharp, 1989, *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984, *Nuc. Acids Res.* 12:387-395).

Another example of algorithm that is suitable for determining percent sequence identity and sequence similarity are the BLAST and BLAST 2.0 algorithms, which are described in Altschul et al., 1977, *Nuc. Acids Res.* 25:3389-3402 and Altschul et al., 1990, *J. Mol. Biol.* 215:403-410, respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For amino acid sequences, the BLASTP program uses as defaults a wordlength of 3, and expectation (E) of 10, and the BLOSUM62 scoring matrix (see Henikoff & Henikoff, 1989, *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance.

A "difference" between sequences refers to an insertion, deletion or substitution of a single residue in a position of the second sequence, compared to the first sequence. Two sequences can contain one, two or more such differences. Insertions, deletions or substitutions in a second sequence which is otherwise identical (100% sequence identity) to a first sequence result in reduced % sequence identity. For example, if the identical sequences are 9 residues long, one substitution in the second sequence results in a sequence identity of 88.9%. If the identical sequences are 17 amino acid residues long, two substitutions in the second sequence results in a sequence identity of 88.2%.

Alternatively, for the purposes of comparing a first, reference sequence to a second, comparison sequence, the number of additions, substitutions and/or deletions made to the first sequence to produce the second sequence may be ascertained. An addition is the addition of one residue into the first sequence (including addition at either terminus of the first sequence). A substitution is the substitution of one residue in the first sequence with one different residue. A deletion is the deletion of one residue from the first sequence (including deletion at either terminus of the first sequence).

Production of Polypeptides of the Invention

Polypeptides of the invention can be obtained and manipulated using the techniques disclosed for example in Green and Sambrook 2012 Molecular Cloning: A Laboratory Manual 4th Edition Cold Spring Harbour Laboratory Press. In particular, artificial gene synthesis may be used to produce polynucleotides (Nambiar et al., 1984, *Science,* 223:1299-1301, Sakamar and Khorana, 1988, *Nucl. Acids Res.,* 14:6361-6372, Wells et al., 1985, Gene, 34:315-323 and Grundstrom et al., 1985, *Nucl. Acids Res.,* 13:3305-3316) followed by expression in a suitable organism to produce polypeptides. A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma and Eckstein, 1998, *Annu. Rev. Biochem.* 67:99-134). These relatively short segments are readily assembled by using a variety of gene amplification methods (Methods Mol Biol., 2012; 834:93-109) into longer DNA molecules, suitable for use in innumerable recombinant DNA-based expression systems. In the context of this invention one skilled in the art would understand that the polynucleotide sequences encoding the polypeptide antigens described in this invention could be readily used in a variety of vaccine production systems, including, for example, viral vectors.

For the purposes of production of polypeptides of the invention in a microbiological host (e.g., bacterial or fungal), nucleic acids of the invention will comprise suitable regulatory and control sequences (including promoters, termination signals etc) and sequences to promote polypeptide secretion suitable for protein production in the host. Similarly, polypeptides of the invention could be produced by transducing cultures of eukaryotic cells (e.g., Chinese hamster ovary cells or drosophila S2 cells) with nucleic acids of the invention which have been combined with suitable regulatory and control sequences (including promoters, termination signals etc) and sequences to promote polypeptide secretion suitable for protein production in these cells.

Improved isolation of the polypeptides of the invention produced by recombinant means may optionally be facilitated through the addition of a stretch of histidine residues (commonly known as a His-tag) towards one end of the polypeptide.

Polypeptides may also be produced synthetically.

Vectors

In additional embodiments, genetic constructs comprising one or more of the nucleic acids of the invention are introduced into cells in vivo such that a polypeptide of the invention is produced in vivo eliciting an immune response. The nucleic acid (e.g., DNA) may be present within any of a variety of delivery systems known to those of ordinary skill in the art, including nucleic acid expression systems, bacteria and some viral expression systems. Numerous gene delivery techniques are well known in the art, such as those described by Rolland, 1998, *Crit. Rev. Therap. Drug Carrier Systems* 15:143-198, and references cited therein. Several of these approaches are outlined below for the purpose of illustration.

Accordingly, there is provided a vector (also referred to herein as a DNA expression construct' or 'construct') comprising a nucleic acid molecule of the invention.

Suitably, the vector comprises nucleic acid encoding regulatory elements (such as a suitable promoter and terminating signal) suitable for permitting transcription of a translationally active RNA molecule in a human host cell. A "translationally active RNA molecule" is an RNA molecule capable of being translated into a protein by a human cell's translation apparatus.

Accordingly, there is provided a vector comprising a nucleic acid of the invention (herein after a "vector of the invention").

In particular, the vector may be a viral vector. The viral vector may be an adenovirus, adeno-associated virus (AAV) (e.g., AAV type 5 and type 2), alphavirus (e.g., Venezuelan equine encephalitis virus (VEEV), Sindbis virus (SIN), Semliki Forest virus (SFV)), herpes virus, arenavirus (e.g., lymphocytic choriomeningitis virus (LCMV)), measles virus, poxvirus (such as modified vaccinia Ankara (MVA)), paramyxovirus, lentivirus, or rhabdovirus (such as vesicular stomatitis virus (VSV)) vector i.e. the vector may be derived from any of the aforementioned viruses. Adenoviruses are particularly suitable for use as a gene transfer vector because of its mid-sized genome, ease of manipulation, high titre, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP is particularly efficient during the late phase of infection, and all the mRNAs trasncribed from this promoter possess a 5'-tripartite leader (TPL) sequence which makes them preferred mRNAs for translation. Replication-deficient adenovirus, which are created by from viral genomes that are deleted for one or more of the early genes are particularly useful, since they have limited replication and less possibility of pathogenic spread within a vaccinated host and to contacts of the vaccinated host.

Other Polynucleotide Delivery

In certain embodiments of the invention, the expression construct comprising one or more polynucleotide sequences may simply consist of naked recombinant DNA plasmids. See Ulmer et al., 1993, *Science* 259:1745-1749 and reviewed by Cohen, 1993, *Science* 259:1691-1692. Transfer of the construct may be performed, for example, by any method which physically or chemically permeabilises the cell membrane. This is particularly applicable for transfer in vitro but it may be applied to in vivo use as well. It is envisioned that DNA encoding a gene of interest may also be transferred in a similar manner in vivo and express the gene product. Multiple delivery systems have been used to deliver DNA molecules into animal models and into man. Some products based on this technology have been licensed for use in animals, and others are in phase 2 and 3 clinical trials in man.

RNA delivery

In other embodiments of the invention, the expression construct comprising one or more polynucleotide sequences may consist of naked, recombinant DNA-derived RNA molecules (Ulmer et al., 2012, Vaccine 30:4414-4418). As for DNA-based expression constructs, a variety of methods can be utilized to introduce RNA molecules into cells in vitro or in vivo. The RNA-based constructs can be designed to mimic simple messenger RNA (mRNA) molecules, such that the introduced biological molecule is directly translated by the host cell's translation machinery to produce its encoded polypeptide in the cells to which it has been introduced. Alternatively, RNA molecules may be designed in a manner that allows them to self-amplify within cells they are introduced into, by incorporating into their structure genes for viral RNA-dependent RNA polymerases. Thus, these types of RNA molecules, known as self-amplifying mRNA (SAM™) molecules (Geall et al. 2012, PNAS, 109:14604-14609), share properties with some RNA-based viral vectors. Either mRNA-based or SAM™ RNAs may be further modified (e.g., by alteration of their sequences, or by use of modified nucleotides) to enhance stability and translation (Schlake et al., RNA Biology, 9: 1319-1330), and both types of RNAs may be formulated (e.g., in emulsions (Brito et al., Molecular Therapy, 2014 22:2118-2129) or lipid nanoparticles (Kranz et al., 2006, *Nature,* 534:396-401)) to facilitate stability and/or entry into cells in vitro or in vivo. Myriad formulations of modified (and non-modified) RNAs have been tested as vaccines in animal models and in man, and multiple RNA-based vaccines are being used in ongoing clinical trials.

Pharmaceutical Compositions

The polypeptides, nucleic acids and vectors of the invention may be formulated for delivery in pharmaceutical compositions such as immunogenic compositions and vaccine compositions (all hereinafter "compositions of the invention"). Compositions of the invention suitably comprise a polypeptide, nucleic acid or vector of the invention together with a pharmaceutically acceptable carrier.

Thus, in an embodiment, there is provided an immunogenic pharmaceutical composition comprising a polypeptide, nucleic acid or vector of the invention together with a pharmaceutically acceptable carrier.

In another embodiment there is provided a vaccine composition comprising a polypeptide, nucleic acid or vector of the invention together with a pharmaceutically acceptable carrier. Preparation of pharmaceutical compositions is generally described in, for example, Powell & Newman, eds., *Vaccine Design* (the subunit and adjuvant approach), 1995. Compositions of the invention may also contain other compounds, which may be biologically active or inactive. Suitably, the composition of the invention is a sterile composition suitable for parenteral administration.

In certain preferred embodiments of the present invention, pharmaceutical compositions of the invention are provided which comprise one or more (e.g., one) polypeptides of the invention in combination with a pharmaceutically acceptable carrier.

In certain preferred embodiments of the present invention, compositions of the invention are provided which comprise one or more (e.g., one) nucleic acids of the invention or one or more (e.g., one) vectors of the invention in combination with a pharmaceutically acceptable carrier.

In an embodiment, the compositions of the invention may comprise one or more (e.g., one) polynucleotide and one or more (e.g., one) polypeptide components. Alternatively, the compositions may comprise one or more (e.g., one) vector and one or more (e.g., one) polypeptide components. Alternatively, the compositions may comprise one or more (e.g., one) vector and one or more (e.g., one) polynucleotide components. Such compositions may provide for an enhanced immune response.

Pharmaceutically Acceptable Salts

It will be apparent that a composition of the invention may contain pharmaceutically acceptable salts of the nucleic acids or polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

Pharmaceutically Acceptable Carriers

While many pharmaceutically acceptable carriers known to those of ordinary skill in the art may be employed in the compositions of the invention, the optimal type of carrier used will vary depending on the mode of administration. Compositions of the present invention may be formulated for any appropriate manner of administration, including for example, parenteral, topical, oral, nasal, intravenous, intracranial, intraperitoneal, subcutaneous or intramuscular administration, preferably parenteral e.g., intramuscular, subcutaneous or intravenous administration. For parenteral administration, the carrier preferably comprises water and may contain buffers for pH control, stabilising agents e.g., surfactants and amino acids and tonicity modifying agents e.g., salts and sugars. If the composition is intended to be provided in lyophilised form for dilution at the point of use, the formulation may contain a lyoprotectant e.g., sugars such as trehalose. For oral administration, any of the above carriers or a solid carrier, such as mannitol, lactose, starch, magnesium stearate, sodium saccharine, talcum, cellulose, glucose, sucrose, and magnesium carbonate, may be employed.

Thus, compositions of the invention may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, solutes that render the formulation isotonic, hypotonic or weakly hypertonic with the blood of a recipient, suspending agents, thickening agents and/or preservatives. Alternatively, compositions of the invention may be formulated as a lyophilizate.

Immunostimulants

Compositions of the invention may also comprise one or more immunostimulants. An immunostimulant may be any substance that enhances or potentiates an immune response (antibody and/or cell-mediated) to an exogenous antigen. Examples of immunostimulants, which are often referred to as adjuvants in the context of vaccine formulations, include aluminium salts such as aluminium hydroxide gel (alum) or aluminium phosphate, saponins including QS21, immunostimulatory oligonucleotides such as CPG, oil-in-water emulsion (e.g., where the oil is squalene), aminoalkyl glucosaminide 4-phosphates, lipopolysaccharide or a derivative thereof e.g., 3-de-O-acylated monophosphoryl lipid A (3D-MPL®) and other TLR4 ligands, TLR7 ligands, TLR8 ligands, TLR9 ligands, IL-12 and interferons. Thus, suitably the one or more immunostimulants of the composition of the invention are selected from aluminium salts, saponins, immunostimulatory oligonucleotides, oil-in-water emulsions, aminoalkyl glucosaminide 4-phosphates, lipopolysaccharides and derivatives thereof and other TLR4 ligands, TLR7 ligands, TLR8 ligands and TLR9 ligands. Immunostimulants may also include monoclonal antibodies which specifically interact with other immune components, for example monoclonal antibodies that block the interaction of immune checkpoint receptors, including PD-1 and CTLA4.

In the case of recombinant-nucleic acid methods of delivery (e.g., DNA, RNA, viral vectors), the genes encoding protein-based immunostimulants may be readily delivered along with the genes encoding the polypeptides of the invention.

Sustained Release

The compositions described herein may be administered as part of a sustained-release formulation (i.e., a formulation such as a capsule, sponge, patch or gel (composed of polysaccharides, for example)) that effects a slow/sustained release of compound following administration.

Storage and Packaging

Compositions of the invention may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a composition of the invention may be stored in a freeze-dried condition requiring only the addition of a sterile liquid carrier (such as water or saline for injection) immediately prior to use.

Dosage

The amount of nucleic acid, polypeptide or vector in each composition of the invention may be prepared is such a way that a suitable dosage for therapeutic or prophylactic use will be obtained. Factors such as solubility, bioavailability, biological half-life, route of administration, product shelf life, as well as other pharmacological considerations will be contemplated by one skilled in the art of preparing such compositions, and as such, a variety of dosages and treatment regimens may be desirable.

Typically, compositions comprising a therapeutically or prophylactically effective amount deliver about 0.1 ug to about 1000 ug of polypeptide of the invention per administration, more typically about 2.5 ug to about 100 ug of polypeptide per administration. If delivered in the form of short, synthetic long peptides, doses could range from 1 to 200ug/peptide/dose. In respect of polynucleotide compositions, these typically deliver about 10 ug to about 20 mg of the nucleic acid of the invention per administration, more typically about 0.1 mg to about 10 mg of the nucleic acid of the invention per administration.

Diseases to be Treated or Prevented

As noted elsewhere, SEQ ID NOs. 1-10 are polypeptide sequences corresponding to CLT antigens which are overexpressed in cutaneous melanoma.

In one embodiment, the invention provides a polypeptide, nucleic acid, vector or composition of the invention for use in medicine.

Further aspects of the invention relate to a method of raising an immune response in a human which comprises administering to said human the polypeptide, nucleic acid, vector or composition of the invention.

The present invention also provides a polypeptide, nucleic acid, vector or composition of the invention for use in raising an immune response in a human.

There is also provided a use of a polypeptide, nucleic acid, vector or composition of the invention for the manufacture of a medicament for use in raising an immune response in a human.

Suitably the immune response is raised against a cancerous tumor expressing a corresponding sequence selected from SEQ ID NOs. 1-10 and variants and immunogenic fragments of any one thereof. By "corresponding" in this context is meant that if the tumor expresses, say, SEQ ID NO. A (A being one of SEQ ID NOs. 1-10) or a variant or immunogenic fragment thereof then the polypeptide, nucleic acid, vector or composition of the invention and medicaments involving these will be based on SEQ ID NO. A or a variant or immunogenic fragment thereof.

Suitably the immune response comprises CD8+ T-cell, a CD4+ T-cell and/or an antibody response, particularly CD8+ cytolytic T-cell response and a CD4+ helper T-cell response.

Suitably the immune response is raised against a tumor, particularly one expressing a sequence selected from SEQ ID NOs. 1-10 and variants thereof and immunogenic fragments thereof.

In a preferred embodiment, the tumor is a melanoma tumor e.g. a cutaneous melanoma tumor.

The tumor may be a primary tumor or a metastatic tumor. Further aspects of the invention relate to a method of treating a human patient suffering from cancer wherein the cells of the cancer express a sequence selected from SEQ ID NOs. 1-10 and immunogenic fragments and variants of any one thereof, or of preventing a human from suffering from cancer which cancer would express a sequence selected from SEQ ID NOs. 1-10 and immunogenic fragments and variants of any one thereof, which method comprises administering to said human a corresponding polypeptide, nucleic acid, vector or composition of the invention.

The present invention also provides a polypeptide, nucleic acid, vector or composition of the invention for use in treating or preventing cancer in a human, wherein the cells of the cancer express a corresponding sequence selected from SEQ ID NOs. 1-10 and immunogenic fragments of any one thereof.

Transcripts corresponding to SEQ ID NOs. 33, 35, 36 and 40 were also overexpressed in uveal melanoma. Consequently, in an alternative embodiment, the tumor is a uveal melanoma tumor and/or the tumor expresses a sequence selected from SEQ ID NOs. 1, 3, 4, 5 and 10.

Thus, the invention provides a method or a polypeptide, nucleic acid, vector or composition for use according to the invention wherein the polypeptide comprises a sequence selected from:

(a) the sequence of any one of SEQ ID NOs. 1, 3, 4, 5 and 10; and (b) a variant of the sequences of (a); and (c) an immunogenic fragment of the sequences of (a).

and for example the polypeptide comprises or consists of a sequence selected from any one of SEQ ID NOs. 11-14, 17-18, 19, 20-22, 30-32, 51-57, 67-74 and 76-77 and for example the nucleic acid comprises or consists of a sequence selected from any one of SEQ ID NOs. 33, 35, 36 or 40 or selected from any one of 41, 43, 44, 45 and 50;

and wherein the cancer is uveal melanoma.

The words "prevention" and "prophylaxis" are used interchangeably herein.

Treatment and Vaccination Regimes

A therapeutic regimen may involve either simultaneous (such as co-administration) or sequential (such as a prime-boost) delivery of (i) a polypeptide, nucleic acid or vector of the invention with (ii) one or more further polypeptides, nucleic acids or vectors of the invention and/or (iii) a further component such as a variety of other therapeutically useful compounds or molecules such as antigenic proteins optionally simultaneously administered with adjuvant. Examples of co-administration include homo-lateral co-administration and contra-lateral co-administration. "Simultaneous" administration suitably refers to all components being delivered during the same round of treatment. Suitably all components are administered at the same time (such as simultaneous administration of both DNA and protein), however, one component could be administered within a few minutes (for example, at the same medical appointment or doctor's visit) or within a few hours.

In some embodiments, a "priming" or first administration of a polypeptide, nucleic acid or vector of the invention, is followed by one or more "boosting" or subsequent administrations of a polypeptide, nucleic acid or vector of the invention ("prime and boost" method). In one embodiment the polypeptide, nucleic acid or vector of the invention is used in a prime-boost vaccination regimen. In an embodiment both the prime and boost are of a polypeptide of the invention, the same polypeptide of the invention in each case. In an embodiment both the prime and boost are of a nucleic acid or vector of the invention, the same nucleic acid or vector of the invention in each case. Alternatively, the prime may be performed using a nucleic acid or vector of the invention and the boost performed using a polypeptide of the invention or the prime may be performed using a polypeptide of the invention and the boost performed using a nucleic acid or vector of the invention. Usually the first or "priming" administration and the second or "boosting" administration are given about 1-12 weeks later, or up to 4-6 months later. Subsequent "booster" administrations may be given as frequently as every 1-6 weeks or may be given much later (up to years later).

Antigen Combinations

The polypeptides, nucleic acids or vectors of the invention can be used in combination with one or more other polypeptides or nucleic acids, vectors of the invention and/or with other antigenic polypeptides (or polynucleotides or vectors encoding them) which cause an immune response to be raised against melanoma e.g. cutaneous or uveal melanoma. These other antigenic polypeptides could be derived from diverse sources, they could include well-described melanoma-associated antigens, such as GPR143, PRAME, MAGE-A3 or pMel (gp100). Alternatively they could include other types of melanoma antigens, including patient-specific neoantigens (Lauss et al. (2017). Nature Communications, 8(1), 1738. http://doi.org/10.1038/s41467-017-01460-0), retained-intron neoantigens (Smart et al. (2018). Nature Biotechnology. http://doi.org/10.1038/nbt.4239), spliced variant neoantigens (Hoyos et al., Cancer Cell, 34(2), 181-183. http://doi.org/10.1016/j.cell.2018.07.008; Kahles et al. (2018). Cancer Cell, 34(2), 211-224. e6. http://doi.org/10.1016/j.ccell.2018.07.001), melanoma antigens that fit within the category known as antigens encoding T-cell epitopes associated with impaired peptide processing (TIEPPs; Gigoux, M., & Wolchok, J. (2018). JEM, 215, 2233, Marijt et al. (2018). JEM 215, 2325), or to-be discovered neoantigens (including CLT antigens). In addition, the antigenic peptides from these various sources could also be combined with (i) non-specific immunostimulant/adjuvant species and/or (ii) an antigen, e.g. comprising universal CD4 helper epitopes, known to elicit strong CD4 helper T-cells (delivered as a polypeptides, or as polynucleotides or vectors encoding these CD4 antigens), to amplify the anti-melanoma-specific responses elicited by co-administered antigens.

Different polypeptides, nucleic acids or vectors may be formulated in the same formulation or in separate formulations. Alternatively, polypeptides may be provided as fusion proteins in which a polypeptide of the invention is fused to a second or further polypeptide (see below).

Nucleic acids may be provided which encode the aforementioned fusion proteins.

More generally, when two or more components are utilised in combination, the components could be presented, for example:

(1) as two or more individual antigenic polypeptide components;
(2) as a fusion protein comprising both (or further) polypeptide components;
(3) as one or more polypeptide and one or more polynucleotide component;
(4) as two or more individual polynucleotide components;
(5) as a single polynucleotide encoding two or more individual polypeptide components; or
(6) as a single polynucleotide encoding a fusion protein comprising both (or further) polypeptide components.

For convenience, it is often desirable that when a number of components are present they are contained within a single fusion protein or a polynucleotide encoding a single fusion protein (see below). In one embodiment of the invention all components are provided as polypeptides (e.g., within a single fusion protein). In an alternative embodiment of the invention all components are provided as polynucleotides (e.g., a single polynucleotide, such as one encoding a single fusion protein).

Fusion Proteins (Fusion Polypeptides)

As an embodiment of the above discussion of antigen combinations, the invention also provides an isolated polypeptide according to the invention fused to a second or further polypeptide of the invention (herein after a "combination polypeptide of the invention"), by creating nucleic acid constructs that fuse together the sequences encoding the individual antigens. Combination polypeptides of the invention are expected to have the utilities described herein for polypeptides of the invention, and may have the advantage of superior immunogenic or vaccine activity or prophylactic or therapeutic effect (including increasing the breadth and depth of responses), and may be especially valuable in an outbred population. Fusions of polypeptides of the invention may also provide the benefit of increasing the efficiency of construction and manufacture of vaccine antigens and/or vectored vaccines (including nucleic acid vaccines).

As described above in the Antigen Combinations section, polypeptides of the invention and combination polypeptides of the invention may also be fused to polypeptide sequences which are not polypeptides of the invention, including one or more of:

(a) other polypeptides which are melanoma associated antigens and thus potentially useful as immunogenic sequences in a vaccine (e.g., GPR143, PRAME, MAGE-A3 and pMel (gp100) referred to supra); and
(b) polypeptide sequences which are capable of enhancing an immune response (i.e. immunostimulant sequences).
(c) Polypeptide sequences, e.g. comprising universal CD4 helper epitopes, which are capable of providing strong CD4+ help to increase CD8+ T-cell responses to CLT antigen epitopes.

Exemplary fusion polypeptides comprises two or more (e.g. two, three or four) sequences selected from the sequences of SEQ ID NOs. 1, 2, 3 and 4; or, in respect of each of the said sequences, a variant of the sequence or an immunogenic fragment of the sequence.

An exemplary fusion polypeptide comprises:

(i) a sequence selected from:
  (a) the sequence of SEQ ID NO. 1; and
  (b) a variant of the sequence of (a); and
  (c) an immunogenic fragment of the sequence of (a) e.g. selected from SEQ ID NOs. 11-14, 55-57 and 73-74; and
(ii) a sequence selected from:
  (a) the sequence of SEQ ID NO. 2; and
  (b) a variant of the sequence of (a); and
  (c) an immunogenic fragment of the sequence of (a) e.g. selected from SEQ ID NOs. 15-16, 58-66, 75 and 78; and
(iii) a sequence selected from:
  (a) the sequence of SEQ ID NO. 3; and
  (b) a variant of the sequence of (a); and
  (c) an immunogenic fragment of the sequence of (a) e.g. selected from SEQ ID NOs. 17-18, 53 and 67-69; and
(iv) a sequence selected from:
  (a) the sequence of SEQ ID NO. 4; and
  (b) a variant of the sequence of (a); and
  (c) an immunogenic fragment of the sequence of (a) e.g. selected from SEQ ID NOs. 19, 51-52, 54, 70-72 and 76-77.

For example the fusion polypeptide comprises the sequences of SEQ ID NOs. 1, 2, 3 and 4.

Another exemplary fusion polypeptide comprises:
(i) a sequence selected from:
(a) the sequence of SEQ ID NO. 1; and
(b) a variant of the sequence of (a); and
(c) an immunogenic fragment of the sequence of (a) e.g. selected from SEQ ID NOs. 11-14, 55-57 and 73-74; and
(ii) a sequence selected from:
(a) the sequence of SEQ ID NO. 2; and
(b) a variant of the sequence of (a); and
(c) an immunogenic fragment of the sequence of (a) e.g. selected from SEQ ID NOs. 15-16, 58-66, 75 and 78; and
(iii) a sequence selected from:
(a) the sequence of SEQ ID NO. 4; and
(b) a variant of the sequence of (a); and
(c) an immunogenic fragment of the sequence of (a) e.g. selected from SEQ ID NOs. 19, 51-52, 54, 70-72 and 76-77.

For example the fusion polypeptide comprises the sequences of SEQ ID NOs. 1, 2 and 4.

The invention also provides nucleic acids encoding the aforementioned fusion polypeptides and other aspects of the invention (vectors, compositions, cells etc) mutatis mutandis as for the polypeptides of the invention.

CLT Antigen-binding Polypeptides

Antigen-binding polypeptides which are immunospecific for tumor-expressed antigens (polypeptides of the invention) may be designed to recruit cytolytic cells to antigen-decorated tumor cells, mediating their destruction. One such mechanism of recruitment of cytolytic cells by antigen-binding polypeptides is known as antibody-dependent cell-mediated cytotoxicity (ADCC). Thus the invention provides an antigen-binding polypeptide which is immunospecific for a polypeptide of the invention. Antigen-binding polypeptides including antibodies such as monoclonal antibodies and fragments thereof e.g., domain antibodies, Fab fragments, Fv fragments, and VHH fragments which may produced in a non-human animal species (e.g., rodent or camelid) and humanised or may be produced in a non-human species (e.g., rodent genetically modified to have a human immune system).

Antigen-binding polypeptides may be produced by methods well known to a skilled person. For example, monoclonal antibodies can be produced using hybridoma technology, by fusing a specific antibody-producing B cell with a myeloma (B cell cancer) cell that is selected for its ability to grow in tissue culture and for an absence of antibody chain synthesis (Köhler and Milstein, 1975, Nature 256(5517): 495-497 and Nelson et al., 2000 (Jun), Mol Pathol. 53(3): 111-7 herein incorporated by reference in their entirety).

A monoclonal antibody directed against a determined antigen can, for example, be obtained by:
a) immortalizing lymphocytes obtained from the peripheral blood of an animal (including a human) previously immunized/exposed with a determined antigen, with an immortal cell and preferably with myeloma cells, in order to form a hybridoma,
b) culturing the immortalized cells (hybridoma) formed and recovering the cells producing the antibodies having the desired specificity.

Monoclonal antibodies can be obtained by a process comprising the steps of:
a) cloning into vectors, especially into phages and more particularly filamentous bacteriophages, DNA or cDNA sequences obtained from lymphocytes especially peripheral blood lymphocytes of an animal (suitably previously immunized with determined antigens),
b) transforming prokaryotic cells with the above vectors in conditions allowing the production of the antibodies,
c) selecting the antibodies by subjecting them to antigen-affinity selection,
d) recovering the antibodies having the desired specificity
e) expressing antibody-encoding nucleic acid molecules obtained from B cells of patients exposed to antigens, or animals experimentally immunized with antigens.

The selected antibodies may then be produced using conventional recombinant protein production technology (e.g., from genetically engineered CHO cells).

The invention provides an isolated antigen-binding polypeptide which is immunospecific for a polypeptide of the invention. Suitably, the antigen-binding polypeptide is a monoclonal antibody or a fragment thereof.

In certain embodiments, the antigen-binding polypeptide is coupled to a cytotoxic moiety. Example cytotoxic moieties include the Fc domain of an antibody, which will recruit Fc receptor-bearing cells facilitating ADCC. Alternatively, the antigen-binding polypeptide may be linked to a biological toxin, or a cytotoxic chemical.

Another important class of antigen-binding polypeptides include T-cell receptor (TCR)-derived molecules that bind to HLA-displayed fragments of the antigens of this invention. In this embodiment, TCR-based biologicals (including TCRs derived directly from patients, or specifically manipulated, high-affinity TCRs) that recognize CLT antigens (or derivatives thereof) on the surface of tumor cells may also include a targeting moiety which recognizes a component on a T-cell (or another class of immune cell) that attract these immune cells to tumors, providing therapeutic benefit. In some embodiments, the targeting moiety may also stimulate beneficial activities (including cytolytic activities) of the redirected immune cells.

Thus, in an embodiment, the antigen-binding polypeptide is immunospecific for an HLA-bound polypeptide that is or is part of a polypeptide of the invention. For example, the antigen-binding polypeptide is a T-cell receptor.

In an embodiment, an antigen-binding polypeptide of the invention may be coupled to another polypeptide that is capable of binding to cytotoxic cells or other immune components in a subject.

In an embodiment, the antigen-binding polypeptide is for use in medicine.

In an embodiment, there is provided a pharmaceutical composition comprising an antigen-binding polypeptide of the invention together with a pharmaceutically acceptable carrier. Such a composition may be a sterile composition suitable for parenteral administration. See e.g., disclosure of pharmaceutical compositions supra.

There is provided by the invention a method of treating a human suffering from cancer wherein the cells of the cancer express a sequence selected from SEQ ID NOs. 1-10 and immunogenic fragments and variants of any one thereof, or of preventing a human from suffering from cancer wherein the cells of the cancer would express a sequence selected from SEQ ID NOs. 1-10 and immunogenic fragments and variants of any one thereof, which comprises administering to said human an antigen-binding polypeptide or composition comprising said antigen-binding polypeptide of the invention.

In an embodiment, there is provided an antigen-binding polypeptide of the invention, which may be coupled to a cytotoxic moiety, or composition comprising said antigen-binding polypeptide of the invention for use in treating or preventing cancer in a human, wherein the cells of the cancer express a corresponding sequence selected from SEQ ID NOs. 1-10 and immunogenic fragments of any one thereof.

Suitably in any of the above embodiments, the cancer is melanoma particularly cutaneous melanoma.

In an embodiment, there is provided a method or an antigen-binding polypeptide or composition for use according to the invention wherein the polypeptide comprises a sequence selected from:

(a) the sequence of any one of SEQ ID NOs. 1, 3, 4, 5 and 10; and (b) a variant of the sequences of (a); and (c) an immunogenic fragment of the sequences of (a).

and for example the polypeptide comprises or consists of a sequence selected from any one of SEQ ID NOs. 11-14, 17-18, 19, 20-22, 30-32, 51-57, 67-74 and 76-77 and for example the nucleic acid comprises or consists of a sequence selected from any one of SEQ ID NOs. 33, 35, 36 or 40 or selected from any one of 41, 43, 44, 45 and 50;

and wherein the cancer is uveal melanoma.

Antigen-binding polypeptides (such as antibodies or fragments thereof may be administered at a dose of e.g. 5-1000 mg e.g. 25-500 mg e.g. 100-300 mg e.g. ca. 200 mg.

Cell Therapies to Facilitate Antigen Presentation In Vivo

Any of a variety of cellular delivery vehicles may be employed within pharmaceutical compositions to facilitate production of an antigen-specific immune response. Thus the invention provides a cell which is an isolated antigen presenting cell modified by ex vivo loading with a polypeptide of the invention or genetically engineered to express the polypeptide of the invention (herein after referred to as a "APC of the invention"). Antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T-cell response and/or to be immunologically compatible with the receiver (i.e., matched HLA haplotype). APCs may generally be isolated from any of a variety of biological fluids and organs, and may be autologous, allogeneic, syngeneic or xenogeneic cells.

Certain preferred embodiments of the present invention use dendritic cells or progenitors thereof as APCs. Thus, in an embodiment, the APC of the invention is a dendritic cell. Dendritic cells are highly potent APCs (Banchereau & Steinman, 1998, *Nature,* 392:245-251) and have been shown to be effective as a physiological adjuvant for eliciting prophylactic or therapeutic immunity (see Timmerman & Levy, 1999, *Ann. Rev. Med.* 50:507-529). In general, dendritic cells may be identified based on their typical shape (stellate in situ, with marked cytoplasmic processes (dendrites) visible in vitro), their ability to take up, process and present antigens with high efficiency and their ability to activate naïve T-cell responses. Dendritic cells may, of course be engineered to express specific cell-surface receptors or ligands that are not commonly found on dendritic cells in vivo or ex vivo, and such modified dendritic cells are contemplated by the present invention. As an alternative to dendritic cells, antigen-loaded secreted vesicles (called exosomes) may be used within an immunogenic composition (see Zitvogel et al., 1998, *Nature Med.* 4:594-600). Thus, in an embodiment, there is provided an exosome loaded with a polypeptide of the invention.

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34-positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorised as "immature" and "mature" cells, which allows a simple way to discriminate between two well-characterised phenotypes. However, this nomenclature should not be construed to exclude all possible intermediate stages of differentiation. Immature dendritic cells are characterised as APCs with a high capacity for antigen uptake and processing, which correlates with the high expression of Fcγ receptor and mannose receptor. The mature phenotype is typically characterized by a lower expression of these markers, but a high expression of cell surface molecules responsible for T-cell activation such as class I and class II MHC, adhesion molecules (e.g., CD54 and CD11) and costimulatory molecules (e.g., CD40, CD80, CD86 and 4-1 BB).

APCs may also be genetically engineered e.g., transfected with a polynucleotide encoding a protein (or portion or other variant thereof) such that the polypeptide is expressed on the cell surface. Such transfection may take place ex vivo, and a pharmaceutical composition comprising such transfected cells may then be used, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., 1997, *Immunology* and *Cell Biology* 75:456-460. Antigen loading of dendritic cells may be achieved by incubating dendritic cells or progenitor cells with the polypeptide, DNA (e.g., a plasmid vector) or RNA; or with antigen-expressing recombinant bacteria or viruses (e.g., an adenovirus, adeno-associated virus (AAV) (e.g., AAV type 5 and type 2), alphavirus (e.g., Venezuelan equine encephalitis virus (VEEV), Sindbis virus (SIN), Semliki Forest virus (SFV), herpes virus, arenavirus (e.g., lymphocytic choriomeningitis virus (LCMV)), measles virus, poxvirus (such as modified vaccinia Ankara (MVA) or fowlpox), paramyxovirus, lentivirus, or rhabdovirus (such as vesicular stomatitis virus (VSV)). Prior to polypeptide loading, the polypeptides may be covalently conjugated to an immunological partner that provides T-cell help (e.g., a carrier molecule). Alternatively, a dendritic cell may be pulsed with a non-conjugated immunological partner, separately or in the presence of the polypeptide or vector.

The invention provides for delivery of specifically designed short, chemically synthesized epitope-encoded fragments of polypeptide antigens to antigen presenting cells. Those skilled in the art will realize that these types of molecules, also known as synthetic long peptides (SLPs) provide a therapeutic platform for using the antigenic polypeptides of this invention to stimulate (or load) cells in vitro (Gornati et al., 2018, Front. Imm, 9:1484), or as a method of introducing polypeptide antigen into antigen-presenting cells in vivo (Melief & van der Burg, 2008, Nat Rev Cancer, 8:351-60).

In an embodiment, there is provided a pharmaceutical composition comprising an antigen-presenting cell of the invention, which is suitably a dendritic cell, together with a pharmaceutically acceptable carrier. Such a composition may be a sterile composition suitable for parenteral administration. See e.g., disclosure of pharmaceutical compositions supra.

In an embodiment, there is provided an antigen-presenting cell of the invention, which is suitably a dendritic cell, for use in medicine.

There is also provided a method of treating a human suffering from cancer wherein the cells of the cancer express a sequence selected from SEQ ID NOs. 1-10 and immunogenic fragments and variants of any one thereof, or of preventing a human from suffering from cancer wherein the cells of the cancer would express a sequence selected from SEQ ID NOs. 1-10 and immunogenic fragments and variants of any one thereof, which comprises administering to said human said antigen presenting cell of the invention, which is suitably a dendritic cell, or composition comprising said antigen presenting cell of the invention.

In an embodiment, there is provided an antigen presenting cell of the invention, which is suitably a dendritic cell, or composition comprising said antigen presenting cell of the invention for use in treating or preventing cancer in a human, wherein the cells of the cancer express a corresponding sequence selected from SEQ ID NOs. 1-10 and immunogenic fragments of any one thereof.

In an embodiment, there is provided a pharmaceutical composition comprising an exosome of the invention together with a pharmaceutically acceptable carrier. Such a composition may be a sterile composition suitable for parenteral administration. See e.g., disclosure of pharmaceutical compositions supra. Compositions may optionally comprise immunostimulants—see disclosure of immunostimulants supra.

In an embodiment, there is provided an exosome of the invention for use in medicine.

There is also provided a method of treating a human suffering from cancer wherein the cells of the cancer express a sequence selected from SEQ ID NOs. 1-10 and immunogenic fragments and variants of any one thereof, or of preventing a human from suffering from cancer wherein the cells of the cancer would express a sequence selected from SEQ ID NOs. 1-10 and immunogenic fragments and variants of any one thereof, which comprises administering to said human said exosome if the invention or composition comprising said exosome of the invention.

In an embodiment, there is provided an exosome of the invention or composition comprising said exosome of the invention for use in treating or preventing cancer in a human, wherein the cells of the cancer express a corresponding sequence selected from SEQ ID NOs. 1-10 and immunogenic fragments of any one thereof. In any one of the above embodiments, suitably the cancer is melanoma particularly cutaneous melanoma.

Stimulated T-cell Therapies

In addition to in vivo or ex vivo APC-mediated production of T-cells immunospecific for polypeptides of the invention, autologous or non-autologous T-cells may be isolated from a subject, e.g., from peripheral blood, umbilical cord blood and/or by apheresis, and stimulated in the presence of a tumor-associated antigens which are loaded onto MHC molecules (signal 1) of APC cells, to induce proliferation of T-cells with a TCR immunospecific for this antigen.

Successful T-cell activation requires the binding of the costimulatory surface molecules B7 and CD28 on antigen-presenting cells and T-cells, respectively (signal 2). To achieve optimal T-cell activation, both signals 1 and 2 are required. Conversely, antigenic peptide stimulation (signal 1) in the absence of costimulation (signal 2) cannot induce full T-cell activation, and may result in T-cell tolerance. In addition to costimulatory molecules, there are also inhibitory molecules, such as CTLA-4 and PD-1, which induce signals to prevent T-cell activation.

Autologous or non-autologous T-cells may therefore be stimulated in the presence of a polypeptide of the invention, and expanded and transferred back to the patient at risk of or suffering from cancer whose cancer cells express a corresponding polypeptide of the invention provided that the antigen-specific TCRs will recognize the antigen presented by the patient's MHC, where they will target and induce the killing of cells of said cancer which express said corresponding polypeptide.

In an embodiment, there is provided a polypeptide, nucleic acid, vector or composition of the invention for use in the ex vivo stimulation and/or amplification of T-cells derived from a human suffering from cancer, for subsequent reintroduction of said stimulated and/or amplified T-cells into the said human for the treatment of the said cancer in the said human.

The invention provides a method of treatment of cancer in a human, wherein the cells of the cancer express a sequence selected from SEQ ID NOs. 1-10 and immunogenic fragments and variants of any one thereof, which comprises taking from said human a population of white blood cells comprising at least T-cells optionally with antigen-presenting cells, stimulating and/or amplifying said T-cells in the presence of a corresponding polypeptide, nucleic acid, vector or composition of the invention, and reintroducing some or all of said white blood cells comprising at least stimulated and/or amplified T-cells into the human.

In any one of the above embodiments, suitably the cancer is melanoma particularly cutaneous melanoma.

In an embodiment, there is provided a process for preparing a T-cell population which is cytotoxic for cancer cells which express a sequence selected from SEQ ID NOs. 1-10 and immunogenic fragments and variants of any one thereof which comprises (a) obtaining T-cells and antigen-presenting cells from a cancer patient and (ii) stimulating and amplifying the T-cell population ex vivo with a corresponding polypeptide, nucleic acid, vector or composition of the invention.

By "corresponding" in this context is meant that if the cancer cells express, say, SEQ ID NO. A (A being one of SEQ ID NOs. 1-10) or a variant or immunogenic fragment thereof then the T-cell population is stimulated and amplified ex vivo with SEQ ID NO. A or a variant or immunogenic fragment thereof in the form of a polypeptide, nucleic acid or vector, or a composition containing one of the foregoing.

For example, in such processes, the culturing and expanding is performed in the presence of dendritic cells. The dendritic cells may be transfected with a nucleic acid molecule or with a vector of the invention and express a polypeptide of the invention.

The invention provides a T-cell population obtainable by any of the aforementioned processes (hereinafter a T-cell population of the invention).

In an embodiment, there is provided a cell which is a T-cell which has been stimulated with a polypeptide, nucleic acid, vector or composition of the invention (hereinafter a T-cell of the invention).

In an embodiment, there is provided a pharmaceutical composition comprising a T-cell population or a T-cell of the invention together with a pharmaceutically acceptable carrier. Such a composition may, for example, be a sterile composition suitable for parenteral administration.

In an embodiment, there is provided a T-cell population or T-cell of the invention for use in medicine.

There is also provided a method of treating a human suffering from cancer wherein the cells of the cancer express a sequence selected from SEQ ID NOs. 1-10 and immunogenic fragments and variants of any one thereof, or of preventing a human from suffering from cancer wherein the cells of the cancer would express a sequence selected from SEQ ID NOs. 1-10 and immunogenic fragments and variants of any one thereof, which comprises administering to said human said T-cell population or T-cell of the invention or composition comprising said T-cell population or T-cell of the invention.

In an embodiment, there is provided a T-cell population of the invention, T-cell of the invention or composition comprising said T-cell population or T-cell of the invention for use in treating or preventing cancer in a human, wherein the cells of the cancer express a corresponding sequence selected from SEQ ID NOs. 1-10 and immunogenic fragments of any one thereof. In any one of the above embodiments, suitably the cancer is melanoma particularly cutaneous melanoma.

In an embodiment, there is provided a process, a method or a T-cell population, T-cell, antigen presenting cell, exosome or composition for use according to the invention wherein the polypeptide comprises a sequence selected from:

(a) the sequence of any one of SEQ ID NOs. 1, 3, 4, 5 and 10; and
(b) a variant of the sequences of (a); and
(c) an immunogenic fragment of the sequences of (a).

and for example the polypeptide comprises or consists of a sequence selected from any one of SEQ ID NOs. 11-14, 17-18, 19, 20-22, 30-32, 51-57, 67-74 and 76-77 and for example the nucleic acid comprises or consists of a sequence selected from any one of SEQ ID NOs. 33, 35, 36 or 40 or selected from any one of 41, 43, 44, 45 and 50;

and wherein the cancer is uveal melanoma.

Engineered Immune Cell Therapies

Derivatives of all types of CLT antigen-binding polypeptides described above, including TCRs or TCR mimetics (see Dubrovsky et al., 2016, Oncoimmunology) that recognize CLT antigen-derived peptides complexed to human HLA molecules, may be engineered to be expressed on the surface of T-cells (autologous or non-autologous), which can then be administered as adoptive T-cell therapies to treat cancer.

These derivatives fit within the category of "chimeric antigen receptors (CARs)," which, as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T-cell, thereby allowing a large number of specific T-cells to be generated, for example, for use in adoptive cell therapy. CARs may direct specificity of the cell to a tumor associated antigen, a polypeptide of the invention, wherein the polypeptide is HLA-bound.

Another approach to treating cancer in a patient is to genetically modify T-cells to target antigens expressed on tumor cells, via the expression of chimeric antigen receptors (CARs). This technology is reviewed in Wendell & June, 2017, Cell, 168: 724-740 (incorporated by reference in its entirety).

Such CAR T-cells may be produced by the method of obtaining a sample of cells from the subject, e.g., from peripheral blood, umbilical cord blood and/or by apheresis, wherein said sample comprises T-cells or T-cell progenitors, and transfecting said cells with a nucleic acid encoding a chimeric T-cell receptor (CAR) which is immunospecific for the polypeptide of the invention, wherein the polypeptide is HLA-bound. Such nucleic acid will be capable of integration into the genome of the cells, and the cells may be administered in an effective amount the subject to provide a T-cell response against cells expressing a polypeptide of the invention. For example, the sample of cells from the subject may be collected.

It is understood that cells used to produce said CAR-expressing T-cells may be autologous or non-autologous.

Transgenic CAR-expressing T-cells may have expression of an endogenous T-cell receptor and/or endogenous HLA inactivated. For example, the cells may be engineered to eliminate expression of endogenous alpha/beta T-cell receptor (TCR).

Methods of transfecting of cells are well known in the art, but highly efficient transfection methods such as electroporation may be employed. For example, nucleic acids or vectors of the invention expressing the CAR constructs may be introduced into cells using a nucleofection apparatus.

The cell population for CAR-expressing T-cells may be enriched after transfection of the cells. For example, the cells expressing the CAR may be sorted from those which do not (e.g., via FACS) by use of an antigen bound by the CAR or a CAR-binding antibody. Alternatively, the enrichment step comprises depletion of the non T-cells or depletion of cells that lack CAR expression. For example, CD56+ cells can be depleted from a culture population.

The population of transgenic CAR-expressing cells may be cultured ex vivo in a medium that selectively enhances proliferation of CAR-expressing T-cells. Therefore, the CAR-expressing T-cell may be expanded ex vivo.

A sample of CAR cells may be preserved (or maintained in culture). For example, a sample may be cryopreserved for later expansion or analysis.

CAR-expressing T-cells may be employed in combination with other therapeutics, for example checkpoint inhibitors including PD-L1 antagonists.

In an embodiment, there is provided a cytotoxic cell that has been engineered to express any of the above antigen-binding polypeptides on its surface. Suitably, the cytotoxic cell is a T-cell.

In an embodiment, there is provided a cytotoxic cell, which is suitably a T-cell, engineered to express any of the above antigen-binding polypeptides on its surface, for use in medicine The invention provides a pharmaceutical composition comprising a cytotoxic cell of the invention, which is suitably a T-cell.

There is provided a method of treating a human patient suffering from cancer wherein the cells of the cancer express a sequence selected from SEQ ID NOs. 1-10 and immunogenic fragments and variants of any one thereof, or of preventing a human from suffering from cancer which cancer would express a sequence selected from SEQ ID NOs. 1-10 and immunogenic fragments and variants of any one thereof, which method comprises administering to said human a cytotoxic cell of the invention, which is suitably a T-cell.

In an embodiment the cytotoxic cell of the invention, which is suitably a T-cell, is for use in treating or preventing cancer in a human, wherein the cells of the cancer express a corresponding sequence selected from SEQ ID NOs. 1-10 and immunogenic fragments of any one thereof.

Combination Therapies

Methods of treating cancer according to the invention may be performed in combination with other therapies, especially checkpoint inhibitors and interferons.

The polypeptides, nucleic acids, vectors, antigen-binding polypeptide and adoptive cell therapies (APC and T-cell-based) can be used in combination with other components designed to enhance their immunogenicity, for example, to improve the magnitude and/or breadth of the elicited immune response, or provide other activities (e.g., activation of other aspects of the innate or adaptive immune response, or destruction of tumor cells).

Accordingly, the invention provides a composition of the invention (i.e. an immunogenic, vaccine or pharmaceutical composition) or a kit of several such compositions comprising a polypeptide, nucleic acid or vector of the invention together with a pharmaceutically acceptable carrier; and (i) one or more further immunogenic or immunostimulant polypeptides (e.g., interferons, IL-12, checkpoint blockade molecules or nucleic acids encoding such, or vectors comprising such nucleic acids), (ii) small molecules (e.g., HDAC inhibitors or other drugs that modify the epigenetic profile of cancer cells) or biologicals (delivered as polypeptides or nucleic acids encoding such, or vectors comprising such nucleic acids) that will enhance the translation and/or presentation of the polypeptide products that are the subject of this invention.

Checkpoint inhibitors, which block normal proteins on cancer cells, or the proteins on the T-cells that respond to them, may be a particularly important class of drugs to combine with CLT-antigen based therapies, since these inhibitors seek to overcome one of cancer's main defences against an immune system attack.

Thus, an aspect of the invention includes administering a polypeptide, nucleic acid, vector, antigen-binding polypeptide, composition, T-cell, T-cell population, or antigen presenting cell of the present invention in combination with a checkpoint inhibitor. Example check point inhibitors are selected from PD-1 inhibitors, such as pembrolizumab, (Keytruda) and nivolumab (Opdivo), PD-L1 inhibitors, such as atezolizumab (Tecentriq), avelumab (Bavencio) and durvalumab (Imfinzi) and CTLA-4 inhibitors such as ipilimumab (Yervoy).

Interferons (e.g., alpha, beta and gamma) are a family of proteins the body makes in very small amounts. Interferons may slow down or stop the cancer cells dividing, reduce the ability of the cancer cells to protect themselves from the immune system and/or enhance multiple aspects of the adaptive immune system. Interferons are typically administered as a subcutaneous injection in, for example the thigh or abdomen.

Thus, an aspect of the invention includes administering a polypeptide, nucleic acid, vector, antigen-binding polypeptide or composition of the present invention in combination with interferon e.g., interferon alpha.

Different modes of the invention may also be combined, for example polypeptides, nucleic acids and vectors of the invention may be combined with an APC, a T-cell or a T-cell population of the invention (discussed infra).

One or more modes of the invention may also be combined with conventional anti-cancer chemotherapy and/or radiation.

Diagnostics

In another aspect, the invention provides methods for using one or more of the polypeptides or nucleic acid of the invention to diagnose cancer, particularly melanoma e.g. cutaneous melanoma, or to diagnose human subjects suitable for treatment by polypeptides, nucleic acids, vectors, antigen-binding polypeptides, adoptive cell therapies, or compositions of the invention.

Thus the invention provides a method of diagnosing that a human suffering from cancer, comprising the steps of: determining if the cells of said cancer express a polypeptide sequence selected from SEQ ID NOs. 1-10 and immunogenic fragments or variants of any one thereof (e.g. selected from the sequences of SEQ ID NOs. 11-32 and 51-78); or a nucleic acid encoding said polypeptide sequence (e.g. selected from the sequences of SEQ ID NOs. 33-40 and SEQ ID NOs. 41-50), and diagnosing said human as suffering from cancer if said polypeptide or corresponding nucleic acid is overexpressed in said cancer cells.

The invention provides a method of diagnosing that a human suffering from cancer which is cutaneous melanoma, comprising the steps of: determining if the cells of said cancer express a polypeptide sequence selected from SEQ ID NO. 2, 6, 7, 8 and 9 and immunogenic fragments or variants thereof; or a nucleic acid encoding said polypeptide sequence, and diagnosing said human as suffering from cancer which is cutaneous melanoma if said polypeptide or corresponding nucleic acid is overexpressed in said cancer cells.

As used herein, "overexpressed" in cancer cells means that the level of expression in cancer cells is higher than in normal cells.

The invention provides a method of diagnosing that a human suffering from cancer which is cutaneous melanoma or uveal melanoma, comprising the steps of: determining if the cells of said cancer express a polypeptide sequence selected from SEQ ID Nos. 1, 3, 4, 5 and 10 and immunogenic fragments or variants of any one thereof; or a nucleic acid encoding said polypeptide sequence, and diagnosing said human as suffering from cancer which is cutaneous melanoma or uveal melanoma if said polypeptide or corresponding nucleic acid is overexpressed in said cancer cells.

The overexpression can be determined by reference to the level of the nucleic acid or polypeptide of the invention in a control human subject known not to have the cancer. Thus overexpression indicates that the nucleic acid or polypeptide of the invention is detected at a significantly higher level (e.g., a level which is 30%, 50%, 100% or 500% higher) in the test subject than in the control subject. In case the control human subject has an undetectable level of the nucleic acid or polypeptide of the invention, then the diagnosis can be arrived at by detecting the nucleic acid or polypeptide of the invention.

The invention also provides a method of treating a human suffering from cancer, comprising the steps of:

(a) determining if the cells of said cancer express a polypeptide sequence selected from SEQ ID NOs. 1-10 and immunogenic fragments or variants of any one thereof (e.g. selected from the sequences of SEQ ID NOs. 11-32 and 51-78) or a nucleic acid encoding said polypeptide (e.g. selected from the sequences of SEQ ID NOs. 33-40 and 41-50); and if so administering to said human a corresponding polypeptide, nucleic acid, vector, composition, T-cell population, T-cell, antigen presenting cell, antigen-binding polypeptide or cytotoxic cell of the invention.

There is also provided use of a polypeptide comprising a sequence selected from:

(a) the sequence of any one of SEQ ID NOs. 1-10; or (b) a variant of the sequences of (a); and (c) an immunogenic fragment of the sequences of (a) isolated from the tumor of a human suffering from cancer, or use of a nucleic acid encoding said polypeptide, as a biomarker for the determination of whether said human would be suitable for treatment by a vaccine comprising a corresponding polypeptide, nucleic acid, vector, composition, T-cell population, T-cell, antigen presenting cell, antigen-binding polypeptide or cytotoxic cell of the invention.

Suitably, the cancer is melanoma particularly cutaneous melanoma.

The invention also provides a method or use according to the invention wherein the polypeptide comprises a sequence selected from:

(a) the sequence of any one of SEQ ID NOs. 1, 3, 4, 5 and 10; and (b) a variant of the sequences of (a); and (c) an immunogenic fragment of the sequences of (a).

and for example the polypeptide comprises or consists of a sequence selected from any one of SEQ ID NOs. 11-14, 17-18, 19, 20-22, 30-32, 51-57, 67-74 and 76-77 and for example the nucleic acid comprises or consists of a sequence selected from any one of SEQ ID NOs. 33, 35, 36 or 40 or selected from any one of 41, 43, 44, 45 and 50;

and wherein the cancer is uveal melanoma.

Suitably the polypeptide of the invention has a sequence selected from SEQ Id NOs. 1-10 or a fragment thereof, such as an immunogenic fragment thereof (e.g. selected from the sequences of SEQ ID NOs. 11-32 and 51-78).

Suitably the nucleic acid of the invention has or comprises a sequence selected from any one of SEQ ID NOs.33-40 or 41-50 or a fragment thereof, such as an immunogenic fragment thereof.

Kits for detecting the presence of nucleic acids are well known. For example, kits comprising at least two oligonucleotides which hybridise to a polynucleotide may be used within a real-time PCR (RT-PCR) reaction to allow the detection and semi-quantification of specific nucleic acids. Such kits may allow the detection of PCR products by the generation of a fluorescent signal as a result of Forster Resonance Energy Transfer (FRET) (for example TaqMan® kits), or upon binding of double stranded DNA (for example, SYBR® Green kits). Some kits (for example, those containing TaqMan® probes which span the exons of the target DNA) allow the detection and quantification of mRNA, for example transcripts encoding nucleic acids of the invention. Assays using certain kits may be set up in a multiplex format to detect multiple nucleic acids simultaneously within a reaction. Kits for the detection of active DNA (namely DNA that carries specific epigenetic signatures indicative of expression) may also be used. Additional components that may be present within such kits include a diagnostic reagent or reporter to facilitate the detection of a nucleic acid of the invention.

Nucleic acids of the invention may also be detected via liquid biopsy, using a sample of blood from a patient. Such a procedure provides a non-invasive alternative to surgical biopsies. Plasma from such blood samples may be isolated and analysed for the presence of nucleic acids of the invention.

Polypeptides of the invention may be detected by means of antigen-specific antibodies in an ELISA type assay to detect polypeptides of the invention in homogenized preparations of patient tumor samples. Alternatively, polypeptides of the invention may be detected by means of immunohistochemical analyses, which identify the presence of the polypeptide antigens by using light microscopy to inspect sections of patient tumor samples that have been stained by using appropriately labeled antibody preparations. As a further alternative, polypeptides of the invention may be detected by means of immunohistochemical analyses, which identify the presence of the polypeptide antigens by using light microscopy to inspect sections of patient tumor samples that have been stained by using appropriately labeled antibody preparations.

Polypeptides of the invention may also be detected by determining whether they are capable of stimulating T-cells raised against the said polypeptide.

Cells of the cancer or tumor e.g., the melanoma e.g. cutaneous melanoma may for example be obtained from a biopsy of the cancer e.g., the melanoma e.g. cutaneous melanoma.

A method of treatment of cancer, particularly melanoma e.g. cutaneous melanoma, in a human comprises (i) detecting the presence of a nucleic acid or polypeptide according to the invention and (ii) administering to the subject a nucleic acid, polypeptide, vector, cell, T-cell or T-cell population or composition according to the invention (and preferably administering the same nucleic acid or polypeptide or fragment thereof that has been detected).

A method of treatment of cancer, particularly melanoma e.g. cutaneous melanoma, in a human also comprises administering to the subject a nucleic acid, polypeptide, vector, cell, T-cell or T-cell population or composition according to the invention, in which subject the presence of a (and preferably the same) nucleic acid or polypeptide according to the invention has been detected.

In particular, the cancer to be diagnosed and if appropriate treated is melanoma e.g. cutaneous melanoma.

Where a polypeptide of the invention of SEQ ID NOs. 1, 3, 4, 5 or 10 or a fragment thereof is detected then the cancer might be cutaneous melanoma or uveal melanoma.

Specific Embodiments

In an embodiment, the CLT antigen polypeptide comprises or consists of SEQ ID NO. 1. Exemplary fragments comprise or consist of any one of SEQ ID NOs. 11-14. Further exemplary fragments comprise two, three or four of SEQ ID NOs. 11-14. Further exemplary fragments comprise or consist of any one of SEQ ID NOs. 55-57 or 73-74. Further exemplary fragments comprise all of SEQ ID NOs. 11-14, 55-57 and 73-74 (allowance being taken for possible sequence overlap so that any overlapping sequence does not need to be present more than once). Exemplary nucleic acids encoding said polypeptide sequence comprise or consists of SEQ ID NO 33 or SEQ ID NO. 41. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma or uveal melanoma. Related methods of diagnosis are also provided.

In an embodiment, the CLT antigen polypeptide comprises or consists of SEQ ID NO. 2. Exemplary fragments comprise or consist of SEQ ID NO. 15 or SEQ ID NO. 16.

Further exemplary fragments comprise SEQ ID NO. 15 and SEQ ID NO. 16. Further exemplary fragments comprise or consist of any one of SEQ ID NOs. 58-66, 75 and 78. Further exemplary fragments comprise all of SEQ ID NOs. 15-16, 58-66, 75 and 78 (allowance being taken for possible sequence overlap so that any overlapping sequence does not need to be present more than once). Exemplary nucleic acids encoding said polypeptide sequence comprise or consists of SEQ ID NO. 34 or SEQ ID NO. 42. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma. Related methods of diagnosis are also provided.

In an embodiment, the CLT antigen polypeptide comprises or consists of SEQ ID NO. 3. Exemplary fragments comprise or consist of SEQ ID NO. 17 or SEQ ID NO. 18. Further exemplary fragments comprise SEQ ID NO. 17 and SEQ ID NO. 18. Further exemplary fragments comprise or consist of any one of SEQ ID NOs. 53 and 67-69. Further exemplary fragments comprise SEQ ID NO. 17, SEQ ID NO. 18 and SEQ ID NO. 53. Further exemplary fragments comprise all of SEQ ID NOs. 17-18, 53 and 67-69 (allowance being taken for possible sequence overlap so that any overlapping sequence does not need to be present more than once). Exemplary nucleic acids encoding said polypeptide sequence comprise or consists of SEQ ID NO. 35 or SEQ ID NO. 43. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma or uveal melanoma. Related methods of diagnosis are also provided.

In an embodiment, the CLT antigen polypeptide comprises or consists of SEQ ID NO. 4. Exemplary fragments comprise or consist of SEQ ID NO. 19. Further exemplary fragments comprise or consist of SEQ ID NO. 51 or SEQ ID NO. 52. Further exemplary fragments comprise or consist of SEQ ID NO. 54. Further exemplary fragments comprise or consist of any one of SEQ ID NOs. 70-72 and 76-77. Further exemplary fragments comprise SEQ ID NO. 19 and either SEQ ID NO. 51 or SEQ ID NO. 52. Further exemplary fragments comprise SEQ ID NO. 54 and either SEQ ID NO. 51 or SEQ ID NO. 52. Further exemplary fragments comprise all of SEQ ID NOs. 19, 51-52, 54, 70-72 and 76-77 (allowance being taken for possible sequence overlap so that any overlapping sequence does not need to be present more than once). Exemplary nucleic acids encoding said polypeptide sequence comprise or consists of SEQ ID NO. 35 or SEQ ID NO. 44. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma or uveal melanoma. Related methods of diagnosis are also provided.

In an embodiment, the CLT antigen polypeptide comprises or consists of SEQ ID NO. 5. Exemplary fragments comprise or consist of any one of SEQ ID NOs. 20-22. Exemplary nucleic acids encoding said polypeptide sequence comprise or consists of SEQ ID NO. 36 or SEQ ID NO. 45. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma or uveal melanoma. Related methods of diagnosis are also provided.

In an embodiment, the CLT antigen polypeptide comprises or consists of SEQ ID NO. 6. Exemplary fragments comprise or consist of SEQ ID NO. 23 or SEQ ID NO. 24. Exemplary nucleic acids encoding said polypeptide sequence comprise or consists of SEQ ID NO. 37 or SEQ ID NO. 46. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma. Related methods of diagnosis are also provided.

In an embodiment, the CLT antigen polypeptide comprises or consists of SEQ ID NO. 7. Exemplary fragments comprise or consist of SEQ ID NO. 25. Exemplary nucleic acids encoding said polypeptide sequence comprise or consists of SEQ ID NO. 38 or SEQ ID NO. 47. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma. Related methods of diagnosis are also provided.

In an embodiment, the CLT antigen polypeptide comprises or consists of SEQ ID NO. 8. Exemplary fragments comprise or consist of SEQ ID NO. 26. Exemplary nucleic acids encoding said polypeptide sequence comprise or consists of SEQ ID NO. 38 or SEQ ID NO. 48. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma. Related methods of diagnosis are also provided.

In an embodiment, the CLT antigen polypeptide comprises or consists of SEQ ID NO. 9. Exemplary fragments comprise or consist of any one of SEQ ID NOs. 27-29. Exemplary nucleic acids encoding said polypeptide sequence comprise or consists of SEQ ID NO. 39 or SEQ ID NO. 49. Corresponding nucleic acids (e.g., DNA or RNA), T-cells, T-cell populations, cytotoxic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma. Related methods of diagnosis are also provided.

In an embodiment, the CLT antigen polypeptide comprises or consists of SEQ ID NO. 10. Exemplary fragments comprise or consist of any one of SEQ ID NOs. 30-32. Exemplary nucleic acids encoding said polypeptide sequence comprise or consists of SEQ ID NO. 40 or SEQ ID NO. 50. Corresponding nucleic acids (e.g., DNA or RNA), T-cells, T-cell populations, cytocotic cells, antigen-binding polypeptides, antigen presenting cells and exosomes as described supra are provided. Said nucleic acids (e.g., DNA or RNA), T-cells, T-cell populations, cytotoxic cells, antigen-binding polypeptides, antigen presenting cells and exosomes may be used in the treatment of cancer especially melanoma e.g. cutaneous melanoma or uveal melanoma. Related methods of diagnosis are also provided.

EXAMPLES

Example 1—CLT Identification

The objective was to identify cancer-specific transcripts that entirely or partially consist of LTR elements.

As a first step, we de novo assembled a comprehensive pan-cancer transcriptome. To achieve this, RNA-sequencing reads from 768 patient samples, obtained from The Cancer Genome Atlas (TCGA) consortium and representing a wide variety of cancer types (24 gender-balanced samples from each of 32 cancer types (31 primary and 1 metastatic melanoma); Table S1), were used for genome-guided assembly. The gender-balanced samples (excluding gender-specific tissues) were adapter and quality (Q20) trimmed and length filtered (both reads of the pair 35 nucleotides) using cutadapt (v1.13) (Marcel M., 2011, EMBnet J., 17:3) and kmer-normalized (k=20) using khmer (v2.0) (Crusoe et al., 2015, F1000Res., 4:900) for maximum and minimum depths of 200 and 3, respectively. Reads were mapped to GRCh38 using STAR (2.5.2b) with settings identical to those used across TCGA and passed to Trinity (v2.2.0) (Trinity, Grabherr, M. G., et al., 2011, Nat. Biotechnol., 29:644-52) for a genome-guided assembly with inbuilt in silico depth normalization disabled. The majority of assembly processes were completed within 256 GB RAM on 32-core HPC nodes, with failed processes re-run using 1.5 TB RAM nodes. Resulting contigs were poly(A)-trimmed (trimpoly within SeqClean v110222) and entropy-filtered (≥0.7) to remove low-quality and artefactual contigs (bbduk within BBMap v36.2). Per cancer type, the original 24 samples were quasi-mapped to the cleaned assembly using Salmon (v0.8.2 or v0.9.2) (Patro, R., et al., 2017, Nat. Methods, 14:417-419), with contigs found expressed at <0.1 transcripts per million (TPM) being removed. Those remaining were mapped to GRCh38 using GMAP (v161107) (Wu et al., 2005, Bioinf., 21:1859-1875), and contigs not aligning with ≥85% identity over ≥85% of their length were removed from the assembly. Finally, assemblies for all cancer types together were flattened and merged into the longest continuous transcripts using gffread (Cufflinks v2.2.1) (Trapnell et al., 2010, Nat. Biotech., 28:511-515). As this assembly process was specifically designed to enable assessment of repetitive elements, monoexonic transcripts were retained, but flagged. Transcript assembly completeness and quality was assessed by comparison with GENCODE v24basic and MiTranscriptome1 (Iyer et al. 2015, Nat. Genet., 47: 199-208). We compiled the list of unique splice sites represented within GENCODE and tested if the splice site was present within the transcriptome assembly within a 2-nucleotide grace window. This process resulted in the identification of 1,001,931 transcripts, 771,006 of which were spliced and 230,925 monoexonic.

Separately, the assembled contigs were overlaid with a genomic repeat sequence annotation to identify transcripts that contain an LTR element. LTR and non-LTR elements were annotated as previously described (Attig et al., 2017, Front. In Microbiol., 8:2489). Briefly, hidden Markov models (HMMs) representing known Human repeat families (Dfam 2.0 library v150923) were used to annotate GRCh38 using RepeatMasker Open-3.0 (Smit, A., R. Hubley, and P. Green, http://www.repeatmasker.org, 1996-2010), configured with nhmmer (Wheeler et al., 2013, Bioinform., 29:2487-2489). HMM-based scanning increases the accuracy of annotation in comparison with BLAST-based methods (Hubley et al., 2016, Nuc. Acid. Res., 44:81-89). RepeatMasker annotates LTR and internal regions separately, thus tabular outputs were parsed to merge adjacent annotations for the same element. This process yielded 181,967 transcripts that contained one or more, complete or partial LTR element.

Transcripts per million (TPM) were estimated for all transcripts using Salmon and expression within each cancer type was compared with expression across 811 healthy tissue samples (healthy tissue-matched controls for all cancer types, where available, from TCGA and, separately from, GTEx (The Genotype-Tissue Expression Consortium, 2015, Science, 348:648-60). Transcripts were considered expressed specifically in cancer if detected at more than 1 TPM in any sample and as cancer-specific if the following criteria were fulfilled: i, expressed in of the 24 samples of each cancer type; ii, expressed at <10 TPM in ≥90% of all healthy tissue samples; iii, expressed in the cancer type of interest ≥3× the median expression in any control tissue type; and iv, expressed in the cancer type of interest ≥3× the 90th percentile of the respective healthy tissue, where available. In addition to these expression thresholds, transcript selection was based on manual inspection, excluding potentially misassembled contigs or transcripts with LTR elements in their 3' untranslated regions (UTRs). Where the direction of transcription could not be unambiguously assigned, transcripts corresponding to both strands were considered.

The list of cancer-specific transcripts was then intersected with the list of transcripts containing complete or partial LTR elements to produce a list of 5,923 transcripts that fulfilled both criteria (referred to as CLTs for Cancer-specific LTR element-spanning Transcripts).

To identify CLTs with protein-coding potential, we run an ORF prediction algorithm, based on length and suitability of dicodon (hexamer) scores. A HMM was trained on hexamers derived from Ensembl CDS sequences and ORFs ≥300 nucleotides were taken forward, where their sense hexamer score exceeded the anti-sense score. This filter identified 885 CLTs potentially encoding a protein of at least 99 amino acids length.

To identify unique protein sequences potentially encoded by CLTs, sequences translated from the largest ORF of selected CLTs were queried against those translated from all ORFs ≥210 nucleotides from the entire transcript assembly using tblastn ($BLAST_{+}$v2.3.0) without soft-maskin. Only CLTs with no hits or with hits with an E-value $>10^{-5}$ were retained.

To further ensure the specificity of cancer-specific antigens encoded by CLTs, we examined their potential cross-reactivity with other proteins that might be expressed in healthy tissue. To this end, translated ORFs with <85% amino acid sequence identity (over the entire length of the protein) with any other predicted protein were retained. For those CLT-encoded proteins showing >85% sequence identity with one or more predicted proteins, we interrogated the expression pattern of transcripts encoding the similar proteins. Where these additional transcripts were also expressed in a cancer-specific manner (based on the criteria listed above), the respective CLT was retained in the list of selected candidates. Where the additional transcripts were also expressed in healthy tissue, the respective CLT was discarded. The combination of these selection criteria yielded a final list of 139 CLTs with the potential to encode proteins with sufficiently unique amino acid sequence.

Of these 139 CLTs, 14 were specific to cutaneous melanoma (i.e. they were found to be upregulated specifically in cutaneous melanoma samples in the TGCA according to the above metholology) and 7 were specific to cutaneous melanoma and uveal melanoma (i.e. they were found to be upregulated specifically in cutaneous melanoma and uveal melanoma samples in TGCA according to the above methodology). Four of these cutaneous melanoma specific CLTs are identified herein as having SEQ ID NO. 34, 37, 38 and 39. Four of these cutaneous melanoma and uveal melanoma specific CLTs are identified herein as having SEQ ID NOs. 33, 35, 36 and 40.

Example 2—Immunopeptidomic Analysis

Immunopeptidomic analysis is a powerful technology that allows the direct detection of specific peptides associated with HLA molecules in cells or tissues. The technique consists of affinity purification of HLA molecules from biological samples, and then elution of bound peptides from the HLA molecules and evaluation of the peptides by nano-ultra performance liquid chromatography mass spectrometry (nUPLC-M$5^2$) (Freudenmann et al., 2018, Immunology 154(3):331-345). The mass spectrometry (MS) spectra produced by this method can be used to precisely identify the short peptides that are bound to HLA Class I and HLA Class II molecules. The software used for spectral interpretation and sequence identification rely on availability of a pre-defined list of protein sequences for spectral matching. Although it is possible to search MS data by using pre-defined lists corresponding to all open reading frames (ORFs) derived from the known transcriptome or even the entire genome (Nesvizhskii et al., 2014, Nat. Methods 11:1114-1125), interrogating these very large sequence databases leads to very high false discovery rates that limit the identification of presented peptides. Further technical issues (e.g., mass of leucine=mass of isoleucine), and theoretical issues (e.g., peptide splicing (Liepe, et al., 2016, *Science* 354(6310): 354-358)) increase the limitations associated with use of very large databases, such as those produced from the known transcriptome or entire genome. Thus, in practice, it is exceptionally difficult to perform immunopeptidoimc analyses to identify novel antigens without reference to a well-defined set of potential polypeptide sequences.

Bassani-Sternberg et al. (Bassani-Sternberg et al., 2016, *Nature Commun.,* 7: 13404) interrogated MS data collected from HLA-bound peptide samples derived from 25 cutaneous melanoma patients against the polypeptides reported for the entire human proteome. These analyses revealed hundreds of thousands of peptides that matched to known human proteins. As expected, these peptides included peptides found within multiple tumor-associated antigens (TAA), including PRAME, MAGEA3, and TRPM1 (melastatin). In addition, the MS data from 5 of these patients were interrogated with a polypeptide list created from patient-specific mutated protein sequences detected by genomic analyses of these 5 patients, revealing patient-specific neoantigens presented on the HLA Class I and HLA Class II molecules of these patients.

Many of the predicted polypeptide sequences (ORFs) derived from the 139 CLTs referred to in Example 1 are not contained within the human proteome. By applying detailed knowledge of immunopeptidomic evaluation, the inventors interrogated the RAW data files of Bassani-Sternberg et al. (database link: https://www.ebi.ac.uk/pride/archive/projects/PXD004894) with this set of novel potential CLT antigen sequences.

To accomplish this analysis, the peptide sequences from all possible ORFs encoded by each CLT were concatenated into a single peptide file for each CLT, or not, and these concatenated files (analysis A) or single peptide files (analysis B) were used to interrogate the raw spectra in the PXD004894 dataset, alongside all polypeptides found in the human proteome (UniProt (analysis A) or UniProt and masDB (analysis B)), by using the Peaks™ software (analysis A) or the Mascot software (analysis B).

In analysis A, the results of these studies identified 14 peptides that were associated with the HLA Class I molecules immunoprecipitated from tumor samples from the 25 patients examined by Bassani-Sternberg et al., which can be attributed to 8 ORFs that were not found in the reported proteome (see Table 1). In analysis B, the results of these studies identified 14 peptides that were associated with the HLA Class I molecules or HLA Class II molecules immunoprecipitated from tumor samples from the 25 patients examined by Bassani-Sternberg et al., which can be attributed to 7 ORFs that were not found in the reported proteome (see Table 2). The detection of these peptides associated with the HLA Class I and HLA Class II molecules from the cited patients confirms that the 10 ORFs from which they were derived (Tables 1 and 2, SEQ ID NOs. 1-10) were translated in melanoma tissue and presented to the immune system complexed with HLA Class I or HLA Class II molecules. On this basis, the polypeptides encoded by these ORFs were defined as CLT antigens. Tables 1 and 2 show the properties of the peptides found in the CLT antigens that were not in the UniProt database. FIGS. 1-32 shows representative mass spectrometry spectra from each of the peptides shown in Table 1 and Table 2. The figures show fragment spectra for indicated peptide sequences as detected in individual patient SKCM tumors by nUPLC-$MS^2$ (from Bassani-Sternberg et al.; image extracted from the PRIDE dataset by the PEAKS software). All fragments that have been detected are indicated in the peptide sequence above the spectrum and the most abundant fragment ions are assigned in each spectrum. In FIGS. 1-15, 29-32 (analysis A), the lower panel of the figures illustrates the sequence annotation to a predicted spectrum, whereas similar data are shown in tabular form on the right side of FIGS. 16-28 (analysis B). Fragment ions are annotated as follows: b: N-terminal fragment ion; y: C-terminal fragment ion; —$H_2O$: water loss; —$NH_3$: loss of ammonia; [2+]: doubly charged peptide ion; pre: unfragmented precursor peptide ion.

A number of the peptides detected in association with HLA Class I from Tables 1 and 2 were assessed to determine the predicted strength of binding to HLA Class I supertypes. Specifically, all HLA Class I-associated peptides referenced in Table 3 that were 9 amino acids or longer were interrogated by using the NetMHC 4.0 prediction software (http://www.cbs.dtu.dk/services/NetMHC/) to predict their binding to HLA Class I type A and B supertypes. The results of these prediction studies showed that all 11 peptides (or 9-mers derived from them) were predicted to bind to at least one of the supertypes tested (see Table 3). Amongst these, many of sequences were predicted to bind with high confidence (low % rank scores) to specific types within the HLA Class I supertypes examined.

Taken together, the data shown in Tables 1-3 and FIGS. 1-32 supply exceptionally strong support for the presentation of the corresponding CLT antigens in melanoma patients.

In summary: the identification of immunopeptidomic peptides derived from the predicted ORFs, demonstrates that these CLTs are translated into polypeptides (SEQ ID NOs. 1-10; referred to as CLT antigens) in tumor tissue. These are then processed by the immune surveillance apparatus of the cells, and loaded onto HLA Class I or HLA Class II molecules, enabling the cell to be targeted for cytolysis by T-cells that recognize the resulting peptide/HLA Class I or peptide/HLA Class II complexes. Thus, these CLT antigens and fragments of them are expected to be useful in a variety of therapeutic modalities for the treatment of melanoma in patients whose tumors express these antigens.

TABLE 1

List of peptides identified by immunopeptidomic analyses (analysis A) of SKCM tumor samples, along with CLT antigen name and cross reference to SEQ ID NOs.

| Peptide sequence[1] | Peptide SEQ ID No. | CLT Antigen No. | CLT Antigen SEQ ID NO. | Patient #[2] | Peptide mass[3] | Peptide length | Area[4] | # of spectra[5] | Ppm[6] |
|---|---|---|---|---|---|---|---|---|---|
| VQQGWFF PR | SEQ ID NO. 11 | 1 | SEQ ID NO. 1 | Mel-3 | 1163.59 | 9 | 350000 | 1 | 9.4 |
| VVRGGAG FAAR | SEQ ID NO. 12 | 1 | SEQ ID NO. 1 | Mel-3 | 1059.59 | 11 | 3970000 | 8 | 5.1 |
| HLADRKLS L | SEQ ID NO. 13 | 1 | SEQ ID NO. 1 | Mel-5 | 1051.61 | 9 | 125000000 | 2 | -1.1 |
| HLADRKLS L | SEQ ID NO. 13 | 1 | SEQ ID NO. 1 | Mel-16 | 1051.61 | 9 | 3290000 | 30 | 5.1 |
| ADSLILDF | SEQ ID NO. 15 | 2 | SEQ ID NO. 2 | Mel-26 | 892.45 | 8 | 83300 | 1 | 0.9 |
| SSFSTLAS LDK | SEQ ID NO. 16 | 2 | SEQ ID NO. 2 | Mel-20 | 1154.58 | 11 | 860000 | 2 | -6.7 |
| NTPNIVSL R | SEQ ID NO. 17 | 3 | SEQ ID NO. 3 | Mel-35 | 1012.57 | 9 | 4690000 | 2 | 3.8 |
| KTKGSLSV FR | SEQ ID NO. 19 | 4 | SEQ ID NO. 4 | Mel-3 | 1121.66 | 10 | 1200000 | 3 | 4.8 |
| AAFDRAV HF | SEQ ID NO. 51 | 4 | SEQ ID NO. 4 | Mel-40 | 1032.51 | 9 | 227000 | 1 | 0.3 |
| AAFDRAV HF | SEQ ID NO. 51 | 4 | SEQ ID NO. 4 | Mel-41 | 1032.514 | 9 | 8700000 | 3 | 7.8 |
| AFDRAVH F | SEQ ID NO. 52 | 4 | SEQ ID NO. 4 | Mel-27 | 961.4769 | 8 | 1240000 | 3 | 7.9 |
| AFDRAVH F | SEQ ID NO. 52 | 4 | SEQ ID NO. 4 | Mel-39 | 961.47 | 8 | 1940000 | 3 | 2.6 |
| DIPIKPW | SEQ ID NO. 21 | 5 | SEQ ID NO. 5 | Mel-5 | 867.49 | 7 | 1280000 | 5 | 5.3 |
| DIPIKPW | SEQ ID NO. 21 | 5 | SEQ ID NO. 5 | Mel-27 | 867.49 | 7 | 1790000 | 6 | 9.1 |
| RVADIPIK PW | SEQ ID NO. 20 | 5 | SEQ ID NO. 5 | Mel-5 | 1193.69 | 10 | 8710000 | 4 | 4.7 |
| RVADIPIK PW | SEQ ID NO. 20 | 5 | SEQ ID NO. 5 | Mel-27 | 1193.69 | 10 | 82000000 | 6 | 9.8 |
| RVADIPIK P | SEQ ID NO. 22 | 5 | SEQ ID NO. 5 | Mel-27 | 1007.61 | 9 | 30300000 | 6 | 8 |
| RSRDNFA VW | SEQ ID NO. 23 | 6 | SEQ ID NO. 6 | Mel-21 | 1149.57 | 9 | 21900000 | 4 | 8.5 |
| RSRDNFA VW | SEQ ID NO. 23 | 6 | SEQ ID NO. 6 | Mel-27 | 1149.57 | 9 | 19800000 | 6 | 7.8 |
| RSRDNFA | SEQ ID NO. 24 | 6 | SEQ ID NO. 6 | Mel-21 | 864.42 | 7 | 41000000 | 3 | 8.8 |

TABLE 1-continued

List of peptides identified by immunopeptidomic analyses (analysis A) of SKCM tumor samples, along with CLT antigen name and cross reference to SEQ ID NOs.

| Peptide sequence[1] | Peptide SEQ ID No. | CLT Antigen No. | CLT Antigen SEQ ID NO. | Patient #[2] | Peptide mass[3] | Peptide length | Area[4] | # of spectra[5] | Ppm[6] |
|---|---|---|---|---|---|---|---|---|---|
| RSRDNFA | SEQ ID NO. 24 | 6 | SEQ ID NO. 6 | Mel-27 | 864.42 | 7 | 2550000 | 3 | 7.9 |
| SPGISLVF | SEQ ID NO. 25 | 7 | SEQ ID NO. 7 | Mel-16 | 818.45 | 8 | 546000 | 1 | 8.3 |
| SSDSTILVL | SEQ ID NO. 26 | 8 | SEQ ID NO. 8 | Mel-41 | 933.50 | 9 | 63600 | 1 | 13.1 |

[1]Peptide identified by mass spectrometry. All peptides are HLA Class I peptides.
[2]Bassani-Sternberg et al, 2016, Nature Comm., 7: 13404
[3]Calculated peptide mass.
[4]Peaks ™ program Area from mass spectrum; selected Area values are shown for peptides for which more than one spectrum was obtained.
[5]Number of spectra in which peptide was detected.
[6]Deviation between observed mass and calculated mass; selected ppm values are shown for peptides for which more than one spectrum was obtained.

TABLE 2

List of peptides identified by immunopeptidomic analyses (analysis B) of SKCM tumor samples, along with CLT antigen name and cross reference to SEQ ID NOs.

| Peptide sequence[1] | Peptide SEQ ID No. | CLT Antigen No. | CLT Antigen SEQ ID NO. | Patient #[2] | Peptide mass[3] | Peptide length | # of spectra[4] | Mass Delta[5] |
|---|---|---|---|---|---|---|---|---|
| HLADRKLSL | SEQ ID NO. 13 | 1 | SEQ ID NO. 1 | Mel-16 | 1051.61 | 9 | 3 | 0.01015 |
| VVRGGAGFAAR | SEQ ID NO. 12 | 1 | SEQ ID NO. 1 | Mel-3 | 1059.59 | 11 | 1 | 0.001564 |
| ARLQGSVTL | SEQ ID NO. 14 | 1 | SEQ ID NO. 1 | Mel-5 | 985.56 | 9 | 1 | 0.007816 |
| SSFSTLASLDK | SEQ ID NO. 16 | 2 | SEQ ID NO. 2 | Mel-20 | 1154.58 | 11 | 2 | 0.004607 |
| QPEVGIIPSVLLMRP* | SEQ ID NO. 18 | 3 | SEQ ID NO. 3 | Mel-18 | 1743.90 | 15 | 1 | -0.052238 |
| KTKGSLSVFR | SEQ ID NO. 19 | 4 | SEQ ID NO. 4 | Mel-3 | 1121.66 | 10 | 2 | 0.005258 |
| RVADIPIKPW | SEQ ID NO. 20 | 5 | SEQ ID NO. 5 | Mel-4 | 1193.69 | 10 | 1 | 0.009444 |
| RVADIPIKPW | SEQ ID NO. 20 | 5 | SEQ ID NO. 5 | Mel-5 | 1193.69 | 10 | 1 | 0.00549 |
| DIPIKPW | SEQ ID NO. 21 | 5 | SEQ ID NO. 5 | Mel-4 | 867.49 | 7 | 1 | 0.008214 |
| AGRMSKSLVIK | SEQ ID NO. 27 | 9 | SEQ ID NO. 9 | Mel-15 | 1188.70 | 11 | 3 | -0.000087 |
| PQSAGRM | SEQ ID NO. 28 | 9 | SEQ ID NO. 9 | Mel-6 | 745.35 | 7 | 1 | 0.007525 |
| AGSQSSSFTRGHTGETPQ* | SEQ ID NO. 29 | 9 | SEQ ID NO 9 | Mel-10 | 1875.83 | 18 | 1 | 0.04998 |
| RSNLSIFL | SEQ ID NO. 30 | 10 | SEQ ID NO. 10 | Mel-4 | 990.55 | 8 | 2 | -0.005184 |
| FSLCLFTL | SEQ ID NO. 31 | 10 | SEQ ID NO. 10 | Mel-18 | 942.49 | 8 | 1 | -0.000214 |

TABLE 2-continued

List of peptides identified by immunopeptidomic analyses (analysis B) of SKCM tumor samples, along with CLT antigen name and cross reference to SEQ ID NOs.

| Peptide sequence[1] | Peptide SEQ ID No. | CLT Antigen No. | CLT Antigen SEQ ID NO. | Patient #[2] | Peptide mass[3] | Peptide length | # of spectra[4] | Mass Delta[5] |
|---|---|---|---|---|---|---|---|---|
| FSLCLFTL | SEQ ID NO. 31 | 10 | SEQ ID NO. 10 | Mel-15 | 942.49 | 8 | 13 | -0.0026 |
| SRRVFSR FSYMTFY SFRSYIKV FV* | SEQ ID NO. 32 | 10 | SEQ ID NO. 10 | Mel-7 | 3370.48 | 24 | 1 | 0.006099 |

[1]Peptide identified by mass spectrometry. All peptides are HLA Class I peptides unless indicated with a * (which ones are HLA Class II)
[2]Bassani-Sternberg et al, 2016, Nature Comm., 7: 13404
[3]Calculated peptide mass.
[4]Number of spectra in which peptide was detected.
[5]Difference between observed mass and calculated mass; selected Mass Delta values are shown for peptides for which more than one spectrum was obtained.
*indicates a HLA Class II peptide

TABLE 3

Predicted NetMHC 4.0 binding of Mass Spectrometry-identified peptides (length ≥9 residues) to 12 HLA Class I Supertype Alleles (HLA-A0101, HLA-A0201, HLA-A0301, HLA-A2402, HLA-A2601, HLA-B0702, HLA-B0801, HLA-B1501, HLA-B2705, HLA-B3901, HLA-B4001, HLA-B5801), along with CLT antigen name and cross reference to SEQ ID NOs.

| predicted to bind 12 human HLA Class I A & B supertypes[1] | Peptide sequence | Number of alleles with a rank score of <5.1%[2] | Number of alleles with a rank score of <2.1%[3] | Peptide SEQ ID NO. | CLT Antigen No. | Patient #[4] |
|---|---|---|---|---|---|---|
| YES | VQQGWFFPR | 2/12 | 1/12 | SEQ ID NO. 11 | 1 | Mel-3 |
| YES | VVRGGFAGFAAR | 3/12 | 0 | SEQ ID NO. 12 | 1 | Mel-3 |
| YES | HLADRKLSL | 6/12 | 3/12 | SEQ ID NO. 13 | 1 | Mel-5/Mel-16 |
| YES | ARLQGSVTL | 7/12 | 3/12 | SEQ ID NO. 14 | 1 | Mel-5 |
| YES | SSFSTLASLDK | 7/12 | 3/12 | SEQ ID NO. 16 | 2 | Mel-20 |
| YES | NTPNIVSLR | 1/12 | 1/12 | SEQ ID NO. 17 | 3 | Mel-35 |
| YES | KTKGSLSVFR | 4/12 | 2/12 | SEQ ID NO. 19 | 4 | Mel-3 |
| YES | AAFDRAVHF | 12/12 | 6/12 | SEQ ID NO. 51 | 4 | Mel-40/Mel-41 |
| YES | RVADIPIKPW | 1/12 | 1/12 | SEQ ID NO. 20 | 5 | Mel-4/Mel-5/Mel-27 |
| YES | RVADIPIKP | 0/12 | 0/12 | SEQ ID NO. 22 | 5 | Mel-27 |
| YES | RSRDNFAVW | 3/12 | 1/12 | SEQ ID NO. 23 | 6 | Mel-21/Mel-27 |

TABLE 3-continued

Predicted NetMHC 4.0 binding of Mass Spectrometry-identified peptides (length ≥9 residues) to 12 HLA Class I Supertype Alleles (HLA-A0101, HLA-A0201, HLA-A0301, HLA-A2402, HLA-A2601, HLA-B0702, HLA-B0801, HLA-B1501, HLA-B2705, HLA-B3901, HLA-B4001, HLA-B5801), along with CLT antigen name and cross reference to SEQ ID NOs.

| predicted to bind 12 human HLA Class I A & B supertypes[1] | Peptide sequence | Number of alleles with a rank score of <5.1%[2] | Number of alleles with a rank score of <2.1%[3] | Peptide SEQ ID NO. | CLT Antigen No. | Patient #[4] |
|---|---|---|---|---|---|---|
| YES | SSDSTILVL | 2/12 | 1/12 | SEQ ID NO. 26 | 8 | Mel-41 |
| YES | AGRMSKSLVIK | 4/12 | 4/12 | SEQ ID NO. 27 | 9 | Mel-15 |

[1]Predicted binding to interrogated HLA Class I supertypes at any Rank score.
[2]Fraction of HLA Class I supertypes that were predicted to bind with a rank score of <5.1% (weak binding).
[3]Fraction of HLA Class I supertypes that were predicted to bind with a rank score of <2.1% (stronger binding).
[4]Bassani-Sternberg et al, 2016, Nature Comm., 7: 13404

Example 2.1—Additional Immunopeptidomic Analysis

In addition to the analyses described in Example 2, the inventors have also identified peptides derived from the predicted ORFs through new immunopeptidomic studies. This additional work, described below, further demonstrates that these CLTs are translated into CLT Antigen polypeptides in tumor tissue.

The inventors procured frozen tumor tissue from 10 patients diagnosed with melanoma. Samples between 0.05-1 g were homogenized, the lysate was centrifugate at high speed and the cleared lysate was mixed with protein A (ProA) beads covalently linked to an anti-human HLA class I monoclonal antibody (W6/32). The mixture was incubated overnight at 4° C. to improve HLA Class I molecule binding to antibody (Ternette et al., 2018 Proteomics 18, 1700465). The HLA Class I-bound peptides were eluted from the antibody by using 10% acetic acid, and the peptides were then separated from other high molecular mass components using reversed-phase column chromatography (Ternette et al., 2018). The purified, eluted peptides were subjected to nUPLC-MS, and specific peptides of defined charge-to-mass ratio (m/z) were selected within the mass spectrometer, isolated, fragmented, and subjected to MS/MS to reveal the m/z of the resulting fragment ions (Ternette et al., 2018), producing an MS/MS dataset corresponding to the immunopeptidome for each of these tumor samples.

By applying detailed knowledge of immunopeptidomics evaluation, the inventors interrogated the spectra of the HLA-Class I dataset for the 10 melanoma tumors prepared by the inventors with the CLT antigens no.1,2,3 and 4 (Table 4; SEQ ID NOs. 1-4), which were searched (for each CLT) alongside all polypeptide sequences found in the human proteome (UniProt) using PEAKS™ software (v8.5 and vX, Bioinformatics Solutions Inc). Since the majority of Class I HLA-bound peptides found in cells are derived from constitutively expressed proteins, the simultaneous interrogation of these databases with the UniProt proteome helps to ensure that assignments of our CLT ORF sequences to MS/MS spectra are correct.

The results of these studies identified 8 individual peptides (Table 4; SEQ ID NOs. 1-4) that were associated with the HLA Class I molecules immunoprecipitated from tumor samples from the 10 melanoma patient samples procured by the inventors. These peptides corresponded to the amino acid sequence of CLT-derived ORFs, and did not correspond to polypeptide sequences present within the known human proteome (UniProt). 2 out of 8 peptides identified from CLT antigens SEQ ID NOs. 1-4 (Table 4) in the inventors' dataset, are in addition to the 10 individual peptides (from the same CLT antigens SEQ ID NOs. 1-4 outlined in Example 2 and Tables 1 & 2) that were associated with the HLA Class I molecules immunoprecipitated from tumor samples from patients examined by Bassani-Sternberg et al.

The detection of these peptides associated with the HLA Class I molecules confirms, that the 4 ORFs from which they were derived, were first translated in melanoma tissues, processed through the HLA Class I pathway and finally presented to the immune system in a complex with HLA Class I molecules. Table 4 shows the properties of the peptides found in the CLT antigens. FIGS. 33-42 show representative MS/MS spectra from each of the peptides shown in Table 4. The top panel of each of these figures shows the MS/MS peptide fragment profile, with standard MS/MS annotations (b: N-terminal fragment ion; y: C-terminal fragment ion; —$H_2O$: water loss; —$NH_3$: loss of ammonia; [2+]: doubly charged peptide ion; pre: unfragmented precursor peptide ion; $a_n$-n: internal fragment ion) shown above the most abundant fragment ion peaks, in an image extracted from the inventors' dataset by the PEAKS software. The lower panel of each Figure shows a rendering of the spectrum indicating the positions of the linear peptide sequences that have been mapped to the fragment ions. Consistent with the high −10 IgP scores assigned to the peptides in Table 4, these spectra contain numerous fragments that precisely match the sequences of the peptides (SEQ ID NOs. 12, 13, 16, 17, 19, 51, 53 and 54) that we discovered in these analyses.

All of the peptides detected in association with HLA Class I from Table 4 that were at least 9 AA in length were assessed to determine their predicted strength of binding to HLA Class I type A and B supertypes by using the NetMHCpan 4.0 prediction software (http://www.cbs.dtu.dk/services/BetMHCpan/). The results of these prediction studies showed that all of the peptides (or 9-mers contained within each full sequence) were predicted to bind to at least one of the supertypes tested (see Table 5). Amongst these, many of sequences were predicted to bind with high confidence (low % rank scores) to specific types within the HLA Class I supertypes examined. The fact that all of the detected peptides were expected to bind to HLA types that were expected to be in the patient population is consistent with their detection. Moreover, every peptide discovered in a tumor sample from the inventors' dataset was predicted by NetMHCpan 4.0 to bind to one of the HLA types we detected in the patient sample.

To provide further certainty of the assignment of tumor tissue-derived MS spectra to the peptide sequences that we discovered in Example 2.1, peptides with these discovered sequences were synthesized and subjected to nUPLC-$MS^2$ using the same conditions applied to the tumor samples in the inventors' data. Comparison of the spectra for selected peptides are shown in FIGS. 43-50. In each figure the upper spectrum corresponds to a tumor sample (from among the inventor's tumor tissue database—FIGS. 33-42) and the lower spectrum corresponds to the synthetically produced peptide of the same sequence. Selected m/z values of detected ion fragments are shown above/below each fragment peak in these MS/MS spectra. These figures reveal a precise alignment of fragments (tiny differences in the experimentally determined m/z values between tumor- and synthetic peptide-derived fragment ions being well within the m/z tolerances of <0.05 Daltons), confirming the veracity of the assignment of each of the tumor tissue-derived spectra to the CLT-encoded peptides.

Taken together, the peptide data shown in Table 4, FIGS. 33-42 and FIGS. 43-50 supply exceptionally strong support for the translation, processing, and presentation of the corresponding CLT antigens in melanoma patients.

To further confirm the cancer-specificity of these CLTs, the inventors processed 37 normal tissue samples (10 normal skin, 9 normal lung and 18 normal breast tissue) and prepared for immunopeptidomic analysis. The inventors interrogated the spectra of the HLA-Class I dataset from these normal tissue samples, searching for all possible peptide sequences derived from the polypeptide sequences of CLT antigens no.1, 2, 3 and 4. No peptides derived from CLT antigens no. 1, 2, 3 and 4 were detected in the set of normal tissue samples (Table 6) providing additional confirmation that the CLTs have cancer-specific expression.

In summary: this additional identification of immunopeptidomic peptides derived from the predicted ORFs, further demonstrates that these CLTs are translated into polypeptides (SEQ ID NOs. 1-4; referred to as CLT antigens) in tumor tissue. Thus, these CLT antigens and fragments of them are expected to be useful in a variety of therapeutic modalities for the treatment of melanoma in patients whose tumors express these antigens.

TABLE 4

List of peptides identified by additional immunopeptidomic analyses of melanoma tumor samples, along with CLT antigen name and cross reference to SEQ ID NOs.

| Peptide sequence[1] | Peptide SEQ ID NO. | CLT Ant. NO. | CLT Ant. SEQ ID NO. | Patient #[2] | Peptide mass[3] | Peptide length | Area[4] | # of spectra[5] | Ppm[6] |
|---|---|---|---|---|---|---|---|---|---|
| HLADRKLSL | SEQ ID NO. 13 | 1 | SEQ ID NO. 1 | 2MT3 | 1051.61 | 9 | 154000 | 2 | -1.4 |
| HLADRKLSL | SEQ ID NO. 13 | 1 | SEQ ID NO. 1 | 2MT10 | 1051.61 | 9 | ND | 1 | 3.4 |
| VVRGGAGFAAR | SEQ ID NO. 12 | 1 | SEQ ID NO. 1 | 2MT3 | 1059.594 | 11 | 985000 | 6 | -0.9 |
| SSFSTLASLDK | SEQ ID NO. 16 | 2 | SEQ ID NO. 2 | 2MT4 | 1154.582 | 11 | 559000 | 1 | 0.9 |
| NTPNIVSLR | SEQ ID NO. 17 | 3 | SEQ ID NO. 3 | 2MT3 | 1012.567 | 9 | 884000 | 1 | -2.8 |
| RPLRIKGVF | SEQ ID NO. 53 | 3 | SEQ ID NO. 3 | 1MT1 | 1084.6869 | 9 | 19400000 | 7 | 0 |
| AAFDRAVHF | SEQ ID NO. 51 | 4 | SEQ ID NO. 4 | 2MT3 | 1032.514 | 9 | ND | 1 | -1.3 |
| KTKGSLSVFR | SEQ ID NO. 19 | 4 | SEQ ID NO. 4 | 2MT3 | 1121.6556 | 10 | 10100000 | 6 | -0.7 |
| KTKGSLSVFR | SEQ ID NO. 19 | 4 | SEQ ID NO. 4 | 2MT1 | 1121.6556 | 10 | 10100000 | 2 | -0.7 |

TABLE 4-continued

List of peptides identified by additional immunopeptidomic analyses of melanoma tumor samples, along with CLT antigen name and cross reference to SEQ ID NOs.

| Peptide sequence[1] | Peptide SEQ ID NO. | CLT Ant. NO. | CLT Ant. SEQ ID NO. | Patient #[2] | Peptide mass[3] | Peptide length | Area[4] | # of spectra[5] | Ppm[6] |
|---|---|---|---|---|---|---|---|---|---|
| KTKGSLSVF | SEQ ID NO. 54 | 4 | SEQ ID NO. 4 | 2MT12 | 965.555 | 9 | 4830000 | 1 | 1.2 |

ND - Not determined
[1]HLA Class I peptides identified by mass spectrometry.
[2]Inventors' dataset (1MT1, 1MT2, 1MT3, 2MT1, 2MT2, 2MT3, 2MT4, 2MT9, 2MT10, 2MT12).
[3]Calculated peptide mass.
[4]Peaks ™ program Area from mass spectrum; selected Area values are shown for peptides for which more than one spectrum was obtained.
[5]Number of spectra in which peptide was detected.
[6]Deviation between observed mass and calculated mass; selected ppm values are shown for peptides for which more than one spectrum was obtained.

TABLE 5

Predicted NetMHC 4.0 binding of Mass Spectrometry-identified peptides (length ≥9 residues) to 12 HLA Class I Supertype Alleles (HLA-A0101, HLA-A0201, HLA-A0301, HLA-A2402, HLA-A2601, HLA-B0702, HLA-B0801, HLA-B1501, HLA-B2705, HLA-B3901, HLA-B4001, HLA-B5801), along with CLT antigen name and cross reference to SEQ ID NOs.

| Predicted to bind 12 human HLA Class I A & B supertypes[1] | Peptide sequence | Number of alleles with a rank score of <5.1%[2] | Number of alleles with a rank score of <2.1%[3] | Peptide SEQ ID NO | CLT Antigen No. | Patient #[4] |
|---|---|---|---|---|---|---|
| YES | HLADRKLSL | 6/12 | 3/12 | SEQ ID NO. 13 | 1 | 2MT3<br>2MT10 |
| YES | VVRGGFAGFAAR | 3/12 | 0 | SEQ ID NO. 12 | 1 | 2MT3 |
| YES | SSFSTLASLDK | 7/12 | 3/12 | SEQ ID NO. 16 | 2 | 2MT4 |
| YES | NTPNIVSLR | 1/12 | 1/12 | SEQ ID NO. 17 | 3 | 2MT3 |
| YES | RPLRIKGVF | 2/12 | 2/12 | SEQ ID NO. 53 | 3 | 2MT1 |
| YES | AAFDRAVHF | 12/12 | 6/12 | SEQ ID NO. 51 | 4 | 2MT3 |
| YES | KTKGSLSVFR | 4/12 | 2/12 | SEQ ID NO. 19 | 4 | 2MT1<br>2MT3 |
| YES | KTKGSLSVF | 7/12 | 4/12 | SEQ ID NO. 54 | 4 | 2MT12 |

[1]Predicted binding to interrogated HLA Class I supertypes at any Rank score.
[2]Fraction of HLA Class I supertypes that were predicted to bind with a rank score of <5.1% (weak binding).
[3]Fraction of HLA Class I supertypes that were predicted to bind with a rank score of <2.1% (stronger binding).
[4]Inventor's database (1MT1, 1MT2, 1MT3, 2MT1, 2M12, 2M13, 2M14, 2M19, 2MT10, 2M112).

TABLE 6

Number of peptides-derived from CLT Antigens 1 to 4 in a set of normal tissue samples.

| Antigen | Skin | Lung | Breast |
|---|---|---|---|
| CLT Antigen 1 | 0/10 | 0/9 | 0/18 |
| CLT Antigen 2 | 0/10 | 0/9 | 0/18 |
| CLT Antigen 3 | 0/10 | 0/9 | 0/18 |
| CLT Antigen 4 | 0/10 | 0/9 | 0/18 |

The results presented here in Examples 1, 2 and 2.1 are in whole or part based upon data generated by the The Cancer Genome Atlas (TCGA) Research Network (http://cancergenome.nih.gov/); and the Genotype-Tissue Expression (GTEx) Project (supported by the Common Fund of the Office of the Director of the National Institutes of Health, and by NCI, NHGRI, NHLBI, NIDA, NIMH, and NINDS).

Example 3—HERVFEST

Functional expansion of specific T-cells (FEST) technology has been used to identify therapeutically relevant tumor-derived epitopes present in the "mutation-associated neoantigen" (MANA) repertoire found in tumor cells of cancer patients based on detection of patient T-cells that react to MANA epitopes (Anagnostou et al., Cancer Discovery 2017; Le et al., Science 2017; Forde et al., NEJM 2018; Danilova et al., Cancer Immunol. Res. 2018). Application of FEST technology to CLT antigens discovered by using the methods elucidated in Example 1, 2, & 2.1 (Tables 1-6, FIGS. 1-50) can be used to identify therapeutically relevant T-cell responses to CLT antigens in cancer patients.

Like other assays (e.g., ELISPOT) to identify epitope-specific T-cells in a subject who has undergone immune exposure, "FEST" technologies derive their specificity by activating/expanding the cognate T-cells in ex vivo cultures that include antigen-presenting cells and suitable antigenic peptides. The technique differs from other immunological assays in that it utilizes next-generation sequencing of the T-cell receptor (TCR) DNA sequences present in these amplified cultures (specifically: TCRseq targeting the TCR-Vβ CDR3 region) to detect the specific TCRs that are expanded in the cells cultured with individual peptides from a panel of target peptides derived from an antigen (or antigens). Application of TCRseq to tumor tissues in the same patient can also be used to demonstrate if TCRs/T-cells detected in the ex vivo, peptide-stimulated cultures are also present within the tumor-infiltrating lymphocytes found in cancer tissues in situ. Thus, MANAFEST has proven to be a powerful technology for identifying MANA epitopes that are recognized by patient T-cells, permitting identification of functionally relevant MANA peptides among the multitude of mutant peptides found by whole-exome sequencing of normal and tumor tissues from cancer patients (Le et al., Science 2017; Forde et al., NEJM 2018; Danilova et al., Cancer Immunol. Res. 2018; Smith et al., J Immunother Cancer 2019).

Application of MANAFEST methodology (Danilova et al., Cancer Immunol. Res. 2018) to CLT antigens was performed as follows. The method, which we will refer to as HERVFEST, consists of the following steps: Step 1: Peptides predicted to contain epitopes that efficiently bind selected HLA Class I alleles were identified in CLT Antigens. Step 2: PBMCs from suitable melanoma patients were matched by HLA Class I type to the peptide library selected in step 1. Step 3: PBMCs from these patients were separated into T-cell and non T-cell fractions. Non T-cells were added back to the patient's T-cells, and then divided into 20-50 wells (containing 250,000 T-cells per culture) and propagated with various T-cell growth factors and individual CLT Antigen-derived synthetic peptides (selected in step ½) for 10 days. Step 4: TCRseq (sequencing of the TCR-Vβ CDR3 sequences) was performed on all wells, and TCR-Vβ CDR3 sequences that were amplified in the presence of individual CLT Antigen-derived peptides (but not amplified in the presence of control peptides or in the absence of peptide stimulation) were identified. The presence of amplified TCR-Vβ CDR3 sequences in individual wells of the assay thus identifies CLT Antigen-derived peptides that elicited an immune response in the melanoma patient. Step 5: TCRseq may also be performed on tumor samples to determine whether the T-cells bearing the CLT-Antigen amplified TCRs homed to patient tumors, providing additional evidence that T-cells bearing these TCRs recognize CLT Antigen-derived peptides within a patient's tumor.

HERVFEST assays were performed with peptides derived from CLT Antigens 1-4 (SEQ ID NOs 1-4). The panel of peptides (see step 1 above) used for these studies was based on NetMHC predictions of CLT Antigen-derived peptides that were predicted to strongly bind the 8 HLA Class I types commonly found in patient tumor samples available for our analyses. CLT Antigen-derived peptides that amplified one or more TCRs in these HERVFEST assays are provided in Table 7. Table 7 also indicates the HLA Class I type(s) of the CLT antigen peptides that were tested with each patient's PBMC-derived cultures. The HLA Class I type of the patients whose PBMCs were tested in these studies and amplified one or more TCRs in the assays, are shown in Table 8.

FIG. 51 panel A shows published data demonstrating TCR amplification with NSCLC patient-specific MANA peptides (Forde et al., NEJM 2018). The vertical axis shows the prevalence of each indicated TCR-Vβ CDR3 sequence for wells of cells cultivated in the presence of the MANA or control peptides listed on the horizontal axis. The amplification in the well containing MANA7 indicates the patient's T-cell repertoire include T-cells that are reactive to this peptide. Panels B and C of FIG. 51 show representative TCR amplification data from PBMCs from 2 melanoma patients that were incubated in the presence of the indicated CLT Antigen peptides and control peptides. As with Panel A, the specific amplifications observed in Panels B & C demonstrate that the T-cell repertoire of these melanoma patients includes T-cells that are reactive with specific CLT Antigen-derived peptides. Panel B shows the frequency of TCRs detected in the LMSSFSTLASL-stimulated well of PBMCs from melanoma patient 222B in all wells stimulated with the panel 15 HLA Class I A*02 peptides from CLT Antigens 1, 2 & 4. Three TCR sequences were amplified. LMSSFSTLASL (SEQ ID NO. 61) is an A*02 binding peptide derived from CLT Antigen 2. Panel C shows the frequency of TCRs detected in the MVACRIKTFR-stimulated well of PBMCs from melanoma patient 224B in all wells stimulated with the panel of 15 HLA Class I A*02 peptides from CLT Antigens 1, 2 & 4 and 24 HLA Class I A*03 peptides from CLT Antigens 1, 2, 3, & 4. One TCR sequence was amplified. MVACRIKTFR (SEQ ID NO. 64) is an A*03 binding peptide derived from CLT Antigen 2.

The control peptides/conditions used in these experiments were as follows: CEF=mixture of CMV, EBV, and influenza peptides; SL9, TV9 and QK1=HIV-1 control peptides; no peptide=cultivation in absence of peptide; Baseline=T-cells before culture.

FIG. 52 shows a summary of all CLT Antigen peptides for CLT Antigens 1-4 which amplified one or more TCRs in studies completed with these patients. Each panel displays the amino acid sequences of CLT Antigens 1-4 overlaid with peptides detected by immunopeptidomic analyses (denoted by dashed underlined or bold text; see Examples 2 & 2.1). Below these sequences, the HERVFEST-detected peptides (see FIG. 51) are displayed with the number of the melanoma patient in which they were detected (Table 8) and the targeted HLA Class I type.

The properties of each HERVFEST detection are defined as follows:

Plain text: Significant amplification of a single TCR

Bold text: Significant amplification of multiple TCRs

Underlined italics text: Significant amplification of a single TCR which was detected in other wells Underlined bold text: Significant amplification of multiple TCRs, at least one of which was detected in other wells These results provide strong evidence that CLT Antigens 1-4 are present in melanoma patients and that peptides derived from these CLT antigens have elicited specific T-cell responses in these melanoma patients, confirming the value of these CLT antigens as targets for therapeutic interventions to treat melanoma.

TABLE 7

CLT Antigen-derived peptides that amplified one or more TCRs in HERVFEST assays

| Reference CLT Antigen | SEQ ID NO. | Peptide sequence | HLA Class I - type for peptide (predicted by NetMHC) | HERVFEST panel reference |
|---|---|---|---|---|
| 1 | SEQ ID NO. 55 | VPANTYNALK | HLA-A*03:01 | 37 |
| 1 | SEQ ID NO. 56 | RLGGCQAWWR | HLA-A*03:01 | 41 |
| 1 | SEQ ID NO. 57 | ANTYNALKSR | HLA-A*11:01 | 60 |
| 1 | SEQ ID NO. 13 | HLADRKLSL | HLA-B*07:02 | 109 |
| 2 | SEQ ID NO. 58 | LVTDMVACRI | HLA-A*01:01 | 8 |
| 2 | SEQ ID NO. 59 | LILDFQPLQL | HLA-A*01:01 | 13 |
| 2 | SEQ ID NO. 60 | MSSFSTLASL | HLA-A*01:01 | 15 |
| 2 | SEQ ID NO. 59 | LILDFQPLQL | HLA-A*02:01 | 25 |
| 2 | SEQ ID NO. 61 | LMSSFSTLASL | HLA-A*02:01 | 27 |
| 2 | SEQ ID NO. 62 | LMSSFSTLA | HLA-A*02:01 | 23 |
| 2 | SEQ ID NO. 63 | QLMSSFSTLA | HLA-A*02:01 | 26 |
| 2 | SEQ ID NO. 64 | MVACRIKTFR | HLA-A*03:01 | 46 |
| 2 | SEQ ID NO. 16 | SSFSTLASLDK | HLA-A*03:01 | 45 |
| 2 | SEQ ID NO. 64 | MVACRIKTFR | HLA-A*11:01 | 67 |
| 2 | SEQ ID NO. 65 | VTDMVACRIK | HLA-A*11:01 | 69 |
| 2 | SEQ ID NO. 66 | SPADSLIL | HLA-B*07:02 | 119 |
| 2 | SEQ ID NO. 78 | SLILDFQPL | HLA-A*02:01 | 20 |
| 3 | SEQ ID NO. 67 | NTPNIVSLRA | HLA-A*01:01 | 18 |
| 3 | SEQ ID NO. 68 | VLLMRPLRIK | HLA-A*11:01 | 78 |
| 3 | SEQ ID NO. 69 | MRPLRIKGVF | HLA-B*07:02 | 124 |
| 4 | SEQ ID NO. 70 | FLFLELWL | HLA-A*02:01 | 30 |
| 4 | SEQ ID NO. 71 | SVFRELHPA | HLA-A*02:01 | 29 |
| 4 | SEQ ID NO. 72 | SPPSSTAPL | HLA-B*07:02 | 132 |

TABLE 8

Characteristics of the melanoma patient PBMCs used in HERVFEST assays

| Patient | HLA allele A1 | HLA allele A2 | HLA allele B1 | HLA allele B2 | HLA allele C1 | HLA allele C2 | HLA(s) targeted in HERVFEST studies |
|---|---|---|---|---|---|---|---|
| 204B | A*01:01 | A*25:01 | B*03:01 | B*16:01 | C*07:01 | C*12:03 | A*01 |
| 222B | A*02:01 | A*30:02 | B*44:02 | Not known | C*05:01 | B*18:01 | A*02 |
| 224B | A*02:01 | A*03:01 | B*35:01 | B*40:02 | C*04:01 | C*02:02 | A*02, A*03 |
| 293B | A*02:01 | A*30:01 | B*13:02 | B*44:02 | C*06:02 | C*05:01 | A*02 |
| 254C | A*11:01 | A*32:01 | B*15:01 | B*56:01/56:55 | C*01:02 | C*03:03 | A*11 |
| 188B | A*02:01 | A*11:01 | B8*7:02 | B*14:02 | C*07:02 | C*08:02 | A*11, B*07 |
| 271B | A*01:01 | A*01:01 | B*08:01 | B*08:01 | C*07:01 | C*07:01 | A*01 |
| 225B | A*02:01 | A*03:01 | B*07:02 | B*51:01 | C*07:02 | C*14:02 | A*03, B*07 |

Figure 56:
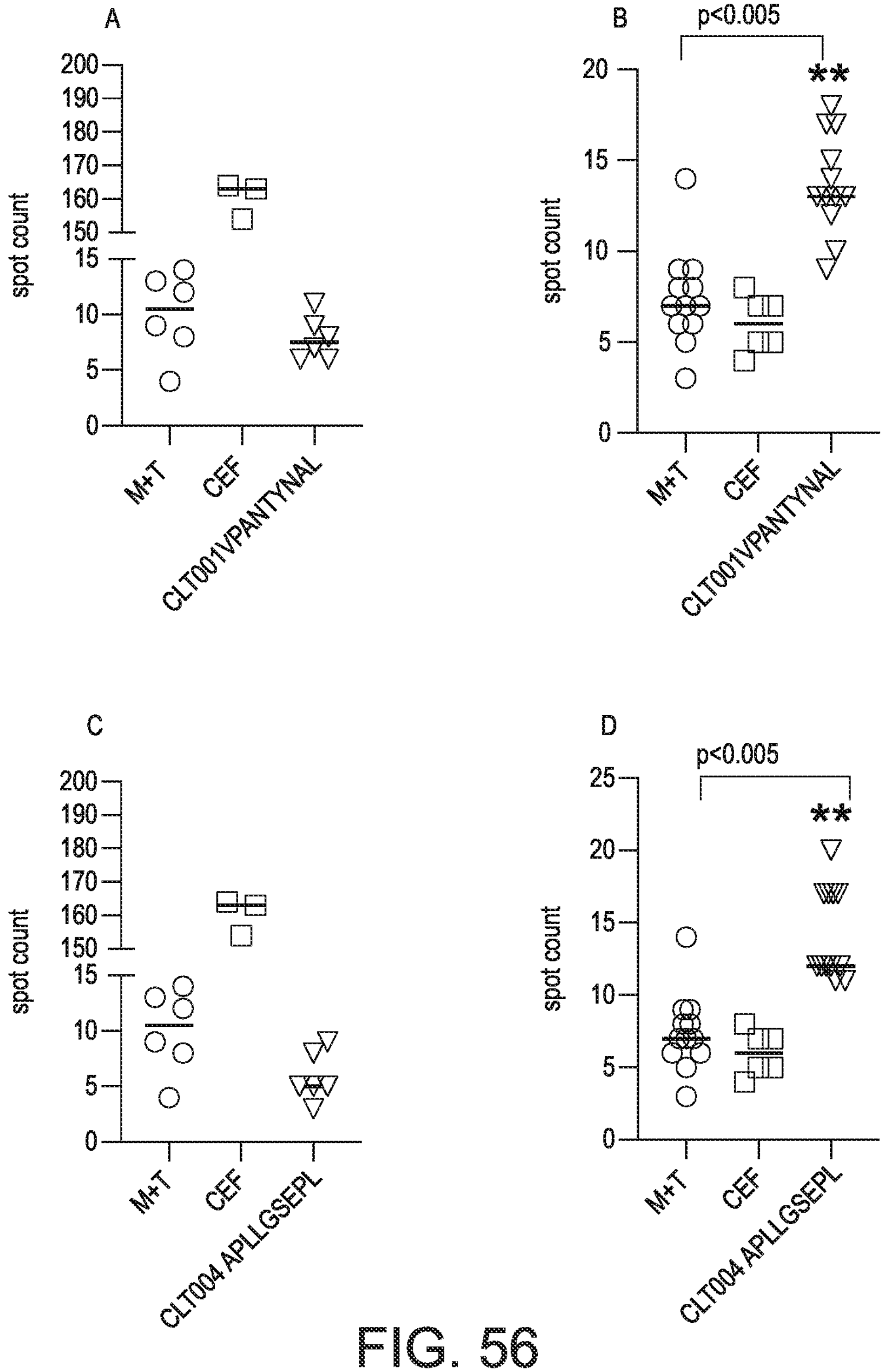

Example 4—Assays to Demonstrate High-affinity T-cells Specific for CLT Antigens have not been Deleted From Normal Subjects' T-cell Repertoire An ELISPOT assay may be used to show that CLT antigen-specific CD8 T-cells are present in the normal T-cell repertoire of healthy individuals, and thus have not been deleted by central tolerance due to the expression of cancer-specific CLT antigens in naïve and thymic tissues in these patients. This type of ELISPOT assay comprises multiple steps. Step 1: CD8 T-cells and CD14 monocytes can be isolated from the peripheral blood of normal blood donors, these cells are HLA typed to match the specific CLT antigens being tested. CD8 T-cells can be further sub-divided into naïve and memory sub-types using magnetically labelled antibodies to the memory marker CD45RO. Step 2: CD14 monocytes are pulsed with individual or pooled CLT antigen peptides for three hours prior to being co-cultured with CD8 T-cells for 14 days. Step 3: Expanded CD8 T-cells are isolated from these cultures and re-stimulated overnight with fresh monocytes pulsed with peptides. These peptides may include; individual CLT antigen peptides, irrelevant control peptides or peptides known to elicit a robust response to infectious (e.g., CMV, EBV, Flu, HCV) or self (e.g. Mart-1) antigens. Re-stimulation is performed on anti-Interferon gamma (IFNγ) antibody-coated plates. The antibody captures any IFNγ secreted by the peptide-stimulated T-cells. Following overnight activation, the cells are washed from the plate and IFNγ captured on the plate is detected with further anti-IFNγ antibodies and standard colorimetric dyes. Where IFNγ-producing cells were originally on the plate, dark spots are left behind. Data derived from such assays includes spot count, median spot size and median spot intensity. These are measures of frequency of T-cells producing IFNγ and amount of IFNγ per cell. Additionally, a measure of the magnitude of the response to the CLT antigen can be derived from the stimulation index (SI) which is the specific response, measured in spot count or median spot size, divided by the background response to monocytes with no specific peptide. A metric of stimulation strength is derived by multiplying the stimulation index for spot number by the stimulation index for spot intensity. In this way, comparisons of the responses to CLT antigens and control antigens can be used to demonstrate that naïve subjects contain a robust repertoire of CLT antigen-reactive T-cells that can be expanded by vaccination with CLT antigen-based immunogenic formulations. Table 9 provides a list of CLT Antigen-derived peptides that induced significant CD8 T-cell responses from HLA-matched normal blood donors. The results are shown in FIGS. 53-56. Horizontal bars represent the mean of the data. Statistical significance was measured with Kruskall Wallis test One-way Anova with correction for repeated measures with Dunns correction. FIG. 53 shows significant CD8 T-cell responses from a normal blood donor to HLA-A*0201-restricted peptides from CLT Antigen 1 (CLT001 in the figure). The example shown in FIG. 54 demonstrates CD8 responses from a normal donor to a peptide derived from CLT Antigen 2 (CLT002 in the figure) also restricted by HLA-A*0201. FIG. 55 shows significant CD8 T-cell responses from a normal blood donor to an HLA-A*0201-restricted peptide from CLT Antigen 4 (CLT004 in the Figure). FIG. 56 shows a lack of response to HLA-B*0702 restricted peptides from CLT Antigens 1 and 4 (CLT001 and CLT004 in the figure) in memory CD45RO-positive CD8 T-cells (panels A and C). By contrast, Naïve CD45RO-negative CD8 T-cells from the same donor respond significantly to peptides from both CLT001 and CLT004 (FIG. 56, panels B and D).

TABLE 9

CLT Antigen-derived peptides that induced significant CD8 T-cell responses from HLA-matched normal blood donors

| Reference CLT Antigen | SEQ ID NO. | Peptide sequence | HLA-type for peptide (predicted by NetMHC) |
|---|---|---|---|
| 1 | SEQ ID. NO. 73 | RLQGSVTLV | HLA-A*02:01 |
| 1 | SEQ ID. NO. 74 | VPANTYNAL | HLA-B*07:02 |
| 2 | SEQ ID. NO. 75 | QLMSSFSTL | HLA-A*02:01 |
| 4 | SEQ ID. NO. 76 | FLELWLPEPML | HLA-A*02:01 |
| 4 | SEQ ID. NO. 77 | APLLGSEPL | HLA-B*07:02 |

Example 5—Staining Reactive T-cells with CLT Antigen Peptide Pentamers

The presence and activity of circulating CD8 T-cells specific for CLT antigens in healthy donors and melanoma patients can be measured by using HLA Class I/peptide-pentamer ("pentamer") staining and/or in vitro killing assays. Thus, application of these methodologies to CLT antigens discovered using the methods elucidated in Example 1, 2 and 2.1 (Tables 1-6, FIGS. 1-50) can be used to demonstrate the existence of therapeutically relevant T-cell responses to the CLT antigens in cancer patients.

For these studies, CD8 T-cells isolated from healthy donor or patient blood are expanded using various cultivation methods, for example anti-CD3 and anti-CD28 coated microscopic beads plus Interleukin-2. Expanded cells can then be stained for specific CLT antigen-reactivity of their T-cell receptors using CLT peptide pentamers, which consist of pentamers of HLA Class I molecules bound to the relevant CLT Antigen peptide in the peptide-binding groove of the HLA molecule. Binding is measured by detection with phycoerythrin or allophycocyanin-conjugated antibody fragments specific for the coiled-coil multimerisation domain of the pentamer structure. In addition to the pentamer stain, further surface markers can be interrogated such as the memory marker CD45RO and the lysosomal release marker CD107a. Association of pentamer positivity with specific surface markers can be used to infer both the number and state (memory versus naive/stem) of the pentamer-reactive T-cell populations Pentamer stained cells may also be sorted and purified using a fluorescence activated cell sorter (FACS). Sorted cells may then be further tested for their ability to kill target cells in in vitro killing assays. These assays comprise a CD8 T-cell population, and a fluorescently labelled target cell population. In this case, the CD8 population is either CLT antigen-specific or CD8 T-cells pentamer-sorted and specific for a positive-control antigen known to induce a strong killing response such as Mart-1. The target cells for these studies may include peptide-pulsed T2 cells which express HLA-A*02, peptide-pulsed C1R cells transfected with HLA-A*02, 03 or B*07 or melanoma cells lines previously shown to express the CLTs/CLT antigens, or patient tumor cells. Peptides used to pulse the T2 or C1R cells include CLT antigen peptides or positive control peptides. Target cells may be fluorescently labelled with carboxyfluorescein succinimidyl ester (CFSE, a cell proliferation dye) and death is indicated by take up of 7AAD. In this way, as target cells are killed, by apoptosis mediated by CD8 T-cells, they gain red fluorescence and become dual red/green positive. Thus, application of such killing assays to pentamer-sorted, CLT antigen-specific CD8 T-cells can be used to enumerate the cytotoxic activity of CLT-antigen-specific T-cells in ex vivo cultures of melanoma patient or healthy donor T-cells. FIG. 57 shows HLA pentamer staining of healthy donor CD8 T-cells with peptides-derived from CLT Antigens 1, 2 and 4 (CLT001, CLT002 and CLT004 in the figure). FIG. 58 shows expanded CLT004 pentamer sorted cells killing CLT004-pulsed C1R-B7 target cells. Significant killing of peptide-pulsed C1R-B7 cells is apparent at 3:1 and 1:1 effector to target cells ratios.

Example 6—Mouse Immunogenicity Studies

To demonstrate the immunogenicity of CLT antigens, mice can be inoculated with replication-defective adenovirus vectors expressing one or more CLT antigens, and T-cells obtained from these mice can be tested for the presence of CLT antigen-specific T-cells using IFNγ ELISPOT assays (Mennuni et al., Int. J. Cancer, 2005). Briefly, mice are inoculated with CLT antigen-expressing recombinant adenoviruses, and at a suitable timepoint they are humanely euthanized, and preparations of spleen cells are loaded into wells of a multiwell dish derivatized with monoclonal antibodies to murine IFNγ, in the presence (or absence) of overlapping peptides corresponding to the CLT antigen. Following a suitable time, the immobilized IFNγ is stained with a different monoclonal antibody, permitting innumeration of the cells/spots which are then compared to total cells loaded into the well to give a quantitative readout of CLT antigen-reactive T-cells.

Example 7—Assays to Validate CLT Expression in Melanoma Cells a) qRT-PCR Validation of CLT Expression in Melanoma Cell Lines Quantitative real-time polymerase chain reaction (qRT-PCR) is a widespread technique to determine the amount of a particular transcript present in RNA extracted from a given biological sample. Specific nucleic acid primer sequences are designed against the transcript of interest, and the region between the primers is subsequently amplified through a series of thermocyle reactions and fluorescently quantified through the use of intercalating dyes (SYBR Green). Primer pairs were designed against the CLTs and assayed against RNA extracted from melanoma cell lines. Non-melanoma cell lines were utilised as negative controls. Specifically, melanoma cell lines COLO 829 (ATCC reference CRL-1974), MeWo (ATCC reference HTB-65), SH-4 (ATCC reference CRL-7724) and control cell lines HepG2 (hepatocellular carcinoma, ATCC reference HB-8065), Jurkat (T-cell leukemia, ATCC reference TIB152) and MCF7 (adenocarcinoma, ATCC reference HTB-22) were expanded in vitro and RNA was extracted from $1\times10^6$ snap-frozen cells and reverse transcribed into cDNA. qRT-PCR analysis WITH SYBR Green detection following standard techniques was performed with primers designed against two regions of each CLT, and reference genes. Relative quantification (RQ) was calculated as:

$$RQ=2[Ct(REFERENCE)-Ct(TARGET)]$$

Figure 59:
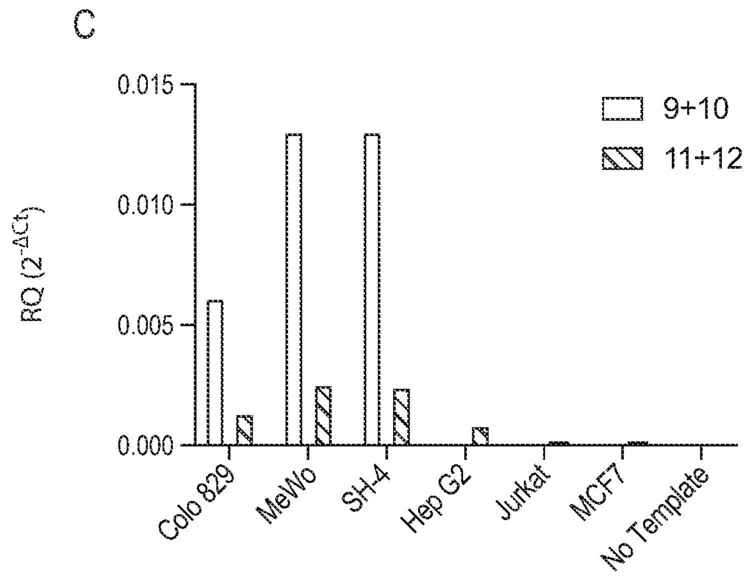

The results of these experiments are presented in FIG. 59. Panel A shows results from a qRT-PCR assay with two primer sets (1+2 and 3+4) targeting different regions of the CLT encoding CLT Antigen 1 (SEQ ID 33) on RNA extracted from three melanoma cell lines and four non-melanoma cell lines. Panel B shows results from qRT-PCR assay with two primer sets (5+6 and 7+8) targeting different regions of the CLT encoding CLT Antigen 2 (SEQ ID 34) on RNA extracted from three melanoma cell lines and four non-melanoma cell lines. Panel C shows results from qRT-PCR assay with two primer sets (9+10 AND 11+12) targeting different regions of the CLT encoding CLT Antigens 3/4 (SEQ ID 35) on RNA extracted from three melanoma cell lines and four non-melanoma cell lines. These results confirmed the specific expression of CLTs in RNA extracted from melanoma cell lines, compared to non-melanoma cells. The CLTs were detected in each of the melanoma cell lines tested.

b) RNAScope Validation of CLT Expression in Melanoma Cells In Situ

In situ hybridisation (ISH) methods of transcript expression analysis allow the presence and expression levels of a given transcript to be visualised within the histopathological context of a specimen. Traditional RNA ISH assays involve the recognition of native RNA molecules in situ with oligonucleotide probes specific to a short stretch of the desired RNA sequence, which are visualised through a signal produced by a combination of antibody or enzymatic-based colorimetric reactions. RNAScope is a recently developed in situ hybridization-based technique with more advanced probe chemistry ensuring specificity of the signal produced and allowing sensitive, single-molecule visulation of target transcripts (Wang et al 2012 J Mol Diagn. 14(1): 22-29). Positive staining for a transcript molecule appears as a small red dot in a given cell, with multiple dots indicative of multiple transcripts present.

RNAScope probes were designed against the CLTs and assayed on sections of 12 formalin-fixed, paraffin-embedded cutaneous melanoma tumour cores. Scoring of the expression signal was performed on representative images from each core as follows:

Estimated % cells with positive staining for the CLT probe, rounded up to the nearest 10

Estimated level of per cell expression across the given section as:

0 =no staining

1=1-2 dots per cell

2=2-6 dots per cell

3=6-10 dots per cell

4=>10 dots per cell

Expression of each of each CLT was detected across a number of different patient tumour cores, independently validating the discovery of CLTs from tumour-derived RNAseq data and confirming homogeneity of expression within tumour tissue across certain samples and also highlighting the presence of at least one CLT in each patient core analysed.

TABLE 10

Scoring of RNAScope in melanoma patient tissue cores

| Tissue | Core | CLT Antigen 1 (SEQ ID 33) % of positive cells | CLT Antigen 1 (SEQ ID 33) Score | CLT Antigen 2 (SEQ ID 34) % of positive cells | CLT Antigen 2 (SEQ ID 34) Score | CLT Antigen 3/4 (SEQ ID 35) % of positive cells | CLT Antigen 3/4 (SEQ ID 35) Score |
|---|---|---|---|---|---|---|---|
| Melanoma | 61 | 10 | 1 | 80 | 4 | 10 | 1 |
| Melanoma | 62 | 80 | 2 | 80 | 2 | 100 | 4 |
| Melanoma | 63 | 100 | 4 | 0 | 0 | 100 | 4 |
| Melanoma | 64 | 0 | 0 | 0 | 0 | 100 | 3 |
| Melanoma | 65 | 70 | 3 | 0 | 0 | 80 | 4 |
| Melanoma | 66 | 100 | 3 | 50 | 2 | 90 | 3 |
| Melanoma | 67 | 100 | 3 | 100 | 4 | 50 | 2 |
| Melanoma | 68 | 0 | 0 | 0 | 0 | 100 | 3 |
| Melanoma | 69 | 90 | 3 | 100 | 4 | 100 | 4 |
| Melanoma | 70 | 0 | 0 | 0 | 0 | 70 | 3 |
| Melanoma | 71 | 0 | 0 | 0 | 0 | 80 | 4 |
| Melanoma | 72 | 100 | 3 | 100 | 4 | 60 | 2 |

Throughout the specification and the claims which follow, unless the context requires otherwise, the word ‘comprise’, and variations such as ‘comprises’ and ‘comprising’, will be understood to imply the inclusion of a stated integer, step, group of integers or group of steps but not to the exclusion of any other integer, step, group of integers or group of steps.

All patents, patent applications and references mentioned throughout the specification of the present invention are herein incorporated in their entirety by reference.

The invention embraces all combinations of preferred and more preferred groups and suitable and more suitable groups and embodiments of groups recited above.

SEQUENCE LISTING

SEQ ID NO. 1 (Polypeptide sequence of CLT Antigen 1)
MWNFFRRELTSNGFPENFSLDVPANTYNALKSRLCDPNADHTSCPSPCSLHAAGALP
GTGRQRWRVELAHLADRKLSLRDVSRLRQGGERRSGIAVKVVRGGAGFAARLQGSV
TLVQQGWFFPRLGGCQAWWRMGAVVWCGELLTCTS SEQ ID NO. 2 (Polypeptide sequence of CLT Antigen 2)
MTGVLIRRGDLVTDMVACRIKTFRGHTEKAAICKTRKESSAETSPADSLILDFQPLQLM
SSFSTLASLDK SEQ ID NO. 3 (Polypeptide sequence of CLT Antigen 3)
MNTPNIVSLRAHQPEVGIIPSVLLMRPLRIKGVFHHIHSPLHGENQGFTLCLQGAPPSSS
V SEQ ID NO. 4 (Polypeptide sequence of CLT Antigen 4)
MAKTKGSLSVFRELHPAAAFDRAVHFLFLELWLPEPMLSSSPPSSTAPLLGSEPLRHW
EASLSR SEQ ID NO. 5 (Polypeptide sequence of CLT Antigen 5)
MKRKANRWRLSLRNGLLPSTPRATQQIPMEFLNSRVADIPIKPW SEQ ID NO. 6 (Polypeptide sequence of CLT Antigen 6)
MRGFLWRVETRGVEGSMRGPQKVLGNRLPGAGRNARSRDNFAVW SEQ ID NO. 7 (Polypeptide sequence of CLT Antigen 7)
MVYYGNPESSPGISLVFGLLRLDRMQPGFSVSQEGDPVGITDHLGC SEQ ID NO. 8 (Polypeptide sequence of CLT Antigen 8)
MPAQLKFTLQVNPATKMRVTLLSQPMETYEGDVLGVQTPYSSDSTILVL SEQ ID NO. 9 (Polypeptide sequence of CLT Antigen 9)
MGSSRVGERMMEEESRTGQKVNPGNTGKLFVGVGISRIAKVKYGECGQGFSDKSDVI
THQRTHTGGKPYVCRECGRALAGSQTSSVTRGHTQGRSLMSAESVSGALAGSQSSS
FTRGHTGETPQSAGRMSKSLVIKPYLNSHKKTNVITTHLHTPALRWLQRKSANPLHSP
RV SEQ ID NO. 10 (Polypeptide sequence of CLT Antigen 10)
MHSLQIFSLCLFTLLIVSFIVQKPFNLIRSNLSIFLLVEIAFEDLVMNYLPKLTSRRVFSRFS
YMTFYSFRSYIKVFVSSQIDFFSLVKGRGPVQAHFSMWFCYSG SEQ ID NO. 11 (peptide sequence derived from CLT Antigen 1)
VQQGWFFPR SEQ ID NO. 12 (peptide sequence derived from CLT Antigen 1)
VVRGGAGFAAR -continued

| SEQUENCE LISTING |
| --- |

SEQ ID NO. 13 (peptide sequence derived from CLT Antigen 1)
HLADRKLSL

SEQ ID NO. 14 (peptide sequence derived from CLT Antigen 1)
ARLQGSVTL

SEQ ID NO. 15 (peptide sequence derived from CLT Antigen 2)
ADSLILDF

SEQ ID NO. 16 (peptide sequence derived from CLT Antigen 2)
SSFSTLASLDK

SEQ ID NO. 17 (peptide sequence derived from CLT Antigen 3)
NTPNIVSLR

SEQ ID NO. 18 (peptide sequence derived from CLT Antigen 3)
QPEVGIIPSVLLMRP

SEQ ID NO. 19 (peptide sequence derived from CLT Antigen 4)
KTKGSLSVFR

SEQ ID NO. 20 (peptide sequence derived from CLT Antigen 5)
RVADIPIKPW

SEQ ID NO. 21 (peptide sequence derived from CLT Antigen 5)
DIPIKPW

SEQ ID NO. 22 (peptide sequence derived from CLT Antigen 5)
RVADIPIKP

SEQ ID NO. 23 (peptide sequence derived from CLT Antigen 6)
RSRDNFAVW

SEQ ID NO. 24 (peptide sequence derived from CLT Antigen 6)
RSRDNFA

SEQ ID NO. 25 (peptide sequence derived from CLT Antigen 7)
SPGISLVF

SEQ ID NO. 26 (peptide sequence derived from CLT Antigen 8)
SSDSTILVL

SEQ ID NO. 27 (peptide sequence derived from CLT Antigen 9)
AGRMSKSLVIK

SEQ ID NO. 28 (peptide sequence derived from CLT Antigen 9)
PQSAGRM

SEQ ID NO. 29 (peptide sequence derived from CLT Antigen 9)
AGSQSSSFTRGHTGETPQ

SEQ ID NO. 30 (peptide sequence derived from CLT Antigen 10)
RSNLSIFL

SEQ ID NO. 31 (peptide sequence derived from CLT Antigen 10)
FSLCLFTL

SEQ ID NO. 32 (peptide sequence derived from CLT Antigen 10)
SRRVFSRFSYMTFYSFRSYIKVFV SEQ ID NO. 33 (cDNA sequence of CLT encoding CLT Antigen 1)
CGGGGCCAGTCTTTCCCGTGCTATTCTCGTGATAGTGAATAAGTCTCACAAGATCT
GATGGGTTTATCAGGGGTTTTCATTTTGCTTCTTCCTCATTTTCTTTTGCTGCTGTAA
TGTAAGAAACGCCTTTTGCCTCCTGCCATAATTCTGAGGCCTCACAGCCATGTGGA
ACTTCTTCAGGAGAGAATTAACATCCAATGGATTCCCAGAAAACTTTTCCCTCGATG
TACCAGCAAACACCTACAATGCCCTGAAAAGCCGCCTCTGCGACCCCAATGCAGA
TCACACGTCCTGTCCCAGCCCCTGCAGCCTCCACGCGGCGGGTGCACTGCCAGG
CACGGGAAGGCAGCGCTGGCGAGTAGAACTGGCCCATCTCGCAGATAGGAAGCT
GAGCCTCAGGGACGTTTCACGCCTTCGTCAAGGTGGTGAGAGGAGGAGCGGGAT
TGCCGTGAAGGTGGTGAGAGGAGGAGCGGGGTTTGCTGCCCGACTTCAGGGATC
TGTCACCCTCGTCCAGCAGGGTTGGTTCTTCCCGAGGCTGGGAGGATGCCAAGCC
TGGTGGAGGATGGGGGCGGTGGTGTGGTGTGGGGAGCTTCTGACTTGCACATCC
TGAGGGAACCTTCTGCAGCTGATGTGTGAACTGGACCCCAGGCCGTGCCTCCGAG
GAATCCCCAAGGCTATGGCCCCTCAGGTCCTGCTGGGGTGTTGGCCCCCACCTCT
GCCTCAGAATGCAGGGGTTCTGCAGGGAAGCCGCAGACCAGCCTGCTGCCTTGG
GCCCTAGGGACACTGCAGCCCCAGAAAGTACTGTGGGGGACAAAAGAGTTGTTTC -continued

SEQUENCE LISTING

TCGGGGGAGAAAACACCTGTGAGGAAATGCAGGTGCCACAGAGGGAAATCCTCCT
GGGGAGGAGGGTACCTGTTCCATCCTCGGCCGACACGGGACTGCCTGGTGCCTG
GTACCCACAGCCGCTACCTGCCGCACGCATCTCTCCATGGTTTGCTAATTACTTCC
ATTAGTTTTAAACAAACTTGACAAGAGACAGAAGGGTCCAGAGAGAAATTAAATCTA
ACTGTTTAAACATGT

SEQ ID NO. 34 (cDNA sequence of CLT encoding CLT Antigen 2)
CACCTCCATCACTGCGAATTATAATTCGACATGAGATTTGGGAGATGACACAAAAC
CAAACCATATCAGTCTTTAAAGAGTTAAGTTAAAATAAGCTCTTTAAAGTGGGCCCT
AATCCAGTATGACTGGTGTTCTTATAAGAAGAGGAGATTTGGTCACAGACATGGTT
GCATGCAGAATAAAGACTTTTCGAGGACACACTGAGAAGGCAGCCATCTGCAAAA
CAAGGAAAGAGTCCTCAGCAGAAACCAGTCCTGCAGACTCCTTGATCTTGGACTTC
CAGCCACTGCAATTGATGTCAAGCTTCAGCACCCTTGCATCTCTGGATAAATGAAA
TGTCACCCCAGCTGCCGTCCTTGTTCAGATCTGTGCAATAAAGAGCAAAGCATAAA
ACCAAGTCAAGGCTTTGAGGGAGTGACCTACAAAATGCATAATGTGAAACAATGCA
AAAGCGAAAGGTGCAAAATCCCCATCAAAGAGCTGGAGGCTGACAGATGCGCCAG
TGATAATTCCCATCTTCCAACACAGGAGCACAGCTTCCATTTTCCATAACAGAACAA
CAGCCAGAGCAGCTGGAAGGCAGGGCCGCATCCCAGACTTCCACCAACAATGGG
ATGAGACTTGACATCTGGAATCACAACCACAACAGACCTGAGAGACCCACCAGCTT
GATGACAAGCTTCTTCTTTCAAAGAAAGGTATCAGTCTGGGGGACCTAGTGCTGCA
AACCATGACAAATTAAGTGTGGCATCCCTCACTTGCATAATGGAACTCAGTGATATT
TTTTAATTAACAAGAGTTATTTTTATGTAAGCTTCTCTCATTCCTCCACTGTGCGTGC
TCGGGGGCTGGTGGTGAGGAAAAAGAAAACAGCTGTGCGGGAAGCATCAAGAAA
AGGCAAGTCATGAAGTCTTAGAGATCAGTGACATGTAAGAAAAAGAGTGAGGAGAA
AAATATTCCTACTAAAGTTTTCCATTTGTTTACCTTCCTTGTCACATAGACTTCCAAG
AGTTAGAAGTCTAGGATTTGATCTCCAAATCTTCCTGGCAGATTACTCATCTTCATT
TCATTCATATAGTCCAGGGGTTTGTACAAAGGAAGATGCCAGTTCTTCCCCAATCA
TAACTAAGATATCAAGAGATATTCTTTTGAAATGTAACAAAGGAGATCTGAAGTTCA
TCTGAAAAAAATAAATGGTTTTAGGCGGTCATGACCATGGGATGCTGGACCAGGAT
GGTAAGCTTCAGGAAACAGAATCTGGAGAATGCCCAGCTGCTCCCACAGGAAGCA
TCAGGGAAGAAGAAGAAGAGGTGTGAAGTCTGCCTTCTGCTCTGCTGGGATCCCT
TTCACATCTCCTTTGCCTCCAGGCAGTTTTGGTTCCTGGCCATTTCCAGGTGTGAC
TCACTCAGGATGGTAAGCATCTTCTCTCCTACCCAGAGTAGAGGATGAAGACCTCA
TCTCAGAGGTTGAAGGGAGCTCCAGAGAGAGGTCTCAAACTTCCAGCATTAACTG
CTAAAGAAGCTTCATGAGCTGCTGGAGAACCTGGGAAATGACCAATTATAGGGACA
GAGCTCAAATACTCTGGGACACTCTAGTAGCTGAGAAAGTTCCAACTCCAGGGTGA
TAGAGGACTGCCTGGCAAACCATCATCAAAGCAGAAGACCTGATACTAACATCACA
GGCTATGGTTTATTACTGAAGATCAGTGCTTACACCCTGCCAGAGGTTCAGAAGCA
AACTTATCATTGTTCTCCCTGGAGATGTTGGCCCACATTCTGAAAAGTGTGGTCAG
TAGTAGCAACAGAAAGCAATTGTGCTTGCCAAGCACAATGTCACTGTCCCCAGCCC
TTCCCCCAACACAACCCAGTAGGTGCTTCCTGGCTGCAAACTTGGGAAAGTCACTT
GACCTGTCTGAGGTTCCACTTCCTAATCTGGCCTGGCGAAGATAAGAAAAACAGTT
TATTTAAAGTGTCTAGCAAAGTGCTTGGACCAAAATAGGACCTCTGAAATGGTTATG
GTAGTGCTGTTAAGGTGATGTTTTAAGTGCTGATGAGCACAAAGATGGGTAAGATA
TTCCTTCTGTTAAAATCTACAGTCTAATGAGAGAGAACAAGATGAATGCACAATAAC
TGTCATTCAGAACAGGATTATGAGAAGGTGTGAATTTCTGTGAAAAATCAGAACAG
GGAGTAATATGATCCCAGGTGATTGGCAGGGGGTGGGGGTCTGGATTCAACTGGA
GAGGGAGCTGGCAGGGAAGGCTTCCTGGAGGATGAGAGTTCAACAAGGGGCAGG
TGTAGGATGTGGGTGGCCAAGTGACTGGGCAGAAGGAGCTGCAGAAGTAAGACC
CCAAATCAGGAAGACAAGGGCCTGCTGAGAAACACGAGCTACAAAGTGCAAGTGC
AGGAAGAGTTGGGATGAGATTAGAAGGGGGTCTGGGGCCAGACTGTGGAAGGCC
CAAATGCCGGGCTAAGGAGTTTGTACTTAATTCAGTGGTCAACGGGGAGTCATTG
GAGGCTGTTGAGCAGGAGAGTTGCTTTCTTTACAGCTGTGCCAGACTAAATTAAAC
CTAAACAGTACTTTATAGCTGGAAAGGGAAGGCCCAGGAATAGCTCTTGACTCAGA
AACAGGCATTGGGGAAGGTAATGAGAAACAGCCGTGACTGATCAAAGCAGAGAGG
TTAATTAAATTTGTAATTATTGTGAAAGGCCATTAAAAACCCTAGTTCACTAGAGATA
ACTGCTCTAGTGGGGCTTCAAAGACAAACGCTTCTTTTAACCTTGAATAGGGGGAT
GTTTGCTTCTCTGTGGAGGAGATATGATTAAGATACTTAATAAATGGTAGATAAACA SEQ ID NO. 35 (cDNA sequence of CLT encoding CLT Antigens 3 and 4)
AAACACACTAAGGGCTTTGTTATGGACTGAAATGTGTCCTCTCCCCAGAGTCACAG
GATTATGAAGCCATAATCCTCAATGTGACTATATTTGGAGCAGGGGCCTTTACAGA
CATAATTAAATTAAATGAGGTCATAAGAGTGGGGCCCTAGTCTGATAGGACTGGTG
TCCTTACAAGAAGAGGGAGAGTCCTCAGAGAGTCCTCTCTCTCGGCATGGACACA
AAAGAAAAGCCATGTGAGGACACAGAGAGAAGGTGGCTGTCTACGAGCTAGGAAG
AAAGGCCTCACCGGAAACCAACCCTCACAGCAGCTCCATCTTGGACTTCCAGCCT
CCGGAACTGTGAGAAAATAAATGTTTGCAATTCAGGTCGGTTGTATTTTGTGAAGG
CCATCCTAGCAAATGAATACTCCTAACATTGTCTCTTTAAGAGCTCACCAGCCTGA
GGTAGGAATCATTCCATCTGTGTTACTAATGAGACCGCTGAGGATCAAAGGGGTTT
TCCACCACATCCACTCACCTCTACATGGCGAAAACCAAGGGTTCACTCTCTGTCTT
CAGGGAGCTCCACCCAGCAGCAGCGTTTGACAGAGCTGTTCACTTCCTCTTCCTG
GAGCTGTGGCTTCCAGAGCCCATGCTCAGCAGTTCCCCTCCTTCTTCGACTGCTC
CTCTCTTAGGCTCAGAGCCACTCAGACATTGGGAAGCAAGTTTGTCAAGATGACAG
AGAACCGAGGTAATGGATTCGAGTGATGAAACAGGAAGTTCATTCATGAGTTTTTG
GCCACACCTCCAAAGTGACGACTTAGCCAGAAATGGGATAACTGGGTTTCCCTACT
TCTCTTTTATCATCCTCAATGAGAGTGACCAAATATTAGAGCTAGATGGAACCTTAG
TGAAAATCTGGCTACTCGTCCCGTCCCACCAGCCTGCCACCCATTTCAAGTTTGAA -continued

SEQUENCE LISTING

GAGACAAAGACACATGGACCTTATGTAATTACTGGGGATTACCCCAGGAGTCTGTG
GCAAAAGTCAGCTTCTTCCCTCCCTGCTTCCCCGCCCTGTCTCTGGTACTTTCTAC
CAACACTGGGCTGTTTCTGTGATCACACTTAAGCGTACCTAACCTGCGAATGCTGT
ATAGAAGGTGCTAATGAACATGATTTAGCTTTAACACTCAGTTTTCTAAAGGGACAC
GTGGGGGCAGCAAATGTTTAGGCAAAAACAATTCCAGTTCTAGCCTCTACTGTCTA
CATATGTGTATACATTTGGGAAACGTTTGGGAAAGGGATATTTGAGAGCTTCTTTTT
CTTTTTTGTGGTTTAGTTATTTGATGATATTGAGATTGTTTCTGAGCCATGTGCTTCA
ACATCGGATTGGGGATTTCAGAAAAAGTTTTAGTCACTGTGATTCCATTTAGCTTCC
AAATGTGTCTCTGCTAAGAGACTTAAAAGCACTCATAAATAGCACGTGTGTCTTCTT
TGCAGTGTTTGCTAATTTTGAGTCACATCTTTTTAGAAAATCATGAGATTTGGTGTC
ACAGAGACTGGAATAAATATAGTCAAACTTATTGGTGAAGATTTCCTTTAGCTGTTT
TCATAATCCATTTCCATTGTTATGATTATTGATGAATAAAACATTTTCTTTAGGTAGA
TACTTCTTTTTTCCCCCCACCTTGATTTAATGTTTCCACTCTTATTGTCAAGTTTCTT
ATTACTCCCTAATAACTCTCAATAAAATAATGATTCCTGGGAGATTATTCCTGCTTTC
CTACTATCACCTGTTGATTTGAAAAGACAGAACAATACCGTAGAAGCTTCACTAATA
CATTGAAAGATAAAATGATAATACTAAATACTAAAATATGAAAAGTGATACTAAAAGT
GGAGTCCTGGCACTAGTATTTTTTTTTTTGAGTCTTTAAATTTTATTTATTTATTTTTG
AATTTTTTAAAATTATATGTTATGTTCTGGGATACATGTGCAGAACGTGCAGGTTTG
TTACATAGGTATACAGGTCTGGCACTAGTATTTTGTTGCCACAAAATATCAAGCATG
TATCCAAACTGCTCAAGACACATTAAAGACACAGGTAATCTGTAGGCATATTCAGG
CTTGTAGTTTGCATTTTTTGGTTTTCTTGTGGCTTTCAGTGCAAGTTGAGGTAATTC
ATGGGAAACAGTCACCAAAGAAGTGCCAGTATTAGAAATCCAAGAGCCATTTCTCT
AGCTTCTTCCAGAATCAAGACTTTAGAGGTAATTTCTATCAACACTGGACATTTCCT
GTCTGCAATTAACAATGAACACATAGCATTATGTTTAATTGCAACCTGTTTAAAGCA
GATTGGATGCTAAGGTTTAAGAACACTCTTCAGTCAAAAAGGTCTTTTAATCAGGTT
TTTAATCTTGAGCACAATCTAGGACACAGCATCATAGACTAACTCATTCGAGAATAG
GTGTTGTCATCTAATCCTAACCACCCCCACCACCAACAAGCTGAATAGCTCTGGGC
TCAGTATATACATTTGTACTGGGCTCAGTACACACACCTAAGCTGGGTTCAGTATAT
GCCACTTTATAGTGAGAGGCATTTTGTAATGAGAGCTCTGGGTTCACTATATACATT
TGTACTGGGCTCA

SEQ ID NO 36 (cDNA sequence of CLT encoding CLT Antigen 5)
GGGAGGGGGCCATGGCGGGGCCACTTCAAAGGAAAAGCTCTAGCTCCCCTACCT
CTCTCACATCCTAAGGCTGCCTTTGTGGGATTCCACACAGAACAGCCTGGAAGCTT
GGGGCCCTGGCTTCCTTTTCTGGCCTGGGAGTCAGGTCATGGGGCCATCGCTTCA
CAGCAATCATGAGGGCCCAGGCCCAAGTGCTCACATGCTCCTCATGGGGACTGCT
CCTCTTAAAGGGTGGGCCCTCCTCACCCAGCTCCCTGCCCTGGCCAAGGAGGAG
GCTGAAAGAGCCTGAGCTGTGCCCTCTCCATTCCACTGCTGTGGCAGGGTCAGAA
ATCTTGGATAGAGAAAACCTTTTGCAAACGGGAATGTATCTTTGTAATTCCTAGCAT
GAAAGACTCTAACAGGTGTTGCTGTGGCCAGTTCACCAACCAGCATATCCCCCCTC
TGCCAAGTGCAACACCCAGCAAAAATGAAGAGGAAAGCAAACAGGTGGAGACTCA
GCCTGAGAAATGGTCTGTTGCCAAGCACACCCAGAGCTACCCAACAGATTCCTAT
GGAGTTCTTGAATTCCAGGGTGGCGGATATTCCAATAAAGCCATGGTGAGAAAGG
CATTCAGACATGGTGCCACTAGGATCACAGCTTTCATTGGCGGCCAGTCTCCCAG
CCCCAAACTGCAGATACCTGGTCTTCTTCATGGCTGTGGCTCAATCTTCCTAGATA
TTTCATTGAAAAACCAAGAGATATATCTGTGCACATGGCTTTTAGCCATGAGGCTTG
GAAACTGGACACCACTGTAAAGAACATCTAGTGTCCCGTAAATCCATACCAAAGCT
CTGAATCCACAAACCAGGCTCTGGCCCAACCCTGCAAACACACTCCATTGCTCCAT
CTTCAGTAAAGGAAGACAAATTCATTTTTCTAATAACTGTGGACCTGCAGCCCCCTT
AGATGTGTTGAGAGTCTTTGGAAATATTTTCCTCTGAGGTCTGTCCACAGCTTCCCT
GGGCCTGCGCTCAGCTGGCCCGAGAAGGACCAAGGTCCCTCACATTTGCATGTAA
ACAGGGAGTGCCCTCTGCCCTTCCAGTGAGCCCTGCCAGCGTGGGGGAGGCTTC
AGCTCTGTGATCCGTTCCAGCTCACTCTGAATTACACTCCTACATGCCCAGTCACA
GACTTTTTGCAATTTCATTTTATTTCACTGGCCCAACATCATTGTTAAAATAAAATTT
AGCTGTGTTCCAAATGCTGCAATATACAGTCTTCTGAAATGGCACCCTACATATTAG
CCCAGACACAAAGAAGCAGTTTATAGGAGACAAGGCATCTGAGCATTATTAGCCTC
CTCCTCACTTTGAAGAGGTCAAGTTCATGGGTGGGCCCATGATCGCCTGACCCATT
TACTCAACAACATCCTCATCCAACTTCTTGGGCCACTGTTCTAGCTAAGCCAGCTTT
GGAACCTATTCCTCCAACATTAGGATTGCCAGATAAAATACAGGACACCCAGTTAT
ATTTGAACTTCAGACATACATTGGATAAATTTTCAGTACAAGTATGTCCCAAATATTG
CATGATTTATTGCATTTAATAAAAATGTTGTACTGAAACATTTTTCATTGTTCCTCTAA
AATTCAAATTTAACTGGGTGTCTTGGTCTGTTTGGCTGCTATAACAAATTGCCTTAG
GCTGGGGAATTTATAAACAACAGAAATTTATTGCTCACATTTCTAGAGTCTGGGAG
GCCCAAGATCAAGGTGCCAGCAGATTTGGTGCCTGGCGAGGGCCCATCCTCTGCT
TCATAGATAGCACCTTCTTGCTGTGTCCTCACATGGCAGAAGCAGAGAACAAGCTC
TCTGAGTCCTC SEQ ID NO 37 (cDNA sequence of CLT encoding CLT Antigen 6)
CTTGGACTTCCCAGCCTCCAGAACTGTGAGAAATAAATTTTTGTTGTTTAATCCATC
CAGTCTGTGATATTTTGTTATGGCAGCTGAAGCAGTCAGGAAAGGATCCTCCCCAT
CTCTGCAGAAGCCTGACCATCCCCCTAGAGGGCCTGGGAGGAAGTGGGTTTTGCA
TACAGTCCCTGTTGACTCTAGTGCCCCCTGCTGGCCCCAGACGCGAGTTCCGGCG
AGGCTTCAGGGTACAGCTCCCCCGCAGCCAGAAGCCGGGCCTGCAGCGCCTCAG
CACCGCTCCGGGACACCCCACCCGCTTCCCAGGCGTGACCTGTCAACAGGTCTGT
ATTGGCGACAAAAGGAGCAGCCCTGAATGTAGGGAAAGCAGGGCGGAGTCCTCT
GCAGGCTCGGGGGAGGGGAGGGGCGTGAATGCGTGGATTTCTGTGGAGAGTGG
AAACACGGGGAGTCGAGGGGAGCATGCGCGGGCCTCAGAAAGTTCTGGGAAACC -continued

SEQUENCE LISTING

GACTCCCGGGAGCAGGGAGGAACGCGCGCTCCAGAGACAACTTCGCGGTGTGGT
GAACTCTCTGAGGAAAAACACGTGCGTGGCAACAAGTGACTGAGACCTAGAAATC
CAAGCGTTGGAGGTCCTGAGGCCAGCCTAAGTCGCTTCAAAATGGAACGAAGGCG
TTTGTGGGGTTCCATTCAGAGCCGATACATCAGCATGAGTGTGTGGACAAGCCCA
CGGAGACTTGTGGAGCTGGCAGGGCAGAGCCTGCTGAAGGATGAGGCCCTGGCC
ATTGCCGCCCTGGAGTTGCTGCCCAGGGAGCTCTTCCCGCCACTCTTCATGGCAG
CCTTTGACGGGAGACACAGCCAGACCCTGAAGGCAATGGTGCAGGCCTGGCCCT
TCACCTGCCTCCCTCTGGGAGTGCTGATGAAGGGACAACATCTTCACCTGGAGAC
CTTCAAAGCTGTGCTTGATGGACTTGATGTGCTCCTTGCCCAGGAGGTTCGCCCCA
GGAGGTGGAAACTTCAAGTGCTGGATTTACGGAAGAACTCTCATCAGGACTTCTG
GACTGTATGGTCTGGAAACAGGGCCAGTCTGTACTCATTTCCAGAGCCAGAAGCA
GCTCAGCCCATGACAAAGAAGCGAAAAGTAGATGGTTTGAGCACAGAGGCAGAGC
AGCCCTTCATTCCAGTAGAGGTGCTCGTAGACCTGTTCCTCAAGGAAGGTGCCTGT
GATGAATTGTTCTCCTACCTCATTGAGAAAGTGAAGCGAAAGAAAAATGTACTACG
CCTGTGCTGTAAGAAGCTGAAGATTTTTGCAATGCCCATGCAGGATATCAAGATGA
TCCTGAAAATGGTGCAGCTGGACTCTATTGAAGATTTGGAAGTGACTTGTACCTGG
AAGCTACCCACCTTGGCGAAATTTTCTCCTTACCTGGGCCAGATGATTAATCTGCG
TAGACTCCTCCTCTCCCACATCCATGCATCTTCCTACATTTCCCCGGAGAAGGAAG
AGCAGTATATCGCCCAGTTCACCTCTCAGTTCCTCAGTCTGCAGTGCCTGCAGGCT
CTCTATGTGGACTCTTTATTTTTCCTTAGAGGCCGCCTGGATCAGTTGCTCAGGCA
CGTGATGAACCCCTTGGAAACCCTCTCAATAACTAACTGCCGGCTTTCGGAAGGG
GATGTGATGCATCTGTCCCAGAGTCCCAGCGTCAGTCAGCTAAGTGTCCTGAGTCT
AAGTGGGGTCATGCTGACCGATGTAAGTCCCGAGCCCCTCCAAGCTCTGCTGGAG
AGAGCCTCTGCCACCCTCCAGGACCTGGTCTTTGATGAGTGTGGGATCACGGATG
ATCAGCTCCTTGCCCTCCTGCCTTCCCTGAGCCACTGCTCCCAGCTTACGACCTTA
AGCTTCTACGGGAATTCCATCTCCATATCTGCCCTGCAGAGTCTCCTGCAGCACCT
CATCGGGCTGAGCAATCTGACCCACGTGCTGTATCCTGTCCCCCTGGAGAGTTAT
GAGGACATCCATGGTACCCTCCACCTGGAGAGGCTTGCCTATCTGCATGCCAGGC
TCAGGGAGTTGCTGTGTGAGTTGGGGCGGCCCAGCATGGTCTGGCTTAGTGCCAA
CCCCTGTCCTCACTGTGGGGACAGAACCTTCTATGACCCGGAGCCCATCCTGTGC
CCCTGTTTCATGCCTAATTAGCTGGGTGCACATATCAAATGCTTCATTCTGCATACT
TGGACACTAAAGCCAGGATGTGCATGCATCTTGAAGCAACAAAGCAGCCACAGTTT
CAGACAAATGTTCAGTGTGAGTGAGGAAAACATGTTCAGTGAGGAAAAAACATTCA
GACAAATGTTCAGTGAGGAAAAAAAGGGGAAGTTGGGGGTAGGCAGATGTTGACT
TGAGGAGTTAATGTGATCTTTGGGGAGATACATCTTATAGAGTTAGAAATAGAATCT
GAATTTCTAAAGGGAGATTCTGGCTTGGGAAGTACATGTAGGAGTTAATCCCTGTG
TAGACTGTTGTAAAGAAACTGTTGAAAATAAAGAGAAGCAATGTGAAGC

SEQ ID NO 38 (cDNA sequence of CLT encoding CLT Antigens 7 and 8)
GAGACAGGTCTCACTCTGTTGCCCGGTCAGGAAAGTGGCACAATCACAGCTCACT
GCAGTCTCAGTCTCCCAGGCTCAAGATGGATACATTTAAGGTATGGTGATCCGGTC
CACCGTGTGGTTAGGATTCCCAAATTTTGTTGACAGCGTCTCGGATATGAACCACA
CGGAAATTTGGCCTGCTGCTTTCTGCGTGGGGAGTGCGATGTGGATCCAGCTGTT
GTACAGTGCCTGCTTCTGGTGGCTGTTTTGCTATGCAGTGGATGCTTATCTGGTGA
TCCGGAGATCGGCAGGACTGAGCACCATCCTGCTGTATCACATCATGGCGTGGGG
CCTGGCCACCCTGCTCTGTGTGGAGGGAGCCGCCATGCTCTACTACCCTTCCGTG
TCCAGGTGTGAGCGGGGCCTGGACCACGCCATCCCCCACTATGTCACCATGTACC
TGCCCCTGCTGCTGGTTCTCGTGGCGAACCCCATCCTGTTCCAAAAGACAGTGAC
TGCAGTGGCCTCTTTACTTAAAGGAAGACAAGGCATTTACACGGAGAACGAGAGG
AGGATGGGAGCCGTGATCAAGATCCGATTTTTCAAAATCATGCTGGTTTTAATTATT
TGTTGGTTGTCGAATATCATCAATGAAAGCCTTTTATTCTATCTTGAGATGCAAACA
GATATCAATGGAGGTTCTTTGAAACCTGTCAGAACTGCAGCCAAGACCACATGGTT
TATTATGGGAATCCTGAATCCAGCCCAGGGATTTCTCTTGTCTTTGGCCTTCTACG
GCTGGACAGGATGCAGCCTGGGTTTTCAGTCTCCCAGGAAGGAGATCCAGTGGGA
ATCACTGACCACCTCGGCTGCTGAGGGGGCTCACCCATCCCCACTGATGCCCCAT
GAAAACCCTGCTTCCGGGAAGGTGTCTCAAGTGGGTGGGCAGACTTCTGACGAAG
CCCTGAGCATGCTGTCTGAAGGTTCTGATGCCAGCACAATTGAAATTCACACTGCA
AGTGAATCCTGCAACAAAAATGAGGGTGACCCTGCTCTCCCAACCCATGGAGACC
TATGAAGGGGATGTGCTGGGGGTCCAGACCCCATATTCCTCAGACTCAACAATTCT
TGTTCTTTAGAACTGTGTTCTCACCTTCCCAACACTGCACTGCCGAAGTGTAGCGG
CCCCCAAACCTTGCTCTCATCACCAGCTAGAGCTTCTTCCCGAAGGGCCTTTAGGA
TAGGAGAAAGGGTTCATGCACACACGTGTGAGA SEQ ID NO 39 (cDNA sequence of CLT encoding CLT Antigen 9)
CCTGTAGTCCCAGCTACTCAGGAGGCTGAGGCAGGAGAATTGCTTGAATCCGGGA
GGCGGAGGTTGCAGTGAGGGGAGATTGTGCCACTGCACTCCAGCCTGGGCGACA
GAGGGAGACTCCATATCAAAAAGAAAAAAAAATCTCTAGAGTTTGGAAACATTTACC
AACCAAACCACTGATTTCTCATCACCTCTTAGTCAAACCTCCTTGGATGGCCTTCAG
AGGAGAACAGAGTAAACACCAGAAGAACTCAGGAGGAAGGAGACTGAAGGAAAGA
TGTATAGCCTGCGAGAAAGAAAGGGTCATGCATACAAAGAGATCAGCGAGCCACA
GGATGATGACTACCTCTATTGTGAGATGTGTCAGAACTTCTTCATTGACAGCTGTG
CTGCTCATGGGCCCCCTACATTTGTAAAGGACAGTGCAGTGGACAAGGGGCATCC
CAACCGTTCAGCCCTCAGTCTGCCCCCGGGGCTGAGAATTGGGCCATCAGGCATC
CCTCAGGCTGGGCTTGGAGTATGGAACGAGGCATCTGATCTGCCACTGGGTCTGC
ACTTTGGCCCCTATGAGGGCCGAATTACAGAAGACGAAGAGGCAGCCAACAGTGG
ATATTCCTGGCTAATCACCAAGGGGAGAAACTGCTATGAGTATGTGGATGGAAAAG
ATAAATCCTCGGCCAACTGGATGAGAACCAAAGCCAGAGATCCATCCATGTCCCTC -continued

SEQUENCE LISTING

ATGCTGTCTGGCCTTTTCAAGTCAAAAATTTCTCAGTCAACATGTGGAACGCAATCA
CTCCTCTCAGAACTTCCCAGGACCATCTGCAAGAAAACTTCTCCAACCAGAGAATC
CCTGCCCAGGGGATCAGAATCAGGAGCGGCAATATTCTGATCCACGCTGCTGTAA
TGACAAAACCAAAGGTCAAGAGATCAAAGAAAGGTCCAAACTCTTGAATAAAAGGA
CATGGCAGAGGGAGATTTCAAGGGCCTTTTCTAGCCCACCCAAAGGACAAATGGG
GAGCTCTAGAGTGGGAGAAAGAATGATGGAAGAAGAGTCCAGAACAGGCCAGAAA
GTGAATCCAGGGAACACAGGCAAATTATTTGTGGGGGTAGGAATCTCAAGAATTGC
GAAAGTCAAATATGGAGAGTGTGGGCAAGGTTTCAGTGATAAGTCAGATGTTATTA
CACACCAAAGGACACACACAGGGGGGAAGCCCTACGTCTGCAGAGAGTGTGGGA
GGGCTTTAGCCGGAAGTCAGACCTCCTCAGTCACCAGAGGACACACACAGGGGA
GAAGCCTTATGTCTGCAGAGAGTGTGAGCGGGGCTTTAGCCGGAAGTCAGTCCTC
CTCATTCACCAGAGGACACACAGGGGAGACGCCCCAGTCTGCAGGAAGGATGAG
TAAGTCATTAGTAATAAAACCTTATCTCAATAGCCACAAGAAGACAAACGTGATCAC
CACACACTTGCACACCCCAGCTCTGAGGTGGCTTCAGCGAAAGTCTGCTAACCCC
TTACATTCCCCGAGAGTGTAAAGAGATCGGAAATAACTAATTAAACAAATCCGCCA
CTTTCATGACTAGAGTTGAGGAAGAACAGGGGATAGTTCTGTAAGTGTTCGGGGG
ACGTCAACATGTGTGGTTGTTTCCCGCACTGATCCCCTCCATTTTTTGTGTTTTGCC
TCCTGTTCTAATTAATTTTGTCTCCATACATATCTGAACCCCAAGTGTGTACCTCATT
CTTCCCTTATCACTGAAGGAAGGAAGAGTCCAGAAGGGCCACAGAGAACTCAAAC
GTTCAGTTCAAGTCTCCACAGGAATTCAACCCCAGAAAGACATAAACTTGGAGTCC
ATCTGGTTTAATTATTGGAGAATCGATTCCCAAGTCCAGGAAGAGAAATGTAGGGT
TTTACAGAGTCGCAGCAGGAAAGAGAGCTCCCTGGTCTCCTGGGAAGTGTGACCT
CTTCTAATGGACCCCTCTCCTCTGCTGCCATACTCCCCCTTGGCTCCCCCTGTCTC
CTCTCCTGATTTCCTCCAATCTCTGTAGCCCCAGAAGTGAACGCCAGACAGGAACA
CGCATGTGTGTATATATGTGTTCACGTGTGCTATGTGTGTTAAGCCTGCATGCATG
GGTGTGGGGGTATGTGCCCTCTGTGTACGTATCTGTGTGAGTGTGGGGGTTTCAA
GGGTGTATTAGGAATAACGCTCAAAATCCTAAGGAAATTGAATACTCTGAGAGAAG
AGAGACAGACCCTCTCATACTGTTTTATATTGTTTTATACTCAGAAAAGGAAAAAGA
AGCAAAACTAAAGGCAGGTAGCCTGGCGCCTAGGAACCAGACCTGAAACCAAGGA
ACCAGACCCGAAACCAGGCCTGGGCCGGCCTGACCTAAGCCTGGTAGTTAAAATT
CGACCCCTGACCTAGCAACTGATGTTATCTATAGATTATAGAAAGACATTGTGAAAC
TTCCCGGTCTGTTCTGTTCCACTCTGACCATCGGTGCATGCAGCCCCTGTCACCTA
CCCCCTGCTTGCTCAATCGATCACGACCCTCTCACGTGGACCCCCTTAGAGTTGTG
AGCCCTTAAAAGGGACAGGAATTGCTCACTCGGGGAGCTCGGCTCTTGAGACAGC
AGTCTTGCTGATGCTCCTGGCCGAATAAACCGCTTCCTTCTTT

SEQ ID NO 40 (cDNA sequence of CLT encoding CLT Antigen 10)
CCCACCTACTGATTTACCAACTCTTTTTCATTTCAACTTTTATTTTAGGTCCAGAGGG
TACATGTGTGAGTTTGTTGCATGAGTATATTGTGTGACACTCATGTATGGGGTACAA
ATAATCCCAACACCAATGTAGAGAACACAATATCCAATAGGCAGTTCTTCAGGCCC
TTTCTCCATCCTGCCCTCCCCCACATGGTAGATCCCAGTGTCTATTGTGCCCATCT
TTATGTCCATGCATAACCAATGTTTAGTTCCCACTTATAAGTGAGAGCATGCAGTAT
TGGGCTTTCTGTGCCCACATTAATTCACTTAAGATAATGGTCTCCAGCTGGATCCAT
ATTGATGCAAAGTACATAATTTCTTTCATTTTATGGCTGCATAGTATTCCATGTTATG
TTTGTACCACATTTTCTTTATCCAGTCCATAGCTGATGGACATCTACATTGATTCCAT
GTCCTCATTAATGTGAATAGTGTTTTGATGAACATATGAATGTATGTGTCTTTTTGGT
AGAATAATTTATTTTCCTTTGGATATAAAGCCAGTAATGGAATTGCTGGGTCGAATC
GTCGTTCTTTTGTAAGTTCTTTGAGATATCTCCAAGTTTCGTTCCACAGGCACTGAA
ATAGTTTACATTCCCACCAATAATGAACACGCATTCCCTTTTCTCCACAACCCTGTC
AACATCTGTTATTTTTTTACTTTTTAATAGTAGCCATTCTGACTGGTGTGTGATGGTA
CTTCATTATGGCTTTCATTCGCATTTCTTTCCTGACTTGTGATTTTGAGTAGTTTTTC
ATATGTTTGTTGGCGACATGTATGTCTTCTGAGAAGAGCCTGTTCATGTTTTTTGCC
CACTTCTTAACAGGGCTGTTCATCTTTTGCTTGTTGATTTGTTCAAGTTTCTTAGAGA
TAGTGGATATTAGATCTCTGTTGGATGCATAGTTTGCAAATATTTTCTCTCTGTCTGT
TTACCCTGTTGATAGTTTCTTTTATTGTGCAGAAACCCTTTAATTTAATCAGGTCCAA
CTTATCCATTTTTCTTTTGGTTGAAATTGCTTTTGAGGACTTAGTTATGAATTATTTG
CCAAAGCTGACGTCAAGAAGGGTATTCTCTAGGTTTTCTTATATGACATTTTATAGT
TTTAGGTCTTATATTAAAGTCTTTGTTTCATCTCAAATTGACTTTTTTTCTCTGGTAAA
AGGTAGGGGTCCAGTTCAAGCTCATTTTTCCATGTGGTTTTGTTACAGTGGGTAGC
TGCAGACATGAGCTGGGCAGGAGAGGCCTCTTCCTAACAGGAATGTCAGGTGACC
A SEQ ID NO. 41 (cDNA sequence encoding CLT Antigen 1)
ATGTGGAACTTCTTCAGGAGAGAATTAACATCCAATGGATTCCCAGAAAACTTTTCC
CTCGATGTACCAGCAAACACCTACAATGCCCTGAAAAGCCGCCTCTGCGACCCCA
ATGCAGATCACACGTCCTGTCCCAGCCCCTGCAGCCTCCACGCGGCGGGTGCACT
GCCAGGCACGGGAAGGCAGCGCTGGCGAGTAGAACTGGCCCATCTCGCAGATAG
GAAGCTGAGCCTCAGGGACGTTTCACGCCTTCGTCAAGGTGGTGAGAGGAGGAG
CGGGATTGCCGTGAAGGTGGTGAGAGGAGGAGCGGGGTTTGCTGCCCGACTTCA
GGGATCTGTCACCCTCGTCCAGCAGGGTTGGTTCTTCCCGAGGCTGGGAGGATGC
CAAGCCTGGTGGAGGATGGGGGCGGTGGTGTGGTGTGGGGAGCTTCTGACTTGC
ACATCC SEQ ID NO. 42 (cDNA sequence encoding CLT Antigen 2)
ATGACTGGTGTTCTTATAAGAAGAGGAGATTTGGTCACAGACATGGTTGCATGCAG
AATAAAGACTTTTCGAGGACACACTGAGAAGGCAGCCATCTGCAAAACAAGGAAAG
AGTCCTCAGCAGAAACCAGTCCTGCAGACTCCTTGATCTTGGACTTCCAGCCACTG -continued

| SEQUENCE LISTING |
|---|

CAATTGATGTCAAGCTTCAGCACCCTTGCATCTCTGGATAAA

SEQ ID NO. 43 (cDNA sequence encoding CLT Antigen 3)
ATGAATACTCCTAACATTGTCTCTTTAAGAGCTCACCAGCCTGAGGTAGGAATCATT
CCATCTGTGTTACTAATGAGACCGCTGAGGATCAAAGGGGTTTTCCACCACATCCA
CTCACCTCTACATGGCGAAAACCAAGGGTTCACTCTCTGTCTTCAGGGAGCTCCAC
CCAGCAGCAGCGTT SEQ ID NO. 44 (cDNA sequence encoding CLT Antigen 4)
ATGGCGAAAACCAAGGGTTCACTCTCTGTCTTCAGGGAGCTCCACCCAGCAGCAG
CGTTTGACAGAGCTGTTCACTTCCTCTTCCTGGAGCTGTGGCTTCCAGAGCCCATG
CTCAGCAGTTCCCCTCCTTCTTCGACTGCTCCTCTCTTAGGCTCAGAGCCACTCAG
ACATTGGGAAGCAAGTTTGTCAAGA SEQ ID NO. 45 (cDNA sequence encoding CLT Antigen 5)
ATGAAGAGGAAAGCAAACAGGTGGAGACTCAGCCTGAGAAATGGTCTGTTGCCAA
GCACACCCAGAGCTACCCAACAGATTCCTATGGAGTTCTTGAATTCCAGGGTGGC
GGATATTCCAATAAAGCCATGG SEQ ID NO. 46 (cDNA sequence encoding CLT Antigen 6)
ATGCGTGGATTTCTGTGGAGAGTGGAAACACGGGGAGTCGAGGGGAGCATGCGC
GGGCCTCAGAAAGTTCTGGGAAACCGACTCCCGGGAGCAGGGAGGAACGCGCGC
TCCAGAGACAACTTCGCGGTGTGG SEQ ID NO 47 (cDNA sequence encoding CLT Antigen 7)
ATGGTTTATTATGGGAATCCTGAATCCAGCCCAGGGATTTCTCTTGTCTTTGGCCTT
CTACGGCTGGACAGGATGCAGCCTGGGTTTTCAGTCTCCCAGGAAGGAGATCCAG
TGGGAATCACTGACCACCTCGGCTGC SEQ ID NO 48 (cDNA sequence encoding CLT Antigen 8)
ATGCCAGCACAATTGAAATTCACACTGCAAGTGAATCCTGCAACAAAAATGAGGGT
GACCCTGCTCTCCCAACCCATGGAGACCTATGAAGGGGATGTGCTGGGGGTCCA
GACCCCATATTCCTCAGACTCAACAATTCTTGTTCTT SEQ ID NO 49 (cDNA sequence encoding CLT Antigen 9)
ATGGGGAGCTCTAGAGTGGGAGAAAGAATGATGGAAGAAGAGTCCAGAACAGGC
CAGAAAGTGAATCCAGGGAACACAGGCAAATTATTTGTGGGGGTAGGAATCTCAA
GAATTGCGAAAGTCAAATATGGAGAGTGTGGGCAAGGTTTCAGTGATAAGTCAGAT
GTTATTACACACCAAAGGACACACACAGGGGGGAAGCCCTACGTCTGCAGAGAGT
GTGGGAGGGCTTTAGCCGGAAGTCAGACCTCCTCAGTCACCAGAGGACACACACA
GGGGAGAAGCCTTATGTCTGCAGAGAGTGTGAGCGGGGCTTTAGCCGGAAGTCA
GTCCTCCTCATTCACCAGAGGACACACAGGGGAGACGCCCCAGTCTGCAGGAAG
GATGAGTAAGTCATTAGTAATAAAACCTTATCTCAATAGCCACAAGAAGACAAACGT
GATCACCACACACTTGCACACCCCAGCTCTGAGGTGGCTTCAGCGAAAGTCTGCT
AACCCCTTACATTCCCCGAGAGTG SEQ ID NO 50 (cDNA sequence encoding CLT Antigen 10)
ATGCATAGTTTGCAAATATTTTCTCTCTGTCTGTTTACCCTGTTGATAGTTTCTTTTA
TTGTGCAGAAACCCTTTAATTTAATCAGGTCCAACTTATCCATTTTTCTTTTGGTTGA
AATTGCTTTTGAGGACTTAGTTATGAATTATTTGCCAAAGCTGACGTCAAGAAGGGT
ATTCTCTAGGTTTTCTTATATGACATTTTATAGTTTTAGGTCTTATATTAAAGTCTTTG
TTTCATCTCAAATTGACTTTTTTTCTCTGGTAAAAGGTAGGGGTCCAGTTCAAGCTC
ATTTTTCCATGTGGTTTTGTTACAGTGGG SEQ ID NO. 51 (peptide sequence derived from CLT Antigen 4)
AAFDRAVHF SEQ ID NO. 52 (peptide sequence derived from CLT Antigen 4)
AFDRAVHF SEQ ID NO. 53 (peptide sequence derived from CLT Antigen 3)
RPLRIKGVF SEQ ID NO. 54 (peptide sequence derived from CLT Antigen 4)
KTKGSLSVF SEQ ID NO.55 (peptide sequence derived from CLT Antigen 1)
VPANTYNALK SEQ ID NO.56 (peptide sequence derived from CLT Antigen 1)
RLGGCQAWWR SEQ ID NO.57 (peptide sequence derived from CLT Antigen 1)
ANTYNALKSR SEQ ID NO.58 (peptide sequence derived from CLT Antigen 2)
LVTDMVACRI

SEQUENCE LISTING

SEQ ID NO.59 (peptide sequence derived from CLT Antigen 2)
LILDFQPLQL

SEQ ID NO.60 (peptide sequence derived from CLT Antigen 2)
MSSFSTLASL

SEQ ID NO.61 (peptide sequence derived from CLT Antigen 2)
LMSSFSTLASL

SEQ ID NO.62 (peptide sequence derived from CLT Antigen 2)
LMSSFSTLA

SEQ ID NO.63 (peptide sequence derived from CLT Antigen 2)
QLMSSFSTLA

SEQ ID NO.64 (peptide sequence derived from CLT Antigen 2)
MVACRIKTFR

SEQ ID NO.65 (peptide sequence derived from CLT Antigen 2)
VTDMVACRIK

SEQ ID NO.66 (peptide sequence derived from CLT Antigen 2)
SPADSLIL

SEQ ID NO.67 (peptide sequence derived from CLT Antigen 3)
NTPNIVSLRA

SEQ ID NO.68 (peptide sequence derived from CLT Antigen 3)
VLLMRPLRIK

SEQ ID NO.69 (peptide sequence derived from CLT Antigen 3)
MRPLRIKGVF

SEQ ID NO.70 (peptide sequence derived from CLT Antigen 4)
FLFLELWL

SEQ ID NO.71 (peptide sequence derived from CLT Antigen 4)
SVFRELHPA

SEQ ID NO.72 (peptide sequence derived from CLT Antigen 4)
SPPSSTAPL

SEQ ID NO.73 (peptide sequence derived from CLT Antigen 1)
RLQGSVTLV

SEQ ID NO.74 (peptide sequence derived from CLT Antigen 1)
VPANTYNAL

SEQ ID NO.75 (peptide sequence derived from CLT Antigen 2)
QLMSSFSTL

SEQ ID NO.76 (peptide sequence derived from CLT Antigen 4)
FLELWLPEPML

SEQ ID NO.77 (peptide sequence derived from CLT Antigen 4)
APLLGSEPL

SEQ ID NO. 78 (peptide sequence derived from CLT Antigen 2)
SLILDFQPL

The invention claimed is:

1. A composition comprising an isolated polypeptide and an immunostimulant selected from the group consisting of aluminum phosphate, saponins, immunostimulatory oligonucleotides, aminoalkyl glucosaminide 4-phosphates, lipopolysaccharides, 3-de-O-acylated monophosphoryl lipid A (3D-MPL), toll-like receptor 4 (TLR4) ligands, toll-like receptor 7 (TLR7) ligands, toll-like receptor 8 (TLR8) ligands, toll-like receptor 9 (TLR9) ligands, interleukin 12 (IL-12), and interferons, wherein:

the isolated polypeptide comprises the amino acid sequence selected from the group consisting of SEQ ID NO: 1, 11-14, 55-57 and 73-74.

2. A fusion protein comprising a first polypeptide and one or more additional polypeptides, wherein the first polypeptide comprises:

(i) the amino acid sequence selected from the group consisting of SEQ ID NO: 1, 11-14, 55-57 and 73-74;

(ii) a melanoma associated antigen;

iii) a universal CD4 helper epitope; or (iv) an immunostimulant polypeptide selected from the group consisting of IL-12, interferons, and checkpoint blockade molecules, wherein the first polypeptide and the one or more additional polypeptides are not the same.

3. A method of making the composition of claim 1, the method comprising combining the immunostimulant with the isolated polypeptide, wherein:

the isolated polypeptide comprises the amino acid sequence selected from the group consisting of SEQ ID NO: 1, 11-14, 55-57 and 73-74.

* * * * *

UNITED STATES PATENT AND TRADEMARK OFFICE
CERTIFICATE OF CORRECTION

Page 1 of 1

PATENT NO. : 12,263,216 B2
APPLICATION NO. : 17/232597
DATED : April 1, 2025
INVENTOR(S) : Kassiotis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 932 days.

Signed and Sealed this
Sixth Day of January, 2026

John A. Squires
*Director of the United States Patent and Trademark Office*